United States Patent
Walsh et al.

(10) Patent No.: US 9,527,830 B2
(45) Date of Patent: Dec. 27, 2016

(54) INHIBITORS OF THE RENAL OUTER MEDULLARY POTASSIUM CHANNEL

(75) Inventors: Shawn Walsh, Bridgewater, NJ (US); Alexander Pasternak, Princeton, NJ (US); Brian Cato, Secaucus, NJ (US); Paul E. Finke, Milltown, NJ (US); Jessica Frie, Princeton, NJ (US); Qinghong Fu, Plainsboro, NJ (US); Dooseop Kim, Seoul (KR); Barbara Pio, West Orange, NJ (US); Aurash Shahripour, Rahway, NJ (US); Zhi-Cai Shi, Monmouth Junction, NJ (US); Haifeng Tang, Metuchen, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 50 days.

(21) Appl. No.: 14/344,681

(22) PCT Filed: Sep. 10, 2012

(86) PCT No.: PCT/US2012/054354
§ 371 (c)(1),
(2), (4) Date: Apr. 15, 2014

(87) PCT Pub. No.: WO2013/039802
PCT Pub. Date: Mar. 21, 2013

(65) Prior Publication Data
US 2014/0235628 A1  Aug. 21, 2014

Related U.S. Application Data

(60) Provisional application No. 61/535,589, filed on Sep. 16, 2011.

(51) Int. Cl.
| | | |
|---|---|---|
| *C07D 403/14* | (2006.01) | |
| *C07D 401/10* | (2006.01) | |
| *C07D 405/14* | (2006.01) | |
| *C07D 413/14* | (2006.01) | |
| *C07D 403/10* | (2006.01) | |
| *C07D 405/06* | (2006.01) | |
| *C07D 405/12* | (2006.01) | |
| *C07D 487/04* | (2006.01) | |
| *C07D 211/28* | (2006.01) | |
| *C07D 211/62* | (2006.01) | |
| *C07D 211/48* | (2006.01) | |
| *C07D 471/08* | (2006.01) | |

(52) U.S. Cl.
CPC .......... *C07D 401/10* (2013.01); *C07D 211/28* (2013.01); *C07D 211/48* (2013.01); *C07D 211/62* (2013.01); *C07D 403/10* (2013.01); *C07D 405/06* (2013.01); *C07D 405/12* (2013.01); *C07D 405/14* (2013.01); *C07D 413/14* (2013.01); *C07D 471/08* (2013.01); *C07D 487/04* (2013.01)

(58) Field of Classification Search
CPC ... C07D 211/58; C07D 405/06; C07D 405/12; C07D 405/14; C07D 409/14; C07D 413/14; C07D 471/10; C07D 471/14; C07D 487/04
USPC .............. 514/252.03, 255.05, 310, 315, 318, 514/320, 322, 339; 544/238, 405; 546/146, 194, 196, 199, 244, 276
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

Yamamoto et al. "Preparation of 1-(2- . . . " CA138:14009 (2002).*

(Continued)

*Primary Examiner* — Celia Chang
(74) *Attorney, Agent, or Firm* — Baerbel R. Brown; Catherine D. Fitch

(57) ABSTRACT

This invention relates to compounds having structural Formula I:

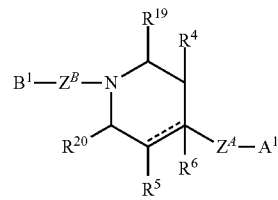

and pharmaceutically acceptable salts thereof which are inhibitors of the Renal Outer Medullary Potassium (ROMK) channel (Kir1.1). The compounds of Formula I are useful as diuretics and natriuretics and therefore are useful for the therapy and prophylaxis of disorders resulting from excessive salt and water retention, including cardiovascular diseases such as hypertension and chronic and acute heart failure.

11 Claims, No Drawings

(56) References Cited

U.S. PATENT DOCUMENTS

| | | | |
|---|---|---|---|
| 5,736,546 A | 4/1998 | Kawashima et al. | |
| 6,258,813 B1 | 7/2001 | Arlt et al. | |
| 6,787,543 B2 | 9/2004 | Take et al. | |
| 6,956,046 B2 * | 10/2005 | Yamamoto | C07D 401/12 514/327 |
| 8,071,602 B2 * | 12/2011 | Sun | 514/253.07 |
| 8,673,920 B2 * | 3/2014 | Pasternak | C07D 295/135 514/218 |
| 2004/0204404 A1 | 10/2004 | Zelle et al. | |
| 2005/0215526 A1 | 9/2005 | Hulme et al. | |
| 2005/0267121 A1 | 12/2005 | Li et al. | |
| 2006/0183739 A1 | 8/2006 | Tsaklakidis et al. | |
| 2006/0183742 A1 | 8/2006 | Mederski et al. | |
| 2006/0211692 A1 | 9/2006 | Mederski et al. | |
| 2007/0004750 A1 | 1/2007 | Lorsbach et al. | |
| 2007/0093472 A1 | 4/2007 | Mederski et al. | |
| 2008/0003214 A1 | 1/2008 | Cezanne et al. | |
| 2010/0286123 A1 | 11/2010 | Pasternak et al. | |
| 2015/0299198 A1 * | 10/2015 | Walsh | A61K 31/4184 514/210.18 |

FOREIGN PATENT DOCUMENTS

| | | | |
|---|---|---|---|
| EP | 1094063 A1 | 4/2001 | |
| EP | 1391452 A1 | 5/2002 | |
| EP | 1939175 A1 | 7/2009 | |
| EP | 2773199 | 5/2013 | |
| FR | 2673182 | 8/1992 | |
| FR | 2673182 A1 | 8/1992 | |
| GB | 949088 A | 2/1964 | |
| GB | 1575310 A | 9/1980 | |
| GB | 2116967 | 7/1986 | |
| JP | 10203986 | 8/1998 | |
| WO | 9744329 | 11/1997 | |
| WO | 0051611 A1 | 9/2000 | |
| WO | 0232874 | 4/2002 | |
| WO | 0204314 A1 | 6/2002 | |
| WO | 0250061 A1 | 6/2002 | |
| WO | 2004020422 A1 | 3/2004 | |
| WO | 2004037817 A1 | 5/2004 | |
| WO | 2004046110 | 6/2004 | |
| WO | 2005037843 | 4/2005 | |
| WO | 2005044797 | 5/2005 | |
| WO | 2006034341 A2 | 3/2006 | |
| WO | 2006034769 A1 | 4/2006 | |
| WO | 2006098342 A1 | 9/2006 | |
| WO | 2006129199 A1 | 12/2006 | |
| WO | 2007075629 A2 | 7/2007 | |
| WO | WO2008040057 | * 4/2008 | |
| WO | 2008147864 | 12/2008 | |
| WO | 2008147864 A2 | 12/2008 | |
| WO | 2009149508 | 11/2009 | |
| WO | 2010129379 A1 | 11/2010 | |
| WO | 2012058116 A1 | 5/2012 | |
| WO | 2012058134 A1 | 5/2012 | |
| WO | 2013028474 A1 | 2/2013 | |
| WO | 2013062892 A1 | 5/2013 | |
| WO | 2013062900 A1 | 5/2013 | |
| WO | 2013066714 A1 | 5/2013 | |
| WO | 2013066717 A1 | 5/2013 | |
| WO | 2013066718 A2 | 5/2013 | |
| WO | 2013090271 A1 | 6/2013 | |
| WO | 2014015495 A1 | 1/2014 | |
| WO | 2014018764 A1 | 1/2014 | |

OTHER PUBLICATIONS

Improper Markush "Fed. Registry" vol. 76(27) p. 71172-75. slide 1, 64-67 (2011).*
Parkin et al. "Structures of piperazine . . . " Acta Cryst. B60, p. 219-227 (2004).*
Bhave et al. "Development of a . . . " Molecular Pharma. v.79, p. 42-50 (2011).*
Patani et al. "Bioisosterism . . . " Chem. Rev. 96 3147-3176 (1996).*
Rubini et al. "Synthesis of isosteric . . . " Tetrhedron 42(21) 6039-45 (1986).*
Feng et al. "Structure-activity . . . " Bioorgan. Med. Chem. 17 p. 2355-60 (2007).*
Swale et al. "ML148: the first selective . . . " ACS Chem. Neurosci p. A-K (2016).*
ACCF/AHA Practice Guideline, 2009 Focused update incorporated into the ACC/AHA 2005 guidelines . . . , Circulation, 2009, e391-e436, 119.
Baltzly, R., The preparation of N-mono-substituted and unsymmetrically disubstituted piperazines, J. Am. Chemoc., 1944, 263-266, 66.
Bhave, G., Small-molecule modulators of inward rectifier K+ channels: recent advances and future possibilities, Future Med Chem, 2010, 757-774, 2(5).
Bhave,G., Development of a selective small-molecule inhibitor Kir1.1, the renal outer medullary potassium channel, Mol. Pharmacol., 2011, 42-50, 79.
Brater et al., Diuretic Therapy, Drug Therapy, 1998, 387-395, 339.
Brewster et al., Antihypertensive 1,4-bis (2-indol-3-ylethyl)piperazines, Chimie Ther., 1973, 169-172 (English trans.), 2.
Cerkvenik-Flajs V, Determination of residues of azaperone in the kidneys by liquid chromatography with fluorescence, Anal. Chim. Acta., 2007, 374-382, 586.
Chemical Abstracts (2004), Abstract No. 697771-49-6, "1,3-Isobenzofurandione 5-[[4-[(5-chloro-2-methoxyphenyl) sulfonyl]-1- . . . "
Cheymol et al., Increase in the effects of epinephrine and acetylcholine . . . , Comptes Rendus des seances de la Societe de Biologie, 1951, 496-499 (English trans.), 145.
Denton, et al., Discovery of a small molecule inhibitor of ROMK with unprecedented selectivity, Molecular Libraries: Probe Report, 2010, pp. 1-10; retrieved on May 2, 2014. Retrieved from the internet: URL :http://www.ncbi.nlm.nih.gov/books/NBK50699/pdf/ml112.pdf.
Fallen, K., The Kir channel immunoglobuling domain is essential for Kir1.1 (ROMK) thermodynamic stability, trafficing and gating, Channels, 2009, 57-66, 3.
Felker et al, Diuretic strategies in patients with acute decompensated heart failure, New Eng. J. Med., 2011, 797-805, 364.
Frank, Managing hypertension using combination therapy, Am. Fam. Physician, 2008, 1279-1286, 77.
International Search Report and Written Opinion for PCT/US2012/54354, mailed Nov. 20, 2012, 7 pages.
Kulkarni, YD, Possible antifertility agents, part III. Synthesis of 4-(substituted aminomethyl)-5,6,7-trimethoxy phthalid . . . (abstract)), Biol. Mem., 1987, 141-144, 13.
Lanyi et al., Piperazine-Derivatives II, Res. Lab. of Chinoin-Fabrik Chemisch-Pharma. Prod., 1968, 1431-1435 (English trans.), 18.
Lewis, L. M., High-throughput screening reveals a small-molecule inhibitor of the Renal Outer Medullary Potassium Channel and Kir7.1, Mol. Pharncol., 2009, 1094-1103, 76.
Lutz, R. E., Antimalarials. Some Piperazine Derivatives, J. Org. Chem., 1947, 771-775, 12, BO.
Miyake et al., Synthesis of 1-substituted isochroman . . . , Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.
Extended European Search Report for 12832050.4 (PCT/US2012/054354) mailed Jan. 27, 2015, 5 pages.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US2012/054354 filed Sep. 10, 2012, which claims priority from U.S. Provisional Application Ser. No. 61/535,589, filed Sep. 16, 2011.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first small molecule selective inhibitors of ROMK were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76 (5): p. 1094-1103.

SUMMARY OF THE INVENTION

One object of the present invention is to provide compounds of Formula I

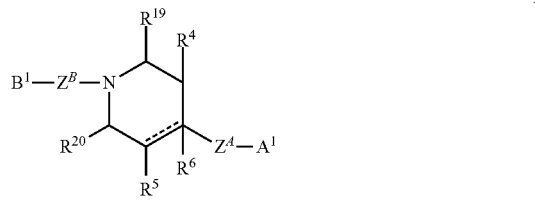

I and the pharmaceutically acceptable salts thereof. The compounds of Formula I are inhibitors of the ROMK (Kir1.1) channel and can act as diuretics and natriuretics and are valuable pharmaceutically active compounds for the therapy and prophylaxis of diseases, including, but not limited to, cardiovascular diseases such as hypertension and conditions resulting from excessive salt and water retention. Therefore, an object of the invention is to provide methods of treatment comprising administering a therapeutically or prophylactically effective amount of a compound of Formula I to a patient in need of a diuretic and/or natriuretic agent. A further object is to provide the use of compounds of Formula I in combination with other therapeutically effective agents, including other drugs useful for the treatment of hypertension and conditions resulting from excessive salt and water retention. The invention furthermore relates to processes for preparing compounds of Formula I, and pharmaceutical compositions which comprise compounds of Formula I. These and other objects will be evident from the description contained herein.

DETAILED DESCRIPTION OF THE INVENTION

The present invention is directed to compounds having structural Formula I:

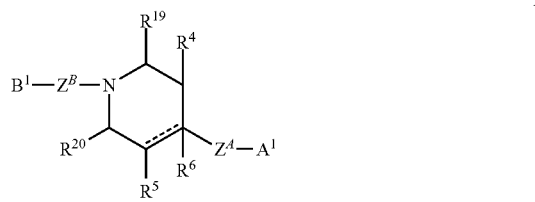

I and the pharmaceutically acceptable salts thereof wherein:
$B^1$—$Z^B$— is $B^1$—$CHR^1CH_2$—, $B^1$—$CHR^1C(O)$—, $B^1$—C(O)—, $B^1$—$CHR^1CH_2C(O)$—, $B^1$—$OCH_2C(O)$—, or $B^1$—$CH(CH_2OH)$—;
—$Z^A$-$A^1$ is $CHR^{21}CR^2R^{22}$-$A^1$, —CH═$CR^2$-$A^1$, —C≡C-$A^1$, —S-$A^1$, —$CH_2O$-$A^1$, —C(O)$CHR^2$-$A^1$, —O-$A^1$, —$NHCHR^2$-$A^1$, —$CH_2N(CH_3)CH_2CH(OH)$-$A^1$, —$CH_2N(CH_3)CH(CH_2OH)$-$A^1$, —$CH_2N(CH_3)$-$A^1$, —$CH_2S$-$A^1$, —$CH_2O$-$A^1$, $CH_2S(O)$-$A^1$, —$CH_2S(O_2)$-$A^1$, or —NH-$A^1$;
$A^1$ is B¹ is
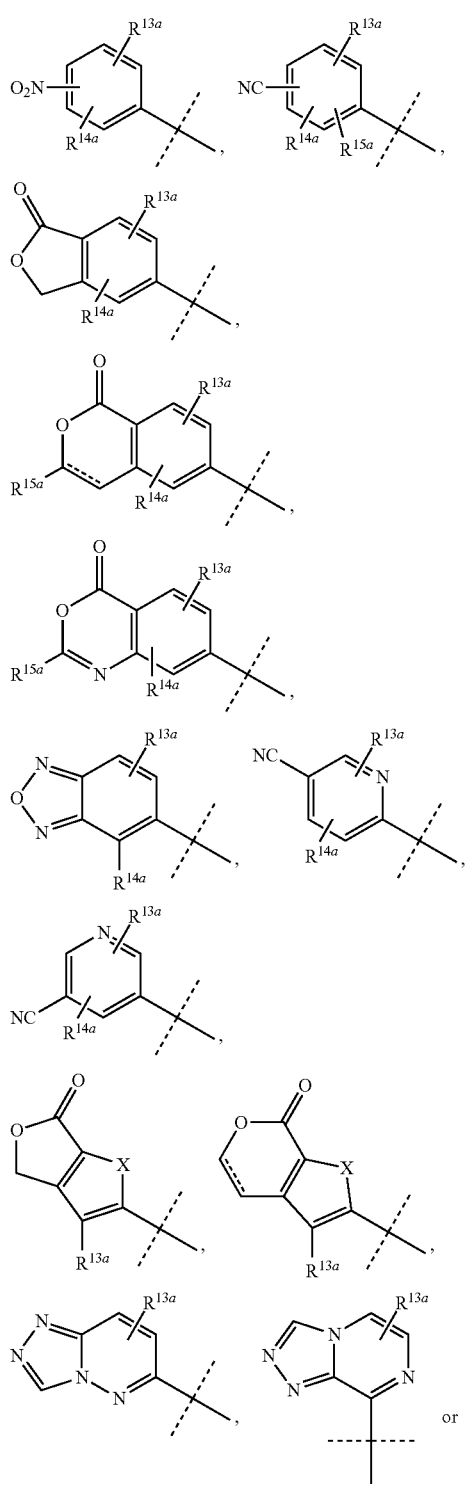
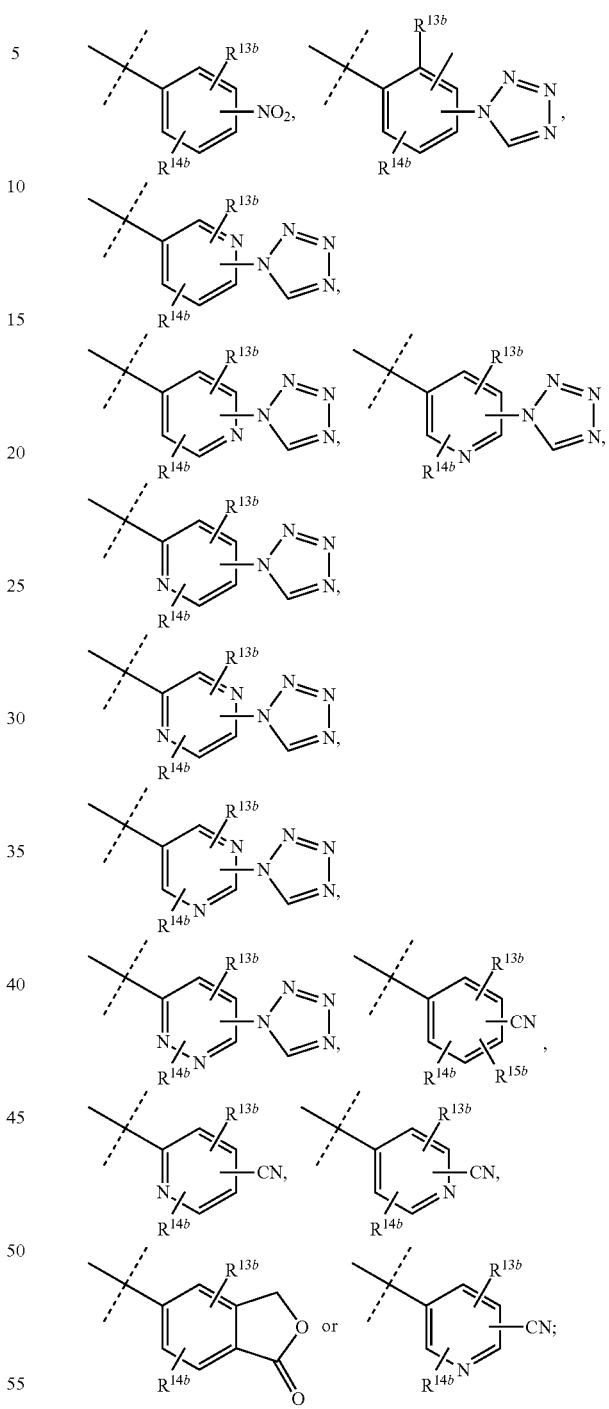
X is O or S;
R¹ is —H, —$C_{1-6}$ alkyl, —$C_{3-6}$ cycloalkyl, —$CF_3$, —OH, F, —$CH_2OH$, —C(O)OH, —C(O)O$C_{1-6}$ alkyl, or
R¹ may be joined with $R^{13b}$ by 2-3 carbon atoms or 1-2 carbon atoms and one heteroatom to form a ring;
R² is —H, —$C_{1-6}$ alkyl, —$C_{3-6}$ cycloalkyl, $CF_3$, —OH, F, —$CH_2OH$, —C(O)OH, —C(O)O$C_{1-6}$ alkyl, or
R² may be joined with $R^{13a}$ by 2-3 carbon atoms or 1-2 carbon atoms and one heteroatom to form a ring;

$R^4$ is H, —OH, F, —O—$C_{1-6}$ alkyl, or —$C_{1-6}$ alkyl, or may be joined with $R^5$ by a bond, or by 1-4 carbon atoms, to form a ring;

$R^5$ is H, —OH, F, —O—$C_{1-6}$ alkyl, or —$C_{1-6}$ alkyl, or may be joined with $R^4$ by a bond, or by 1-4 carbon atoms to form a ring;

$R^6$ is —H, —$C_{1-6}$ alkyl, —C(O)O$C_{1-6}$ alkyl, —OH, halogen, —OC(O)$C_{1-6}$ alkyl, —CH$_2$OH, —CHF$_2$, —N($C_{1-6}$ alkyl)$_2$, —C$_6$H$_5$, —CF$_3$, or a 5 or 6 membered heteroaryl ring having 1, 2, 3, or 4 heteroatoms;

$R^{13a}$ is —H, —$C_{1-6}$ alkyl, —$C_{3-6}$ cycloalkyl, -halogen, CF$_3$, —CH$_2$OH, —CO$_2$R$^{16a}$, —OR$^{16a}$, —SR$^{16a}$, —CN, -aryl, -heterocycle, —NR$^{16a}$R$^{18a}$, or $R^{13a}$ may be joined with $R^2$ by 2-3 carbon atoms or 1-2 carbon atoms and one heteroatom to form a ring, or $R^{13a}$ may be joined with $R^{14a}$ by 3-4 carbon atoms or 2-3 carbon atoms and one heteroatom to form a ring;

$R^{13b}$ is —H, —$C_{1-6}$ alkyl, —$C_{3-6}$ cycloalkyl, -halogen, CF$_3$, —CH$_2$OH, —CO$_2$R$^{16b}$, —OR$^{16b}$, —SR$^{16b}$, —CN, -aryl, -heterocycle, —NR$^{16b}$R$^{18b}$, or $R^{13b}$ may be joined to $R^1$ by 2-3 carbon atoms or 1-2 carbon atoms and one heteroatom to form a ring, or $R^{13b}$ may be joined to $R^{14b}$ by 3-4 carbon atoms or 2-3 carbon atoms and one heteroatom to form a ring;

$R^{14a}$ is —H, —$C_{1-6}$ alkyl, —$C_{3-6}$ cycloalkyl, -halogen, CF$_3$, —CH$_2$OH, —CO$_2$R$^{17a}$, —OR$^{17a}$, —SR$^{17a}$, —CN, -aryl, -heterocycle, or $R^{14a}$ may be joined to $R^{13a}$ by 3-4 carbon atoms or 2-3 carbon atoms and one heteroatom to form a ring;

$R^{14b}$ is —H, —$C_{1-6}$ alkyl, —$C_{3-6}$ cycloalkyl, -halogen, CF$_3$, —CH$_2$OH, —CO$_2$R$^{17b}$, —OR$^{17b}$, —SR$^{17b}$, —CN, -aryl, -heterocycle, or $R^{14b}$ may be joined to $R^{13b}$ by 3-4 carbon atoms or 2-3 carbon atoms and one heteroatom to form a ring;

$R^{15a}$ is —H, halogen, —$C_{1-6}$ alkyl, $C_{3-6}$ cycloalkyl, —O$C_{1-6}$ alkyl, or —CF$_3$;

$R^{15b}$ is —H, halogen, —$C_{1-6}$ alkyl, $C_{3-6}$ cycloalkyl, —O$C_{1-6}$ alkyl, or —CF$_3$;

$R^{16a}$, $R^{16b}$, $R^{17a}$, $R^{17b}$, $R^{18a}$, and $R^{18b}$ are independently —H, —$C_{1-6}$ alkyl, or —$C_{3-6}$ cycloalkyl;

$R^{19}$ and $R^{20}$ are H, or may be joined by a bond or 1-2 carbon atoms, to form a 4-5-membered ring; and $R^{21}$ and $R^{22}$ are H, or, together with carbon atom to which they are attached, form —$C_{3-6}$ cycloalkyl.

In one embodiment of the invention are compounds, and pharmaceutically acceptable salts thereof, where,

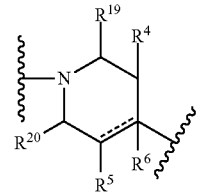

is

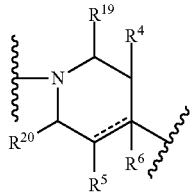 , 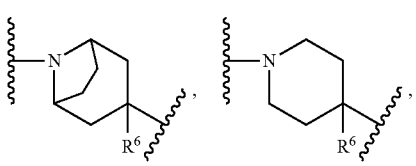

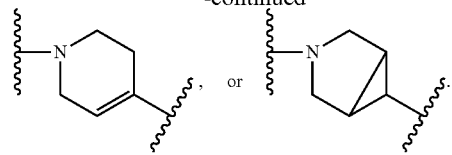

In one class of this embodiment are compounds, and pharmaceutically acceptable salts thereof, where,

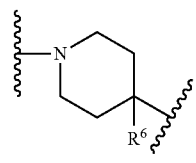

is

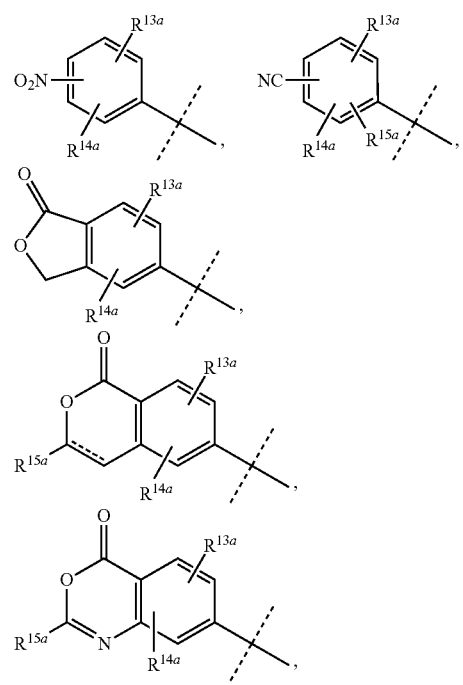

In another class of this embodiment, $R^6$ is H, —C(O)OCH$_3$, C(O)OCH$_2$CH$_3$, —OC(O)CH$_3$, —CH$_2$OH, OH, —CHF$_3$, —N(CH$_3$)$_2$, —CH$_3$, —C$_6$H$_5$, or F.

In another embodiment of the invention are compounds, and pharmaceutically acceptable salts thereof, where $A^1$ is -continued

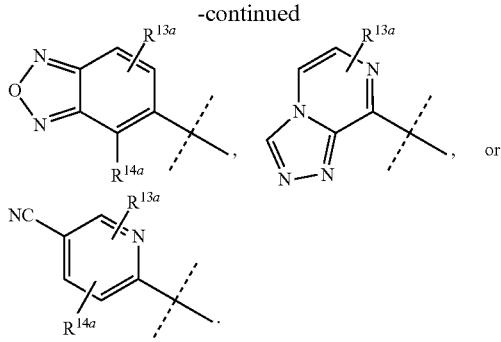

In a class of this embodiment,
$A^1$ is

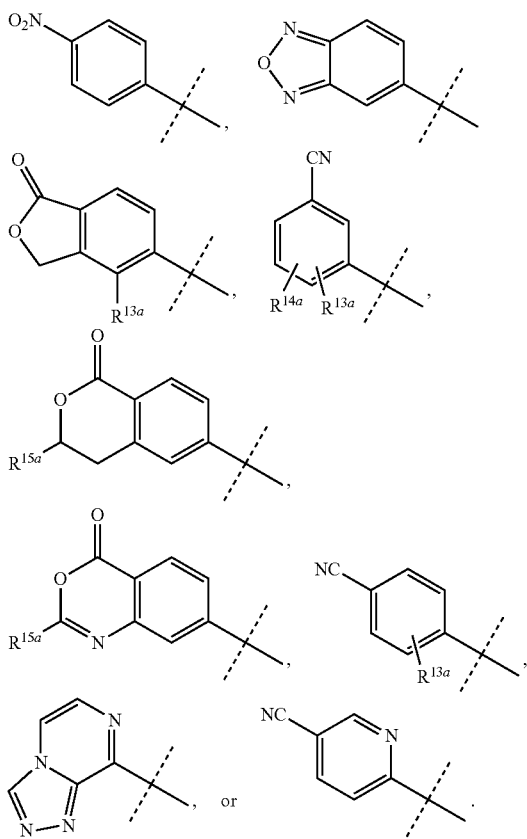

In a subclass of this class, $R^{13a}$ is H, F, Br, Cl, $CH_3$, or $-OCH_3$; $R^{14a}$ is H or F; and $R^{15a}$ is H or $CH_3$.

In another subclass of this class
$A^1$ is

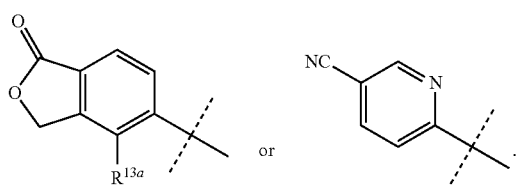

In another subclass of this class, $R^{13a}$ is H or $CH_3$.

In another embodiment of the invention are compounds, and pharmaceutically acceptable salts thereof, where $B^1$ is

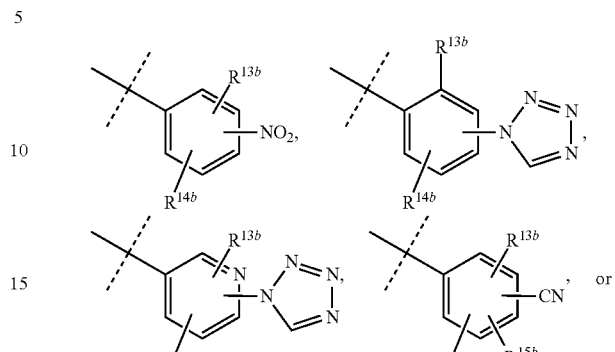

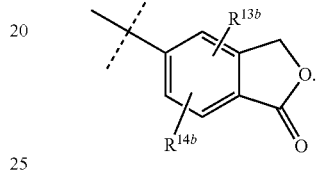

In a class of this embodiment,
$B^1$ is

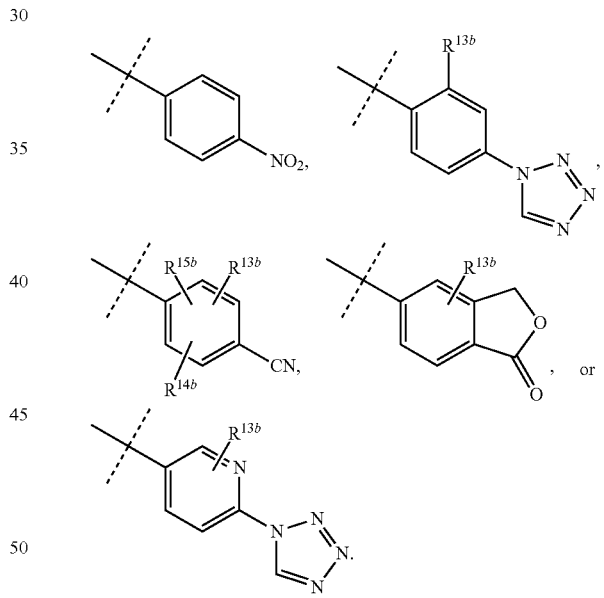

In a subclass of this class, $R^{13b}$ is H, F, Br, Cl, $-CF_3$, $-CH_3$ or $-OCH_3$; $R^{14b}$ is H or Cl; and $R^{15b}$ is H or F.

In another subclass of this embodiment,
$B^1$ is

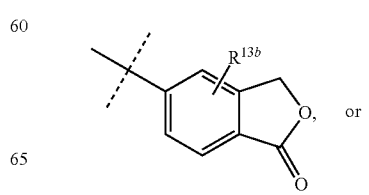

-continued

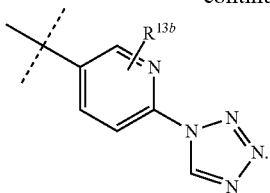

In another embodiment of the invention are compounds, and pharmaceutically acceptable salts thereof, where $B^1—Z^B—$ is $B^1—CH_2CH_2—$, $B^1—CHR^1C(O)—$, $B^1—C(O)—$, $B^1—CH_2CH_2C(O)—$, $B^1—OCH_2C(O)—$, $B^1—CH(OH)CH_2—$, or $B^1—CH(CH_2OH)—$;

In a class of this embodiment, $B^1—Z^B—$ is $B^1—CH_2CH_2—$, $B^1—CHR^1C(O)—$ or $B^1—CH(OH)CH_2—$.

In another embodiment of the invention are compounds, and pharmaceutically acceptable salts thereof, where $—Z^A-A^1$ is $CHR^{21}CR^2R^{22}-A^1$, $—CH=CH-A^1$, $—C≡C-A^1$, $—S-A^1$, $—CH_2O-A^1$, $—C(O)CH_2-A^1$, $—O-A^1$, $—CH_2CH(OH)-A^1$, $—NHCH_2-A^1$, $—CH_2N(CH_3)CH_2CH(OH)-A^1$, $—CH_2N(CH_3)CH(CH_2OH)-A^1$, $—CH_2N(CH_3)-A^1$, $—CH_2S-A^1$, $—CH_2O-A^1$, $CH_2S(O)-A^1$, $—CH_2S(O)_2-A^1$, or $—NH-A^1$;

In a class of this embodiment, $—Z^A-A^1$ is $—CH_2CH_2-A^1$, $—CH_2O-A^1$, or $—CH_2CH(OH)-A^1$.

Another embodiment of the invention are compounds, and pharmaceutically acceptable salts thereof, which are
Methyl 1,4-bis[2-(4-nitrophenyl)ethyl]piperidine-4-carboxylate,
4-[(E)-2-(4-Nitrophenyl)ethenyl]-1-[2-(4-nitrophenyl)ethyl]piperidine,
1,4-bis[2-(4-Nitrophenyl)ethyl]piperidine,
2-(4-(1H-Tetrazol-1-yl)phenyl)-1-(4-(4-nitrophenethyl)piperidin-1-yl)ethanone,
1-{4-[(E)-2-(2,1,3-Benzoxadiazol-5-yl)ethenyl]piperidin-1-yl}-2-[4-(1H)tetrazol-1-yl)phenyl]ethanone,
5-[(E))-2-(1-{[4-(1H)-tetrazol-1-yl)phenyl]acetyl}piperidin-4-yl)ethenyl]-2-benzofuran-1(3H)-one,
5-[2-(1-{[4-(1H-Tetrazol-1-yl)phenyl]acetyl}piperidin-4-yl)ethyl]-2-benzofuran-1(3H)-one,
1-{4-[2-(2,1,3-Benzoxadiazol-5-yl)ethyl]-4-hydroxypiperidin-1-yl}-2-[4-(1H-tetrazol-1-yl)phenyl]ethanone,
5-[2-(1-{[4-(1H-Tetrazol-1-yl)phenyl]acetyl}-1,2,3,6-tetrahydropyridin-4-yl)ethyl]-2-benzofuran-1(3H)-one,
2-Fluoro-5-[(4-hydroxy-1-{[4-(1H-tetrazol-1-yl)phenyl]acetyl}piperidin-4-yl)ethynyl]benzonitrile,
5-[2-(4-fluoro-1-{[4-(1H-tetrazol-1-yl)phenyl]acetyl}piperidin-4-yl)ethyl]-2-benzofuran-1(3H)-one,
1-{4-[(4-Nitrophenyl)sulfanyl]piperidin-1-yl}-2-[4-(1H-tetrazol-1-yl)phenyl]ethanone,
2-Fluoro-5-[2-(4-hydroxy-1-{[4-(1H-tetrazol-1-yl)phenyl]acetyl}piperidin-4-yl)ethyl]benzonitrile,
2-Fluoro-5-[2-(4-fluoro-1-{[4-(1H-tetrazol-1-yl)phenyl]acetyl}piperidin-4-yl)ethyl]benzonitrile,
Ethyl 4-[2-(3-cyano-4-fluorophenyl)ethyl]-1-{[4-(1H-tetrazol-1-yl)phenyl]acetyl}piperidine-4-carboxylate,
4-[2-(3-Cyano-4-fluorophenyl)ethyl]-1-{[4-(1H-tetrazol-1-yl)phenyl]acetyl}piperidin-4-yl acetate,
2-Fluoro-5-[2-(1-{[4-(1H-tetrazol-1-yl)phenyl]acetyl}-1,2,3,6-tetrahydropyridin-4-yl)ethyl]benzonitrile,
2-Fluoro-5-[2-(4-hydroxy-1-{[2-methyl-4-(1H-tetrazol-1-yl)phenyl]acetyl}piperidin-4-yl)ethyl]benzonitrile,
2-Fluoro-5-(2-{4-hydroxy-1-[(4-nitrophenyl)acetyl]piperidin-4-yl}ethyl)benzonitrile,
2-Fluoro-5-[2-(4-hydroxy-1-{[5-(1H-tetrazol-1-yl)-2,3-dihydro-1H-inden-1-yl]carbonyl}piperidin-4-yl)ethyl]benzonitrile,
5-[(4-Hydroxy-1-{[4-(1H-tetrazol-1-yl)phenyl]acetyl}piperidin-4-yl)ethynyl]-2-methoxybenzonitrile,
3-[2-(4-Hydroxy-1-{[4-(1H-tetrazol-1-yl)phenyl]acetyl}piperidin-4-yl)ethyl]benzonitrile,
3-[2-(4-Fluoro-1-{[4-(1H-tetrazol-1-yl)phenyl]acetyl}piperidin-4-yl)ethyl]benzonitrile,
3-[(4-Hydroxy-1-{[4-(1H-tetrazol-1-yl)phenyl]acetyl}piperidin-4-yl)ethynyl]-4-methylbenzonitrile,
2-Chloro-4-(2-{4-[2-(3-cyano-4-fluorophenyl)ethyl]-4-hydroxypiperidin-1-yl}-2-oxoethyl)benzonitrile,
2-Fluoro-5-{2-[4-(hydroxymethyl)-1-{[4-(1H-tetrazol-1-yl)phenyl]acetyl}piperidin-4-yl]ethyl}benzonitrile,
5-{2-[4-(Difluoromethyl)-1-{[4-(1H-tetrazol-1-yl)phenyl]acetyl}piperidin-4-yl]ethyl}-2-fluorobenzonitrile,
5-[2-(3-{[4-(1H-Tetrazol-1-yl)phenyl]acetyl}-3-azabicyclo[3.1.0]hex-6-yl)ethyl]-2-benzofuran-1(3H)-one,
2-Fluoro-5-[(E)-2-(4-hydroxy-1-{[4-(1H-tetrazol-1-yl)phenyl]acetyl}piperidin-4-yl)ethenyl]benzonitrile,
2-Fluoro-5-(2-{4-hydroxy-1-[2-(1-oxo-1,3-dihydro-2-benzofuran-5-yl)ethyl]piperidin-4-yl}ethyl)benzonitrile,
2-Fluoro-5-[2-(4-hydroxy-1-{[4-(1H-tetrazol-1-yl)-2-(trifluoromethyl)phenyl]acetyl}piperidin-4-yl)ethyl]benzonitrile,
2-Fluoro-5-[2-(4-hydroxy-1-{[4-(1H-tetrazol-1-yl)phenyl]acetyl}piperidin-4-yl)cyclopropyl]benzonitrile,
2,6-Difluoro-3-[(4-hydroxy-1-{[4-(1H-tetrazol-1-yl)phenyl]acetyl}piperidin-4-yl)ethynyl]benzonitrile,
2,6-Difluoro-3-[2-(4-hydroxy-1-{[4-(1H-tetrazol-1-yl)phenyl]acetyl}piperidin-4-yl)ethyl]benzonitrile,
3-[(4-Hydroxy-1-{[4-(1H-tetrazol-1-yl)phenyl]acetyl}piperidin-4-yl)ethynyl]-6-methoxy-2-methylbenzonitrile,
6-Fluoro-3-[(4-hydroxy-1-{[4-(1H-tetrazol-1-yl)phenyl]acetyl}piperidin-4-yl)ethynyl]-2-methylbenzonitrile,
6-Fluoro-3-[2-(4-hydroxy-1-{[4-(1H-tetrazol-1-yl)phenyl]acetyl}piperidin-4-yl)ethyl]-2-methylbenzonitrile,
3-[2-(4-Hydroxy-1-{[4-(1H-tetrazol-1-yl)phenyl]acetyl}piperidin-4-yl)ethyl]-6-methoxy-2-methylbenzonitrile,
2-Chloro-6-fluoro-3-[(4-hydroxy-1-{[4-(1H-tetrazol-1-yl)phenyl]acetyl}piperidin-4-yl)ethynyl]benzonitrile,
2-Chloro-6-fluoro-3-[2-(4-hydroxy-1-{[4-(1H-tetrazol-1-yl)phenyl]acetyl}piperidin-4-yl)ethyl]benzonitrile,
4-Methyl-5-[(E)-2-(1-{[4-(1H-tetrazol-1-yl)phenyl]acetyl}piperidin-4-yl)ethenyl]-2-benzofuran-1(3H)-one,
4-Methyl-5-[2-(1-{[4-(1H-tetrazol-1-yl)phenyl]acetyl}piperidin-4-yl)ethyl]-2-benzofuran-1(3H one,
3-[(4-Hydroxy-1-{[4-(1H-tetrazol-1-yl)phenyl]acetyl}piperidin-4-yl)ethynyl]-2-methylbenzonitrile,
3-[2-(4-Hydroxy-1-{[4-(1H-tetrazol-1-yl)phenyl]acetyl}piperidin-4-yl)ethynyl]-2-methylbenzonitrile,
2-Fluoro-3-[(4-hydroxy-1-{[4-(1H-tetrazol-1-yl)phenyl]acetyl}piperidin-4-yl)ethynyl]-6-methoxybenzonitrile,
2-Fluoro-3-[2-(4-hydroxy-1-{[4-(1H-tetrazol-1-yl)phenyl]acetyl}piperidin-4-yl)ethyl]-6-methoxybenzonitrile,
5-[(E)-2-{1-[(1-oxo-1,3-dihydro-2-benzofuran-5-yl)acetyl]piperidin-4-}ethenyl]-2-benzofuran-1(3H)-one,
2-Fluoro-5-[(E)-2-{1-[(1-oxo-1,3-dihydro-2-benzofuran-5-yl)acetyl]piperidin-4-yl}ethenyl]benzonitrile,
2-Fluoro-5-(2-{1-[(1-oxo-1,3-dihydro-2-benzofuran-5-yl)acetyl]piperidin-4-yl}ethyl)benzonitrile,
5-(2-{1-[(1-oxo-1,3-dihydro-2-benzofuran-5-yl)acetyl]piperidin-4-yl}ethyl)-2-benzofuran-1(3H)-one, 5-[(1-{[4-(1H-Tetrazol-1-yl)phenyl]acetyl}piperidin-4-yl)sulfanyl]-2-benzofuran-1(3H)-one,
2-Methoxy-4-(2-oxo-2-(4-[(E)-2-(1-oxo-1,3-dihydro-2-benzofuran-5-yl)ethenyl]piperidin-1-yl]ethyl]benzonitrile,
2-Methoxy-4-(2-oxo-2-(4-[2-(1-oxo-1,3-dihydro-2-benzofuran-5-yl)ethyl]piperidin-1-yl]ethyl]benzonitrile,
5-[2-(4-{1-Hydroxy-2-[4-(1H-tetrazol-1-yl)phenyl]ethyl}piperidin-1-yl)ethyl]-2-benzofuran-1(3H)-one,
5-[(1-{[4-(1H-Tetrazol-1-yl)phenyl]acetyl}piperidin-4-yl)methoxy]-2-benzofuran-1(3H)-one,
5-Fluoro-2-methoxy-4-(2-oxo-2-{4-[2-(1-oxo-1,3-dihydro-2-benzofuran-5-yl)ethyl]piperidin-1-yl}ethyl)benzonitrile,
4-Fluoro-5-[2-(1-{[4-(1H-tetrazol-1-yl)phenyl]acetyl}piperidin-4-yl)ethyl]-2-benzofuran-1(3H)-one,
4-Methyl-5-[(1-{[4-(1H-tetrazol-1-yl)phenyl]acetyl}piperidin-4-yl)sulfanyl]-2-benzofuran-1(3H)-one,
4-Bromo-5-[2-(1-{[4-(1H-tetrazol-1-yl)phenyl]acetyl}piperidin-4-yl)ethyl]-2-benzofuran-1(3H)-one,
4-Bromo-5-[(Z)-2-(1-{[4-(1H-tetrazol-1-yl)phenyl]acetyl}piperidin-4-yl)ethenyl]-2-benzofuran-1(3H)-one,
3-Chloro-2-fluoro-4-(2-oxo-2-{4-[2-(1-oxo-1,3-dihydro-2-benzofuran-5-yl)ethyl]piperidin-1-yl}ethyl)benzonitrile,
2-Methoxy-4-[2-oxo-2-(4-{[(1-oxo-1,3-dihydro-2-benzofuran-5-yl)oxy]methyl}piperidin-1-yl)ethyl]benzonitrile,
2-Fluoro-3-methyl-4-(2-oxo-2-{4-[2-(1-oxo-1,3-dihydro-2-benzofuran-5-yl)ethyl]piperidin-1-yl}ethyl)benzonitrile,
2-Bromo-4-[2-oxo-2-[4-[2-(1-oxo-3H-isobenzofuran-5-yl)ethyl]-1-piperidyl]ethyl]benzonitrile,
6-[2-(1-{[4-(1H-tetrazol-1-yl)phenyl]acetyl}piperidin-4-yl)ethyl]-3,4-dihydro-1H-isochromen-1-one,
6-[2-(1-{[5-(1H-Tetrazol-1-yl)-2,3-dihydro-1H-inden-1-yl]carbonyl}piperidin-4-yl)ethyl]-3,4-dihydro-1H-isochromen-1-one,
5-Fluoro-2-methoxy-4-(2-oxo-2-{4-[2-(1-oxo-3,4-dihydro-1H-isochromen-6-yl)ethyl]piperidin-1-yl}ethyl)benzonitrile,
4-Bromo-5-[(E)-2-(1-{[4-(1H-tetrazol-1-yl)phenyl]acetyl}piperidin-4-yl)ethenyl]-2-benzofuran-1(3H)-one,
5-[2-(4-{[4-(1H-Tetrazol-1-yl)phenyl]acetyl}piperidin-1-yl)ethyl]-2-benzofuran-1(3H)-one,
2-Fluoro-5-methoxy-4-(2-oxo-2-{4-[2-(1-oxo-1,3-dihydro-2-benzofuran-5-yl)ethyl]piperidin-1-yl}ethyl)benzonitrile,
2-Methoxy-4-(2-{4-[2-(1-oxo-1,3-dihydro-2-benzofuran-5-yl)ethyl]piperidin-1-yl}ethyl)benzonitrile,
5-[2-(1-{[5-(1H-Tetrazol-1-yl)-2,3-dihydro-1H-inden-1-yl]carbonyl}piperidin-4-yl)ethyl]-2-benzofuran-1(3H)-one,
2-Fluoro-4-(3-oxo-3-{4-[(1-oxo-1,3-dihydro-2-benzofuran-5-yl)sulfanyl]piperidin-1-yl}propyl)benzonitrile,
2,5-Difluoro-3-methoxy-4-(2-oxo-2-{4-[2-(1-oxo-1,3-dihydro-2-benzofuran-5-yl)ethyl]piperidin-1-yl}ethyl)benzonitrile,
5-[(1-{[(1-oxo-1,3-dihydro-2-benzofuran-5-yl)oxy]acetyl}piperidin-4-yl)oxy]-2-benzofuran-1(3H)-one,
2-Fluoro-4-(3-oxo-3-{4-[(1-oxo-1,3-dihydro-2-benzofuran-5-yl)oxy]piperidin-1-yl}propyl)benzonitrile,
2-Fluoro-3-methoxy-4-(2-oxo-2-{4-[2-(1-oxo-1,3-dihydro-2-benzofuran-5-yl)ethyl]piperidin-1-yl}ethyl)benzonitrile,
2-Methyl-7-[(E)-2-(1-{[4-(1H-tetrazol-1-yl)phenyl]acetyl}piperidin-4-yl)ethenyl]-4H-3,1-benzoxazin-4-one,
3-Methyl-6-[(E)-2-(1-{[4-(1H-tetrazol-1-yl)phenyl]acetyl}piperidin-4-yl)ethenyl]-3,4-dihydro-1H-isochromen-1-one,
3-Methyl-6-[2-(1-{[4-(1H-tetrazol-1-yl)phenyl]acetyl}piperidin-4-yl)ethyl]-3,4-dihydro-1H-isochromen-1-one,
5-[2-(1-{[6-(1H-tetrazol-1-yl)pyridin-3-yl]acetyl}piperidin-4-yl)ethyl]-2-benzofuran-1(3H)-one,
5-{2-[4-(Dimethylamino)-1-{[4-(1H-tetrazol-1-yl)phenyl]acetyl}piperidin-4-yl]ethyl}-2-fluorobenzonitrile,
4-[(E)-2-{1-[2-(1-oxo-1,3-dihydro-2-benzofuran-5-yl)ethyl]piperidin-4-yl}ethenyl]benzonitrile,
4-[(E)-2-{1-[2-(1-oxo-1,3-dihydro-2-benzofuran-5-yl)ethyl]piperidin-4-yl}ethenyl]benzonitrile,
5-({1-[2-hydroxy-2-(1-oxo-1,3-dihydro-2-benzofuran-5-yl)ethyl]piperidin-4-yl}sulfanyl)-2-benzofuran-1(3H)-one,
5-[(1R)-1-Hydroxy-2-{4-[2-hydroxy-2-(4-methyl-1-oxo-1,3-dihydro-2-benzofuran-5-yl)ethyl]piperidin-1-yl}ethyl]-4-methyl-2-benzofuran-1(3H)-one,
5-[(1R)-1-Hydroxy-2-{4-[1-hydroxy-2-(4-methyl-1-oxo-1,3-dihydro-2-benzofuran-5-yl)ethyl]piperidin-1-yl}ethyl]-4-methyl-2-benzofuran-1(3H)-one,
4-Methyl-5-[2-(4-{[(1-oxo-1,3-dihydro-2-benzofuran-5-yl)methyl]amino}piperidin-1-yl)ethyl]-2-benzofuran-1(3H)-one,
5-(2-{4-[(2,1,3-Benzoxadiazol-5-ylmethyl)amino]piperidin-1-yl}ethyl)-4-methyl-2-benzofuran-1(3H)-one,
2-Fluoro-4-[({1-[2-(4-methyl-1-oxo-1,3-dihydro-2-benzofuran-5-yl)ethyl]piperidin-4-yl}amino)methyl]benzonitrile,
5-{(1R)-1-Hydroxy-2-[4-({[(2R)-2-hydroxy-2-(1-oxo-1,3-dihydro-2-benzofuran-5-yl)ethyl](methyl)amino}methyl)piperidin-1-yl]ethyl}-4-methyl-2-benzofuran-1(3H)-one,
5-{(1R)-1-Hydroxy-2-[4-({[2-hydroxy-1-(1-oxo-1,3-dihydro-2-benzofuran-5-yl)ethyl](methyl)amino}methyl)piperidin-1-yl]ethyl}-4-methyl-2-benzofuran-1(3H)-one,
6-[({1-[(2R)-2-Hydroxy-2-(4-methyl-1-oxo-1,3-dihydro-2-benzofuran-5-yl)ethyl]piperidin-4-yl}methyl)(methyl)amino]pyridine-3-carbonitrile,
5-[({1-[(2R)-2-Hydroxy-2-(4-methyl-1-oxo-1,3-dihydro-2-benzofuran-5-yl)ethyl]piperidin-4-yl}methyl)sulfanyl]-4-methyl-2-benzofuran-1(3H)-one,
5-({1-[(2R)-2-Hydroxy-2-(4-methyl-1-oxo-1,3-dihydro-2-benzofuran-5-yl)ethyl]piperidin-4-yl}methoxy)-4-methyl-2-benzofuran-1(3H)-one,
5-[({1-[(2R)-2-Hydroxy-2-(4-methyl-1-oxo-1,3-dihydro-2-benzofuran-5-yl)ethyl]piperidin-4-yl}methoxy)-4-methyl-2-benzofuran-1(3H)-one,
5-[({1-[2-Hydroxy-1-(4-methyl-1-oxo-1,3-dihydro-2-benzofuran-5-yl)ethyl]piperidin-4-yl}methyl)sulfinyl]-4-methyl-2-benzofuran-1(3H)-one,
4-Methyl-5-{[(1-{[6-(1H-tetrazol-1-yl)pyridin-3-yl]acetyl}piperidin-4-yl)methyl]sulfanyl}-2-benzofuran-1(3H)-one,
5-({1-[(2R)-2-Hydroxy-2-(4-methyl-1-oxo-1,3-dihydro-2-benzofuran-5-yl)ethyl]piperidin-4-yl}methyl)sulfonyl]-4-methyl-2-benzofuran-1(3H)-one,
6-[({1-[(2R)-2-Hydroxy-2-(4-methyl-1-oxo-1,3-dihydro-2-benzofuran-5-yl)ethyl]piperidin-4-yl}methyl)sulfanyl]pyridine-3-carbonitrile,
6-[({1-[(2R)-2-Hydroxy-2-(4-methyl-1-oxo-1,3-dihydro-2-benzofuran-5-yl)ethyl]piperidin-4-yl}methyl)sulfinyl]pyridine-3-carbonitrile,
6-({4-Fluoro-1-[(2R)-2-hydroxy-2-(4-methyl-1-oxo-1,3-dihydro-2-benzofuran-5-yl)ethyl]piperidin-4-yl}methoxy)pyridine-3-carbonitrile,
6-[({1-[(2R)-2-Hydroxy-2-(4-methyl-1-oxo-1,3-dihydro-2-benzofuran-5-yl)ethyl]piperidin-4-yl}methyl)sulfanyl]-3,4-dihydro-1H-isochromen-1-one, 6-[({1-[(2R)-2-Hydroxy-2-(4-methyl-1-oxo-1,3-dihydro-2-benzofuran-5-yl)ethyl]piperidin-4-yl}methyl)sulfinyl]-3,4-dihydro-1H-isochromen-1-one,
6-[({1-[(2R)-2-Hydroxy-2-(4-methyl-1-oxo-1,3-dihydro-2-benzofuran-5-yl)ethyl]-4-phenylpiperidin-4-yl}methoxy)pyridine-3-carbonitrile,
6-({3-[(2R)-2-Hydroxy-2-(4-methyl-1-oxo-1,3-dihydro-2-benzofuran-5-yl)ethyl]-3-azabicyclo[3.1.0]hex-6-yl}methoxy)pyridine-3-carbonitrile,
6-[({1-[(2R)-2-Hydroxy-2-(4-methyl-1-oxo-1,3-dihydro-2-benzofuran-5-yl)ethyl]-4-methylpiperidin-4-yl}methoxy)pyridine-3-carbonitrile,
6-({4-Fluoro-1-[(2R)-2-hydroxy-2-(4-methyl-1-oxo-1,3-dihydro-2-benzofuran-5-yl)ethyl]piperidin-4-yl}methyl)sulfanyl]pyridine-3-carbonitrile,
6-[({1-[(2R)-2-Hydroxy-2-(4-methyl-1-oxo-1,3-dihydro-2-benzofuran-5-yl)ethyl]piperidin-4-yl}methyl)sulfonyl]-3,4-dihydro-1H-isochromen-1-one,
5-[1-Hydroxy-2-(1-{[6-(1H-tetrazol-1-yl)pyridin-3-yl]acetyl}piperidin-4-yl)ethyl]-4-methyl-2-benzofuran-1(3H)-one,
(R)-6-(1-(2-Hydroxy-2-(4-methyl-1-oxo-1,3-dihydroisobenzofuran-5-yl)ethyl)piperidin-4-ylamino)nicotinonitrile,
6-((1R,5S)-8-((R)-2-Hydroxy-2-(4-methyl-1-oxo-1,3-dihydroisobenzofuran-5-yl)ethyl)-8-azabicyclo[3.2.1]octan-3-ylamino)nicotinonitrile,
5-((1R)-2-(6-([1,2,4]Triazolo[4,3-c]pyrazin-8-ylamino)-3-azabicyclo[3.1.0]hexan-3-yl)-1-hydroxyethyl)-4-methyl-isobenzofuran-1(3H)-one, or
(R)-5-(2-(4-([1,2,4]Triazolo[4,3-c]pyrazin-8-ylamino)piperidin-1-yl)-1-hydroxyethyl)-4-methylisobenzofuran-1(3H)-one.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule.

In some instances the number of substituents which may be optionally present on a moiety is specified, for example but not limited to, 1 to 3 of —F (fluoro). For example, an alkyl group that can be optionally substituted with 1-3 of —F includes, but is not limited to, —CH$_3$, —CH$_2$F, —CHF$_2$, —CF$_3$, —CH$_2$CH$_3$, —CH$_2$—CH$_2$F, —CH$_2$—CHF$_2$, —CHF—CH$_2$F, —CH$_2$CF$_3$, —CHF—CHF$_2$, —(CH$_2$)$_2$CH$_3$, —CH(CF$_3$)—CH$_3$, —(CH$_2$)$_3$—CF$_3$, —(CH$_2$)$_2$CH(CF$_3$)CH$_3$, and —(CH$_2$)$_5$—CF$_3$, as appropriate for the defined number of carbon atoms for the given alkyl group.

Halo or halogen refers to —F (fluoro), —Cl (chloro), —Br (bromo) and —I (iodo). In one embodiment, halogens are —F and —Cl.

The term "heteroaryl", alone or in combination, means six-membered aromatic rings containing one to four nitrogen atoms; benzofused six-membered aromatic rings containing one to three nitrogen atoms; five-membered aromatic rings containing one oxygen, one nitrogen or one sulfur atom; benzofused five-membered aromatic rings containing one oxygen, one nitrogen or one sulfur atom; five-membered aromatic rings containing two heteroatoms independently selected from oxygen, nitrogen and sulfur and benzofused derivatives of such rings; five-membered aromatic rings containing three nitrogen atoms and benzofused derivatives thereof; a tetrazolyl ring; a thiazinyl ring; or coumarinyl. Examples of such ring systems are furanyl, thienyl, pyrrolyl, pyridinyl, pyrimidinyl, indolyl, quinolinyl, isoquinolinyl, imidazolyl, triazinyl, thiazolyl, isothiazolyl, pyridazinyl, pyrazolyl, oxazolyl, isoxazolyl, benzothienyl, quinazolinyl and quinoxalinyl.

Unless expressly depicted or described otherwise, variables depicted in a structural formula with a "floating" bond, such as each of substituents $R^{13a}$, $R^{13b}$, $R^{14a}$ and $R^{14b}$, are permitted on any available carbon atom in the ring to which each is attached.

The image "---", when present in a ring, represents a single, double or aromatic bond.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO$^-$ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and are therefore useful as diuretic and/or natriuretic agents. ROMK inhibitors help to increase urination and increase urine volume and also to prevent or reduce reabsorption of sodium in the kidneys leading to increased excretion of sodium and water. Therefore, the compounds are useful for treatment or prophylaxis of disorders that benefit from increased excretion of water and sodium from the body. Accordingly, an object of the instant invention is to provide a method for inhibiting ROMK comprising administering a compound of Formula I in a ROMK-inhibitory effective amount to a patient in need thereof. The inhibition of ROMK by the compounds of Formula I can be examined, for example, in any of the activity assays described below. Another object is to provide a method for causing diuresis, natriuresis or both, comprising administering a compound of Formula I in a therapeutically effective amount to a patient in need thereof.

Due to their activity as diuretics and natriuretic agents, this invention further provides the use of compounds of Formula I in methods for treatment of, prevention of or reduction of risk for developing medical conditions that benefit from increased excretion of water and sodium, such as but not limited to one or more of hypertension, heart failure (both acute and chronic, also known as congestive heart failure) and/or other conditions resulting from excessive salt and water retention. Compounds of Formula I are useful for treating both primary (essential) and secondary hypertension. Hypertensive conditions include, but are not limited to, systolic hypertension, isolated systolic hypertension, diastolic hypertension, isolated diastolic hypertension, renovascular hypertension, endocrine disorder hypertension (including hyperaldosteronism and pheochromocytoma), malignant hypertension, resistant hypertension, hypertension in obesity/diabetes/metabolic syndrome, hypertension in heart failure, hypertension in pregnancy, and accelerated hypertension, and prehypertension associated with any of these conditions. It further includes the use of the compounds of Formula I in methods for treatment of, prevention of or reduction of risk for developing one or more disorders such as pulmonary arterial hypertension (PAH), cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, nephrotic syndrome, acute and chronic kidney insufficiency, hypercalcemia, Dent's disease, Meniere's disease, edetamous states, and other conditions for which a diuretic would have therapeutic or prophylactic benefit. The compounds of the invention can be administered to a patient having, or at risk of having, one or more conditions for which a diuretic would have therapeutic or prophylactic benefit such as those described herein.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) the $^{86}Rb^+$ Efflux Assay, 2) the Thallium Flux Assay, 3) the Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a pharmaceutically active agent (or agents) that is active in the body, including pro-drugs that convert to pharmaceutically active form after administration, which is different from the compound of Formula I, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible.

Several methods for preparing the compounds of this invention are described in the following Schemes and Examples. Starting materials and intermediates are purchased, made from known procedures, or as otherwise illustrated.

Schemes

Compounds of the formula I are prepared in a variety of ways as exemplified by the examples below. Some frequently applied routes to the compounds of the formula I are described by the Schemes below.

Several methods for preparing the compounds of this invention are described in the following Schemes and Examples. Starting materials and intermediates are purchased, made from known procedures, or as otherwise illustrated. The Ar group shown in the below schemes is a substituted aromatic or substituted heterocyclic group as previously defined. The A group shown in the schemes is O, OH, halogen, OS(O)$_2$R$^{23}$, OP(O)$_2$R$^{23}$, OR$^{23}$, or SR$^{23}$ where R$^{23}$ is —C$_{1-6}$ alkyl or Ar. Z is B$^1$—Z$^B$—. X is OH, NH$_2$ or SH$_2$. n is 0 or 1. [r] represents a reduction step.

The preparation of the compounds I1 and I2 is detailed in Scheme 1. Treatment of the electrophile 1-1 (such as aryl halide or trifluoromethanesulfonate) with 1-Boc piperazine 1-2 or similar olefin metal catalyzed coupling conditions (such as standard Heck conditions, including trans-dichlorobis(tri-o-tolylphosphine) palladium (II) and triethylamine) affords the olefin product 1-3. The Boc protecting group (Greene, T.; Wuts, P. G. M. *protective Groups in Organic Synthesis*, John Wiley and Sons, Inc., New York, N.Y. 1991) of 1-3 can be removed under acidic conditions, such as with TFA or HCl. Alternatively, the piperazine may be protected with another protecting group such as Cbz, and subsequently removed by hydrogenolysis. Subsequent alkylation of 1-4 with an electrophile 1-5 (examples include alkyl halides, mesylates, trifluoromethanesulfonates, etc. or aldehydes) in the presence of appropriate base (such as triethylamine) or reducing agent (such as sodium cyanoborohydride) gives rise to compounds I1. The olefin of I1 can be reduced to the corresponding saturated alkyl compound with standard reducing conditions such as heterogenous palladium hydrogenation to yield I2.

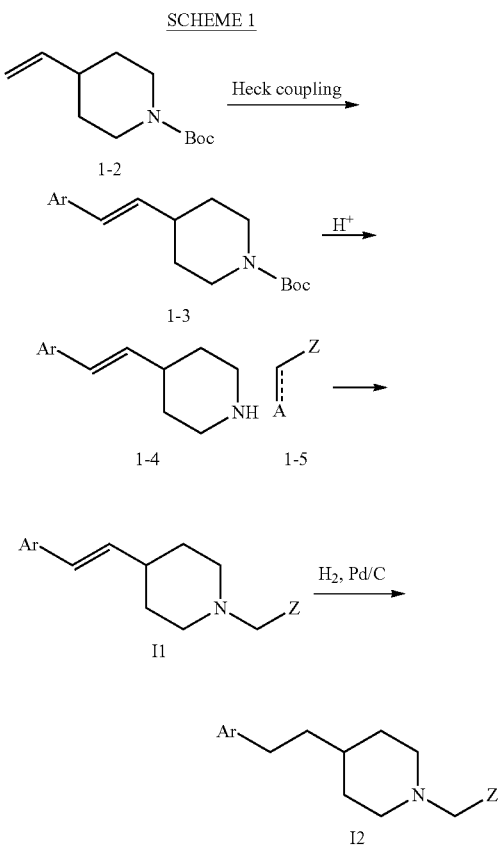

SCHEME 1

Additionally, compounds of formulas I3 and I4 can also be prepared by the sequence detailed in Scheme 2. Treatment previously described intermediate 1-4 with the appropriate electrophile 2-1 (such as carboxylic acid or ester) under standard amide bond forming conditions (such as EDC, HOBt, triethylamine) gives rise to I3. Alternatively, the piperazine may be protected with another protecting group such as Cbz. Similarly, the olefin may be reduced to the saturated alkyl compound using standard reducing conditions such as heterogenous palladium hydrogenation to yield I4.

SCHEME 2

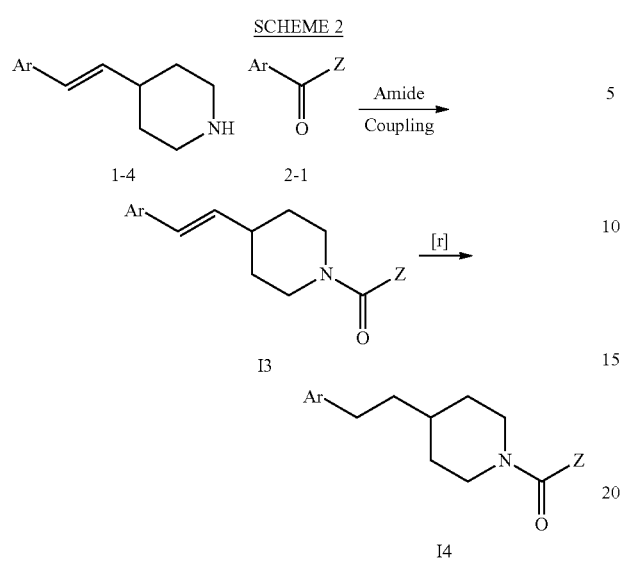

The preparation of compounds of formulas I5 and I6 begins with the addition of the alkylmetal species generated from trimethylsilylacetylene 3-1 (such as the alkyllithium generated from treatment with n-butyllithium) to commercially available tert-butyl 4-piperidone-1-carboxylate, 3-2, to produce the alcohol 3-3 (Scheme 3). The Boc group can be removed under acidic conditions to afford piperidine 3-4, which can then be coupled to electrophile 3-5 via standard amide bond forming conditions described above in Scheme 2. The resulting terminal alkyne 3-6 can then undergo metal catalyzed cross coupling (such as Sonogashira conditions) with the appropriate aryl or heteroaryl halide, trifluoromethanesulfonate, phosphonate, or other reactive intermediate to furnish I-5. Reduction (or partial reduction) of the alkyne in I-5 (such as under heterogeneous metal catalysed hydrogenation) can provide I-6.

SCHEME 3

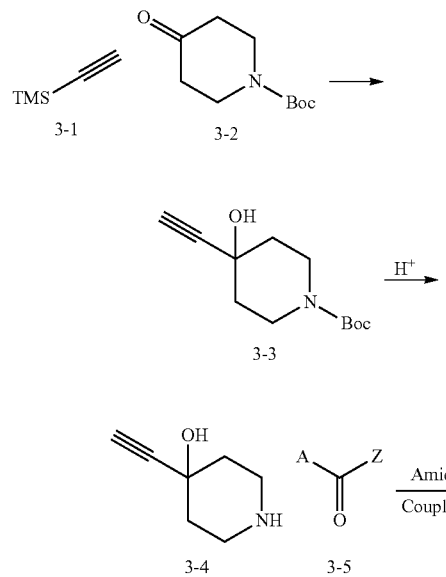

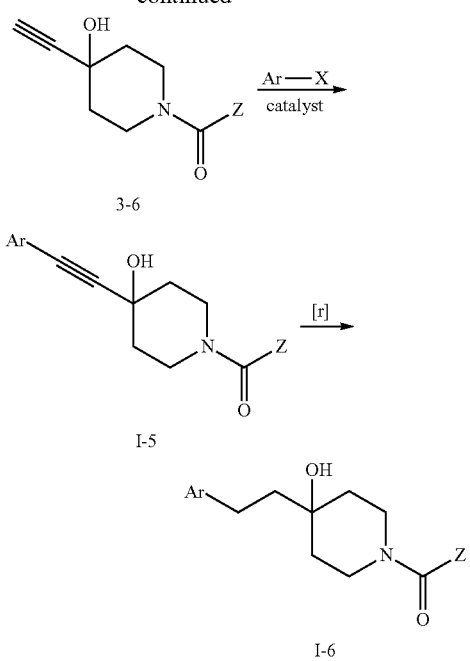

The related piperidines I-7 can be prepared following the method detailed in Scheme 4. Treatment of 3-3 (as described above in Scheme 3) with the appropriate aryl or heteroaryl halide, trifluoromethanesulfonate, phosphonate, or other reactive intermediate under metal catalyzed cross coupling (such as Sonogashira conditions) affords 4-1. The Boc group can be removed under acidic conditions to afford piperidine 4-2, which can then be coupled to electrophile 4-3 (examples include alkyl halides, mesylates, trifluoromethanesulfonates, etc. or aldehydes) in the presence of appropriate base (such as triethylamine) or reducing agent (such as sodium cyanoborohydride) to furnish piperidine 4-4. Reduction (or partial reduction) of the alkyne in 4-4 (such as under heterogeneous metal catalysed hydrogenation) can provide I-7.

SCHEME 4

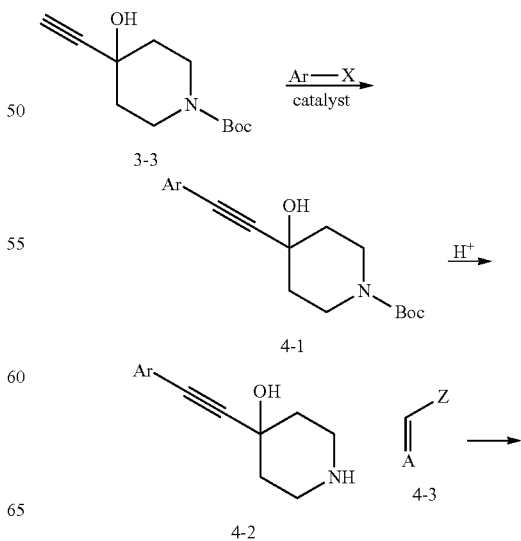

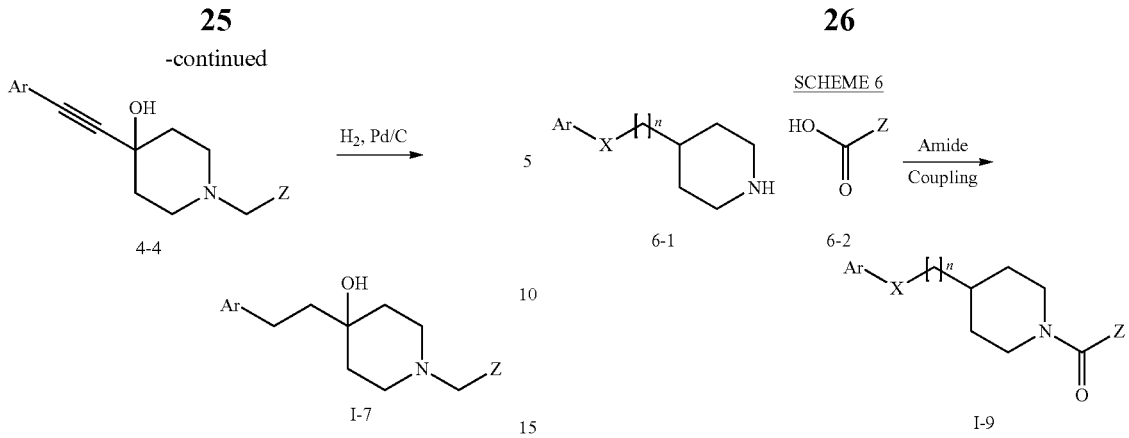

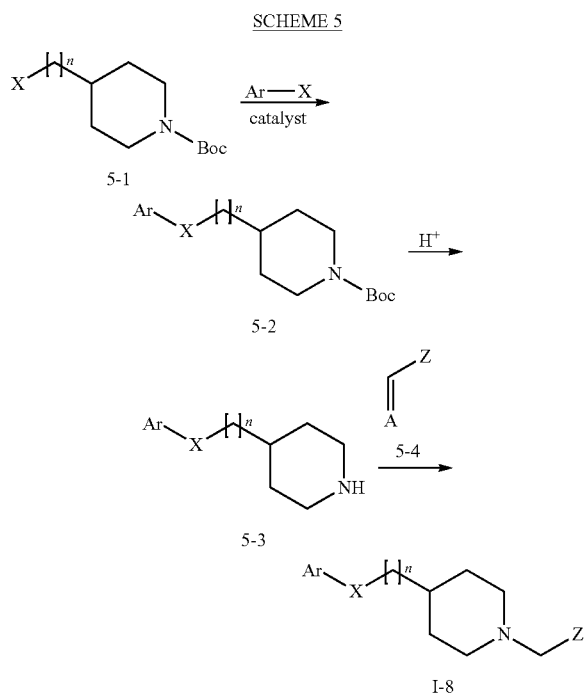

Piperidines I-8 can be prepared as shown in Scheme 5. Treatment of the heteroatom containing piperidines 5-1 (such as thio, amino, hydroxyl, thiomethyl, amino methyl, or hydroxylmethyl) with a heteroaryl halide, trifluoromethanesulfonate, phosphonate, or other reactive intermediate under the appropriate metal catalyzed or base conditions (such as Ullman coupling, palladium or copper catalysis, or triethylamine or cesium carbonate) provides the piperazines 5-2. The Boc group can be removed under acidic conditions to afford piperidine 5-3, which can then be coupled to electrophile 5-4 (examples include alkyl halides, mesylates, trifluoromethanesulfonates, etc. or aldehydes) in the presence of appropriate base (such as triethylamine) or reducing agent (such as sodium cyanoborohydride) to furnish piperidine I-8.

Alternatively, piperadines I-9, containing an amide linkage can be prepared starting from intermediate 5-1. Coupling of 5-1 with appropriate electrophiles 3-5 via standard amide bond forming conditions can be carried out as described above in Scheme 2 to furnish I-9.

General Procedures.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detetor, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250× 4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions. Celite® (Fluka) diatomite is diatomaceous earth, and can be referred to as "celite".

Abbreviations used herein include: —C(O)CH$_3$ (Ac); acetic acid (AcOH); —OC(O)CH$_3$ (OAc); aqueous (aq); Cbz (benzyloxycarbonyl); N,N-diisopropylethylamine (DIEA); N,N-dimethylformamide (DMF); ethyl acetate (EtOAc); diethyl ether (ether or Et$_2$O); petroleum ether (PE); gram(s) (g); hour(s) (h or hr); 2-propanol (IPA); mass spectrum (ms or MS); microliter(s) (IL); milligram(s) (mg); milliliter(s) (mL); millimole (mmol); minute(s) (min); methyl t-butylether (MTBE); (benzotriazol-1-yloxy)tripyrrolidino-phosphonium hexafluorophosphate (PyBOP); retention time (R$_t$); room temperature (rt or RT); saturated aq sodium chloride solution (brine); trifluoroacetic acid (TFA); hydrochloric acid (HCl); tetrahydrofuran (THF); flash chromatography (FC); medium pressure liquid chromatography (MPLC); liquid chromatography (LC); liquid chromatography-mass spectrometry (LCMS or LC-MS); supercritical fluid chromatography (SFC); t-butyloxycarbonyl (Boc or BOC); Diethylaminosulfur trifluoride (DAST); dichloromethane (DCM); dimethylacetamide (DMA); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); thin layer chromatography (TLC); N-(3-dimethylaminopropyl)-N'-ethylcarbdiimide hydrochloride (EDC); lithium diisopropylamide (LDA); toluenesulfonylmethyl isocyanide (TosMIC); trimethylsilyl (TMS); N,N-diisopropylethylamine (DIPEA); diethylaminosulfur trifluoride (DAST); 2-(7-Aza-1H-benzotriazole-1-yl)-1,1,3,3-tetramethyluronium hexafluorophosphate (HATU).

The following are representative procedures for the preparation of the compounds used in the following Examples, or which can be substituted for the compounds used in the following Examples which may not be commercially available.

Intermediate 1

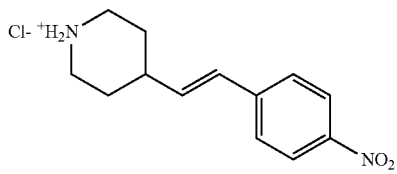 [SMILES: [Cl-] ; O=[N+]([O-])c1ccc(/C=C/C2CC[NH2+]CC2)cc1]

4-[(E)-2-(4-nitrophenyl)ethenyl]piperidinium Chloride

Step A: tert-Butyl 4-[(E)-2-(4-nitrophenyl)ethenyl]piperidine-1-carboxylate tert-Butyl 4-ethenylpiperidine-1-carboxylate (0.50 g, 2.4 mmol), trans-dichlorobis(tri-o-tolylphosphine) palladium (II) (0.050 g, 0.064 mmol), 1-bromo-4-nitrobenzene (0.57 g, 2.8 mmol), and triethylamine (1.6 mL, 12 mmol) were added to a microwave tube, diluted with DMF (2 mL) and degassed under a stream of nitrogen. The tube was sealed and heated in the microwave to 130° C. for 30 min. The resulting mixture was diluted with diethyl ether and washed successively with saturated sodium bicarbonate, water (2×), 1 N hydrochloric acid, and brine, then dried (MgSO$_4$), filtered and concentrated. The resulting tert-butyl 4-[(E)-2-(4-nitrophenyl)ethenyl]piperidine-1-carboxylate was used directly in the next step.

LC/MS: [(M+1)]$^+$=333.

Step B: 4-[(E)-2-(4-nitrophenyl)ethenyl]piperidinium Chloride tert-butyl 4-[(E)-2-(4-nitrophenyl)ethenyl]piperidine-1-carboxylate (0.16 g, 0.48 mmol) was dissolved in 1,4-dioxane (1 mL) and treated at room temperature with a solution of 4 N hydrochloric acid in dioxane (0.12 mL, 0.48 mmol). After 30 minutes the mixture was concentrated. The resulting 4-[(E)-2-(4-nitrophenyl)ethenyl]piperidinium chloride was used directly in the next step. LC/MS: [(M+1)]$^+$=233.

Intermediate 2

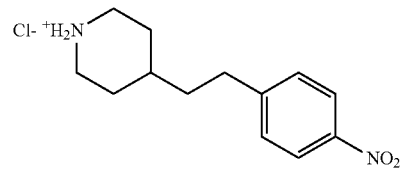 [SMILES: [Cl-] ; O=[N+]([O-])c1ccc(CCC2CC[NH2+]CC2)cc1]

4-[2-(4-Nitrophenyl)ethyl]piperidinium Chloride

Step A: tert-Butyl 4-[2-(4-aminophenyl)ethyl]piperidine-1-carboxylate

To a solution of tert-butyl 4-[(E)-2-(4-nitrophenyl)ethenyl]piperidine-1-carboxylate (0.78 g, 2.3 mmol) in methanol (5 mL) was added palladium hydroxide (0.25 g, 0.36 mmol) and the mixture was stirred under an atmosphere of hydrogen for 12 hours. The mixture was filtered through diatomaceous earth and concentrated. The resulting tert-butyl 4-[2-(4-aminophenyl)ethyl]piperidine-1-carboxylate was used directly in the next step.

LC/MS: [(M+1)]$^+$=305.

Step B: tert-Butyl 4-[2-(4-nitrophenyl)ethyl]piperidine-1-carboxylate

To a solution of tert-butyl 4-[2-(4-aminophenyl)ethyl]piperidine-1-carboxylate (0.43 g, 1.4 mmol) in acetone (25 mL) was added a solution of saturated sodium bicarbonate (40 mL). The resulting mixture was cooled to 0° C. and slowly treated with a solution of oxone (4 g, 6.5 mmol) in water (40 mL). After 2 hours the cooling bath was removed and the mixture diluted with diethyl ether. The layers were separated and the organics washed successively with saturated sodium sulfite, water and brine, then dried (MgSO$_4$), filtered and concentrated. The resulting tert-butyl 4-[2-(4- nitrophenyl)ethyl]piperidine-1-carboxylate was used directly without further purification. LC/MS: [(M+1)]⁺=335.

Step C: 4-[2-(4-Nitrophenyl)ethyl]piperidinium Chloride tert-butyl 4-[2-(4-nitrophenyl)ethyl]piperidine-1-carboxylate (0.40 g, 1.2 mmol) was dissolved in 1,4-dioxane (1 mL) and treated at room temperature with a solution of 4 N hydrochloric acid in dioxane (0.30 mL, 1.2 mmol). After 30 minutes the mixture was concentrated. The resulting 4-[2-(4-nitrophenyl)ethyl]piperidinium chloride was used directly in the next step. LC/MS: [(M+1)]⁺=235.

Intermediate 3

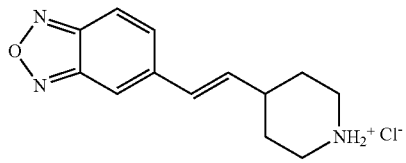 [SMILES: C(=C\C1CC[NH2+]CC1)/c1ccc2nonc2c1 ; [Cl-]]

4-[(E)-2-(2,1,3-Benzoxadiazol-5-yl)ethenyl]piperidinium Chloride

Step A: tert-Butyl 4-[(E)-2-(2,1,3-benzoxadiazol-5-yl)ethenyl]piperidine-1-carboxylate In a 15 mL microwave tube was added 5-bromo-2,1,3-benzoxadiazole (0.94 g, 4.7 mmol), tert-butyl 4-ethenylpiperidine-1-carboxylate (1.0 g, 4.7 mmol), triethylamine (0.66 ml, 4.7 mmol), palladium (II) acetate (0.11 mg, 0.47 mmol) and DMF (5 mL). The solution was degassed and filled with nitrogen (3×), then heated to 100° C. for 2 hr. The reaction was diluted with ethyl acetate, washed with water, filtered through a pad of diatomaceous earth and a plug of silica gel. The organic phase was dried over MgSO₄, concentrated and purified by MPLC (eluted with gradient 0→30% EtOAc/Hexane) to provide tert-butyl 4-[(E)-2-(2,1,3-benzoxadiazol-5-yl)ethenyl]piperidine-1-carboxylate as a mixture with the Z-olefin. LC-MS (IE, m/z): 352 [M+Na]⁺.

Step B: 4-[(E)-2-(2,1,3-Benzoxadiazol-5-yl)ethenyl]piperidinium Chloride

In a 4 mL reaction vial was added tert-butyl 4-[(E)-2-(2,1,3-benzoxadiazol-5-yl)ethenyl]piperidine-1-carboxylate (0.12 mg, 0.37 mmol) and HCl (4 N in dioxane, 93 uL, 0.37 mmol). The reaction was stirred at room temperature for 10 min. The desired product precipitated as white solid. The product was filtered and washed with dichloromethane to provide 4-[(E)-2-(2,1,3-benzoxadiazol-5-yl)ethenyl]piperidinium chloride. LC-MS (IE, m/z): 230.3 [M+1]⁺.

Intermediate 4

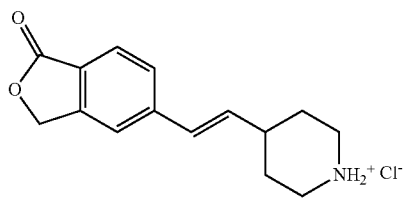 [SMILES: O=C1OCc2cc(/C=C/C3CC[NH2+]CC3)ccc21 ; [Cl-]]

4-[(E)-2-(1-Oxo-1,3-dihydro-2-benzofuran-5-yl)ethenyl]piperidinium Chloride

4-[(E)-2-(1-oxo-1,3-dihydro-2-benzofuran-5-yl)ethenyl]piperidinium chloride was prepared in a similar fashion to that described for the synthesis of INTERMEDIATE 3 starting from tert-butyl 4-ethenylpiperidine-1-carboxylate and 5-bromo-2-benzofuran-1(3H)-one.
LC-MS (IE, m/z): 244 [M+1]⁺.

Intermediate 5

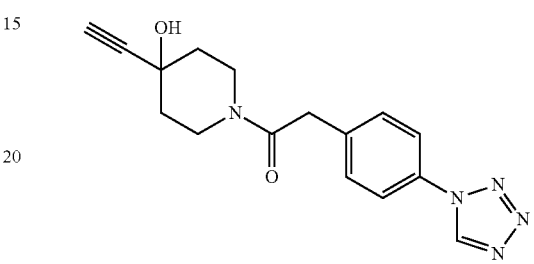

1-(4-Ethynyl-4-hydroxypiperidin-1-yl)-2-[4-(1H-tetrazol-1-yl)phenyl]ethanone

Step A: tert-Butyl 4-hydroxy-4-[(trimethylsilyl)ethynyl]piperidine-1-carboxylate To a solution of n-butyllithium (2.5 M, 107 mL, 270 mmol) in THF (250 mL) at −78° C. was added trimethylsilylacetylene (25 g, 0.260 mmol) dropwise. After 1 hour a solution of tert-butyl 4-piperidone-1-carboxylate (26 g, 130 mmol) in THF (65 mL) was added dropwise and the mixture stirred at −78° C. for one additional hour. The mixture then warmed to rt and was poured into saturated ammonium chloride and extracted with diethyl ether (3×). The combined organic layers were washed with brine, dried (MgSO₄), filtered and concentrated to provide tert-butyl 4-hydroxy-4-[(trimethylsilyl)ethynyl]piperidine-1-carboxylate which was used without further purification in the next step. ¹H-NMR (CDCl₃, 500 MHz), δ 3.82 (m, 2H), 3.23 (m, 2H), 2.14 (br s, 1H), 1.91 (m, 2H), 1.72 (m, 1H), 1.43 (s, 9H), 0.20 (s, 3H).

Step B: 4-Hydroxy-4-[(trimethylsilyl)ethynyl]piperidinium Chloride

To a solution of tert-butyl 4-hydroxy-4-[(trimethylsilyl)ethynyl]piperidine-1-carboxylate (80 g, 130 mmol) in 1,4-dioxane (200 mL) was added 4 N HCl in dioxane (38 mL, 150 mmol) at room temperature. The mixture stirred 48 hours, after which the solvent was evaporated to provide 4-hydroxy-4-[(trimethylsilyl)ethynyl]piperidinium chloride which was used in the next step without further purification. ¹H-NMR (CD₃OD, 500 MHz), δ 3.34 (m, 2H), 3.21 (m, 2H), 2.09 (m, 2H), 1.99 (m, 2H), 0.19 (s, 3H).

Step C: 1-{4-Hydroxy-4-[(trimethylsilyl)ethynyl]piperidin-1-yl}-2-[4-(1H-tetrazol-1-yl)phenyl]ethanone A solution of 4-hydroxy-4-[(trimethylsilyl)ethynyl]piperidinium chloride (14 g, 29 mmol) in dichloromethane (90 mL) was cooled to 5° C. and treated sequentially with EDC (6.7 g, 35 mmol), [4-(1H-tetrazol-1-yl)phenyl]acetic acid (5.9 g, 29 mmol), and triethyl amine (16 mL, 12 mmol). The cooling bath was removed and the mixture stirred 12 hours. The mixture was washed sequentially with 1 N HCl, saturated aq. sodium bicarbonate, and brine, then dried (MgSO$_4$), filtered and concentrated. 1-{4-hydroxy-4-[(trimethylsilyl)ethynyl]piperidin-1-yl}-2-[4-(1H-tetrazol-1-yl)phenyl]ethanone was used directly in the next step without further purification. $^1$H-NMR (CD$_3$OD, 500 MHz), δ 9.01 (s, 1H), 7.71 (d, J=8.5 Hz, 2H), 7.51 (d, J=8.5 Hz, 2H), 4.12 (m, 1H), 3.86 (s, 2H), 3.76 (m, 1H), 3.46 (m, 2H), 1.93 (m, 2H), 1.76 (m, 2H), 1.66 (br s, 1H), 0.21 (s, 3H). LC-MS (IE, m/z): 384 [M+1]$^+$.

Step D: 1-(4-Ethynyl-4-hydroxypiperidin-1-yl)-2-[4-(1H-tetrazol-1-yl)phenyl]ethanone A solution of 1-{4-hydroxy-4-[(trimethylsilyl)ethynyl]piperidin-1-yl}-2-[4-(1H-tetrazol-1-yl)phenyl]ethanone (11 g, 29 mmol) in THF (60 mL) was cooled to 5° C. and slowly treated with a solution of tetrabutylammonium fluoride in THF (1.0 N, 36 mL, 36 mmol). After complete addition the cooling bath was removed and the reaction stirred an additional 2 hours. The mixture was poured into water and extracted with ethyl acetate (4×) and dichloromethane (1×). The combined organic layers were concentrated in vacuo and the resulting residue purified by MPLC (eluent gradient 20→100% EtOAc:heptane) to provide 1-(4-ethynyl-4-hydroxypiperidin-1-yl)-2-[4-(1H-tetrazol-1-yl)phenyl]ethanone. $^1$H-NMR (CD$_3$OD, 500 MHz), δ 8.98 (s, 1H), 7.67 (d, J=8.5 Hz, 2H), 7.47 (d, J=8.5 Hz, 2H), 4.04 (m, 1H), 3.82 (s, 2H), 3.71 (m, 1H), 3.46 (m, 2H), 2.57 (s, 1H), 1.91 (m, 2H), 1.74 (m, 2H), 1.63 (br s, 1H). LC-MS (IE, m/z): 312 [M+1]$^+$.

Intermediate 6

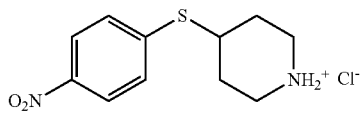 [SMILES: O=[N+]([O-])c1ccc(SC2CC[NH2+]CC2)cc1 ; [Cl-]]

4-[(4-Nitrophenyl)sulfanyl]piperidinium Chloride

Step A: tert-Butyl 4-[(4-nitrophenyl)sulfanyl]piperidine-1-carboxylate

To a solution of tert-butyl 4-hydroxypiperidine-1-carboxylate (8.0 g, 40 mmol) in 100 mL of DCM was added triethylamine (8.0 g, 80 mmol) and the mixture was cooled to 0° C. Methanesulfonyl chloride (5.0 g, 44 mmol) was added dropwise, and the reaction mixture was stirred at r.t. for 12 h. The mixture was concentrated in vacuo and the resulting residue redissolved in DMF (150 mL). 4-Nitrobenzenethiol (2.5 g, 16 mmol) was added, followed by triethylamine (4.9 g, 36 mmol) and the mixture was heated at 100° C. overnight. The mixture was cooled to r.t., diluted with water and extracted with ethyl acetate. The organic layer was dried over anhydrous Na$_2$SO$_4$ and concentrated. The residue was purified by via chromatography (PE/EtOAc 10:1) to provide tert-butyl 4-[(4-nitrophenyl)sulfanyl]piperidine-1-carboxylate. $^1$H-NMR (400 MHz, CDCl$_3$) δ ppm 8.13 (d, J=9.1 Hz, 2H), 7.39 (d, J=9.1 Hz, 2H), 3.95~4.0 (m, 2H), 3.45~3.52 (m, 1H), 3.01~3.06 (m, 2H), 1.99~2.03 (m, 2H), 1.56~1.63 (m, 2H), 1.45 (s, 9H).

Step B: 4-[(4-Nitrophenyl)sulfanyl]piperidinium Chloride

A solution of tert-butyl 4-[(4-nitrophenyl)sulfanyl]piperidine-1-carboxylate (1.0 g, 3.0 mmol) in 10 mL of 1,4-dioxane was treated with 40 mL of HCl/Et$_2$O and the mixture was stirred at ambient temperature for 2 hours. The reaction was concentrated to provide 4-[(4-Nitrophenyl)sulfanyl]piperidinium chloride which was used directly without further purification.

Intermediate 7

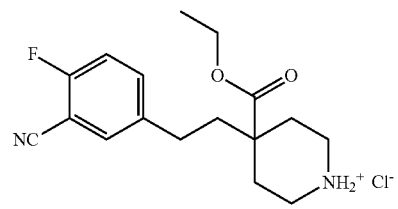 [SMILES: CCOC(=O)C1(CCc2ccc(F)c(C#N)c2)CC[NH2+]CC1 ; [Cl-]]

4-[2-(3-Cyano-4-fluorophenyl)ethyl]-4-(ethoxycarbonyl)piperidinium Chloride

Step A: 2-Fluoro-5-(2-hydroxyethyl)benzonitrile

A solution of compound 2-fluoro-5-(2-oxoethyl)benzonitrile (7.6 g, 47 mmol) in 100 mL of MeOH was cooled to 0° C. and treated with NaHB$_4$ (2.67 g, 70.22 mmol) in portions. The reaction mixture was allowed to warm to ambient temperature slowly and stirred for 1 h. The solvent was removed under vacuum, and the residue was partitioned in EtOAc and water. The aqueous phase was extracted with EtOAc and the combined organic phases were washed with brine, dried over anhydrous sodium sulfate and concentrated. The resulting residue was purified by flash column chromatograph to provide 2-fluoro-5-(2-hydroxyethyl)benzonitrile.

$^1$H-NMR (300 MHz, CDCl$_3$) δ ppm 7.44~7.51 (m, 2H), 7.14 (dd, J=8.7, 8.7 Hz, 1H), 3.85 (dd, J=6.4, 6.4 Hz, 1H), 2.89 (dd, J=6.4, 6.4 Hz, 1H).

Step B: 5-(2-Bromoethyl)-2-fluorobenzonitrile

A solution of 2-fluoro-5-(2-hydroxyethyl)benzonitrile (3.1 g, 19 mmol) and triethylamine (2.9 mL, 21 mmol) in anhydrous DCM (30 mL) was cooled to −5° C., and treated with methanesulfonyl chloride (1.6 mL, 21 mmol). The resulting mixture was stirred at 0° C. for 2 h, then diluted with PE/EtOAc (20/1, 100 mL) and filtered. The filtrate was concentrated under vacuum. The resulting residue was dissolved in 100 mL of acetone and LiBr (4.9 g, 57 mmol) was added. The mixture was heated at reflux for 12 h under a nitrogen atmosphere. The solvent was removed under vacuum, and the residue was partitioned between water and EtOAc. The organic phase was washed with brine, dried over anhydrous sodium sulfate and concentrated. The resulting residue was purified by flash chromatograph to provide 5-(2-bromoethyl)-2-fluorobenzonitrile. $^1$H-NMR (300 MHz, CDCl$_3$) δ ppm 7.41~7.56 (m, 2H), 7.18~7.21 (m, 1H), 3.53 (dd, J=6.8, 6.8 Hz, 2H), 3.16 (dd, J=6.8, 6.8 Hz, 2H).

Step C: 1-tert-Butyl 4-ethyl 4-[2-(3-cyano-4-fluorophenyl)ethyl]piperidine-1,4-dicarboxylate A solution of diisopropylamine (1.6 g, 15 mmol) in anhydrous THF (10 mL) was cooled to −78° C. under nitrogen atmosphere and a solution of n-butyllithium in hexanes (2.5 M, 6.2 mL, 15 mmol) was added dropwise via a syringe. The resulting solution was allowed to warm to room temperature slowly, after which it was recooled to −78° C. A solution of 1-tert-butyl 4-ethyl piperidine-1,4-dicarboxylate (3.6 g, 14 mmol) in anhydrous THF (10 mL) was added dropwise via a syringe, and the reaction mixture was stirred at −78° C. for 1 h. A solution of 542-bromoethyl)-2-fluorobenzonitrile (3.37 g, 14.78 mmol) in anhydrous THF (10 mL) was added dropwise via a syringe. The reaction mixture was allowed to warm to ambient temperature slowly and stirred overnight. Then mixture was poured into water, and extracted with EtOAc. The organic phase was washed with brine, dried over anhydrous sodium sulfate and concentrated. The resulting residue was purified by flash chromatography and preparative HPLC to provide 1-tert-butyl 4-ethyl 4-[2-(3-cyano-4-fluorophenyl)ethyl]piperidine-1,4-dicarboxylate. $^1$H-NMR (400 MHz, CDCl$_3$) δ ppm 7.33~7.37 (m, 1H), 7.28~7.30 (m, 1H), 7.11 (dd, J=8.6, 8.6 Hz, 1H), 4.43 (m, 1H), 4.19 (dd, J=7.1, 14.2 Hz, 2H), 4.09~4.14 (dd, J=7.1, 14.2 Hz, 1H), 3.87~3.91 (m, 2H), 2.86~2.92 (m, 2H), 2.80 (s, 1H), 2.52 (m, 1H), 2.03~2.16 (m, 2H), 1.73~1.79 (m, 2H), 1.44 (s, 9H), 1.35~1.41 (m, 4H).

Step D: 4-[2-(3-Cyano-4-fluorophenyl)ethyl]-4-(ethoxycarbonyl)piperidinium Chloride A solution of 1-tert-butyl 4-ethyl 4-[2-(3-cyano-4-fluorophenyl)ethyl]piperidine-1,4-dicarboxylate (2.4 g, 5.8 mmol) in 50 mL of HCl/Et$_2$O was stirred at ambient temperature for 12 h. The solvent was concentrated to provide 4-[2-(3-Cyano-4-fluorophenyl)ethyl]-4-(ethoxycarbonyl)piperidinium chloride which was used directly without further purification.

Intermediate 8

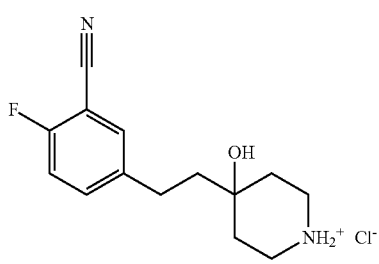 [SMILES: N#Cc1cc(CCC2(O)CC[NH2+]CC2)ccc1F ; [Cl-]]

4-[2-(3-Cyano-4-fluorophenyl)ethyl]-4-hydroxypiperidinium Chloride

Step A: tert-Butyl 4-ethynyl-4-hydroxypiperidine-1-carboxylate

A solution of tert-butyl 4-hydroxy-4-[(trimethylsilyl)ethynyl]piperidine-1-carboxylate (20 g, 67 mmol) in dry THF (150 mL) was added a solution of 1.0 M solution of tetrabutylammonium fluoride (19 g in 100 mL THF) at 0° C. The mixture was stirred at 0° C. for 1 hr and then poured into water (500 mL) and the products were extracted with EtOAc (3×300 mL). The combined organic layers were washed with brine (500 mL), dried (Na$_2$SO$_4$), filtered and concentrated to provide tert-butyl 4-ethynyl-4-hydroxypiperidine-1-carboxylate which was used directly in the next step without further purification.

Step B: tert-Butyl 4-[(3-cyano-4-fluorophenyl)ethynyl]-4-hydroxypiperidine-1-carboxylate A solution of tert-butyl 4-ethynyl-4-hydroxypiperidine-1-carboxylate (8.2 g, 36 mmol) and 2-fluoro-5-iodobenzonitrile (8.72 g, 43.6 mmol) in N,N-diethylamine (200 mL), was added tetrakis(triphenylphosphine)palladium dichloride (0.80 mg) and copper (I) iodide (0.34 mg). The mixture was stirred at room temperature under N$_2$ for 12 h and then evaporated. The residue was partitioned between water and EtOAc. The combined organic solutions were washed with brine (500 mL), dried (Na2SO4), filtered and concentrated to provide tert-butyl 4-[(3-cyano-4-fluorophenyl)ethynyl]-4-hydroxypiperidine-1-carboxylate which was used directly in the next step without further purification.

Step C: tert-Butyl 4-[2-(3-cyano-4-fluorophenyl)ethyl]-4-hydroxypiperidine-1-carboxylate A mixture of tert-butyl 4-[(3-cyano-4-fluorophenyl)ethynyl]-4-hydroxypiperidine-1-carboxylate (7.0 g, 20 mmol) and 1 g of palladium on carbon in 150 mL of MeOH was stirred at ambient temperature under H$_2$ atmosphere overnight. The reaction mixture was filtered and concentrated to provide tert-butyl 4-[2-(3-cyano-4-fluorophenyl)ethyl]-4-hydroxypiperidine-1-carboxylate. $^1$H-NMR (400 MHz, CDCl$_3$) δ ppm 7.38~7.42 (m, 2H), 7.1 (t, J=8.6 Hz, 1H), 3.78~3.86 (m, 2H), 3.12~3.21 (m, 2H), 2.7~2.75 (m, 2H), 1.7~1.76 (m, 2H), 1.55~1.6 (m, 4H), 1.44 (s, 9H).

Step D: 4-[2-(3-Cyano-4-fluorophenyl)ethyl]-4-hydroxypiperidinium Chloride

A solution of tert-butyl 4-[2-(3-cyano-4-fluorophenyl)ethyl]-4-hydroxypiperidine-1-carboxylate (2.7 g, 7.8 mmol) in 50 mL of dioxane was treated with 50 mL of HCl/Et$_2$O and stirred at room temperature overnight. The reaction mixture was concentrated and the resulting residue was purified by flash chromatography to provide 4-[2-(3-cyano-4-fluorophenyl)ethyl]-4-hydroxypiperidinium chloride which was used directly in the next step without further purification.

Intermediate 9

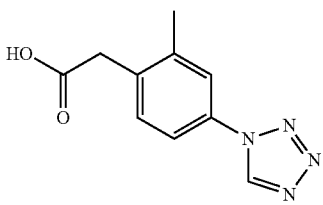 [SMILES: Cc1cc(-n2cnnn2)ccc1CC(=O)O]

[2-Methyl-4-(1H-tetrazol-1-yl)phenyl]acetic Acid

To a solution of (4-amino-2-methylphenyl)acetic acid (0.10 g, 0.61 mmol) and triethyl orthoformate (0.16 ml, 0.97 mmol) in acetic acid (1 ml) was added sodium azide (0.059 g, 0.91 mmol). The resulting mixture was heated to reflux for 4 hours. The mixture was poured into ice water and the resulting solid collected by filtration and dried under vacuum to provide [2-methyl-4-(1H-tetrazol-1-yl)phenyl]acetic acid. LC-MS (IE, m/z): 219 [M+1]⁺.

Intermediate 10

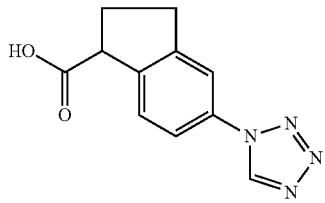 [SMILES: O=C(O)C1CCc2cc(-n3cnnn3)ccc21]

5-(1H-Tetrazol-1-yl)-2,3-dihydro-1H-indene-1-carboxylic Acid

Step A: N-(2,3-Dihydro-1H-inden-5-yl)acetamide

A solution of indan-5-amine (43 g, 0.31 mol) and TEA (51 mL, 0.37 mol) in 400 mL of anhydrous DCM was added a solution of AcCl (24 mL, 0.34 mol) in 100 mL of anhydrous DCM dropwise at 0° C. then and stirred for 0.5 h at r.t. After the reaction was completed, the reaction mixture was added 500 mL of DCM, washed with water, 10% HCl solution, 10% NaHCO₃ and brine. The organic phase was dried over anhydrous Na₂SO₄ and concentrated to give N-(2,3-dihydro-1H-inden-5-yl)acetamide. ¹H-NMR (300 MHz, CDCl₃) δ ppm 7.43 (s, 1H), 7.13~7.14 (m, 2H), 2.86 (q, J=7.9 Hz, 4H), 2.15 (s, 3H), 2.0~2.10 (m, 2H).

Step B: N-(1-Oxo-2,3-dihydro-1H-inden-5-yl)acetamide

A solution of N-(2,3-dihydro-1H-inden-5-yl)acetamide (50 g, 0.29 mol) in 150 mL of acetic acid and 40 ml, of acetic anhydride was added a solution of chromium trioxide in a mixed solution (30 mL of water and 140 mL of acetic acid) dropwise at 10° C. by external cooling. After stirring overnight, the solution was poured into 2 L of ice water under vigorously stirring. The resulting solid was filtered, washed with cooled EtOH to give N-(1-oxo-2,3-dihydro-1H-inden-5-yl)acetamide. ¹H-NMR (300 MHz, CDCl₃) δ ppm 7.90 (s, 1H), 7.66~7.70 (m, 2H), 7.22~7.25 (m, 1H), 3.09~3.13 (m, 2H), 2.66~2.70 (m, 2H), 2.22 (s, 3H).

Step C: N-(1-Cyano-2,3-dihydro-1H-inden-5-yl)acetamide

To a stirring ice-cooled mixture of N-(1-cyano-2,3-dihydro-1H-inden-5-yl)acetamide (10 g, 53 mmol), TosMIC (16 g, 80 mmol) in 100 mL of anhydrous DME was added a solution of NaOMe (1.8 g of Na in 20 mL of anhydrous MeOH) dropwise. After the addition was completed, the mixture was stirred overnight at ambient temperature. The reaction mixture was quenched with 4 N HCl at 0° C. and extracted with DCM. The extract was washed with bine, dried over anhydrous Na₂SO₄ and concentrated. The residue was purified with silica gel column chromatograph to give N-(1-cyano-2,3-dihydro-1H-inden-5-yl)acetamide. ¹H-NMR (300 MHz, CDCl₃) δ ppm 7.90 (s, 1H), 7.66~7.70 (m, 2H), 7.22~7.25 (m, 1H), 4.03~4.05 (m, 1H), 3.10~3.15 (m, 2H), 2.35~2.43 (m, 2H), 2.17 (s, 3H).

Step D: 5-Aminoindane-1-carboxylic Acid

A mixture of N-(1-cyano-2,3-dihydro-1H-inden-5-yl)acetamide (20 g, 0.11 mol) in 180 mL of concentrated hydrogen chloride was refluxed for two days. The reaction mixture was concentrated under reduce pressure, and the residue was basified with saturated NaOH to Ph 4~5. The mixture was extracted with EtOAc and the extract was dried over anhydrous Na₂SO₄ and concentrated. The residue was purified with silica gel column chromatograph to afford 5-aminoindane-1-carboxylic acid. ¹H-NMR (300 MHz, CDCl₃) δ ppm 6.95~7.05 (m, 1H), 6.66~6.68 (m, 1H), 6.51~6.53 (m, 1H), 4.11~4.16 (m, 1H), 3.06~3.27 (m, 4H).

Step E: 5-(1H-Tetrazol-1-yl)-2,3-dihydro-1H-indene-1-carboxylic Acid

A solution of 5-aminoindane-1-carboxylic acid (2.95 g, 16.7 mmol), sodium azide (1.20 g, 18.3 mmol) and triethyl orthoformate (7.42 g, 50.1 mmol) in 20 mL of acetic acid was heated to 100° C. for 3 hrs. After the reaction was completed, the mixture was cooled to ambient temperature. The solution was removed under vacuum and the residue was diluted with EtOAc, washed with brine, dried over anhydrous Na₂SO₄ and concentrated. The residue was purified with silica gel column chromatograph to give the crude product, then re-crystallization from DCM to yield 5-(1H-tetrazol-1-yl)-2,3-dihydro-1H-indene-1-carboxylic acid. ¹H-NMR (400 MHz, DMSO) δ ppm 10.0 (s, 1H), 7.75 (s, 1H), 7.66~7.69 (m, 1H), 7.55 (d, J=8.1 Hz, 1H), 4.02~4.06 (m, 1H), 2.88~3.08 (m, 2H), 2.31 (q, J=8.1 Hz, 2H).

Intermediate 11

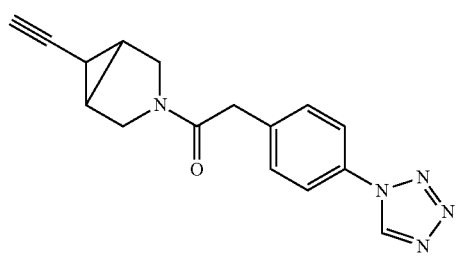 [SMILES: C#CC1C2CN(C(=O)Cc3ccc(-n4cnnn4)cc3)CC12]

1-(6-Ethynyl-3-azabicyclo[3.1.0]hex-3-yl)-2-[4-(1H-tetrazol-1-yl)phenyl]ethanone Step A: 1-[6-(Hydroxymethyl)-3-azabicyclo[3.1.0]hex-3-yl]-2-[4-(1H-tetrazol-1-yl)phenyl]ethanone EDC (250 mg, 1.3 mmol) was added to a stirred, cooled 0° C. mixture of [4-(1H-tetrazol-1-yl)phenyl]acetic acid (200 mg, 1.0 mmol) in dichloromethane (10 ml) and the mixture was stirred at room temperature for 15 min. 3-Azabicyclo[3.1.0]hex-6-ylmethanol (110 mg, 1.0 mmol)

was added followed by triethylamine (0.56 mL, 4.0 mmol) and the solution stirred 12 h. The reaction mixture was diluted with water and extracted with DCM (3×). The combined organic layers were washed successively with 1N NaHSO$_4$, saturated aqueous sodium bicarbonate, and brine, then dried (Na$_2$SO$_4$), filtered and concentrated to provide 1-[6-(hydroxymethyl)-3-azabicyclo[3.1.0]hex-3-yl]-2-[4-(1H-tetrazol-1-yl)phenyl]ethanone which was used directly without further purification. $^1$H NMR (500 MHz, CD$_3$OD): δ 9.76 (s, 1H), 7.84 (d, J=8.5 Hz, 2H), 7.52 (d, J=8.5 Hz, 2H), 3.80 (s, 2H), 3.77 (m, 2H), 3.69 (m, 1H), 3.44 (m, 3H), 1.63 (m, 1H), 1.59 (m, 1H), 0.83 (m, 1H).

Step B: 1-(6-Ethynyl-3-azabicyclo[3.1.0]hex-3-yl)-2-[4-(1H-tetrazol-1-yl)phenyl]ethanone Dess-Martin periodinane (160 mg, 0.38 mmol) was added to a solution of 1-[6-(hydroxymethyl)-3-azabicyclo[3.1.0]hex-3-yl]-2-[4-(1H-tetrazol-1-yl)phenyl]ethanone (89 mg, 0.30 mmol) in dichloromethane (2 ml) at rt. After 2 h, the reaction was diluted with saturated aqueous sodium bicarbonate and saturated aqueous sodiumthiosulfate and the resulting mixture stirred 30 min. The layers were separated and the aqueous layer extracted with EtOAc (3×). The combined organic layers were dried (Na$_2$SO$_4$), filtered and concentrated. The resulting aldehyde was dissolved in methanol (5 mL) and treated successively with dimethyl (1-diazo-2-oxopropyl)phosphonate (110 mg, 0.60 mmol) and potassium carbonate (94 mg, 0.68 mmol). The resulting reaction stirred 12 h at room temperature, then was diluted with water and extracted with extracted with EtOAc (3×). The combined organic layers were washed with brine, dried (Na$_2$SO$_4$), and concentrated to provide 1-(6-ethynyl-3-azabicyclo[3.1.0]hex-3-yl)-2-[4-(1H-tetrazol-1-yl)phenyl]ethanone which was used directly without further purification. $^1$H NMR (500 MHz, CDCl$_3$): δ 9.02 (s, 1H), 7.72 (d, J=8.5 Hz, 2H), 7.48 (d, J=8.5 Hz, 2H), 3.90 (m, 1H), 3.88 (s, 2H), 3.71 (m, 2H), 2.68 (m, 1H), 2.25 (s, 1H), 1.99 (m, 2H).

Intermediate 12

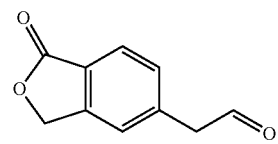

4-[(E)-2-(3-Cyano-4-fluorophenyl)ethenyl]-4-hydroxypiperidine

Step A: tert-Butyl 4-[(E)-2-(3-cyano-4-fluorophenyl)ethenyl]-4-hydroxypiperidine-1-carboxylate To a solution of 1 (1.0 g, 2.9 mmol) in 50 ml of THF was added sodium bis(2-methoxyethoxy)aluminum hydride (1.8 g, 5.8 mmol) at −10° C. The mixture was allowed to warm to room temperature and stirred overnight. The reaction was quenched by the addition of saturated citric acid to adjust pH 3, and partitioned between water and EtOAc. The organic layer was washed with brine (100 ml), dried over anhydrous sodium sulfate, filtered and concentrated. The resulting residue was purified by prep-TLC to provide tert-butyl 4-[(E)-2-(3-cyano-4-fluorophenyl)ethenyl]-4-hydroxypiperidine-1-carboxylate which was used directly in the next step.

Step A: 4-[(E)-2-(3-Cyano-4-fluorophenyl)ethenyl]-4-hydroxypiperidine

A solution of tert-butyl 4-[(E)-2-(3-cyano-4-fluorophenyl)ethenyl]-4-hydroxypiperidine-1-carboxylate (280 mg, 0.80 mmol) in 5 mL of EtOAc was added 5M HCl/dioxane (9 ml) at 0° C. After stirring for 3 h at 0° C., the mixture was poured into a 2N aqueous solution of potassium carbonate (20 ml). The aqueous phase was separated and extracted with EtOAc. The combined organic layers were washed with brine (100 ml), dried over anhydrous sodium sulfate, filtered, and concentrated. The resulting residue was purified by prep-TLC to provide 4-[(E)-2-(3-cyano-4-fluorophenyl)ethenyl]-4-hydroxypiperidine.

Intermediate 13

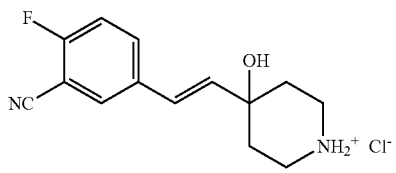 [SMILES: N#Cc1cc(/C=C/C2(O)CC[NH2+]CC2)ccc1F ; [Cl-]]

Oxo-1,3-dihydro-2-benzofuran-5-yl)acetaldehyde

Step A: 5-(1,3-dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.7 mmol), palladium (II) acetate (250 mg, 1.1 mmol) and 5-bromo-2-benzofuran-1(3H)-one (100 g, 470 mmol). DMF (1.9 L) was added to the flask, and the mixture was degassed three times by alternating vacuum and nitrogen purge. Commercially available bromo(1,3-dioxolan-2-ylmethyl)zinc solution (1.0 L, 520 mmol) was added via canula and the mixture was again degassed three times. The mixture was then heated at 85° C. for 5 h. Analysis by HPLC-MS indicated the reaction was not complete. The mixture was stirred at 85° C. for 5 more h. The mixture was then allowed to return to room temperature for overnight. 2-methyltetrahydrofuran (2.0 L) and brine were added, and the mixture was stirred for 5 min. The layers were separated and the aqueous layer was extracted again with 2-methyltetrahydrofuran. The organic layers were combined, washed three times with brine (100 ml), dried over MgSO$_4$, filtered, and concentrated. The resulting residue was purified by flash chromatography (1.5 kg silica cartridge), eluting with 0→20% ethyl acetate in dichloromethane to afford 5-(1,3-dioxolan-2-ylmethyl)-2-benzofuran-1(3H)-one. MS: m/z 221 (M+1)$^+$.

Step B: Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.1 L, 2.3 mol) was added and the resulting mixture was heated at 40° C. for 8 h. Then the mixture was stirred overnight at room temperature. The mixture was extracted three times with 2 L of ethyl acetate. The combined organic layers were concentrated to provide oxo-1,3-dihydro-2-benzofuran-5-yl)acetaldehyde. MS: m/z 177 (M+1)⁺.

Intermediate 14

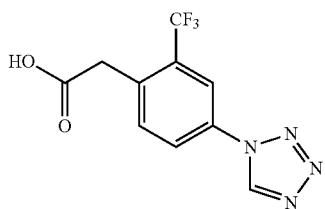 [SMILES: O=C(O)Cc1ccc(-n2cnnn2)cc1C(F)(F)F]

[4-(1H-Tetrazol-1-yl)-2-(trifluoromethyl)phenyl]acetic Acid

[4-(1H-tetrazol-1-yl)-2-(trifluoromethyl)phenyl]acetic acid was prepared in a similar fashion to that described for the synthesis of INTERMEDIATE 9 starting from [4-amino-2-(trifluoromethyl)phenyl]acetic acid. LC-MS (IE, m/z): 273 [M+1]⁺.

Intermediate 15

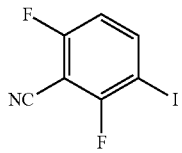 [SMILES: N#Cc1c(F)ccc(I)c1F]

3-bromo-2,6-difluorobenzonitrile

A solution of compound 2,6-difluorobenzonitrile (5.0 g, 36 mmol) in concentrated sulfuric acid (25 mL) was added with N-bromosuccinimide (7.0 g, 40 mmol) at 0° C. and the resulting mixture was stirred at ambient temperature for 2 days. The reaction was poured over ice and the resulting mixture was extracted with EtOAc. The organic layer was washed with water, saturated NaHCO₃ solution, brine, dried over anhydrous sodium sulfate and concentrated. The residue was purified with fast column chromatograph to give compound 3-bromo-2,6-difluorobenzonitrile.
¹H-NMR (400 MHz, CDCl₃) δ ppm 7.78~7.83 (m, 1H), 6.98~7.03 (m, 1H).

Intermediate 16

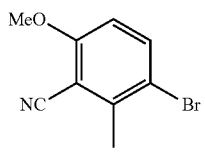

3-Bromo-6-methoxy-2-methylbenzonitrile

A solution of bromine (260 mg, 1.6 mmol) in carbon tetrachloride (1.0 mL) was added over 15 min to a solution of 2-methoxy-6-methylbenzonitrile (240 mg, 1.6 mmol) in carbon tetrachloride (3.0 mL) at −10° C. containing 4.0 mg of Fe powder. After 45 min the reaction was poured into ice water. The organic layer was washed with Na₂SO₃ (aq.) solution (×2), brine and dried (Na₂SO₄), filtered and concentrated to provide 3-bromo-6-methoxy-2-methylbenzonitrile which was used directly without further purification.

Intermediate 17

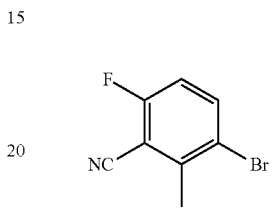

3-Bromo-6-fluoro-2-methylbenzonitrile

To a cooled (0° C.) solution of 2-fluoro-6-methylbenzonitrile (5.0 g, 37 mmol) in 100 mL of concentrated H₂SO₄ was added NBS (6.93 g, 38.9 mmol). Then the mixture was stirred at 0° C. for 3 hrs and poured into ice-water (1 L). The solution was extracted three times with EtOAc (200 mL) and the combined organic layers were washed with water and brine, dried over anhydrous sodium sulfate, filtered and concentrated. The residue was purified by silica gel fash chromatography to give 3-bromo-6-fluoro-2-methylbenzonitrile.
¹H-NMR (400 MHz, CDCl₃) δ ppm 7.71~7.74 (m, 1H), 6.95 (t, J=8.6 Hz, 1H), 2.62 (s, 3H).

Intermediate 18

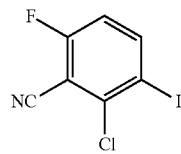 [SMILES: N#Cc1c(F)ccc(I)c1Cl]

2-Chloro-6-fluoro-3-iodobenzonitrile

Step A: 2-Chloro-6-fluoro-3-iodobenzaldehyde

A solution of diisopropylamine (870 mg, 8.6 mmol) in anhydrous THF was added n-butyllithium (2.5 M in hexanes, 3.1 mL, 7.8 mmol) dropwise over 5 min under nitrogen at 0° C. After 10 min, the reaction mixture was cooled to −78° C. and 2-chloro-4-fluoro-1-iodobenzene (2.0 g, 7.8 mmol) was added dropwise over 5 min. After 1 h at −78° C., DMF (640 mg, 8.6 mmol) was added dropwise over 5 min. After a further 10 min at −78° C., the reaction mixture was quenched by the rapid addition of acetic acid (2.0 mL), followed quickly by water (50 mL). The cold solution was extracted with diethyl ether and the organic extracts were washed with diluted HCl (0.2 M, 25 mL), water, brine and dried over anhydrous sodium sulfate. The solvent was removed under reduce pressure and the resulting residue was then purified by silica gel chromatography to provide 2-chloro-6-fluoro-3-iodobenzaldehyde.

¹HNMR (400 MHz, CDCl₃) δ 10.34 (s, 1H), 8.04 (m, 1H), 6.92 (dd, J=9.4, 9.4 Hz, 1H).

Step B: 2-Chloro-6-fluoro-3-iodobenzonitrile

A suspension of 2-chloro-6-fluoro-3-iodobenzaldehyde (500 mg, 1.3 mmol) and hydroxylamine-o-sulfonic acid (290 mg, 2.6 mmol) in 10 mL of water was heated at 50° C. overnight. The suspension was cooled and the solid was collected and dried under vacuum to provide 2-chloro-6-fluoro-3-iodobenzonitrile. 1H-NMR (400 MHz, CDCl₃) δ 8.06 (m, 1H), 6.94 (m, 1H).

Intermediate 19

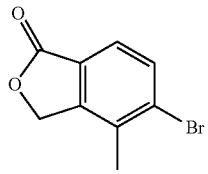

5-Bromo-4-Methyl-2-benzofuran-1(3H)-one

Step A: (3-Bromo-2-methylphenyl)methanol

To a solution of 3-bromo-2-methyl benzoic acid (35 g, 160 mmol) in THF (200 mL) was added borane THF complex (1.0 M, 210 mL, 210 mmol). The mixture was allowed to stir for 24 h. The reaction was quenched with water. The solvent THF was removed under reduced pressure. The resulting solid was dissolved in ethyl acetate (500 mL), washed with 1N hydrochloric acid, saturated sodium bicarbonate, and brine. The combined organic layers were dried over sodium sulfate and concentrated to afford (3-bromo-2-methylphenyl)methanol.

Step B: 5-Bromo-4-methyl-2-benzofuran-1(3H)-one

To a flask charged with (3-bromo-2-methylphenyl)methanol (6.0 g, 30 mmol) was added a 1M trifluoroacetic acid solution of thallium trifluoroacetate (16.2 g, 29.8 mmol). The mixture was stirred at RT overnight. The solvent was removed under vacuum, and the residue was pumped under high vacuum for 30 min to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and methanol (150 mL). The reaction was flushed with CO twice, and kept under CO at room temperature. Analysis by LC showed a big product spot within 2 hours. To this solution was added ethyl acetate to precipitate the salts. The black solution was filtered through a diatomaceous earth pad, washed with EtOAc, adsorbed onto silica and purified by silica gel chromatography to afford 5-bromo-4-methyl-2-benzofuran-1(3H)-one. ¹H-NMR (500 MHz, CDCl₃) δ ppm 7.71 (d, J=8.0 Hz, 1H), 7.58 (d, J=8.0 Hz, 1H), 5.25 (s, 2H), 2.37 (s, 3H).

Intermediate 20

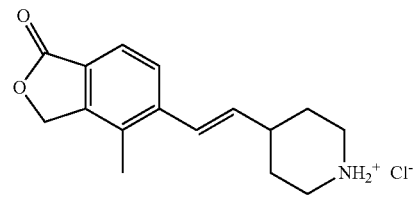 [SMILES: Cc1c(/C=C/C2CC[NH2+]CC2)ccc2c1COC2=O ; [Cl-]]

4-[(E)-2-(4-Methyl-1-oxo-1,3-dihydro-2-benzofuran-5-yl)ethenyl]piperidinium Chloride 4-[(E)-2-(4-Methyl-1-oxo-1,3-dihydro-2-benzofuran-5-yl)ethenyl]piperidinium chloride was prepared in a similar fashion to that described for the synthesis of INTERMEDIATE 3 starting from tert-butyl 4-ethenylpiperidine-1-carboxylate and 5-bromo-4-methyl-2-benzofuran-1(3H)-one. LC-MS (IE, m/z): 258 [M+1]⁺.

Intermediate 21

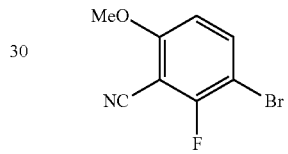

3-Bromo-2-fluoro-6-methoxybenzonitrile

3-Bromo-2-fluoro-6-methoxybenzonitrile was prepared in a similar fashion to the synthesis previously described for INTERMEDIATE 16 starting form 2-fluoro-6-methoxybenzonitrile. LC-MS (IE, m/z): 230 [M+1]⁺.

Intermediate 22

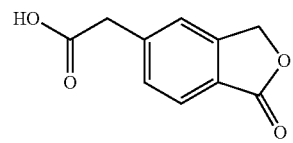 [SMILES: O=C(O)Cc1ccc2c(c1)COC2=O]

(1-Oxo-1,3-dihydro-2-benzofuran-5-yl)acetic acid

Step A: tert-Butyl (1-oxo-1,3-dihydro-2-benzofuran-5-yl)acetate

To a 20 mL microwave tube charged with 5-bromo-2-benzofuran-1(3H)-one (500 mg, 2.4 mmol) and palladium tetrakis triphenylphosphine (140 mg, 0.12 mmol) in THF (5 mL) was added (2-tert-butoxy-2-oxoethyl)(chloro)zinc (6.6 mL, 0.5 M, 3.3 mmol). The mixture was purged with nitrogen 3 times, and heated to 105° C. for 30 minutes in a microwave reactor. The reaction mixture was poured into water and filtered then extracted with ethyl acetate twice.

The organic layer was washed with brine, dried, and evaporated to dryness. The residue was purified by MPLC on a 40 g ISCO Redi-Sep column to yield tert-butyl (1-oxo-1,3-dihydro-2-benzofuran-5-yl)acetate. $^1$H-NMR (500 MHz, CDCl$_3$) δ ppm 7.89 (d, J=7.7 Hz, 1H), 7.46 (d, J=8.3 Hz, 1H), 7.44 (s, 1H), 5.33 (s, 2H), 3.69 (s, 2H), 1.47 (s, 9H).

Step B:
(1-Oxo-1,3-dihydro-2-benzofuran-5-yl)acetic acid tert-Butyl (1-oxo-1,3-dihydro-2-benzofuran-5-yl)acetate (1.2 g, 4.8 mmol) was dissolved in TFA and stirred at room temperature for one h. The reaction mixture was concentrated and pumped under vacuum overnight to afford (1-oxo-1,3-dihydro-2-benzofuran-5-yl)acetic acid. LC-MS (IE, m/z): 193 [M+1]$^+$.

Intermediate 23

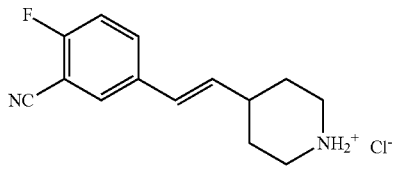 [SMILES: N#Cc1cc(/C=C/C2CC[NH2+]CC2)ccc1F ; [Cl-]]

4-[(E)-2-(3-Cyano-4-fluorophenyl)ethenyl]piperidinium Chloride

4-[(E)-2-(3-Cyano-4-fluorophenyl)ethenyl]piperidinium chloride was prepared in a similar fashion to that described for the synthesis of INTERMEDIATE 3 starting from tert-butyl 4-ethenylpiperidine-1-carboxylate and 3-bromo-6-fluoro-2-methylbenzonitrile.
LC-MS (IE, m/z): 231 [M+1]$^+$.

Intermediate 24

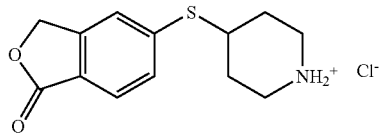 [SMILES: O=C1OCc2cc(SC3CC[NH2+]CC3)ccc21 ; [Cl-]]

4-[(1-Oxo-1,3-dihydro-2-benzofuran-5-yl)sulfanyl]piperidinium chloride

Step A: tert-Butyl 4-(Acetylsulfanyl)piperidine-1-carboxylate

A solution of tert-butyl 4-hydroxypiperidine-1-carboxylate (5.0 g, 25 mmol) in 20 mL of anhydrous DCM was treated with triethylamine (4.2 mL, 30 mmol) followed by cooling to 0° C. and dropwise addition of methanesulfonyl chloride (1.9 mL, 25 mmol). The resulting mixture stirred at rt for 12 h, then was diluted with DCM, washed with brine, dried over anhydrous sodium sulfate and concentrated. The resulting residue was dissolved in 20 mL of DMF, treated with potassium thioacetate (4.3 g, 37 mmol) and the mixture was stirred at 65° C. under a nitrogen atmosphere overnight. The reaction mixture was cooled to room temperature, poured into water and extracted with diethyl ether (3×). The combined organic extracts were washed with water and brine, dried over anhydrous sodium sulfate and concentrated to provide tert-butyl 4-(acetylsulfanyl)piperidine-1-carboxylate, which was used directly in the next step without further purification. $^1$H-NMR (400 MHz, CDCl$_3$) δ ppm 3.80~2.86 (m, 2H), 3.58 (m, 1H), 2.99~3.06 (m, 2H), 2.35 (s, 3H), 1.81~1.88 (m, 2H), 1.51~1.56 (m, 2H), 1.40 (s, 9H).

Step B: tert-Butyl 4-Sulfanylpiperidine-1-carboxylate

A solution of sodium methoxide (prepared from 570 mg of sodium in 20 mL of anhydrous methanol, 25 mmol) was added dropwise to a stirred solution of tert-butyl 4-(acetylsulfanyl)piperidine-1-carboxylate (5.2 g, 21 mmol) in 80 mL of anhydrous methanol at 0° C. After 1 h at 0° C. for the mixture was allowed to warm to room temperature and then stirred for an additional 4 h. The solvent was removed in vacuo and the residue was partitioned between EtOAc and water. The aqueous phase was extracted with EtOAc and the combined extracts were washed with brine, dried over sodium sulfate and concentrated. The residue was purified by flash chromatography (Petrol ether/EtOAc=4:1) to provide tert-butyl 4-sulfanylpiperidine-1-carboxylate. $^1$H-NMR (400 MHz, CDCl$_3$) δ ppm 4.83 (m, 1H), 3.93~3.97 (m, 2H), 2.71~2.82 (m, 3H), 1.90~1.93 (m, 2H), 1.43~1.50 (m, 2H), 1.39 (s, 9H).

Step C: tert-Butyl 4-[(1-oxo-1,3-dihydro-2-benzofuran-5-yl)sulfanyl]piperidine-1-carboxylate A solution of tert-butyl 4-sulfanylpiperidine-1-carboxylate (490 mg, 2.3 mmol) in 20 mL of anhydrous 1,4-dioxane was added 5-bromo-2-benzofuran-1(3H)-one (500 mg, 2.3 mmol), DIEA (596 mg, 4.62 mmol), tris(dibenzylideneacetone)dipalladium (0) (190 mg, 0.12 mmol) and Xantphos (67 mg, 0.12 mmol), and the mixture was heated at reflux under a nitrogen atmosphere overnight. The reaction mixture was concentrated under vacuum, and the resulting residue was purification by prep-TLC (Petrol ether/EtOAc=2:1) to provide tert-butyl 4-[(1-oxo-1,3-dihydro-2-benzofuran-5-yl)sulfanyl]piperidine-1-carboxylate.
$^1$H-NMR (400 MHz, CDCl$_3$) δ ppm 7.72 (d, J=8.4 Hz, 1H), 7.60~7.62 (m, 2H), 5.23 (s, 2H), 3.93~3.97 (m, 2H), 2.72~2.82 (m, 3H), 1.89~1.93 (m, 2H), 1.43~1.49 (m, 2H), 1.39 (s, 9H).

Step D: 4-[(1-Oxo-1,3-dihydro-2-benzofuran-5-yl)sulfanyl]piperidinium chloride

A solution of tert-butyl 4-[(1-oxo-1,3-dihydro-2-benzofuran-5-yl)sulfanyl]piperidine-1-carboxylate (200 mg, 0.58 mmol) in 10 mL of THF was added 5 mL of 4 M HCl/ether, and the solution was stirred at ambient temperature overnight. The solvent was removed under vacuum to provide 4-[(1-oxo-1,3-dihydro-2-benzofuran-5-yl)sulfanyl]piperidinium chloride, which was directly without further purification.

Intermediate 25

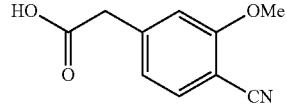 [SMILES: COc1cc(CC(=O)O)ccc1C#N]

(4-Cyano-3-methoxyphenyl)acetic Acid

Step A: Ethyl(3-Methoxy-4-{[(trifluoromethyl)sulfonyl]oxy}phenyl)acetate

Ethyl (4-hydroxy-3-methoxyphenyl)acetate (12.0 g, 57 mmol) was dissolved in anhydrous dichloromethane (200 mL). 4-Dimethylaminopyridine (0.70 g, 0.10 equiv) was added, followed by triethylamine (9.6 mL, 69 mmol). The solution was then cooled to in a dry ice and acetone bath while under nitrogen. Trifluoromethanesulfonic anhydride (9.6 mL, 57 mmol) was slowly added and the reaction mixture was allowed to warm to ambient temperature. The reaction mixture was then diluted with dichloromethane (200 mL) and washed with water (2×100 mL). The organic layer was dried over magnesium sulfate, filtered, and concentrated to dryness under reduced pressure to provide ethyl (3-methoxy-4-{[(trifluoromethyl)sulfonyl]oxy}phenyl)acetate which was used directly in the next step without further purification. LC/MS [(M+1)– $CO_2Et]^+$=269.0.

Step B: Ethyl (4-Cyano-3-methoxyphenyl)acetate

The ethyl (3-methoxy-4-{[(trifluoromethyl)sulfonyl]oxy}phenyl)acetate (17 g) produced in the previous step was dissolved in anhydrous dimethylformamide (100 mL). Zinc cyanide (3.4 g, 29 mmol) was added, and the solution was purged thoroughly with nitrogen.

Tetrakis(triphenylphosphine)palladium(0) (5.6 g, 4.9 mmol) was then added and the reaction mixture was heated to 80° C. for 4 h. After allowing the mixture to cool to ambient temperature and diluting with water (200 mL), ethyl acetate (400 mL) was added. The combined layers were filtered to remove any solids, the filtrate transferred to a separatory funnel, and the layers separated. The aqueous layer was re-extracted with ethyl acetate (2×100 mL), the organic portions were combined and dried over magnesium sulfate. The dry organics were then filtered and evaporated to dryness under reduced pressure and excess dimethylformamide was removed by evaporation in vacuo at 65° C. for 1.5 h. The resulting residue was purified through silica gel chromatography (ethyl acetate/hexanes, 2:3) to provide ethyl (4-cyano-3-methoxyphenyl)acetate. NMR (500 MHz, DMSO-$d_6$), δ 7.67 (d, J=8.0 Hz, 1H), 7.18 (s, 1H), 7.0 (d, J=8.0 Hz, 1H), 4.10 (q, J=7.1 Hz, 2H), 3.89 (s, 3H), 3.78 (s, 2H), 1.19 (t, J=7.1 Hz, 3H); LC/MS $(M+1)^+$=220.17;

Step C: (4-Cyano-3-methoxyphenyl)acetic Acid

Aqueous LiOH (0.096 g, 2.9 mmol, in 2 mL of water) was added to a stirred solution of ethyl (4-cyano-3-methoxyphenyl)acetate (0.50 g, 2.9 mmol) in THF:$CH_3OH$ 5:1 (23 mL), and the solution was stirred at room temperature overnight. After acidification to pH 3 with 1 N HCl, the aqueous was extracted with AcOEt (2×50 mL). The organic phase was washed with brine, dried ($MgSO_4$), and evaporated under reduced pressure to give the (4-cyano-3-methoxyphenyl) acetic acid, which was used directly in the next step without further purification.

NMR (500 MHz, DMSO-$d_6$), δ 12.52 (s, 1H), 7.65 (d, J=8.0 Hz, 1H), 7.17 (s, 1H), 7.0 (d, J=7.8.0 Hz, 1H), 3.89 (s, 3H), 3.69 (s, 2H); LC/MS $(M+1)^+$=192.16.

Intermediate 26

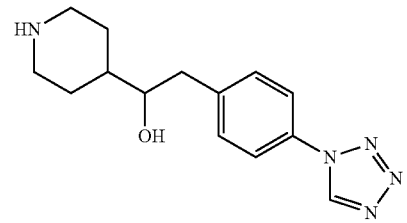 [SMILES: OC(Cc1ccc(-n2cnnn2)cc1)C1CCNCC1]

1-(Piperidin-4-yl)-2-[4-(1H-tetrazol-1-yl)phenyl]ethanol

Step A: tert-Butyl 4-[2-(4-Bromophenyl)-1-hydroxyethyl]piperidine-1-carboxylate Magnesium turnings were suspended in 20 mL of diethyl ether, to which a solution of 1-bromo-4-(bromomethyl) benzene (10 g, 40 mmol) in 80 mL of diethyl ether was added dropwise at 0~10° C. After addition was completed, the reaction was heated at reflux for 30 min. tert-butyl 4-[methoxy(methyl)carbamoyl]piperidine-1-carboxylate (11 g, 40 mmol) was dissolved in 40 mL of THF, and added to the reaction mixture, maintaining the temperature below 10° C. After addition was completed, the mixture was stirred for 2 hours. The reaction was quenched with saturated $NH_4Cl$ solution and the resulting aqueous was with EtOAc (2×). The combined organic layers were washed with brine (100 mL), dried over $Na_2SO_4$, and concentrated in vacuo. The resulting residue was purified by MPLC to provide tert-butyl 4-[2-(4-bromophenyl)-1-hydroxyethyl]piperidine-1-carboxylate. LC-MS (IE, m/z): 283, 384 $[M+1]^+$.

Step B: tert-Butyl 4-{[4-(Acetylamino)phenyl]acetyl}piperidine-1-carboxylate tert-Butyl 4-[2-(4-bromophenyl)-1-hydroxyethyl]piperidine-1-carboxylate (100 mg, 0.26 mmol), ammonium acetate (18 mg, 0.31 mmol), palladium(II)acetate (6.9 mg, 0.030 mmol), Xantphos (26 mg, 0.045 mmol), and cesium carbonate (130 mg, 0.39 mmol) were mixed with 2 mL of 1,4-dioxane and the mixture was degassed with argon three times. The reaction mixture was heated at reflux for 6 hours. The mixture was then diluted with EtOAc, washed with water, then brine, dried over $Na_2SO_4$, filtered and concentrated. The resulting residue was purified by prep-TLC to provide tert-butyl 4-{[4-(acetylamino)phenyl]acetyl}piperidine-1-carboxylate.
LC-MS (IE, m/z): 361 $[M+1]^+$.

Step C: tert-Butyl 4-{2-[4-(Acetylamino)phenyl]-1-hydroxyethyl}piperidine-1-carboxylate tert-Butyl 4-{[4-(acetylamino)phenyl]acetyl}piperidine-1-carboxylate (50 mg, 0.14 mmol) was dissolved in MeOH (5 mL), to which sodium borohydride (5.2 mg, 0.14 mmol) was added in one portion. After 30 min, the mixture was diluted with EtOAc, washed with water and brine, then dried over $Na_2SO_4$, filtered and concentrated to provide tert-butyl 4-{2-[4-(acetylamino)phenyl]-1-hydroxyethyl}piperidine-1-carboxylate which was used directly in the next step without further purification. LC-MS (IE, m/z): 363 $[M+1]^+$.

Step D: tert-Butyl 4-[2-(4-Aminophenyl)-1-hydroxyethyl]piperidine-1-carboxylate tert-Butyl 4-{2-[4-(acetylamino)phenyl]-1-hydroxyethyl}piperidine-1-carboxylate (30 mg, 0.080 mmol), potassium hydroxide (45 mg, 0.80 mmol), ethanol (0.5 mL), and H$_2$O (0.8 mL) were mixed and heated at reflux for 24 hours. The reaction mixture was extracted with EtOAc. The organic layer was washed with water and brine, dried over Na$_2$SO$_4$, filtered and concentrated in vacuo to provide tert-butyl 4-[2-(4-aminophenyl)-1-hydroxyethyl]piperidine-1-carboxylate. LC-MS (IE, m/z): 321 [M+1]$^+$.

Step E: tert-Butyl 4-{1-Hydroxy-2-[4-(1H-tetrazol-1-yl)phenyl]ethyl}piperidine-1-carboxylate To a solution of tert-butyl 4-[2-(4-aminophenyl)-1-hydroxyethyl]piperidine-1-carboxylate (50 mg, 0.16 mmol) in ethanol (1.0 mL) was added triethylorthoformate (140 mg, 0.96 mmol) followed by sodium azide (11 mg, 0.17 mmol) and the mixture was heated to 60~70° C. After 1.5 hours, the solution was diluted with water, and extracted with EtOAc. The organic layer was washed with brine, dried over Na$_2$SO$_4$, filtered and concentrated. The resulting residue was purified by prep-TLC to provide tert-butyl 4-{1-hydroxy-2-[4-(1H-tetrazol-1-yl)phenyl]ethyl}piperidine-1-carboxylate. LC-MS (IE, m/z): 374 [M+1]$^+$.

Step F: 1-(Piperidin-4-yl)-2-[4-(1H-tetrazol-1-yl)phenyl]ethanol tert-Butyl 4-{1-hydroxy-2-[4-(1H-tetrazol-1-yl)phenyl]ethyl}piperidine-1-carboxylate (180 mg, 0.48 mmol) was dissolved in 10 mL of HCl/EtOAc (3M), and the mixture was stirred for 30 min. The mixture was concentrated in vacuo and the residue was dissolved in water (10 mL) and 10 mL of NaHCO$_3$ (sat.), and extracted with 30 mL of CH$_2$Cl$_2$/i-PrOH (v/v, 3:1). After dried over Na$_2$SO$_4$, the solution was concentrated in vacuo to provide 1-(piperidin-4-yl)-2-[4-(1H-tetrazol-1-yl)phenyl]ethanol.
$^1$H-NMR (DMSO-d6, 400 Hz) δ: 10.04 (s, 1H), 7.78 (d, J=6.6 Hz, 2H), 7.48 (d, J=6.6 Hz, 2H), 3.47~3.50 (m, 1H), 3.23~3.28 (m, 3H) 2.76~2.83 (m, 3H), 2.61~2.66 (m, 1H), 1.88~1.90 (m, 3H), 1.69~1.72 (m, 1H), 1.53~1.69 (m, 4H).

Intermediate 27

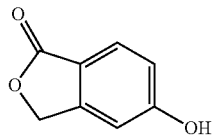 [SMILES: O=C1OCc2cc(O)ccc21]

5-Hydroxy-2-benzofuran-1-(3H)-one

Step A: tert-Butyl 4-tert-Butoxy-2-methylbenzoate

A suspension of 4-hydroxy-2-methylbenzoic acid (5.0 g, 33 mmol) in dioxane (50 mL) in a 500 ml, pressure bottle was cooled until the dioxane started to freeze, then sulfuric acid (conc., 1 mL) was added, followed by liquid isobutylene (100 mL, condensed in a graduated cylinder cooled in a dry ice bath). The pressure bottle was sealed and the reaction was warmed to room temperature. After 2 hours, all the acid was in solution and the mixture was stirred for 2.5 days. It was then recooled in a dry ice bath and slowly quenched into a large, stirred flask containing excess aq. sodium bicarbonate solution and diethyl ether and the mixture was stirred for 30 minutes. The ether layer was separated and washed with another portion of aq. sodium bicarbonate solution. The aqueous layers were back extracted with a second portion of ether and the ether layers were washed with brine, dried over sodium sulfate and evaporated in vacuo. The residue was purified by flash chromatography (5 to 25% ethyl acetate in hexanes) to afford tert-butyl 4-tert-butoxy-2-methylbenzoate as the higher Rf band.

Higher: $^1$H-NMR (400 MHz, CDCl$_3$) δ ppm 7.79 (d, J=8.3 Hz, 1H), 6.82 (dd, J=2.5, 8.3 Hz, 1H), 6.81 (br s, 1H), 2.54 (s, 3H), 1.58 (s, 9H), 1.38 (s, 9H).

Lower: $^1$H-NMR (400 MHz, CDCl$_3$) δ ppm 7.80 (d, J=9.2 Hz, 1H), 6.66 (m, 2H), 5.46 (br s, 1H), 2.54 (s, 3H), 1.58 (s, 9H).

Step B: tert-Butyl 2-Bromomethyl 4-tert-butoxybenzoate tert-Butyl 4-tert-butoxy-2-methylbenzoate (2.5 g, 9.5 mmol) from Step A was taken up in carbon tetrachloride (50 mL) under nitrogen and 2,5-dibromo-3,3-dimethylhydantoin (1.5 g, 5.2 mmol) was added and the reaction was heated in a 90° C. oil bath with addition of a few crystals of dibenzoyl peroxide 3 times. After about 30 min, the reaction was cooled and filtered to remove the hydantoin by-product. The mother liquor was evaporated in vacuo and the resulting tert-butyl 2-bromomethyl 4-tert-butoxybenzoate was used directly in the next step.

LC/MS (M+1-56)$^+$=287/289, (M+1-56-56)$^+$=231/233.

Step C: 5-tert-Butoxy-2-benzofuran-1-(3H)-one and tert-Butyl 2-Hydroxymethyl 4-tert-butoxybenzoate tert-Butyl 2-bromomethyl 4-tert-butoxybenzoate (~4.0 g, assumed 9.5 mmol) was taken up in 1,4-dioxane (125 mL) and silver nitrate (2.5 g, 15 mmol) dissolved in water (25 mL) was added and the mixture was stirred at rt for three days. The reaction was diluted with water and extracted twice with diethyl ether. The ether layers were washed with brine, dried over sodium sulfate and evaporated in vacuo. The residue was purified by careful flash chromatography (1→10% ethyl acetate in hexanes) to elute starting material and then aldehyde by-product (from some di-bromide). Further elution with 10→15% provided tert-butyl 2-hydroxymethyl 4-tert-butoxybenzoate and then with 20→30% afforded 5-tert-butoxy-2-benzofuran-1-(3H)-one.

Higher hydroxymethyl: $^1$H-NMR (400 MHz, CDCl$_3$) δ ppm 7.79 (d, J=8.6 Hz, 1H), 7.00 (d, J=2.5 Hz, 1H), 6.93 (dd, J=2.4, 8.6 Hz, 1H), 4.69 (d, J=7.3 Hz, 2H), 4.14 (t, J=7.4 Hz, 1H), 1.59 (s, 9H), 1.40 (s, 9H).

Lower lactone: $^1$H-NMR (400 MHz, CDCl$_3$) δ ppm 7.80 (d, J=8.4 Hz, 1H), 7.10 (dd, J=1.9, 8.5 Hz, 1H), 7.03 (d, J=1.1 Hz, 1H), 5.25 (s, 2H), 1.44 (s, 9H).

Step D: 5-Hydroxy-2-benzofuran-1-(3H)-one

To a solution of 5-t-butoxy-2-benzofuran-1-(3H)-one (600 mg, 2.9 mmol) in ether (20 mL) was added 2M hydrogen chloride in ether (10 mL, 20 mmol). The mixture was aged for 5 days to afford pure title 5-hydroxy lactone intermediate (390 mg) in 3 crops as a white solid. Alternatively, the hydroxymethyl product from Step C could be treated similarly with 2M hydrogen chloride in ether to provide 5-hydroxy-2-benzofuran-1-(3H)-one.

$^1$H-NMR (400 MHz, CDCl$_3$) δ ppm 7.66 (d, J=8.2 Hz, 1H), 6.95 (dd, J=2.0, 8.2 Hz, 1H), 6.94 (s, 1H), 5.19 (s, 2H).

Intermediate 28

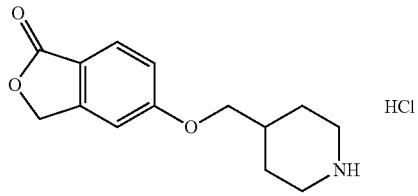 [SMILES: O=C1OCc2cc(OCC3CCNCC3)ccc21 ; Cl]

4-{[(1-Oxo-1,3-dihydro-2-benzofuran-5-yl)oxy]methyl}piperidinium Chloride

Step A: tert-Butyl 4-{[(methylsulfonyl)oxy]methyl}piperidine-1-carboxylate

To a solution of tert-butyl 4-hydroxymethylpiperidine-1-carboxylate (1.0 g, 4.7 mmol) in DCM (20 mL) was added DIPEA (2.5 mL, 14 mmol) and methanesulfonyl chloride (0.45 mL, 5.8 mmol). The reaction was stirred at rt for 3 hours, then was diluted with water and extracted twice with DCM. The combined organic layers were washed with brine, dried over sodium sulfate and evaporated in vacuo. The residue was purified by flash chromatography (20→40% ethyl acetate in hexanes) to provide tert-butyl 4-{[(methylsulfonyl)oxy]methyl}piperidine-1-carboxylate. LC/MS (M+1-56)$^+$=238.

Step B: tert-Butyl 4-{[(1-Oxo-1,3-dihydro-2-benzofuran-5-yl)oxy]methyl}piperidine-1-carboxylate To a solution of 5-hydroxy-2-benzofuran-1-(3H)-one (100 mg, 0.67 mmol) and tert-butyl 4-{[(methylsulfonyl)oxy]methyl}piperidine-1-carboxylate (200 mg, 0.67 mmol) from Step A in DMF (2 mL) was added sodium hydride (60% in mineral oil, 27 mg, 0.67 mmol) and sodium iodide (20 mg, 0.13 mmol). The reaction was stirred at rt for 16 hours, then heated at 55° C. for 3 days. The mixture was diluted with water, acidified with citric acid and extracted three times with ethyl acetate. The organic layers were washed with brine, dried over sodium sulfate and evaporated. The residue was taken up in 1:1 DCM:methanol and treated with excess trimethylsilyl diazomethane and re-evaporated. The residue was separated by flash chromatography (60% ethyl acetate in hexanes) to provide a mixture of mesyl starting material, methyl ester and tert-Butyl 4-{[(1-oxo-1,3-dihydro-2-benzofuran-5-yl)oxy]methyl}piperidine-1-carboxylate.

Alternatively, the reaction can be done on the same scale using sodium hexamethyldisilazide (1M) as base at 55-65° C. for 9 hours to afford a better mix of acid/methyl ester and lactone products after FC.

The combined mixtures were used directly in the next step.

Methyl ester: LC/MS (M+1-100)$^+$=280, (M+1-56)$^+$=324, (M+1-56-18)$^+$=306 (100%).

Lactone: LC/MS (M+1-100)$^+$=248, (M+1-56)$^+$=292, (M+1-197)$^+$=151 (phenol, 100%), Step C: 4-{[(1-Oxo-1,3-dihydro-2-benzofuran-5-yl)oxy]methyl}piperidinium Chloride The combined product fractions from Step B (~1.3 mmol) were taken up in 2M hydrogen chloride in ether (5 mL). The mixture was aged for 16 hours at which time there was a precipitate (75 mg) which was centrifuged, washed with diethyl ether and dried to provide 4-{[(1-oxo-1,3-dihydro-2-benzofuran-5-yl)oxy]methyl}piperidinium chloride which was used directly in the next step without further purification. LC/MS (M+1)$^+$=248.

Intermediate 29

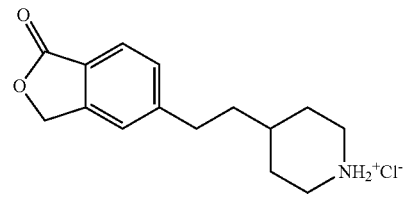

4-[2-(1-Oxo-1,3-dihydro-2-benzofuran-5-yl)ethyl]piperidinium Chloride tert-Butyl 4-[2-(1-Oxo-1,3-dihydro-2-benzofuran-5-yl)ethyl]piperidine-1-carboxylate was prepared in a similar fashion to the previously described synthesis of INTERMEDIATE 8, steps C and D, starting from tert-butyl 4-[(E)-2-(1-oxo-1,3-dihydro-2-benzofuran-5-yl)ethenyl]piperidine-1-carboxylate. LC/MS (M+1)$^+$=246.

Intermediate 30

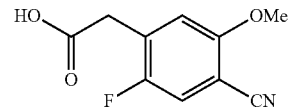 [SMILES: COc1cc(CC(=O)O)c(F)cc1C#N]

(4-Cyano-2-fluoro-5-methoxyphenyl)acetic Acid

Step A: di-tert-Butyl (4-cyano-2-fluoro-5-methoxyphenyl)propanedioate

A suspension of NaH (60% in mineral oil, 0.33 g, 8.3 mmol) in dry DMF (20 mL) was stirred and cooled to 0° C., and di-tert-butyl malonate (1.5 g, 7.1 mmol) was added. The mixture was allowed to warm to room temperature before addition of 4,5-difluoro-2-methoxybenzonitrile (1.0 g, 5.9 mmol). The mixture was heated at 80° C. for 4 h with stirring, then the reaction mixture was cooled to room temperature and poured into a mixture of ice-water (100 mL) and AcOEt (100 mL). The layers were separated, and the organic layer was washed successively with water, and brine, then dried over Na$_2$SO$_4$ and concentrated. The residue was purified by flash chromatography (silica gel, EtOAc/hexanes, 0→10%) to give the di-tert-butyl (4-cyano-5-fluoro-2-methoxyphenyl)propanedioate. LCMS: [(M+1)-t-Bu, CO2-t-Bu]$^+$=210.

Step B: (4-cyano-2-fluoro-5-methoxyphenyl)acetic acid

Trifluoroacetic acid (5 mL) was added to a solution of di-tert-butyl (4-cyano-5-fluoro-2-methoxyphenyl) propanedioate (1.3 g, 28.3 mmol) in of dichloromethane (5 mL) at room temperature. The reaction mixture was stirred over night, then concentrated under reduced pressure, and the residue was treated with Et$_2$O (10 mL) to induce crystallization. The crystals were collected by filtration to give 4-cyano-2,5-difluorophenyl)acetic acid.

$^1$H NMR (500 MHz, CD$_3$OD) δ 7.44 (d, J=5.3 Hz, 1H), 7.19 (d, J=5.4 Hz, 1H), 3.96 (s, 3H), 3.78 (s, 2H); LC/MS: [(M+1)]$^+$=210.

Intermediate 31

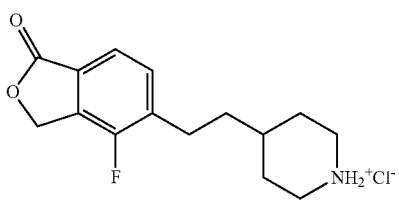

4-[2-(4-Fluoro-1-oxo-1,3-dihydro-2-benzofuran-5-yl)ethyl]piperidinium Chloride

Step A: 5-Bromo-4-fluoro-2-benzofuran-1(3H)-one

A mixture of (3-bromo-2-fluorophenyl)methanol (1.4 g, 6.8 mmol), thallium(II)trifluoroacetate (4.4 g, 8.2 mmol) and trifluoroacetic acid (40 mL) was stirred at room temperature for 12 h. The solution was concentrated to dryness under reduced pressure and azeotroped with dichloroethane (2×). The reaction mixture was then treated with palladium(II) chloride (0.10 g, 0.68 mmol), lithium chloride (0.50 g, 14 mmol), magnesium oxide (0.50 g, 14 mmol) and methanol (40 mL); the reaction mixture was then degassed and purged with CO several times and stirred under CO for 3 h. To the flask was then added a 1:1 mixture of DCM and EtOAc (200 mL) and the mixture passed through a pad of diatomaceous earth; the solution was adsorbed into silica gel and purified by MPLC (hexanes/EtOAc 1/1) to provide 5-bromo-4-fluoro-2-benzofuran-1(3H)-one. LC/MS: [(M+2)]$^+$=233.

Step B: tert-Butyl 4-[(E)-2-(4-Fluoro-1-oxo-1,3-dihydro-2-benzofuran-5-yl)ethenyl]piperidine-1-carboxylate To a flask added 5-bromo-4-fluoro-2-benzofuran-1(3H)-one (0.10 g, 0.43 mmol) palladium(II)acetate (0.097 g, 0.043 mmol), triethylamine (0.12 mL, 0.88 mmol) and tert-butyl 4-ethenylpiperidine-1-carboxylate (0.27 g, 1.2 mmol); the resulting mixture was then dissolved in DMF (15 mL) and heated in an oil bath at 130° C. for 2 h. The flask was cooled to room temperature, diluted with EtOAc and washed with saturated sodium bicarbonate and water, then dried (Na$_2$SO$_4$), filtered and adsorbed into silica gel. MPLC (hexanes/EtOAc=1/1) purification provided tert-butyl 4-[(E)-2-(4-fluoro-1-oxo-1,3-dihydro-2-benzofuran-5-yl) ethenyl]piperidine-1-carboxylate. LC/MS: [(M+2)]$^+$=233.

Step C: tert-Butyl 4-[2-(4-Fluoro-1-oxo-1,3-dihydro-2-benzofuran-5-yl)ethyl]piperidine-1-carboxylate tert-Butyl 4-[(E)-2-(4-fluoro-1-oxo-1,3-dihydro-2-benzofuran-5-yl)ethenyl]piperidine-1-carboxylate (0.050 g, 0.13 mmol) was added to a flask containing a stir bar followed by palladium on carbon (0.010 g, 0.090 mmol); the mixture was dissolved in ethanol (10 mL) and few drops of AcOH; the flask was degassed and purged with H$_2$ and stirred under H$_2$ for 12 h. The reaction mixture was filtered through a pad of diatomaceous earth and concentrated to dryness under reduced pressure to provide tert-butyl 4-[2-(4-fluoro-1-oxo-1,3-dihydro-2-benzofuran-5-yl)ethyl]piperidine-1-carboxylate. LC/MS: [(M+2)]$^+$=364.

Step D: 4-[2-(4-Fluoro-1-oxo-1,3-dihydro-2-benzofuran-5-yl)ethyl]piperidinium Chloride tert-Butyl 4-[2-(4-fluoro-1-oxo-1,3-dihydro-2-benzofuran-5-yl]piperidine-1-carboxylate (0.030 g, 0.090 mmol) in trifluoroacetic acid (4 mL) was added to a flask and stirred for 20 min. at room temperature. The solution was concentrated to dryness under reduced pressure to provide a residue which was azeotropped with dichloroethane (2×) to afford 4-[2-(4-fluoro-1-oxo-1,3-dihydro-2-benzofuran-5-yl)ethyl] piperidinium chloride which was used directly in the next step without further purification. LC/MS: [(M+1)]$^+$=264.

Intermediate 32

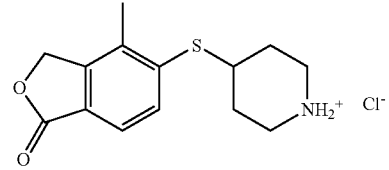 [SMILES: Cc1c(SC2CC[NH2+]CC2)ccc2c1COC2=O ; [Cl-]]

4-[(4-Methyl-1-oxo-1,3-dihydro-2-benzofuran-5-yl) sulfanyl]piperidinium Chloride 4-[(4-Methyl-1-oxo-1,3-dihydro-2-benzofuran-5-yl)sulfanyl]piperidinium chloride was prepared in a similar fashion to that previously described for the synthesis of INTERMEDIATE 24 starting from tert-butyl 4-sulfanylpiperidine-1-carboxylate and 5-bromo-4-methyl-2-benzofuran-1(3H)-one.

Intermediate 33

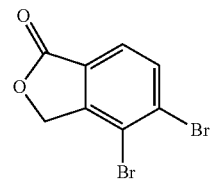 [SMILES: O=C1OCc2c1ccc(Br)c2Br]

4,5-Dibromo-2-benzofuran-1(3H)-one

To a mixture of 5-bromo-2-benzofuran-1(3H)-one (2.0 g, 9.4 mmol) and NBS (2.2 g, 12 mmol) was added trifluoromethanesulfonic acid (10 ml) and the mixture was heated to 60° C. for 16 hours. TLC showed two new spots, along with some unreacted SM. MPLC purification provided 4,5-dibromo-2-benzofuran-1(3H)-one. LC-MS (IE, m/z): 292 [M+1]⁺.

Intermediate 34

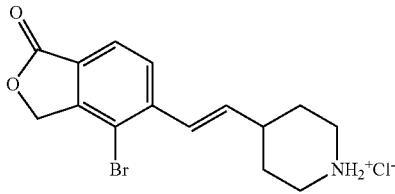

4-[(E)-2-(4-bromo-1-oxo-1,3-dihydro-2-benzofuran-5-yl)ethenyl]piperidinium Chloride 4-[(E)-2-(4-bromo-1-oxo-1,3-dihydro-2-benzofuran-5-yl)ethenyl]piperidinium chloride was prepared in a similar fashion to that previously described for the synthesis of INTERMEDIATE 3 starting from tert-butyl 4-ethenylpiperidine-1-carboxylate and 4,5-dibromo-2-benzofuran-1(3H)-one. LC-MS (IE, m/z): 322 [M+1]⁺.

Intermediates 35 and 36

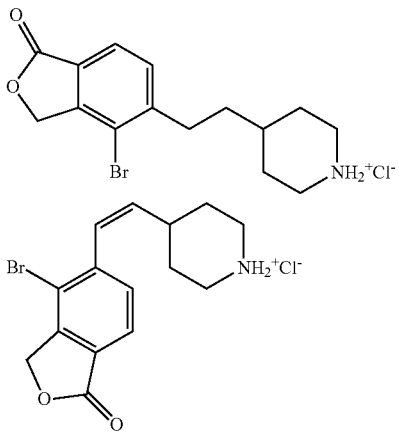

4-[2-(4-Bromo-1-oxo-1,3-dihydro-2-benzofuran-5-yl)ethyl]piperidinium Chloride and 4-[(Z)-2-(4-bromo-1-oxo-1,3-dihydro-2-benzofuran-5-yl)ethenyl]piperidinium Chloride A solution of tert-butyl 4-[(E)-2-(4-bromo-1-oxo-1,3-dihydro-2-benzofuran-5-yl)ethenyl]piperidine-1-carboxylate was treated with Wilkinson's catalyst (21 mg, 0.024 mmol) under an atmosphere of hydrogen and the reaction was run for 48 hours. LC showed some reduction, but SM remained, and also a new peak with the same molecule weight of the SM emerged, which was identified as the Z-olefin adduct generated under the reaction conditions. The reaction was stopped at that point, and purified by MPLC to afford tert-Butyl 4-[2-(4-bromo-1-oxo-1,3-dihydro-2-benzofuran-5-yl)ethyl]piperidine-1-carboxylate (LC-MS (IE, m/z): 424 [M+1]⁺) and tert-butyl 4-[(Z)-2-(4-bromo-1-oxo-1,3-dihydro-2-benzofuran-5-yl)ethenyl]piperidine-1-carboxylate (LC-MS (IE, m/z): 422 [M+1]⁺) as a co-eluting mixture. The products collected were further treated with 4N HCl to remove the Boc group and carried on to the next step without further purification.

Intermediate 37

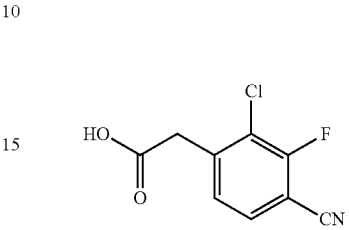

(2-Chloro-4-cyano-3-fluorophenyl)acetic Acid

Step A: Di-tert-butyl (2-chloro-4-cyano-3-fluorophenyl)propanedioate

A dry flask was charged with sodium hydride (60% suspension in mineral oil, 3.8 g, 94 mmol) and 150 ml of dry DMF, and cooled to 0° C. followed by dropwise addition of di-tert-butyl malonate via syringe. After 30 min at 0° C., a solution of 3-chloro-2,4-difluorobenzonitrile in DMF (10 ml) was added over a period of 15 minutes. The ice bath was removed and the reaction mixture was subjected to heating at 80° C. in an oil bath for 12 hrs. The mixture was cooled to RT, quenched with saturated ammonium chloride, and partitioned between water and ethyl acetate. The organic layer was concentrated and the resulting residue purified by flash chromatography (eluted with 2→10% hexanes/ethyl acetate) to provide di-tert-butyl (2-chloro-4-cyano-3-fluorophenyl)propanedioate. ¹H-NMR (400 MHz, CDCl₃) δ ppm 7.68 (m, 1H), 7.53 (m, 1H), 5.06 (s, 1H), 1.52 (s, 18H). LC-MS (IE, m/z): 370 [M+1]⁺.

Step B: (2-Chloro-4-cyano-3-fluorophenyl)acetic Acid

To di-tert-butyl (2-chloro-4-cyano-3-fluorophenyl)propanedioate in DCM 50 ml was added trifluoroacetic acid (25 ml) and the mixture was allowed to stir at room temperature for 3 hours. The reaction mixture was evaporated to dryness under reduced pressure, and high vacuum pump then azeotroped with toluene (2×) to provide (2-chloro-4-cyano-3-fluorophenyl)acetic acid which was used directly in the next step without further purification. ¹H-NMR (400 MHz, DMSO-d₆) δ ppm 8.18 (m, 1H), 7.82 (m, 1H), 3.82 (s, 2H). LC-MS (IE, m/z): 214 [M+1]⁺.

Intermediate 38

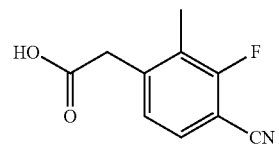

(4-Cyano-3-fluoro-2-methylphenyl)acetic Acid (4-Cyano-3-fluoro-2-methylphenyl)acetic acid was prepared in a similar fashion to the previously described synthesis of INTERMEDIATE 37 starting from di-tert-butyl malonate and 2,4-difluoro-3-methylbenzonitrile.

$^1$H-NMR (400 MHz, CD$_3$OD) δ ppm 7.62 (m, 1H), 7.43 (m, 1H), 2.32 (s, 2H).

Intermediate 39

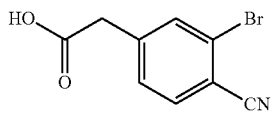 [SMILES: N#Cc1ccc(CC(=O)O)cc1Br]

(3-Bromo-4-cyanophenyl)acetic Acid (3-Bromo-4-cyanophenyl)acetic acid was prepared in a similar fashion to the previously described synthesis of INTERMEDIATE 37 starting from di-tert-butyl malonate and 3-bromo-4-fluorobenzonitrile. LC-MS (IE, m/z): 240 [M+1]$^+$.

Intermediate 40

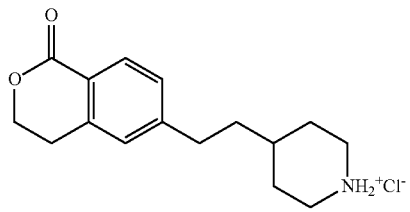

4-[2-(1-oxo-3,4-dihydro-1H-isochromen-6-yl)ethyl]piperidinium chloride

4-[2-(1-oxo-3,4-dihydro-1H-isochromen-6-yl)ethyl]piperidinium chloride was prepared in a similar fashion to the previously described synthesis of INTERMEDIATE 31, steps B, C and D, starting from tert-butyl 4-ethyenylpiperidine-1-carboxylate and 6-bromo-3,4-dihydro-1H-isochromen-1-one. LC-MS (IE, m/z): 260 [M+1]$^+$.

Intermediate 41

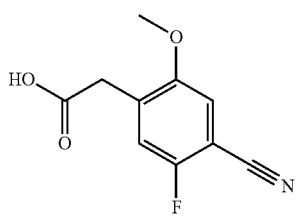

(4-Cyano-5-fluoro-2-methoxyphenyl)acetic Acid (4-Cyano-5-fluoro-2-methoxyphenyl)acetic acid was prepared in a similar fashion to the previously described synthesis of INTERMEDIATE 37 starting from di-tert-butyl malonate and 2,4-difluoro-5-methoxybenzonitrile. LC-MS (IE, m/z): 208 [M−1]$^+$.

Intermediate 42

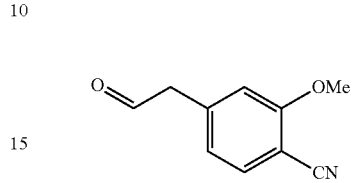

2-Methoxy-4-(2-oxoethyl)benzonitrile

Step A: 2-(Methyoxy)-4-prop-2-en-1-ylbenzonitrile

To a 50 mL flask containing a stir bar were added 2-methoxy-4-bromobenzonitrile (0.30 g, 1.4 mmol), palladium tetrakis (82 mg, 0.071 mmol), allyltri-n-butyltin (0.88 mL, 2.8 mmol), and lithium chloride (0.12 g, 2.8 mmol). The resulting mixture was then dissolved in anhydrous toluene (16 mL); the flask was placed in an oil bath and heated at 130° C. LC as well as TLC (hexanes/EtOAc=1/0.3) indicated that reaction had gone to completion. The flask was taken out of the oil bath and cooled to room temperature. To the flask was added EtOAc (40 mL) and the mixture was transferred into a separatory funnel and washed with brine. The organic phase was dried over Na$_2$SO$_4$, filtered and concentrated to dryness. It was then dissolved in DCM and absorbed into silica gel. The silica gel was then loaded onto a silica column for separation with the solvent systems of hexanes/EtOAc (1/0.3) to provide 2-(methyloxy)-4-prop-2-en-1-ylbenzonitrile. LC-MS (IE, m/z): 174 [M+1]$^+$.

Step B: 2-Methoxy-4-(2-oxoethyl)benzonitrile

To a 25 mL flask containing a stir bar was added 2-(methyoxy)-4-prop-2-en-1-ylbenzonitrile (0.15 g, 0.87 mmol) and MeOH (8 mL). The flask was placed in a cold bath of −78° C. Ozone was bubbled through the flask for about 10 min. followed by addition of dimethyl sulfide (1.5 mL, 24 mmol). The flask was taken out of the cold bath and stirred at room temperature for 1 h; LC indicated completion of the reaction. The reaction mixture was concentrated to dryness to provide 2-methoxy-4-(2-oxoethyl)benzonitrile which was used directly in the next step without further purification. LC-MS (IE, m/z): 176 [M+1]$^+$.

Intermediate 43

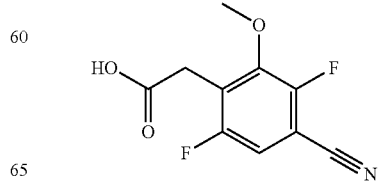

(4-Cyano-3,6-difluoro-2-methoxyphenyl)acetic Acid (4-Cyano-3,6-difluoro-2-methoxyphenyl)acetic acid was prepared in a similar fashion to the previously described synthesis of INTERMEDIATE 37 starting from di-tert-butyl malonate and 2,4,5-trifluoro-3-methoxybenzonitrile. LC-MS (IE, m/z): 228 [M−1]⁺.

Intermediate 44

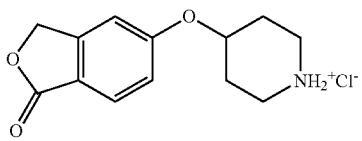

4-[(1-Oxo-1,3-dihydro-2-benzofuran-5-yl)oxy]piperidinium Chloride

Step A: 5-(4,4,5,5-tetramethyl-1,3,2-dioxaborolan-2-yl)-2-benzofuran-1(3H)-one To a microwave tube containing a stir bar was added 5-bromo-2-benzofuran-1(3H)-one (0.10 g, 0.47 mmol), Bis(pinacolato)diboron (0.12 g, 0.47 mmol), bis(diphenylphosphino)palladium(II) (0.010 g, 0.014 mmol), potassium acetate (0.14 g, 1.4 mmol) and anhydrous toluene (10 mL). The resulting mixture was capped and heated at 80° C. for 2 h. The reaction mixture was diluted with benzene and washed successively with water and brine. The organic layer was then dried (Na₂SO₄), filtered, and concentrated. The resulting residue was purified by silica gel column chromatography (hexanes/EtOAc=1/1) to provide 5-(4,4,5,5-tetramethyl-1,3,2-dioxaborolan-2-yl)-2-benzofuran-1(3H)-one. LC/MS: [(M+1)]⁺=261.

Step B: (1-Oxo-1,3-dihydro-2-benzofuran-5-yl)boronic acid

To a flask containing a stir bar were added 5-(4,4,5,5-tetramethyl-1,3,2-dioxaborolan-2-yl)-2-benzofuran-1(3H)-one (0.20 g, 0.77 mmol) and sodium periodate (0.16 g, 0.77 mmol) followed by addition of a 4:1 mixture of THF (4 mL) and Water (1 mL); the resulting mixture was stirred for 30 min. To the reaction mixture was then added 1N hydrochloric acid (0.20 mL) and subsequently stirred overnight at room temperature indicated completion of the reaction. The reaction mixture was diluted with water and the layers were separated. The aqueous layer was extracted with EtOAc(2×) and the combined organic layers were washed successively with water and brine, then dried (Na₂SO₄), filtered and concentrated to provide (1-oxo-1,3-dihydro-2-benzofuran-5-yl)boronic acid, which was used for the next step with out further purification. LC/MS: [(M+1)]⁺=178.

Step C: tert-Butyl 4-[(1-Oxo-1,3-dihydro-2-benzofuran-5-yl)oxy]piperidine-1-carboxylate A dry round bottomed flask was charged with (1-oxo-1,3-dihydro-2-benzofuran-5-yl)boronic acid (0.20 g, 1.12 mmol), copper (II) acetate (0.20 g, 1.12 mmol) tert-butyl 4-hydroxy-1-piperidinecarboxylate (0.45 g, 2.25 mmol), pyridine (0.4 mL, 4.5 mmol), DIEA (0.8 mL, 4.8 mmol) and 4 Å molecular sieves (0.5 g) and the resulting mixture was dissolved in dichloromethane (15 mL) and stirred at room temperature overnight. The reaction mixture was passed through a pad of diatomaceous earth followed by concentration to dryness; the resulting residue was dissolved in EtOAc, washed with water and brine, then dried (Na₂SO₄), filtered and concentrated. The resulting residue was purified by silica gel column chromatography (hexanes/EtOAc=1/1) to provide tert-butyl 4-[(1-Oxo-1,3-dihydro-2-benzofuran-5-yl)oxy]piperidine-1-carboxylate. LC/MS: [(M+1)]⁺=334.

Step D: 4-[(1-Oxo-1,3-dihydro-2-benzofuran-5-yl)oxy]piperidinium Chloride tert-Butyl 4-[(1-oxo-1,3-dihydro-2-benzofuran-5-yl)oxy]piperidine-1-carboxylate (0.20 g, 0.60 mmol) was stirred in trifluoroacetic acid (6.0 mL) for 30 min at room temperature. The solution was concentrated to dryness under reduced pressure to provide a residue which was azeotroped with dichloroethane (2×) to provide 4-[(1-oxo-1,3-dihydro-2-benzofuran-5-yl)oxy]piperidinium chloride. LC/MS: [(M+1)]⁺=234.

Intermediate 45

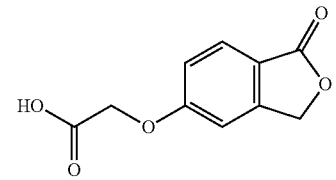 [SMILES: O=C(O)COc1ccc2c(c1)COC2=O]

[(1-Oxo-1,3-dihydro-2-benzofuran-5-yl)oxy]acetic Acid

Step A: tert-Butyl [(1-oxo-1,3-dihydro-2-benzofuran-5-yl)oxy]acetate

To a solution of 5-hydroxy-2-benzofuran-1(3H)-one (120 mg, 0.80 mmol) in DMF (5 ml) was added sodium hexamethyldisylazide (1.0 M, 0.80 ml, 0.80 mmol) at 0° C. The reaction was stirred for 15 minutes before tert-butyl bromoacetate (390 mg, 2.0 mmol) was added. After 15 minutes the reaction was quenched with saturated ammonium chloride and extracted with EtOAc.

The organic layer was washed with brine, concentrated and purified by MPLC to provide tert-butyl [(1-oxo-1,3-dihydro-2-benzofuran-5-yl)oxy]acetate. LC/MS: [(M+1)]⁺=265.

Step B: [(1-Oxo-1,3-dihydro-2-benzofuran-5-yl)oxy]acetic Acid

A solution of tert-butyl [(1-oxo-1,3-dihydro-2-benzofuran-5-yl)oxy]acetate (0.17 g, 0.64 mmol) in trifluoroacetic acid (2 mL) and DCM (2 mL) was stirred for 1 h. The solvent was removed under reduced pressure to provide [(1-oxo-1,3-dihydro-2-benzofuran-5-yl)oxy]acetic acid which was used directly in the next step without further purification.

Intermediate 46

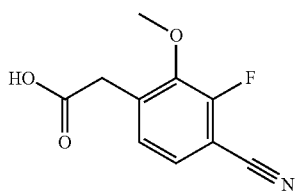

(4-Cyano-3-fluoro-2-methoxyphenyl)acetic Acid (4-Cyano-3-fluoro-2-methoxyphenyl)acetic Acid was prepared in a similar fashion to the previously described synthesis of INTERMEDIATE 37 starting from di-tert-butyl malonate and 2,4-difluoro-3-methoxybenzonitrile. LC-MS (IE, m/z): 208 [M+1]$^+$.

Intermediate 47

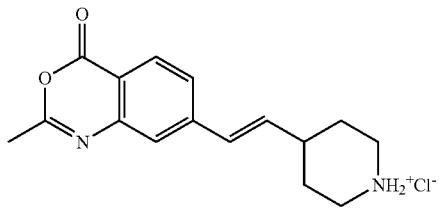

4-[(E)-2-(2-Methyl-4-oxo-4H-3,1-benzoxazin-7-yl) ethenyl]piperidinium Chloride

4-[(E)-2-(3-Methyl-1-oxo-3,4-dihydro-1H-isochromen-6-yl)ethenyl]piperidinium chloride was prepared in a similar fashion to the previously described synthesis of INTERMEDIATE 3 starting from tert-butyl 4-ethenylpiperidine-1-carboxylate and 6-bromo-3-methyl-3,4-dihydro-1H-isochromen-1-one. LC-MS (IE, m/z): 271 [M+1]$^+$.

Intermediate 48

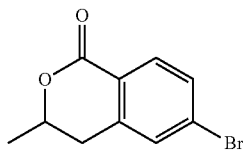

6-Bromo-3-methyl-3,4-dihydro-1H-isochromen-1-one

A solution of diisopropylamine (13 ml, 93 mmol) in THF (160 ml) at −78° C. was treated with a solution of n-butyllithium (1.6 M in Hexanes; 58 ml, 93 mmol) over a period of 15 minutes using a syringe pump.

In a separate flask, a solution of 2-methyl-4-bromo benzoic acid (10 g, 46 mmol) and hexamethylphosphoramde (8.3 ml, 46 mmol) in THF (160 ml) was cooled to −78° C. A solution of methyllithium (29 ml, 46 mmol) was added slowly via syringe to the cooled solution. The resulting mixture was stirred for 10 minutes and then transferred via cannula to the LDA solution at −78° C. The resulting bright red solution was stirred at −78° C. for an additional 1 hour before addition of anhydrous acetaldehyde (7.9 ml, 140 mmol) (color changed from red to orange to clear yellow). After complete addition, the mixture was allowed to warm to room temperature and stir for an additional 1 hour.

The flask containing the reaction mixture was then resubmerged in the dry ice acetone bath before it was quenched with 4M HCl in 1,4-dioxane (50 mL) followed by 25 mL of MeOH. The reaction was stirred at room temp for an additional 1 hour. The crude reaction was partitioned between 200 mL EtOAc and 200 mL water. The organic layer was washed with waster, brine, dried over anhydrous magnesium sulfate, filtered and concentrated. Purification of the resulting residue via MPLC (30-70% DCM/Hexanes) afforded 6-bromo-3-methyl-3,4-dihydro-1H-isochromen-1-one.
$^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). LC-MS (IE, m/z): 241 [M+1]$^+$.

Intermediate 49

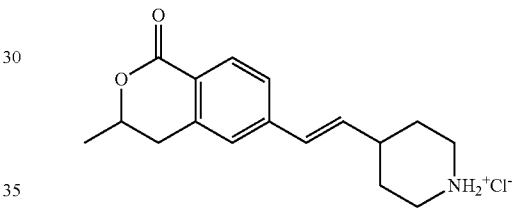

4-[(E)-2-(3-Methyl-1-oxo-3,4-dihydro-1H-isochromen-6-yl)ethenyl]piperidinium Chloride 4-[(E)-2-(3-Methyl-1-oxo-3,4-dihydro-1H-isochromen-6-yl)ethenyl]piperidinium chloride was prepared in a similar fashion to the previously described synthesis of INTERMEDIATE 3 starting from tert-butyl 4-ethenylpiperidine-1-carboxylate and 6-bromo-3-methyl-3,4-dihydro-1H-isochromen-1-one. LC-MS (IE, m/z): 272 [M+1]$^+$.

Intermediate 50

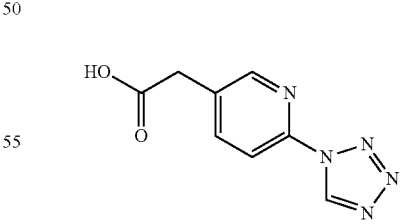

[6-(1H-Tetrazol-1-yl)pyridin-3-yl]acetic Acid

Step A: 5-Chloro-2-nitropyridine

To concentrated H$_2$SO$_4$ (50 mL) was added 30% H$_2$O$_2$ (25 mL) at 0° C. and a solution of 5-chloropyridin-2-amine (5.0 g, 39 mmol) in concentrated H$_2$SO$_4$ (20 mL) was added at 0° C. The mixture was stirred for 20 hours at room temperature. The mixture was poured into ice water under vigorous stirring and the resulting solid was filtered. The solid was recrystallized from ethanol to give 5-chloro-2-nitropyridine. ¹H-NMR (400 MHz, CDCl₃) δ 8.58 (d, J=2.8 Hz, 1H), 8.23 (d, J=8.8 Hz, 1H), 8.00 (dd, J=2.8 Hz, 8.8 Hz, 1H). LC/MS m/z 159 (M+1)⁺.

Step B: tert-Butyl Ethyl (6-Nitropyridin-3-yl)propanedioate

To a suspension of NaH (60% in oil, 0.65 g, 16 mmol) in DMF (40 mL) was added tert-butyl ethyl propanedioate (2.8 g, 15 mmol) at room temperature. The mixture was stirred for 30 min. A solution of 5-chloro-2-nitropyridine (2.0 g, 13 mmol) in DMF (10 mL) was added. The mixture was heated to 80° C. and stirred for 4 hours. The solvent was removed under reduce pressure. Water was added and the mixture was extracted with EtOAc. The combined organic layer was washed with brine, dried over anhydrous Na₂SO₄, concentrated and the residue was purified by column chromatography with silica gel to give tert-butyl ethyl (6-nitropyridin-3-yl)propanedioate. ¹H-NMR (400 MHz, CDCl₃) δ 8.58 (s, 1H), 8.20~8.27 (m, 2H), 4.69 (s, 1H), 4.21~4.26 (m, 2H), 1.45 (s, 9H), 1.28 (t, J=7.2 Hz, 2H).

Step C: Ethyl (6-Nitropyridin-3-yl)acetate

A mixture of tert-butyl ethyl (6-nitropyridin-3-yl)propanedioate (1.4 g, 4.5 mmol) in a mixed solution of TFA/DCM (10 mL/10 mL) was stirred for 5 hours at room temperature. The mixture was concentrated under reduce pressure. The residue was dissolved with DCM, washed with saturated sodium bicarbonate solution, dried over anhydrous Na₂SO₄ and concentrated to give ethyl (6-nitropyridin-3-yl)acetate. ¹H-NMR (400 MHz, CDCl₃) δ 8.57 (s, 1H), 8.27 (d, J=8.4 Hz, 1H), 8.03 (dd, J=2.4 Hz, 8.4 Hz, 1H), 4.22 (q, J=7.2 Hz, 2H), 3.81 (s, 2H), 1.30 (t, J=7.2 Hz, 3H).

Step D: Ethyl (6-Aminopyridin-3-yl)acetate

A mixture of ethyl (6-nitropyridin-3-yl)acetate (0.90 g, 4.28 mmol), Pd/C (10%, 0.1 g) in MeOH (50 mL) was stirred for 2 hours under H₂ atmosphere at room temperature. The mixture was filtered and concentrated to give ethyl (6-aminopyridin-3-yl)acetate.
¹H-NMR (400 MHz, CDCl₃) δ 7.93 (s, 1H), 7.38 (dd, J=2.4 Hz, 8.4 Hz, 1H), 6.46 (d, J=8.4 Hz, 1H), 4.48 (br, 2H), 4.13 (q, J=7.2 Hz, 2H), 3.44 (s, 2H), 1.23 (t, J=7.2 Hz, 3H).

Step E: Ethyl [6-(1H-Tetrazol-1-yl)pyridin-3-yl]acetate

To a mixture of ethyl (6-aminopyridin-3-yl)acetate (0.55 g, 3.1 mmol), CH(OEt)₃ (1.4 g, 9.2 mmol) in AcOH (20 mL) was added NaN₃ (0.24 g, 3.7 mmol) at room temperature. The mixture was heated to 80° C. and stirred for 3 hours. The mixture was concentrated under reduce pressure. Water was added, and the mixture was extracted with EtOAc. The combined organic layer was washed with brine, dried over anhydrous Na₂SO₄, concentrated and the residue was purified by column chromatography via silica gel to provide ethyl [6-(1H-tetrazol-1-yl)pyridin-3-yl]acetate. ¹H-NMR (400 MHz, CDCl₃) δ 9.52 (s, 1H), 8.44 (s, 1H), 8.06 (d, J=8.4 Hz, 1H), 7.94 (dd, J=2.4 Hz, 8.4 Hz, 1H), 4.20 (q, J=7.2 Hz, 2H), 3.72 (s, 2H), 1.27 (t, J=7.2 Hz, 3H).

Step F: [6-(1H-tetrazol-1-yl)pyridin-3-yl]acetic acid

To a mixture ethyl [6-(1H-tetrazol-1-yl)pyridin-3-yl]acetate (0.42 g, 1.8 mmol) in THF (3 mL) was added 1.4 M LiOH (aq.) (5 mL) at room temperature. The mixture was stirred 3 hours at room temperature. The reaction was acidified with citric acid until Ph about 3-4. The mixture was extracted with EtOAc. The combined organic layer was washed with brine, dried over anhydrous Na₂SO₄, concentrated to provide [6-(1H-tetrazol-1-yl)pyridin-3-yl]acetic acid. ¹H-NMR (400 MHz, DMSO) δ 12.62 (s, 1H), 10.16 (s, 1H), 8.54 (s, 1H), 8.01~8.09 (m, 2H), 3.80 (s, 2H).

Intermediate 50

Method 2

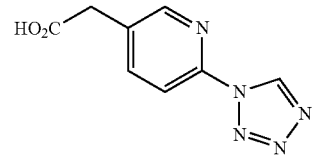 [SMILES: O=C(O)Cc1ccc(-n2cnnn2)nc1]

[6-(1H-Tetrazol-1-yl)pyridin-3-yl]acetic acid

Step A: Ethyl (6-Nitropyridin-3-yl)acetate

To a suspension of NaH (60% in mineral oil, 14 g, 350 mmol) in 250 mL DMF in a 1 L flask with a magnetic stir bar was added tert-butyl ethyl propanedioate (65 mL, 350 mmol) maintaining the temperature below +12° C. in an ice bath over 20 min (gas evolution). After 20 min, the ice bath was removed, allowed to warm to rt over 30 min. Solid commercially available 5-bromo-2-nitropyridine (50 g, 250 mmol) was added. A red suspension formed immediately. After 15 min, the reaction flask was placed in a 60° C. oil bath. After 1 h, the heating was turned off. The red-black slurry was allowed to stir overnight while cooling down. After 15 h at rt, the mixture was cooled in an ice bath. Additional 0.7 equiv NaH (60% in mineral oil, 6.9 g, 170 mmol) was added in ~10 portions below +10° C. (internal) to keep the foaming under control. After 30 min and ⅔ through the addition of NaH, the mixture turned very thick. Additional 100 mL DMF (2 volumes) was added to facilitate stirring. The rest of NaH was added over 10 min. Stirring in the ice bath was continued for additional 10 min. It is important to add NaH slowly in order to keep the exotherm and foaming under control. If all of NaH is added at the beginning of the reaction, it results in low yield and extensive decomposition. The cooling bath was removed, the mixture was allowed to stir to rt for 1 h. The reaction mixture was heated to 60° C. over 30 min, then heated for the total of 3.5 h at 60° C. whereupon ~95% of the bromide had been consumed. The flask was then cooled in an ice bath. After 20 min in the ice bath, 100 mL MTBE was added followed by 300 mL of 1 M aqueous H₃PO₄ below +15° C. (pH=5). The red-black color of the reaction mixture sharply turned to light brown. The mixture was combined with 750 mL EtOAc, washed with 4×1 L water. The organic phase was concentrated to an oil and carried directly into the next step.

The resulting crude tert-butyl ethyl (6-nitropyridin-3-yl) propanedioate was dissolved in 153 mL DCM, and TFA (95 mL, 1200 mmol) was added. The mixture was stirred at 25°

C. for 2 h, then was heated at 35° C. for 2 h, (80% conversion). An additional 2 equiv of TFA (39 mL, 490 mmol) was added. The mixture was heated at 35° C. for 1 h, then was kept at rt overnight (>95% conversion). The reaction was quenched with 1.0 L of 1 M aq $K_3PO_4$ in an ice bath below +20° C. to pH=6. The layers were separated, and the aqueous phase was extracted with an additional 200 mL of DCM. The organic phase was dried ($MgSO_4$), filtered, and concentrated. The residue was dissolved in 200 mL MTBE and the solution was filtered through 20 g of silica gel to remove tar. The silica plug was eluted with additional 750 mL MTBE. The filtrate was concentrated, the oily residue was suspended in ~100 mL of 3:1 Hexane/EtOAc. Crystallized occurred upon stirring/seeding. The suspension was filtered, and the filter cake washed with 100 mL of 5:1 hexane/EtOAc to provide the desired product. The mother liquors were concentrated, purified by flash chromatography on 7.5×18 cm silica (Hexane:EtOAc 3:1 to 3:2). The purest fractions were collected, concentrated to an oil, and treated with ~100 mL hexane to crystallize additional product. The slurry was stirred at rt for 1 h, filtered, the filter cake was washed with hexane to afford additional ethyl (6-nitropyridin-3-yl)acetate.

Step B: Ethyl (6-Aminopyridin-3-yl)acetate

A suspension of 10% Pd on carbon (9.2 g, 8.7 mmol) in a solution of the ethyl (6-nitropyridin-3-yl)acetate (36 g, 170 mmol) in EtOH (360 mL) was hydrogenated at 20 psi and 25° C. for 2 h. The suspension was filtered through Solka Floc eluting with 200 mL EtOH. The filtrate was concentrated and solvent switched with EtOAc, then concentrated to afford the title compound.

Step C: Ethyl [6-(1H-Tetrazol-1-yl)pyridin-3-yl]acetate

A 1 L 3-neck flask was purged with nitrogen and charged with a solution of ethyl (6-aminopyridin-3-yl)acetate (32 g, 180 mmol) in EtOAc (320 mL) at +22° C. Then 30 mL of TMS trifluoroacetate was added (1.0 equiv) while cooling in a water bath. A mild exotherm to +25° C. and partial crystallization was observed. After 5 min, triethylorthoformate was added (44 mL, 260 mmol) followed by TMS-azide (28 mL, 210 mmol). The resulting suspension was stirred at +23° C. After 15 min, an additional 10 mL of TMS trifluoroacetate was added (0.30 equiv). A clear solution formed after ~10 min. The mixture was stirred for 3 days at +20° C. whereupon a thin, light yellow suspension had formed. The mixture was cooled in an ice bath, and 200 ml of 1M aq $K_3PO_4$ was added while maintaining the temperature below +20° C. Then 460 mL EtOAc was added to solubilize the product. The layers were separated (pH of aq~8), then the organic phase was washed with 2×250 mL water, and concentrated to a thick slurry. Then 400 mL of n-heptane was added to the concentrated organic phase over 20 min. After 30 min, the suspension was filtered to afford the title tetrazole product.

Step D: [6-(1H-tetrazol-1-yl)pyridin-3-yl]acetic acid

To a suspension of ethyl [6-(1H-tetrazol-1-yl)pyridin-3-yl]acetate (30.0 g, 130 mmol) in 150 mL of water was added 28 mL of 5M aq NaOH (140 mmol) over 5 min while cooled in a water bath. A very mild exotherm to +22° C. was observed. The mixture was stirred for 40 min at rt whereupon 106 mL of 2M aq $H_3PO_4$ was added over 30 min at rt.

The resulting suspension was filtered, and the filter cake was washed with 2×50 mL water and dried on the frit under a stream of nitrogen overnight to afford [6-(1H-tetrazol-1-yl)pyridin-3-yl]acetic acid. This material was identical by H NMR to that synthesized according to method 1 above.

Intermediate 51

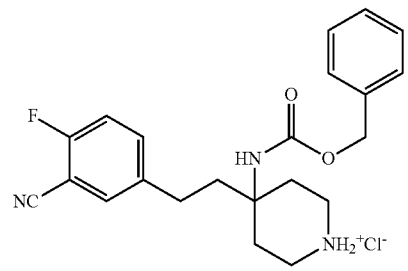

4-{[(Benzyloxy)carbonyl]amino}-4-[2-(3-cyano-4-fluorophenyl)ethyl]piperidinium Chloride Step A: 1-tert-Butyl 4-[2-(3-cyano-4-fluorophenyl) ethyl]piperidine-1,4-dicarboxylate A solution of 1-tert-butyl 4-ethyl 4-[2-(3-cyano-4-fluorophenyl)ethyl]piperidine-1,4-dicarboxylate (900 mg, 2.225 mmol) in methanol (12 mL), water (6 mL), and THF (12 mL) was treated with solid lithium hydroxide (530 mg, 22 mmol) and was stirred at rt for 3 days. The reaction was concentrated in vacuo, diluted with water, and extracted with ether. The aqueous layer was acidified with 18% citric acid and extracted twice with ethyl acetate. The organic layers were washed with brine, dried over sodium sulfate and evaporated. The residue was purified by MPLC (20% ethyl acetate in hexanes, then 20-50% ethyl acetate with 1% acetic acid in hexanes) to provide 1-tert-Butyl 4-[2-(3-cyano-4-fluorophenyl)ethyl]piperidine-1,4-dicarboxylate. $^1$H-NMR (400 MHz, $CDCl_3$) δ ppm 7.35-7.45 (m, 2H), 7.12 (t, J=8.6 Hz, 1H), 3.90 (br d, J=13 Hz, 2H), 2.95-3.05 (m, 2H), 2.55-2.65 (m, 2H), 2.15 (br d, J=13.4 Hz, 2H), 1.8-1.9 (m, 2H), 1.46 (s, 9H), 1.4-1.5 (m, 2H). LC/MS (M+1-56)$^+$=321, (M+1-100)$^+$=277 (100%).

Step B: tert-Butyl 4-[2-(3-cyano-4-fluorophenyl) ethyl]-4-[(benzyloxycarbonyl)amino]piperidine-1-carboxylate To a solution of 1-tert-butyl 4-[2-(3-cyano-4-fluorophenyl)ethyl]piperidine-1,4-dicarboxylate (180 mg, 0.48 mmol) in 1,4-dioxane (2 mL) was added diphenylphosphoryl azide (0.155 mL, 0.717 mmol), DIPEA (0.251 mL, 1.435 mmol) and benzyl alcohol (0.398 mL, 3.83 mmol). The mixture was heated at 80° C. for 7.5 hours. The reaction was concentrated in vacuo, acidified with 18% citric acid and extracted twice with ethyl acetate. The organic layers were washed with brine, dried over sodium sulfate and evaporated. The residue was purified by MPLC (eluent: 5→40% ethyl acetate in hexanes) to provide tert-butyl 4-[2-(3-cyano-4-fluorophenyl)ethyl]-4-[(benzyloxycarbonyl)amino]piperidine-1-carboxylate.

$^1$H-NMR (400 MHz, $CDCl_3$) δ ppm 7.20-7.40 (2 m, 7H), 7.07 (t, J=8.5 Hz, 1H), 5.07 (s, 2H), 4.58 (s, 1H), 3.80-3.90

(br s, 2H), 2.95-3.10 (m, 2H), 2.25-2.35 (m, 2H), 1.9-2.1 (m, 4H), 1.5-1.6 (m, 2H), 1.46 (s, 9H). LC/MS (M+1-100)=382.

Step C: 4-{[(Benzyloxy)carbonyl]amino}-4-[2-(3-cyano-4-fluorophenyl)ethyl]piperidinium Chloride To tert-butyl 4-[2-(3-cyano-4-fluorophenyl)ethyl]-4-[(benzyloxycarbonyl)amino]piperidine-1-carboxylate (140 mg, 0.30 mmol) was added 2 N HCl in diethyl ether (2.5 mL, 5 mmol) and stirred overnight. The volatiles were evaporated and an additional portion of 2M HCl in ether was added and stirred 4 additional hours. The volatiles were again evaporated and the white solid was dried under vacuum to provide 4-{[(benzyloxy)carbonyl]amino}-4-[2-(3-cyano-4-fluorophenyl)ethyl]piperidinium chloride which was used directly in the next step without further purification.

Intermediate 52

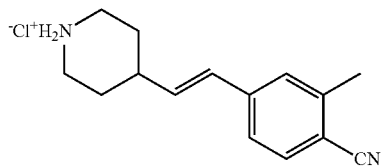

4-[(E)-2-(4-Cyano-3-methylphenyl)ethenyl]piperidinium Chloride

4-[(E)-2-(4-Cyano-3-methylphenyl)ethenyl]piperidinium chloride was prepared in a similar fashion to the previously described synthesis of INTERMEDIATE 3 starting from tert-butyl 4-ethenylpiperidine-1-carboxylate and 4-iodo-2-methylbenzonitrile. LC-MS (IE, m/z): 227 [M+1]+.

Intermediate 53

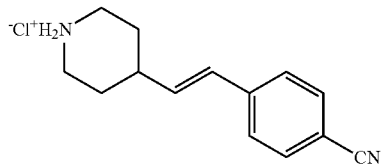

4-[(E)-2-(4-Cyano-3-methylphenyl)ethenyl]piperidinium Chloride

4-[(E)-2-(4-Cyano-3-methylphenyl)ethenyl]piperidinium chloride was prepared in a similar fashion to the previously described synthesis of INTERMEDIATE 3 starting from tert-butyl 4-ethenylpiperidine-1-carboxylate and 4-iodobenzonitrile. LC-MS (IE, m/z): 213 [M+1]+.

Intermediate 54

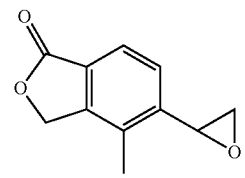

4-Methyl-5-oxiran-2-yl-2-benzofuran-1(3H)-one

Step A:
5-Ethenyl-4-methyl-2-benzofuran-1(3H)-one

5-Bromo-4-methyl-2-benzofuran-1(3H)-one (600 mg, 4.5 mmol), potassium vinyl trifluoroborate (510 mg, 2.2 mmol), PdCl$_2$(dppf)-CH$_2$Cl$_2$ Adduct (180 mg, 0.220 mmol), and TEA (0.62 mL, 4.5 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography (0-80% ETOAC/Hexane solvent system) to yield 5-ethenyl-4-methyl-2-benzofuran-1(3H)-one.

$^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H). LC-MS: [M+1]=175.

Step B: 4-Methyl-5-oxiran-2-yl-2-benzofuran-1(3H)-one 5-ethenyl-4-methyl-2-benzofuran-1(3H)-one (1.5 g, 8.4 mmol) was added to DCM (25 mL) at 0° C. then meta-chloroperbenzoic acid (2.9 g, 17 mmol) was added and the mixture was stirred at RT overnight. The reaction mixture was washed once each with saturated aqueous Na$_2$S$_2$O$_3$, saturated sodium bicarbonate, and brine. The organic layer was dried over Na$_2$SO$_4$, filtered, and evaporated to dryness. The crude material was purified by MPLC chromatography (eluting with 0-80% EtOAc/hexane solvent system) to yield 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.74 (dd, J=2.2, 5.5 Hz, 1H), 2.43 (s, 3H).

LC-MS: [M+1]=191.

Intermediates 54A and 54B

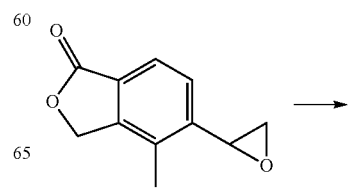

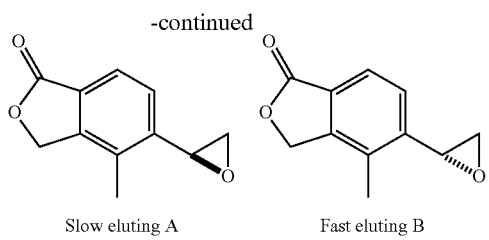

Slow eluting A      Fast eluting B

A: 4-Methyl-5-[(2S)-oxiran-2-yl]-2-benzofuran-1(3H)-one

B: 4-Methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/ml in 1:1 DCM:MeOH. The separation was accomplished using 10% EtOH/CO2, flow rate 200 ml/min, 100 bar, 25° C. 500 ul Injections were spaced every 2.12 mins. The fast epoxide (4-methyl-5-[(2R)-oxiran-2-yl]-2-benzofuran-1(3H)-one, 3B) eluted at 5.2 min, and the slow epoxide (4-methyl-5-[(2S)-oxiran-2-yl]-2-benzofuran-1(3H)-one, 3A) eluted at 5.6 min.

Alternatively, the resolution could also be achieved using a mobile phase of 8% MeOH/98% $CO_2$ with a flow rate of 100 ml/min. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer was inferred based on the X-ray crystal structure determination of a derivative made with 3B, and by Mosher ester and Trost ester $^1$HNMR analysis of an ester made starting from 3B. The B epoxide isomer finds utility in the present invention.

Intermediates 55 and 56

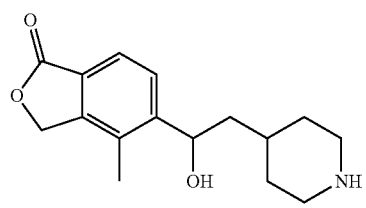

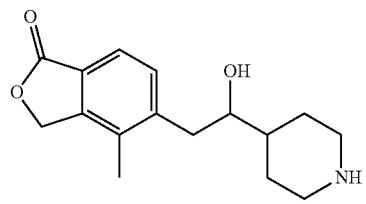

5-[1-Hydroxy-2-(piperidin-4-yl)ethyl]-4-methyl-2-benzofuran-1(3H)-one and 5-[2-Hydroxy-2-(piperidin-4-yl)ethyl]-4-methyl-2-benzofuran-1(3H)-one Step A: tert-Butyl 4-[2-hydroxy-2-(4-methyl-1-oxo-1,3-dihydro-2-benzofuran-5-yl)ethyl]piperidine-1-carboxylate and tert-Butyl 4-[1-hydroxy-2-(4-methyl-1-oxo-1,3-dihydro-2-benzofuran-5-yl)ethyl]piperidine-1-carboxylate To a solution of tert-butyl 4-[(E)-2-(4-methyl-1-oxo-1,3-dihydro-2-benzofuran-5-yl)ethenyl]piperidine-1-carboxylate (300 mg, 0.84 mmol) in THF (2 mL) was added borane tetrahydrofuran complex (1.3 ml, 1.3 mmol) at 0° C. The mixture was allowed to stir for 16 hours. The reaction mixture was then treated with sodium hydroxide (2.0 N, 0.84 ml, 1.7 mmol) and hydrogen peroxide (0.15 ml, 1.7 mmol). The reaction was carefully quenched with water, diluted with EtOAc, washed with brine, dried over sodium sulfate, adsorbed onto silica gel, and purified by flash chromatography to deliver an inseparable mixture of regio-isomeric products, tert-butyl 4-[2-hydroxy-2-(4-methyl-1-oxo-1,3-dihydro-2-benzofuran-5-yl)ethyl]piperidine-1-carboxylate and tert-butyl 4-[1-hydroxy-2-(4-methyl-1-oxo-1,3-dihydro-2-benzofuran-5-yl)ethyl]piperidine-1-carboxylate. LC-MS (IE, m/z): 376 [M+1]$^+$.

Step C: 5-[1-hydroxy-2-(piperidin-4-yl)ethyl]-4-methyl-2-benzofuran-1(3H)-one and 5-[2-hydroxy-2-(piperidin-4-yl)ethyl]-4-methyl-2-benzofuran-1(3H-one A mixture of tert-butyl 4-[2-hydroxy-2-(4-methyl-1-oxo-1,3-dihydro-2-benzofuran-5-yl)ethyl]piperidine-1-carboxylate and tert-butyl 4-[1-hydroxy-2-(4-methyl-1-oxo-1,3-dihydro-2-benzofuran-5-yl)ethyl]piperidine-1-carboxylate was treated with trifluoroacetic acid at RT to remove the Boc group. When LC suggested complete reaction, the volatiles were removed. The residue was purified by mass-directed HPLC. The faster eluting peak was 5-[1-hydroxy-2-(piperidin-4-yl)ethyl]-4-methyl-2-benzofuran-1(3H)-one, and the slower peak was 5-[2-hydroxy-2-(piperidin-4-yl)ethyl]-4-methyl-2-benzofuran-1(3H)-one.

5-[1-hydroxy-2-(piperidin-4-yl)ethyl]-4-methyl-2-benzofuran-1(3H)-one TFA salt (INTERMEDIATE 55): $^1$H-NMR (500 MHz, DMSO) δ ppm 8.72 (bs, 1H), 8.41 (bs, 1H), 7.68 (m, 2H), 6.45 (bs, 1H), 5.39 (m, 2H), 4.97 (d, J=9.0 Hz, 1H), 3.39 (bs, 1H), 3.27 (dd, J=22, 12 Hz, 1H), 2.87 (bs, 1H), 2.23 (s, 3H), 2.04 (d, J=14 Hz, 1H), 1.87 (bs, 1H), 1.78 (d, J=14 Hz, 1H), 1.50 (m, 1H), 1.35 (m, 2H).

5-[2-hydroxy-2-(piperidin-4-yl)ethyl]-4-methyl-2-benzofuran-1(3H)-one TFA salt (INTERMEDIATE 56): $^1$H-NMR (500 MHz, DMSO) δ ppm 8.60 (bs, 1H), 8.24 (bs, 1H), 7.60 (d, J=7.0 Hz, 1H), 7.42 (d, J=7.0 Hz, 1H), 5.38 (m, 2H), 4.78 (m, 1H), 3.48 (m, 1H), 2.86 (m, 2H), 2.71 (t, J=11 Hz, 1H), 2.25 (s, 3H), 1.95 (d, J=14 Hz, 1H), 1.76 (d, J=11 Hz, 1H), 1.58 (m, 1H), 1.51 (m, 1H).

Intermediate 55A

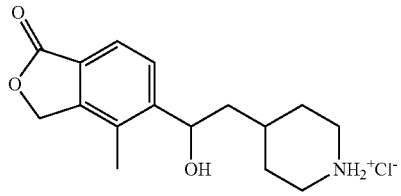

4-[2-Hydroxy-2-(4-methyl-1-oxo-1,3-dihydro-2-benzofuran-5-yl)ethyl]piperidinium Chloride An alternative preparation of the HCl salt of INTERMEDIATE 55 was also used:

Step A: tert-Butyl 4-hydroxy-4-[2-(4-methyl-1-oxo-1,3-dihydro-2-benzofuran-5-yl)-2-oxoethyl]piperidine-1-carboxylate To a THF solution (7 mL) of cerium (III) chloride (460 mg, 1.9 mmol) and sodium iodide (840 mg, 5.6 mmol) was added a 5-(bromoacetyl)-4-methyl-2-benzofuran-1(3H)-one (500 mg, 1.9 mmol) and tert-butyl 4-oxopiperidine-1-carboxylate (370 mg, 1.9 mmol) simultaneously at ambient temperature. The reaction was stirred at ambient temperature for one hour and then quenched by the addition of aqueous sodium thiosulfate. The aqueous layer was extracted with DCM (3×). The combined organic layers were then dried over sodium sulfate, filtered and concentrated. The resulting residue was purified via MPLC (0-80% EtOAc/Hex gradient) to afford tert-butyl 4-hydroxy-4-[2-(4-methyl-1-oxo-1,3-dihydro-2-benzofuran-5-yl)-2-oxoethyl]piperidine-1-carboxylate. $^1$H NMR (500 MHz, CDCl$_3$): 7.82 (m, 1H), 7.70 (m, 1H), 5.3 (s, 2H), 3.8-3.9 (broad m, 2H), 3.7 (s, 1H), 3.2-3.3 (broad m, 2H), 3.1 (s, 2H), 2.4 (s, 3H), 1.8 (broad d, 2H), 1.6 (m, 2H), 1.45 (s, 9H). LC-MS (IE, m/z): 210 [M−100]$^+$.

Step B: tert-Butyl 4-[2-(4-methyl-1-oxo-1,3-dihydro-2-benzofuran-5-yl)-2-oxoethyl]-4-[(methylsulfonyl)oxy]piperidine-1-carboxylate To an ice cooled solution of tert-butyl 4-hydroxy-4-[2-(4-methyl-1-oxo-1,3-dihydro-2-benzofuran-5-yl)-2-oxoethyl]piperidine-1-carboxylate (240 mg, 0.62 mmol) in 4 mL of dichloromethane was added triethylamine (180 μL, 1.3 mmol) and methanesulfonyl chloride (73 μL, 0.94 mmol) respectively. The reaction was allowed to warm to ambient temperature over a period of two hours and then quenched by the addition of aqueous sodium bicarbonate. The aqueous layer was extracted with DCM (3×). The combined organic layers were then dried over sodium sulfate, filtered and concentrated in vacuo to provide tert-butyl 4-[2-(4-methyl-1-oxo-1,3-dihydro-2-benzofuran-5-yl)-2-oxoethyl]-4-[(methylsulfonyl)oxy]piperidine-1-carboxylate which was used directly in the next step without further purification.

Step C: tert-Butyl 4-[2-(4-methyl-1-oxo-1,3-dihydro-2-benzofuran-5-yl)-2-oxoethylidene]piperidine-1-carboxylate To a solution of tert-butyl 4-[2-(4-methyl-1-oxo-1,3-dihydro-2-benzofuran-5-yl)-2-oxoethyl]-4-[(methylsulfonyl)oxy]piperidine-1-carboxylate (290 mg, 0.63 mmol) in THF (2.4 mL) was added DBU (200 μL, 1.3 mmol). The reaction was allowed to stir at ambient temperature for 15 hours and then quenched by the addition of water. The aqueous layer was extracted with ethyl acetate (3×). The combined organic layers were then dried over sodium sulfate, filtered and concentrated in vacuo. The resulting residue was purified via MPLC (0-100% EtOAc/Hex gradient) to provide tert-butyl 4-[2-(4-methyl-1-oxo-1,3-dihydro-2-benzofuran-5-yl)-2-oxoethylidene]piperidine-1-carboxylate. $^1$H NMR (500 MHz, CDCl$_3$): 7.8 (m, 1H), 7.6 (m, 1H), 6.4 (s, 1H), 5.3 (s, 2H), 3.6 (dd, 2H), 3.5 (broad t, 2H), 2.9 (broad s, 2H), 2.38~2.42 (broad m, 5H), 1.5 (s, 9H). LC-MS (IE, m/z): 272 [M−100]$^+$.

Step D: tert-Butyl 4-[2-(4-methyl-1-oxo-1,3-dihydro-2-benzofuran-5-yl)-2-oxoethyl]piperidine-1-carboxylate A solution tert-butyl 4-[2-(4-methyl-1-oxo-1,3-dihydro-2-benzofuran-5-yl)-2-oxoethylidene]piperidine-1-carboxylate (160 mg, 0.42 mmol) in DCM (5 mL) was added to a slurry of 10% palladium on carbon (13 mg, 0.13 mmol) in DCM (5 mL). This solution was then subjected to hydrogenation conditions (50 psi @ 23° C. for two hours) using a Parr shaker. After two hours, the reaction was filtered over a pad of diatomaceous earth and concentrated in vacuo to provide tert-butyl 4-[2-(4-methyl-1-oxo-1,3-dihydro-2-benzofuran-5-yl)-2-oxoethyl]piperidine-1-carboxylate which was used directly without further purification.

LC-MS (IE, m/z): 274 [M−100]$^+$.

Step E: tert-Butyl 4-[2-hydroxy-2-(4-methyl-1-oxo-1,3-dihydro-2-benzofuran-5-yl)ethyl]piperidine-1-carboxylate To a solution of tert-butyl 4-[2-(4-methyl-1-oxo-1,3-dihydro-2-benzofuran-5-yl)-2-oxoethyl]piperidine-1-carboxylate (160 mg, 0.42 mmol) in 3 mL of methanol was added sodium borohydride (16 mg, 0.42 mmol) portionwise. The reaction was allowed to stir at ambient temperature for one hour, quenched by the addition of water and then concentrated in vacuo. The resulting residue was redissolved in DCM/water mixture. The aqueous layer was extracted three times with DCM. The combined organic layers were dried over sodium sulfate, filtered and concentrated in vacuo to provide tert-butyl 4-[2-hydroxy-2-(4-methyl-1-oxo-1,3-dihydro-2-benzofuran-5-yl)ethyl]piperidine-1-carboxylate which was used directly in the next step without further purification.

Step F: 4-[2-Hydroxy-2-(4-methyl-1-oxo-1,3-dihydro-2-benzofuran-5-yl)ethyl]piperidinium Chloride To a solution of tert-butyl 4-[2-hydroxy-2-(4-methyl-1-oxo-1,3-dihydro-2-benzofuran-5-yl)ethyl]piperidine-1-carboxylate (160 mg, 0.42 mmol) in 1 mL methanol was added an excess amount of a 4 N HCl in dioxane solution. After addition, the reaction was allowed to stir at ambient temperature for one hour and then concentrated in vacuo to provide 4-[2-hydroxy-2-(4-methyl-1-oxo-1,3-dihydro-2- benzofuran-5-yl)ethyl]piperidinium chloride which was used directly in the next step without further purification.

Intermediate 57

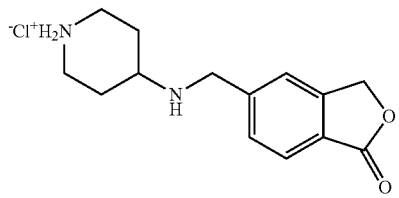

4-{[(1-Oxo-1,3-dihydro-2-benzofuran-5-yl)methyl] amino}piperidinium Chloride

Step A: tert-butyl 4-{[(1-oxo-1,3-dihydro-2-benzofuran-5-yl)methyl]amino}piperidine-1-carboxylate To a solution of tert-butyl 4-amino-1-piperidinecarboxylate (60 mg, 0.30 mmol) in methanol (3 ml) was added 1-oxo-1,3-dihydro-2-benzofuran-5-carbaldehyde (49 mg, 0.30 mmol) at rt. The mixture was left to stir for 10 min, and then sodium cyanoborohydride (28 mg, 0.45 mmol) was added to the mixture at rt. 10% acetic acid (0.4 ml, 7.0 mmol) was then added dropwise to help with solubility. The reaction mixture was left to stir at rt overnight. The mixture was concentrated, and the residue was purified by prep-TLC (silica gel; 10% MeOH/DCM) to provide tert-butyl 4-{[(1-oxo-1,3-dihydro-2-benzofuran-5-yl)methyl] amino}piperidine-1-carboxylate. LC-MS (IE, m/z): 347 [M+1]$^+$.

Step B: 4-{[(1-Oxo-1,3-dihydro-2-benzofuran-5-yl) methyl]amino}piperidinium Chloride tert-butyl 4-{[(1-oxo-1,3-dihydro-2-benzofuran-5-yl) methyl]amino}piperidine-1-carboxylate was dissolved in 7 ml of 4M HCl in 1,4-dioxane at rt. A few drops of MeOH were added to help with solubility. The solution was stirred at rt for 1.5 h. The mixture was then concentrated in vacuo to provide 4-{[(1-Oxo-1,3-dihydro-2-benzofuran-5-yl) methyl]amino}piperidinium Chloride. LC-MS (IE, m/z): 247 [M+1]$^+$.

Intermediate 58

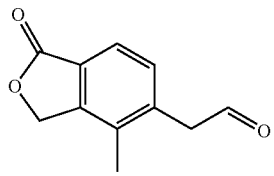

(4-Methyl-1-oxo-1,3-dihydro-2-benzofuran-5-yl) acetaldehyde

Step A: 4-Methyl-5-prop-2-en-1-yl-2-benzofuran-1 (3H)-one

To a flask charged with 5-bromo-4-methyl-2-benzofuran-1(3H)-one (320 mg, 1.4 mmol) and a stir bar was added allyl tri-n-butyltin (0.66 mL, 2.1 mmol), Pd(PPh$_3$)$_4$ (240 mg, 0.21 mmol), lithium chloride (180 mg, 4.2 mmol), and toluene (15 mL). The reaction was purged with nitrogen 2 times then was heated at reflux for 4 hours. The reaction mixture was diluted with DCM, adsorbed onto silica gel, and purified by silica gel chromatography to provide 4-methyl-5-prop-2-en-1-yl-2-benzofuran-1(3H)-one.

Step B: (4-methyl-1-oxo-1,3-dihydro-2-benzofuran-5-yl)acetaldehyde

A solution of 4-methyl-5-prop-2-en-1-yl-2-benzofuran-1 (3H)-one (220 mg, 1.2 mmol) in MeOH (20 mL) was cooled to −78° C. To this solution was bubbled ozone until the reaction turned blue.

Nitrogen was bubbled through the reaction to drive off excess ozone, followed by addition of DMS (0.87 mL, 12 mmol). The reaction was allowed to warm up to RT. The solvents were removed under reduced pressure. The resulting residue was purified by flash chromatography to afford (4-methyl-1-oxo-1,3-dihydro-2-benzofuran-5-yl)acetaldehyde.

$^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Intermediate 59

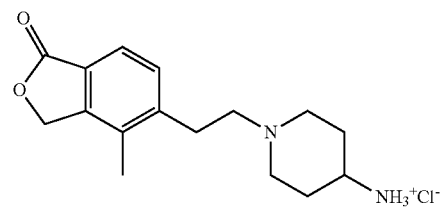

1-[2(4-Methyl-1-oxo-1,3-dihydro-2-benzofuran-5-yl)ethyl]piperidin-4-aminium Chloride Step A: tert-Butyl {1-[2-(4-Methyl-1-oxo-1,3-dihydro-2-benzofuran-5-yl)ethyl]piperidin-4-yl}carbamate To a solution of tert-butyl piperidin-4-ylcarbamate (1.5 g, 7.5 mmol) in methanol (35 ml) was added (4-methyl-1-oxo-1,3-dihydro-2-benzofuran-5-yl)acetaldehyde (1.6 g, 8.2 mmol) at room temperature. The mixture was left to stir for 10 min, and then sodium cyanoborohydride (0.71 g, 11 mmol) was added to the mixture at room temperature. 10% Acetic acid (10 ml, 180 mmol) was then added dropwise to help with solubility. The reaction mixture was left to stir at rt for 2 h. The mixture was concentrated, and the residue was purified by MPLC (eluent: EtOAc/Hexanes 0% to 100%, then MeOH/DCM 0% to 10%) to provide tert-butyl {1-[2-(4-methyl-1-oxo-1,3-dihydro-2-benzofuran-5-yl)ethyl]piperidin-4-yl}carbamate.

LC-MS (IE, m/z): 375 [M+1]$^+$.

Step B: 1-[2-(4-Methyl-1-oxo-1,3-dihydro-2-benzofuran-5-yl)ethyl]piperidin-4-aminium Chloride tert-butyl {1-[2-(4-methyl-1-oxo-1,3-dihydro-2-benzofuran-5-yl)ethyl]piperidin-4-yl}carbamate (2.0 g, 5.5 mmol)

was dissolved in 40 ml of 4M HCl in 1,4-dioxane at rt. A few drops of methanol was added to help with solubility. The solution was stirred at rt for 3 h. The mixture was then concentrated to provide 1-[2-(4-methyl-1-oxo-1,3-dihydro-2-benzofuran-5-yl)ethyl]piperidin-4-aminium chloride, which was used directly in the next reaction without further purification. LC-MS (IE, m/z): 275 [M+1]+.

Intermediate 60

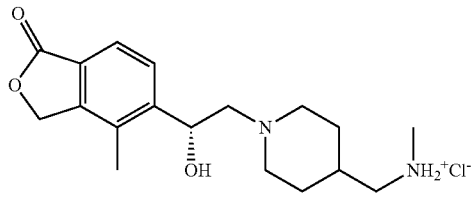

{1-[(2R)-2-hydroxy-2-(4-methyl-1-oxo-1,3-dihydro-2-benzofuran-5-yl)ethyl]piperidin-4-yl}-N-methyl-methanaminium chloride Step A: tert-Butyl ({1-[(2R)-2-Hydroxy-2-(4-methyl-1-oxo-1,3-dihydro-2-benzofuran-5-yl)ethyl]piperidin-4-yl}methyl)methylcarbamate A solution of 4-methyl-5-[(2R)-oxiran-2-yl]-2-benzofuran-1(3H)-one (76 mg, 0.40 mmol) in 2 mL of ethanol was added to tert-butyl methyl(piperidin-4-ylmethyl)carbamate (91 mg, 0.40 mmol). The reaction mixture was heated at 140° C. in the microwave for 55 minutes. The solvents were removed in vacuo to provide tert-butyl ({1-[(2R)-2-hydroxy-2-(4-methyl-1-oxo-1,3-dihydro-2-benzofuran-5-yl)ethyl]piperidin-4-yl}methyl)methylcarbamate which was used directly in the next step without further purification.

Step B: 5-[(1R)-1-hydroxy-2-{4-[(methylamino)methyl]piperidin-1-yl}ethyl]-4-methyl-2-benzofuran-1(3H)-one A suspension of tert-butyl ({1-[(2R)-2-hydroxy-2-(4-methyl-1-oxo-1,3-dihydro-2-benzofuran-5-yl)ethyl]piperidin-4-yl}methyl)methylcarbamate (83 mg, 0.20 mmol) in dioxane (200 uL) was treated with a solution of hydrochloric acid in dioxane (4.0 M, 200 uL). After shaking 3 h, the solution was treated with additional hydrochloric acid in dioxane (4.0 M, 100 uL). After shaking an additional sixteen hours, the solvents were removed in vacuo to provide 5-[(1R)-1-hydroxy-2-{4-[(methylamino)methyl]piperidin-1-yl}ethyl]-4-methyl-2-benzofuran-1(3H)-one which was used directly in the next step without further purification.

Intermediate 61

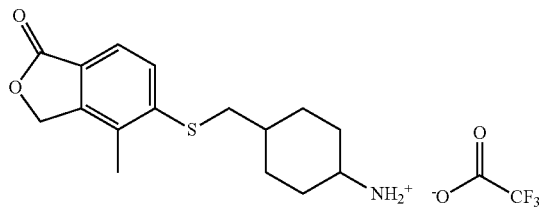

4-{[(4-Methyl-1-oxo-1,3-dihydro-2-benzofuran-5-yl)sulfanyl]methyl}piperidinium Trifluoroacetate Step A:
4-Methyl-5-sulfanyl-2-benzofuran-1(3H)-one A sealable tube was charged with 4-methyl-1-oxo-1,3-dihydro-2-benzofuran-5-yl trifluoromethanesulfonate (4.2 g, 14 mmol), triisopropylsilanethiol (4.1 g, 21 mmol), CS$_2$CO$_3$ (6.9 g, 21 mmol) and toluene (50 mL). After degassing with bubbling argon for 10 minutes, tris(triphenylphosphine)palladium(0)tetrakis (1.6 g, 1.4 mmol) was added and mixture was heated at 100° C. for 4 hours. After cooling, the reaction mixture was transferred to a round bottom flask and solvent was removed in vacuo. The resulting residue was redissolved in EtOAc and treated with 100 mL of 1N HCl. The layers were separated and the aqueous phase was extracted with EtOAc (2×). The combined organic layers were dried over anhydrous Na$_2$SO$_4$, filtered and concentrated. The resulting residue was purified by MPLC (0→10% MeOH/DCM gradient) to provide 4-methyl-5-sulfanyl-2-benzofuran-1(3H)-one. LC-MS (IE, m/z): 181 [M+1]+.

Step B: tert-Butyl 4-{[(4-Methyl-1-oxo-1,3-dihydro-2-benzofuran-5-yl)sulfanyl]methyl}piperidine-1-carboxylate 4-Methyl-5-sulfanyl-2-benzofuran-1(3H)-one (400 mg, 2.2 mmol) and tert-butyl 4-(bromomethyl)piperidine-1-carboxylate (700 mg, 2.5 mmol) were dissolved in DMF (4 ml) and were mixed with potassium carbonate (610 mg, 4.4 mmol) at room temperature. The mixture was put on microwave reactor and heated at 145° C. for 20 minutes. After cooling to room temperature, the reaction mixture was diluted with EtOAc and water. The layers were separated and the aqueous layer extracted with EtOAc. The combined organic phases were dried over Na$_2$SO$_4$, filtered and concentrated. The resulting residue was purified by MPLC (0→50% EtOAc/Hexane gradient) to provide tert-butyl 4-{[(4-methyl-1-oxo-1,3-dihydro-2-benzofuran-5-yl)sulfanyl]methyl}piperidine-1-carboxylate. $^1$H NMR (500 MHz, CDCl$_3$): δ 7.71 (d, J=8.1 Hz, 1H), 7.33 (d, J=8.1 Hz, 1H), 5.23 (s, 2H), 4.14 (br, 2H), 2.95 (d, J=6.8 Hz, 2H), 2.70 (m, 2H), 2.28 (s, 3H), 1.89 (m, 2H), 1.81-1.73 (m, 1H), 1.46 (s, 9H), 1.34-1.19 (m, 2H).

Step C: 4-{[(4-Methyl-1-oxo-1,3-dihydro-2-benzofuran-5-yl)sulfanyl]methyl}piperidinium Trifluoroacetate tert-Butyl 4-{[(4-methyl-1-oxo-1,3-dihydro-2-benzofuran-5-yl)sulfanyl]methyl}piperidine-1-carboxylate (90 mg, 0.24 mmol) was dissolved in DCM (2 mL) and was treated with trifluoromethanesulfonic acid (1.0 mL, 13 mmol). After 2 hours, the solvent was removed under reduced pressure and the resulting residue was re-dissolved in a small amount of DCM. The solvent was removed to eliminate any remaining TFA. The resulting 4-{[(4-methyl-1-oxo-1,3-dihydro-2-benzofuran-5-yl)sulfanyl]methyl}piperidinium trifluoroacetate was dried under high vacuum and used directly in the next step without further purification.

LC-MS (IE, m/z): 278 [M+1]+.

Intermediate 62

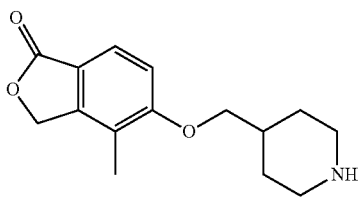 [SMILES: Cc1c(OCC2CCNCC2)ccc2c1COC2=O]

4-Methyl-5-(piperidin-4-ylmethoxy)-2-benzofuran-1(3H)-one

Step A: tert-Butyl 4-{[(4-methyl-1-oxo-1,3-dihydro-2-benzofuran-5-yl)oxy]methyl}piperidine-1-carboxylate 5-Hydroxy-4-methyl-2-benzofuran-1(3H)-one (80 mg, 0.49 mmol) and tert-butyl 4-(bromomethyl)piperidine-1-carboxylate (200 mg, 0.72 mmol) were mixed together in DMF (5 mL). Potassium carbonate (140 mg, 0.98 mmol) was added and the mixture was stirred at 80° C. overnight. The reaction was diluted with EtOAc and water and the layers separated. The organic phase was washed with brine, dried ($Na_2SO_4$), filtered and concentrated. The resulting residue was purified by MPLC (0-50% EtOAc/Hexane) to provide tert-butyl 4-{[(4-methyl-1-oxo-1,3-dihydro-2-benzofuran-5-yl)oxy]methyl}piperidine-1-carboxylate.

$^1$H NMR (500 MHz, $CDCl_3$), δ 7.74 (d, J=8.4 Hz, 1H), 6.96 (d, J=8.4 Hz, 1H), 5.20 (s, 2H), 4.19 (m, 2H), 3.92 (d, J=6.2 Hz, 2H), 2.77 (m, 2H), 2.16 (s, 3H), 2.06-2.00 (m, 1H), 1.83 (d, J=13.1 Hz, 2H), 1.47 (s, 9H), 1.40-1.28 (m, 2H). LC-MS (IE, m/z): 384 [M+23]$^+$.

Step B: 4-Methyl-5-(piperidin-4-ylmethoxy)-2-benzofuran-1(3H)-one tert-Butyl 4-{[(4-methyl-1-oxo-1,3-dihydro-2-benzofuran-5-yl)oxy]methyl}piperidine-1-carboxylate (71 mg, 0.20 mmol) was dissolved in DCM (2 mL) and was treated by trifluoroacetic acid (1.0 mL, 13 mmol) at room temperature for 3 hours. The solvent was removed under reduced pressure and the residue was re-dissolved in EtOAc, then washed with of saturated sodium bicarbonate solution. The aqueous layer was extracted with EtOAc (2×) and the combined organic layers were dried ($Na_2SO_4$), filtered and concentrated to provide 4-methyl-5-(piperidin-4-ylmethoxy)-2-benzofuran-1(3H)-one which was used directly in the next step without further purification. LC-MS (IE, m/z): 262 [M+1]$^+$.

Intermediate 63

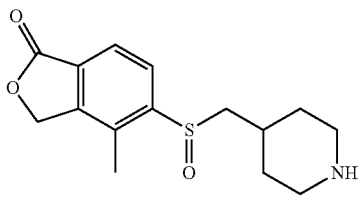 [SMILES: Cc1c(S(=O)CC2CCNCC2)ccc2c1COC2=O]

4-Methyl-5-[(piperidin-4-ylmethyl)sulfinyl]-2-benzofuran-1(3H)-one

Step A: tert-butyl 4-{[(4-methyl-1-oxo-1,3-dihydro-2-benzofuran-5-yl)sulfinyl]methyl}piperidine-1-carboxylate tert-Butyl 4-{[(4-methyl-1-oxo-1,3-dihydro-2-benzofuran-5-yl)sulfanyl]methyl}piperidine-1-carboxylate (81 mg, 0.22 mmol) was dissolved in DCM (2 mL) and was treated by meta-chloroperbenzoic acid (48 mg, 0.22 mmol) at room temperature for 4 hours. The reaction mixture was diluted with dichloromethane, washed with saturated sodium bicarbonate solution (2×), then dried over $Na_2SO_4$, filtered and concentrated to provide tert-butyl 4-{[(4-methyl-1-oxo-1,3-dihydro-2-benzofuran-5-yl)sulfinyl]methyl}piperidine-1-carboxylate.

LC-MS (IE, m/z): 394 [M+1]$^+$; 392 [M−1]$^+$.

Step B: 4-Methyl-5-[(piperidin-4-ylmethyl)sulfinyl]-2-benzofuran-1(3H)-one tert-Butyl 4-{[(4-methyl-1-oxo-1,3-dihydro-2-benzofuran-5-yl)sulfinyl]methyl}piperidine-1-carboxylate (4.2 mg, 0.21 mmol) was dissolved in dichloromethane (2 mL) and was treated with trifluoromethylacetic acid (1 mL) at room temperature for 2 hours. The solvent was removed in vacuo and the residue was re-dissolved in 1 mL of THF and was mixed with 1 mL of sat NaHCO3. After stirring at room temperature for 10 minutes, the mixture was concentrated in vacuo, and the resulting solid extracted with 10 mL 1:2 MeOH/DCM. The combined organics were concentrated in vacuo to provide 4-methyl-5-[(piperidin-4-ylmethyl)sulfinyl]-2-benzofuran-1(3H)-one which was used directly in the next step without further purification. LC-MS (IE, m/z): 294 [M+1]$^+$.

Intermediate 64

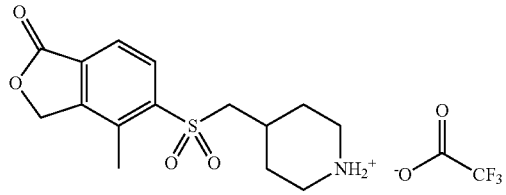

4-{[(4-Methyl-1-oxo-1,3-dihydro-2-benzofuran-5-yl)sulfonyl]methyl}piperidinium Trifluoroacetate Step A: tert-Butyl 4-{[(4-methyl-1-oxo-1,3-dihydro-2-benzofuran-5-yl)sulfonyl]methyl}piperidine-1-carboxylate tert-Butyl 4-{[(4-methyl-1-oxo-1,3-dihydro-2-benzofuran-5-yl)sulfanyl]methyl}piperidine-1-carboxylate (180 mg, 0.48 mmol) was dissolved in dichloromethane (2 mL) at room temperature and was treated with meta-chloroperbenzoic acid (240 mg, 0.96 mmol) for 3 hours. The reaction was then diluted with DCM and washed with saturated sodium bicarbonate solution. Then organic phase was dried over anhydrous $Na_2SO_4$, filtered, and concentrated. The resulting residue was purified by MPLC (eluted by 0→10% MeOH/

DCM gradient) to provide tert-butyl 4-{[(4-methyl-1-oxo-1,3-dihydro-2-benzofuran-5-yl)sulfonyl]methyl}piperidine-1-carboxylate. LC-MS (IE, m/z): 432 [M+23]+.

Step B: 4-{[(4-Methyl-1-oxo-1,3-dihydro-2-benzofuran-5-yl)sulfonyl]methyl}piperidinium Trifluoroacetate tert-Butyl 4-{[(4-methyl-1-oxo-1,3-dihydro-2-benzofuran-5-yl)sulfonyl]methyl}piperidine-1-carboxylate (160 mg, 0.40 mmol) was dissolved in DCM (2 mL) at room temperature and was treated with trifluoromethylacetic acid (1.0 ml, 13 mmol) for 2 hours. Then solvent was removed and was dried on high vacuum pump to provide 4-{[(4-methyl-1-oxo-1,3-dihydro-2-benzofuran-5-yl)sulfonyl]methyl}piperidinium trifluoroacetate which was used directly in the next step without further purification. LC-MS (IE, m/z): 309 [M+1]+.

Intermediate 65

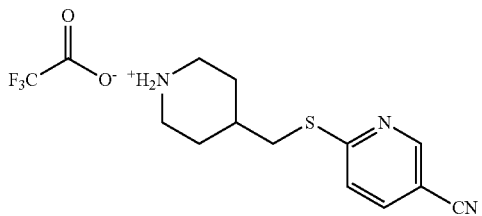 [SMILES: O=C([O-])C(F)(F)F ; N#Cc1ccc(SCC2CC[NH2+]CC2)nc1]

4-{[(5-Cyanopyridin-2-yl)sulfanyl]methyl}piperidinium Trifluoroacetate

Step A: 6-Sulfanylpyridine-3-carbonitrile

6-Chloro-3-Nitrilpyridine (4.0 g, 29 mmol) was dissolved in DMF (50 mL) and was treated with sodium sulfide hydrate (6.42 g, 87 mmol) at room temperature and the mixture stirred over night. The reaction was then poured into 300 mL of water and white precipitate was collected by filtration. The filter cake was washed with a small amount of water and was dried by air flow for 30 minutes. The resulting solid was transferred to a round bottom flask and dried under high vacuum for 12 h to provide 6-sulfanylpyridine-3-carbonitrile. LC-MS (IE, m/z): 135 [M+1]+.

Step B: tert-Butyl 4-{[(5-cyanopyridin-2-yl)sulfanyl]methyl}piperidine-1-carboxylate 6-Sulfanylpyridine-3-carbonitrile (220 mg, 1.6 mmol) was dissolved in DMF (10 mL) in a round bottom flask at room temperature. tert-butyl 4-(bromomethyl)piperidine-1-carboxylate (530 mg, 1.9 mmol) was added, followed by potassium carbonate (440 mg, 3.2 mmol). The resulting mixture was heated to 80° C. and stirred over night. The reaction mixture was diluted with EtOAc, washed with water and brine, then dried over anhydrous sodium sulfate, filtered and concentrated. The resulting residue was purified by MPLC (eluent: 0→100% EtOAc/Hexane gradient) to provide tert-Butyl 4-{[(5-cyanopyridin-2-yl)sulfanyl]methyl}piperidine-1-carboxylate. $^1$H NMR δ (ppm) (500 Hz, CDCl$_3$): 8.64 (d, J=2.1 Hz, 1H), 7.64 (dd, J=8.4, 2.2 Hz, 1H), 4.11 (m, 2H), 3.17 (d, J=6.8 Hz, 2H), 2.68 (m, 2H), 1.84-1.80 (m, 2H), 1.80-1.72 (m, 1H), 1.55 (s, 9H), 1.28-1.16 (m, 2H). LC-MS (IE, m/z): 356 [M+23]+.

Step C: 4-{[(5-Cyanopyridin-2-yl)sulfanyl]methyl}piperidinium Trifluoroacetate tert-Butyl 4-{[(5-cyanopyridin-2-yl)sulfanyl]methyl}piperidine-1-carboxylate (100 mg, 0.30 mmol) was dissolved in DCM (1 mL) at room temperature in a clear vial. Trifluoromethylacetic acid (1.0 mL, 13 mmol) was added and the mixture stirred for 2 hours. The solvent was removed under reduced pressure and the resulting residue was re-dissolved in DCM and concentrated in vacuo to remove excess TFA. The resulting residue was triturated with diethyl ether and dried under high vacuum to provide 4-{[(5-cyanopyridin-2-yl)sulfanyl]methyl}piperidinium trifluoroacetate which was used directly in the next step without further purification.

LC-MS (IE, m/z): 234 [M+1]+.

Intermediate 66

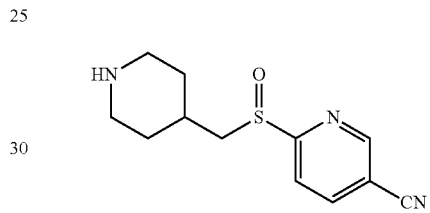

6-[(Piperidin-4-ylmethyl)sulfinyl]pyridine-3-carbonitrile

6-[(Piperidin-4-ylmethyl)sulfinyl]pyridine-3-carbonitrile was prepared in a similar fashion the synthesis of INTERMEDIATE 63 starting from tert-Butyl 4-{[(5-cyanopyridin-2-yl)sulfanyl]methyl}piperidine-1-carboxylate. LC-MS (IE, m/z): 234 [M+1]+.

Intermediate 67

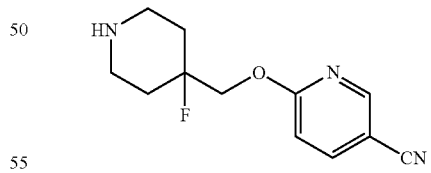

6-[(4-Fluoropiperidin-4-yl)methoxy]pyridine-3-carbonitrile

6-[(4-Fluoropiperidin-4-yl)methoxy]pyridine-3-carbonitrile was prepared in a similar fashion to the synthesis previously described for INTERMEDIATE 62 starting from tert-butyl 4-fluoro-4-(hydroxymethyl)piperidine-1-carboxylate and 6-chloro-3-nitrilpyridine. LC-MS (IE, m/z): 236 [M+1]+.

Intermediate 68

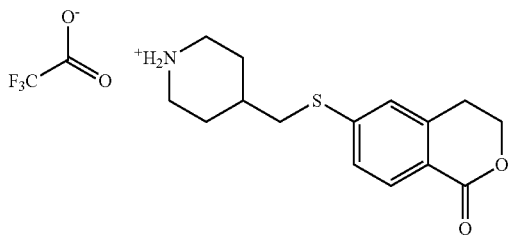 [SMILES: O=C([O-])C(F)(F)F ; O=C1OCCc2cc(SCC3CC[NH2+]CC3)ccc21]

4-{[(1-Oxo-3,4-dihydro-1H-isochromen-6-yl)sulfanyl]methyl}piperidinium Trifluoroacetate 4-{[(1-Oxo-3,4-dihydro-1H-isochromen-6-yl)sulfanyl]methyl}piperidinium Trifluoroacetate was prepared in a similar fashion to the synthesis previously described for INTERMEDIATE 61 starting from tert-butyl 4-(bromomethyl)piperidine-1-carboxylate and 6-bromo-3,4-dihydro-1H-isochromen-1-one. LC-MS (IE, m/z): 278 [M+1]$^+$.

Intermediate 69

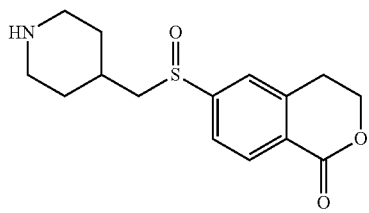

6-[(Piperidin-4-ylmethyl)sulfinyl]-3,4-dihydro-1H-isochromen-1-one

6-[(Piperidin-4-ylmethyl)sulfinyl]-3,4-dihydro-1H-isochromen-1-one was prepared in a similar fashion to the synthesis previously described for INTERMEDIATE 63 starting from tert-butyl 4-{[(1-oxo-3,4-dihydro-1H-isochromen-6-yl)sulfanyl]methyl}piperidine-1-carboxylate.
LC-MS (IE, m/z): 294 [M+1]$^+$.

Intermediate 70

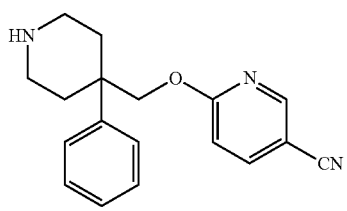 [SMILES: N#Cc1ccc(OCC2(c3ccccc3)CCNCC2)nc1]

6-[(4-Phenylpiperidin-4-yl)methoxy]pyridine-3-carbonitrile

6-[(4-Phenylpiperidin-4-yl)methoxy]pyridine-3-carbonitrile was prepared in a similar fashion to the synthesis previously described for INTERMEDIATE 62 starting from tert-butyl 4-phenyl-4-(hydroxymethyl)piperidine-1-carboxylate and 6-chloro-3-nitrilpyridine. LC-MS (IE, m/z): 294 [M+1]$^+$.

Intermediate 71

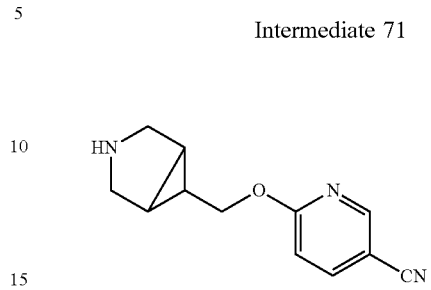

6-(3-Azabicyclo[3.1.0]hex-6-ylmethoxy)pyridine-3-carbonitrile 6-(3-Azabicyclo[3.1.0]hex-6-ylmethoxy)pyridine-3-carbonitrile was prepared in a similar fashion to the synthesis previously described for INTERMEDIATE 65 starting from tert-butyl 6-(hydroxymethyl)-3-azabicyclo[3.1.0]hexane-3-carboxylate and 6-chloro-3-nitrilpyridine.
LC-MS (IE, m/z): 216 [M+1]$^+$.

Intermediate 72

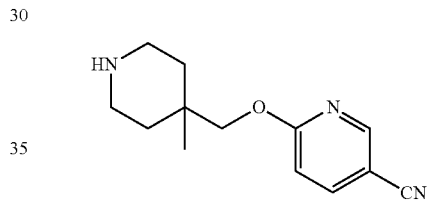

6-[(4-Methylpiperidin-4-yl)methoxy]pyridine-3-carbonitrile

6-[(4-Methylpiperidin-4-yl)methoxy]pyridine-3-carbonitrile was prepared in a similar fashion to the synthesis previously described for INTERMEDIATE 62 starting from tert-butyl 4-methyl-4-(hydroxymethyl)piperidine-1-carboxylate and 6-chloro-3-nitrilpyridine. LC-MS (IE, m/z): 232 [M+1]$^+$.

Intermediate 73

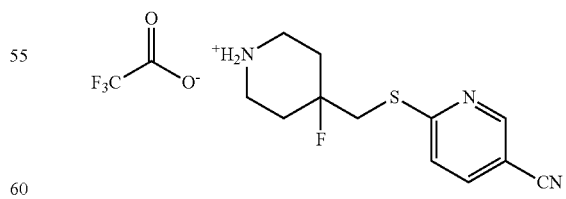

4-{[(5-Cyanopyridin-2-yl)sulfanyl]methyl}-4-fluoropiperidinium Trifluoroacetate

4-{[(5-Cyanopyridin-2-yl)sulfanyl]methyl}-4-fluoropiperidinium trifluoroacetate was prepared in a similar fashion to the synthesis previously described for INTERMEDIATE 61 starting from tert-butyl 4-fluoro-4-(hydroxymethyl)piperidine-1-carboxylate and 6-chloro-3-nitrilpyridine. LC-MS (IE, m/z): 252 [M+1]⁺.

Intermediate 74

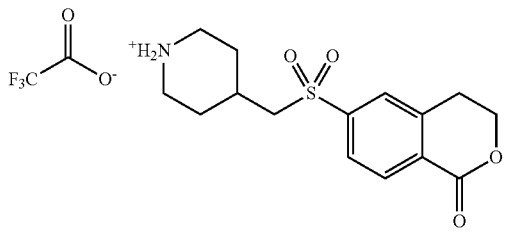 [SMILES: O=C([O-])C(F)(F)F ; O=C1OCCc2cc(S(=O)(=O)CC3CC[NH2+]CC3)ccc21]

4-{[(1-Oxo-3,4-dihydro-1H-isochromen-6-yl)sulfonyl]methyl}piperidinium Trifluoroacetate 4-{[(1-Oxo-3,4-dihydro-1H-isochromen-6-yl)sulfonyl]methyl}piperidinium trifluoroacetate was prepared in a similar fashion to the synthesis previously described for INTERMEDIATE 64 starting from tert-butyl 4-{[(1-oxo-3,4-dihydro-1H-isochromen-6-yl)sulfanyl]methyl}piperidine-1-carboxylate. LC-MS (IE, m/z): 310 [M+1]⁺.

Intermediate 75

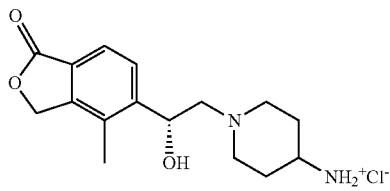

(R)-5-(2-4-Aminopiperidin-1-yl)-1-hydroxyethyl)-4-methylisobenzofuran-1(3-one hydrochloride (R)-5-(2-(4-Aminopiperidin-1-yl)-1-hydroxyethyl)-4-methylisobenzofuran-1(3H)-one hydrochloride was prepared in a similar fashion to that described for the synthesis of INTERMEDIATE 59 starting from tert-butyl piperidin-4-ylcarbamate and 4-methyl-5-[(2R)-oxiran-2-yl]-2-benzofuran-1(3H)-one. LC-MS (IE, m/z): 291 [M+1]⁺.

Intermediate 76

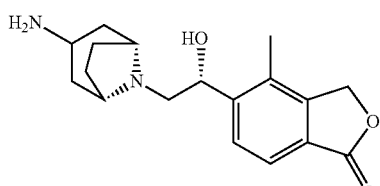

5-((1R)-2-((1R,5S)-3-Amino-8-azabicyclo[3.2.1]octan-8-yl)-1-hydroxyethyl)-4-methylisobenzofuran-1(3H)-one Hydrochloride 5-((1R)-2-((1R,5S)-3-Amino-8-azabicyclo[3.2.1]octan-8-yl)-1-hydroxyethyl)-4-methylisobenzofuran-1(3H)-one hydrochloride was prepared in a similar fashion to that described for the synthesis of INTERMEDIATE 59 starting from tert-butyl (1R,5S)-8-azabicyclo[3.2.1]octan-3-ylcarbamate and 4-methyl-5-[(2R)-oxiran-2-yl]-2-benzofuran-1(3H)-one. LC-MS (IE, m/z): 303 [M+1]⁺.

Intermediate 77

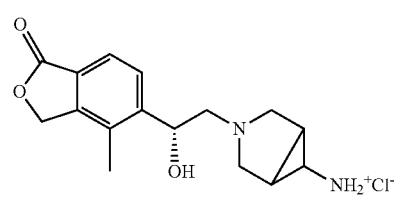

5-((1R)-2-(6-Amino-3-azabicyclo[3.1.0]hexan-3-yl)-1-hydroxyethyl)-4-methylisobenzofuran-1(3H)-one Hydrochloride 5-((1R)-2-(6-Amino-3-azabicyclo[3.1.0]hexan-3-yl)-1-hydroxyethyl)-4-methylisobenzofuran-1(3H)-one hydrochloride was prepared in a similar fashion to that described for the synthesis of INTERMEDIATE 59 starting from tert-butyl 3-azabicyclo[3.1.0]hexan-6-ylcarbamate and 4-methyl-5-[(2R)-oxiran-2-yl]-2-benzofuran-1(3H)-one.

Example 1

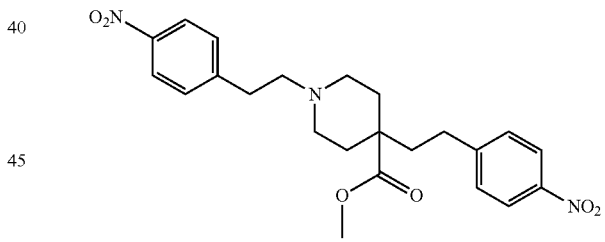

Methyl 1,4-bis[2-(4-nitrophenyl)ethyl]piperidine-4-carboxylate

Step A: 1-tert-Butyl 4-methyl 4-[2-(4-nitrophenyl)ethyl]piperidine-1,4-dicarboxylate A solution of 1-tert-butyl 4-methyl piperidine-1,4-dicarboxylate (0.50 g, 2.1 mmol) in THF (30 mL) was slowly dropped into a fresh batch of LDA solution (prepared from diisopropylamine (0.35 mL, 2.5 mmol) and n-butyllithium (2.5 M, 0.9 mL, 2.3 mmol) at −78° C. After stirring the mixture for 30 minutes, a solution of 1-(2-iodoethyl)-4-nitrobenzene (0.57 g, 2.1 mmol) in THF (30 mL) was dropped into the solution. 1-tert-butyl 4-methyl 4-[2-(4-nitrophenyl)ethyl]piperidine-1,4-dicarboxylate was isolated after chromatography.

LC-MS (IE, m/z): 393 [M+1]⁺.

Step B: Methyl 1,4-bis[2-(4-nitrophenyl)ethyl]piperidine-4-carboxylate

To a flask charged with 1-tert-butyl 4-methyl 4-[2-(4-nitrophenyl)ethyl]piperidine-1,4-dicarboxylate (0.22 g, 0.55 mmol) was added TFA (2 mL). The mixture was allowed to stir at RT for 30 minutes, at which point LC indicated complete removal of the Boc group. The volatiles were removed in vacuo. To the resulting amine was added (4-nitrophenyl)acetaldehyde (0.16 g, 0.55 mmol) and titanium (IV) isopropoxide (1.3 ml, 4.4 mmol). The mixture was allowed to stir for 15 minutes before ethanol (3 mL) and sodium cyanoborohydride (0.28 g, 4.4 mmol) were added to the reaction. The mixture stirred at RT for 16 hours. After work-up, mass-directed HPLC provided methyl 1,4-bis[2-(4-nitrophenyl)ethyl]piperidine-4-carboxylate.
LC-MS (IE, m/z): 442 [M+1]+.

Example 2

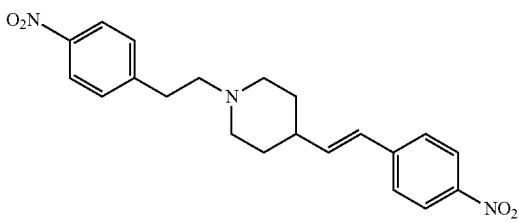 [SMILES: O=[N+]([O-])c1ccc(/C=C/C2CCN(CCc3ccc([N+](=O)[O-])cc3)CC2)cc1]

4-[(E)-2-(4-Nitrophenyl)ethenyl]-1-[2-(4-nitrophenyl)ethyl]piperidine

A mixture of 4-[(E)-2-(4-nitrophenyl)ethenyl]piperidinium chloride (0.13 g, 0.48 mmol), 1-(2-bromoethyl)-4-nitrobenzene (0.22 g, 0.96 mmol), and triethylamine (0.40 mL, 2.9 mmol) in DMF was stirred at 60° C. for 30 hours. The mixture was cooled and diluted with water and ethyl acetate and the layers separated. The organic layer was washed successively with water (3×) and brine, then dried (MgSO4), filtered and concentrated. Purification by prep-TLC (9:0.8:0.2 DCM:MeOH:TEA) provided 4-[(E)-2-(4-nitrophenyl)ethenyl]-1-[2-(4-nitrophenyl)ethyl]piperidine.
LC-MS (IE, m/z): 382 [M+1]+.

Example 3

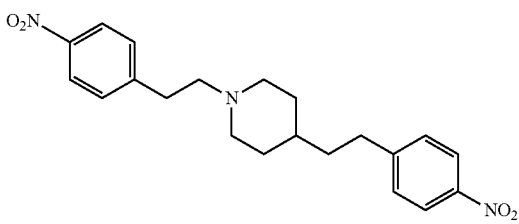 [SMILES: O=[N+]([O-])c1ccc(CCC2CCN(CCc3ccc([N+](=O)[O-])cc3)CC2)cc1]

1,4-bis[2-(4-Nitrophenyl)ethyl]piperidine 1,4-bis[2-(4-nitrophenyl)ethyl]piperidine was prepared in a similar fashion to that described for the synthesis of EXAMPLE 2 starting from 4-[2-(4-nitrophenyl)ethyl]piperidinium chloride. LC-MS (IE, m/z): 384 [M+1]+.

Example 4

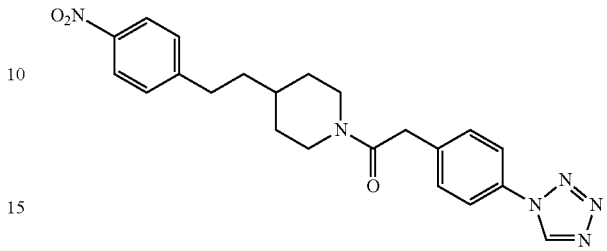

2-(4-(1H-Tetrazol-1-yl)phenyl)-1-(4-(4-nitrophenethyl)piperidin-1-yl)ethanone

[4-(1H-Tetrazol-1-yl)phenyl]acetic acid (57 mg, 0.28 mmol) and 4-[(E)-2-(4-nitrophenyl)ethenyl]piperidinium chloride (75 mg, 0.28 mmol) were dissolved in dichloromethane (30 ml) and treated with EDC (53 mg, 0.28 mmol) and diisopropylethyl amine (0.058 ml, 0.33 mmol). The reaction was stirred for 16 hrs.

The reaction was washed with 1 N hydrochloric acid, saturated aqueous NaHCO3, and brine, then dried over Na2SO4 then filtered and concentrated. The residue was purified by mass directed HPLC to yield 2-(4-(1H-tetrazol-1-yl)phenyl)-1-(4-(4-nitrophenethyl)piperidin-1-yl)ethanone. 1H NMR (500 MHz, DMSO): δ 10.06 (s, 1H), 8.13 (d, J=8.4 Hz, 2H), 7.82 (d, J=8.2 Hz, 2H), 7.49 (d, J=5.5 Hz, 2H), 7.47 (d, J=5.5 Hz, 2H), 4.37 (d, J=13 Hz, 1H), 3.97 (d, J=13.9 Hz, 1H), 3.81 (s, 2H), 2.97 (t, J=12 Hz, 1H), 2.72 (t, J=7.75 Hz, 2H), 2.52 (t, J=12.5 Hz, 1H), 1.71 (b, 2H), 1.71 (b, 1H), 1.44-1.54 (m, 2H), 0.94-1.04 (m, 2H). LC/MS (M+1)+=421.

Example 5

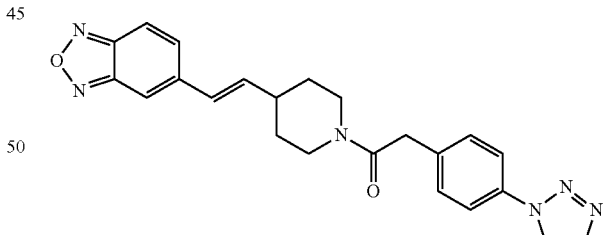

1-{4-[(E)-2-(2,1,3-Benzoxadiazol-5-yl)ethenyl]piperidin-1-yl}-2-[4-(1H)tetrazol-1-yl)phenyl]ethanone In a 8 ml, reaction vial, was added [4-(1H-tetrazol-1-yl)phenyl]acetic acid (45 mg, 0.22 mmol), EDC (43 mg, 0.22 mmol), 1H-benzotriazol-1-ol hydrate (34.1 mg, 0.222 mmol) and dichloromethane (2 mL). The reaction was stirred at room temperature for 10 min. To above reaction was added 4-[(E)-2-(2,1,3-benzoxadiazol-5-yl)ethenyl]piperidinium chloride (51 mg, 0.22 mmol) and triethylamine (0.031 mL, 0.22 mmol) in dichloromethane (1.0 mL). The reaction was stirred at room temperature under $N_2$ for 18 hr, diluted with dichloromethane, washed with aqueous sodium bicarbonate, brine and water. The organic phase was dried over $MgSO_4$, filtered and concentrated. 1-{4-[(E)-2-(2,1,3-benzoxadiazol-5-yl)ethenyl]piperidin-1-yl}-2-[4-(1H)tetrazol-1-yl)phenyl]ethanone was obtained after purification by flash column chromatography. $^1$H NMR (500 MHz, DMSO-$d_6$): 10.06 (s, 1H), 7.4-8.0 (m, 7H), 6.4-6.8 (m, 2H), 4.44 (m, 1H), 4.06 (m, 1H), 3.86 (s, 2H), 1.0-3.4 (m, 7H). LC-MS (IE, m/z): 416 [M+1]$^+$.

Example 6

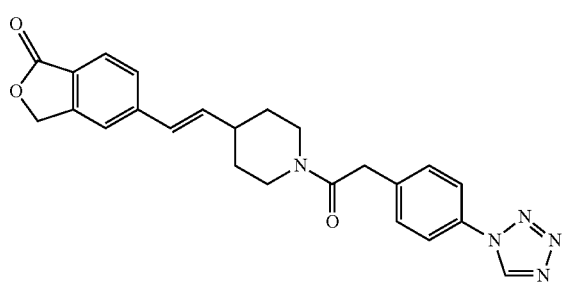 [SMILES: O=C1OCc2cc(/C=C/C3CCN(C(=O)Cc4ccc(-n5cnnn5)cc4)CC3)ccc21]

5-[(E))-2-(1-{[4-(1H)-tetrazol-1-yl)phenyl]acetyl}piperidin-4-yl)ethenyl]-2-benzofuran-1(3H)-one 5-[(E)-2-(1-{[4-(1H)-tetrazol-1-yl)phenyl]acetyl}piperidin-4-yl)ethenyl]-2-benzofuran-1(3H)-one was prepared in a similar fashion to that described for the synthesis of EXAMPLE 5 starting from 4-[(E)-2-(1-oxo-1,3-dihydro-2-benzofuran-5-yl)ethenyl]piperidinium chloride and [4-(1H-tetrazol-1-yl)phenyl]acetic acid.

$^1$H NMR (500 MHz, CDCl$_3$): 9.01 (s, 1H), 7.3-7.9 (m, 7H), 6.2-6.6 (m, 2H), 5.27 (s, 2H), 4.68 (m, 1H), 3.96 (m, 1H), 3.83 (s, 2H), 1.1-2.3 (m, 7H). LC-MS (IE, m/z): 430 [M+1]$^+$.

Example 7

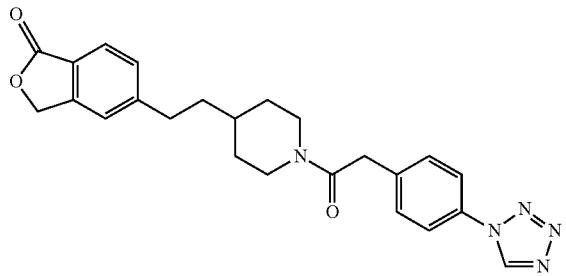 [SMILES: O=C1OCc2cc(CCC3CCN(C(=O)Cc4ccc(-n5cnnn5)cc4)CC3)ccc21]

5-[2-(1-{[4-(1H-Tetrazol-1-yl)phenyl]acetyl}piperidin-4-yl)ethyl]-2-benzofuran-1(3H)-one 5-[(E)-2-(1-{[4-(1H-Tetrazol-1-yl)phenyl]acetyl}piperidin-4-2-benzofuran-1(3H)yl)ethyenyl] (39 mg, 0.091 mmol) was dissolved in methanol (5 mL), and treated with palladium on carbon (5%, 9.6 mg, 0.091 mmol). The reaction was stirred under $H_2$ at 1 atm for 18 hr. The reaction was filtered through a pad of diatomaceous earth and concentrated to provide 5-[2-(1-{[4-(1H-tetrazol-1-yl)phenyl]acetyl}piperidin-4-yl)ethyl]-2-benzofuran-1(3H)-one.

$^1$H NMR (500 MHz, CDCl$_3$, δ in ppm): 9.05 (s, 1H), 7.85 (d, J=8.0 Hz, 1H), 7.70 (d, J=8.2 Hz, 2H), 7.49 (d, J=8.2 Hz, 2H), 7.36 (d, J=8.0 Hz, 1H), 7.30 (s, 1H), 5.30 (s, 2H), 4.69 (m, 1H), 3.94 (m, 1H), 3.84 (s, 2H), 3.07 (m, 1H), 2.78 (m, 2H), 2.62 (m, 1H), 1.1-2.3 (m, 7H). LC-MS (IE, m/z): 432 [M+1]$^+$.

Example 8

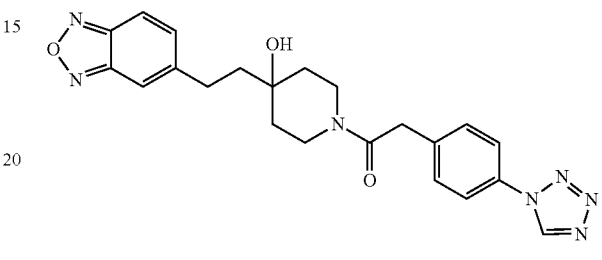

1-{4-[2-(2,1,3-Benzoxadiazol-5-yl)ethyl]-4-hydroxypiperidin-1-yl}-2-[4-(1H-tetrazol-1-yl)phenyl]ethanone Step A: 1-[4-(2,1,3-Benzoxadiazol-5-ylethynyl)-4-hydroxypiperidin-1-yl]-2-[4-(1H-tetrazol-1-yl)phenyl]ethanone 5-bromo-2,1,3-benzoxadiazole (0.11 g, 0.55 mmol), 1-(4-ethynyl-4-hydroxypiperidin-1-yl)-2-[4-(1H-tetrazol-1-yl)phenyl]ethanone (0.16 g, 0.50 mmol), copper (I) iodide (0.0048 g, 0.025 mmol), dichlorobis(triphenylphosphine)palladium (II) (0.070 g, 0.1 mmol) were combined in DMF (2 mL) and flushed with nitrogen. Triethylamine (0.14 mL, 1.0 mmol) was added, the vessel sealed and the mixture heated in an oil bath at 80° C. for 12 h. The mixture was cooled, diluted with water and extracted with ethyl acetate (3×). The combined organic layers were washed successively with water (2×) and brine, then dried (Na$_2$SO$_4$), filtered and concentrated. Purification by MPLC (eluent gradient 10→50% EtOAc:hex.) provided 1-[4-(2,1,3-benzoxadiazol-5-ylethynyl)-4-hydroxypiperidin-1-yl]-2-[4-(1H-tetrazol-1-yl)phenyl]ethanone. $^1$H NMR (500 MHz, CDCl$_3$, δ in ppm): 9.06 (s, 1H), 7.93 (s, 1H), 7.82 (d, J=9.5 Hz, 1H), 7.70 (d, J=8.5 Hz, 2H), 7.50 (d, J=8.5 Hz, 2H), 7.36 (d, J=9.0 Hz, 1H), 4.02 (m, 1H), 3.88 (s, 2H), 3.81 (m, 1H), 3.68 (m, 1H), 3.58 (m, 1H), 3.07 (br s, 1H), 2.06 (m, 2H), 1.90 (m, 2H). LC-MS (IE, m/z): 430 [M+1]$^+$.

Step B: 1-{4-[2-(2,1,3-benzoxadiazol-5-yl)ethyl]-4-hydroxypiperidin-1-yl}-2-[4-(1H-tetrazol-1-yl)phenyl]ethanone A mixture of 1-[4-(2,1,3-benzoxadiazol-5-ylethynyl)-4-hydroxypiperidin-1-yl]-2-[4-(1H-tetrazol-1-yl)phenyl]ethanone (14 mg, 0.033 mmol) and palladium on carbon (7.0 mg, 0.0065 mmol) in ethyl acetate (1 mL) was stirred under a hydrogen atmosphere (1 atm) for 12 h. The mixture was filtered through a pad of diatomaceous earth and concentrated to provide 1-{4-[2-(2,1,3-benzoxadiazol-5-yl)ethyl]-4-hydroxypiperidin-1-yl}-2-[4-(1H-tetrazol-1-yl)phenyl]ethanone. $^1$H NMR (500 MHz, CDCl$_3$, δ in ppm): 9.03 (s, 1H), 7.80 (d, J=9.5 Hz, 1H), 7.71 (d, J=8.5 Hz, 2H), 7.60 (s, 1H), 7.52 (d, J=8.5 Hz, 2H), 7.29 (d, J=9.5 Hz, 1H), 4.48 (m, 1H), 3.87 (s, 2H), 3.77 (m, 1H), 3.55 (m, 1H), 3.16 (m, 1H), 2.87 (m, 2H), 2.37 (m, 2H), 2.06 (m, 2H), 1.88 (m, 2H). LC-MS (IE, m/z): 434 [M+1]$^+$.

Example 9

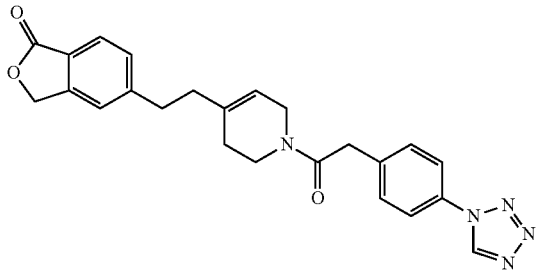 [SMILES: O=C1OCc2cc(CCC3=CCN(C(=O)Cc4ccc(-n5cnnn5)cc4)CC3)ccc21]

5-[2-(1-{[4-(1H-Tetrazol-1-yl)phenyl]acetyl}-1,2,3,6-tetrahydropyridin-4-yl)ethyl]-2-benzofuran-1(3H)-one Step A: 5-[(4-Hydroxy-1-{[4-(1H-tetrazol-1-yl)phenyl]acetyl}piperidin-4-yl)ethynyl]-2-benzofuran-1(3H)-one 5-bromo-2-benzofuran-1(3H)-one (0.064 g, 0.30 mmol), 1-(4-ethynyl-4-hydroxypiperidin-1-yl)-2-[4-(1H-tetrazol-1-yl)phenyl]ethanone (0.093 g, 0.30 mmol), triphenylphosphine (0.016 g, 0.060 mmol), tris(dibenzylideneacetonedipalladium(0) (0.014 g, 0.015 mmol) were combined in THF (2 mL) and flushed with nitrogen. Tetrabutylammonium fluoride solution in THF (1 M, 0.60 mL, 0.60 mmol) was added, the vessel sealed and the mixture heated in an oil bath at 60° C. for 3 h. The mixture was cooled, diluted with water and extracted with ethyl acetate (3×). The combined organic layers were washed successively with water (2×) and brine, then dried (Na$_2$SO$_4$), filtered and concentrated. Purification by MPLC (eluent gradient 10→50% EtOAc:hex.) provided 5-[(4-hydroxy-1-{[4-(1H-tetrazol-1-yl)phenyl]acetyl}piperidin-4-yl)ethynyl]-2-benzofuran-1(3H)-one. LC-MS (IE, m/z): 444 [M+1]$^+$.

Step B: 5-[2-(4-Hydroxy-1-{[4-(1H-tetrazol-1-yl)phenyl]acetyl}piperidin-4-yl)ethyl]-2-benzofuran-1(3H)-one A mixture of 5-[(4-hydroxy-1-{[4-(1H-tetrazol-1-yl)phenyl]acetyl}piperidin-4-yl)ethynyl]-2-benzofuran-1(3H)-one (28 mg, 0.063 mmol) and palladium on carbon (13 mg, 0.0065 mmol) in ethanol (2 mL) was stirred under a hydrogen atmosphere (1 atm) for 12 h. The mixture was filtered through a pad of diatomaceous earth and concentrated. Purification by prep-TLC (2% MeOH in EtOAc eluent) provided 5-[2-(4-hydroxy-1-{[4-(1H-tetrazol-1-yl)phenyl]acetyl}piperidin-4-yl)ethyl]-2-benzofuran-1(3H)-one.
$^1$H NMR (500 MHz, CDOD$_3$, δ in ppm): 9.77 (s, 1H), 7.85 (d, J=8.5 Hz, 2H), 7.76 (d, J=8 Hz, 1H), 7.55 (d, J=8.5 Hz, 2H), 7.46 (s, 1H), 7.43 (d, J=8 Hz, 1H), 5.35 (s, 2H), 4.30 (m, 1H), 3.94 (s, 2H), 3.86 (m, 1H), 3.52 (m, 1H), 3.19-3.15 (overlapping m's, 3H), 2.85 (m, 2H), 1.79 (m, 2H), 1.69 (m, 2H). LC-MS (IE, m/z): 448 [M+1]$^+$.

Step C: 5-[2-(1-{[4-(1H-Tetrazol-1-yl)phenyl]acetyl}-1,2,3,6-tetrahydropyridin-4-yl)ethyl]-2-benzofuran-1(3H)-one Toluenesulfonic acid (1.6 mg, 8.6 μmol) was added to a stirred mixture of 5-[2-(4-hydroxy-1-{[4-(1H-tetrazol-1-yl)phenyl]acetyl}piperidin-4-yl)ethyl]-2-benzofuran-1(3H)-one (3.0 mg, 6.7 μmol) in benzene (0.5 mL) and the mixture was heated at reflux for 12 h. The mixture was cooled and concentrated, then purified by prep-TLC (2% MeOH in EtOAc eluent) to provide 5-[2-(1-{[4-(1H-Tetrazol-1-yl)phenyl]acetyl}-1,2,3,6-tetrahydropyridin-4-yl)ethyl]-2-benzofuran-1(3H)-one. $^1$H NMR (500 MHz, CDCl$_3$, δ in ppm): 9.04 (s, 1H), 7.87 (d, J=8 Hz, 1H), 7.71 (d, J=8.5 Hz, 2H), 7.50 (d, J=8.5 Hz, 2H), 7.36 (d, J=8 Hz, 1H), 7.30 (s, 1H) 5.35 (m, 1H), 5.32 (s, 2H), 4.12 (m, 1H), 4.00 (m, 1H), 3.88 (s, 2H), 3.78 (m, 1H), 3.61 (m, 1H), 3.01 (m, 2H), 2.89 (m, 2H), 2.39 (m, 2H). LC-MS (IE, m/z): 430 [M+1]$^+$.

Example 10

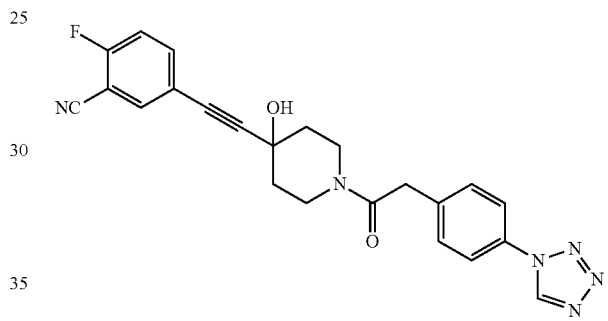

2-Fluoro-5-[(4-hydroxy-1-{[4-(1H-tetrazol-1-yl)phenyl]acetyl}piperidin-4-yl)ethynyl]benzonitrile 2-Fluoro-5-iodobenzonitrile (0.41 mg, 1.7 mmol), triphenylphosphine (0.088 g, 0.33 mmol), and tris(dibenzylideneacetone)dipalladium (0) (0.076 mg, 0.084 mmol) were dissolved in THF (15 ml) and flushed with nitrogen. The mixture was treated with 1-(4-ethynyl-4-hydroxypiperidin-1-yl)-2-[4-(1H-tetrazol-1-yl)phenyl]ethanone (520 mg, 1.7 mmol) followed by tetrabutylammonium fluoride solution in THF (1.0 M, 3.3 ml, 3.3 mmol), sealed and placed in an oil bath at 60° C. for 3 h. The mixture was cooled, diluted with water and ethyl acetate, and the layers separated. After the aqueous was extracted with additional ethyl acetate (2×), the combined organics were washed successively with water (2×) and brine, dried (Na$_2$SO$_4$) and concentrated. The resulting residue was purified by MPLC (eluent gradient 10→50% EtOAc:hex.) to provide 2-fluoro-5-[(4-hydroxy-1-{[4-(1H-tetrazol-1-yl)phenyl]acetyl}piperidin-4-yl)ethynyl]benzonitrile. $^1$H NMR (500 MHz, CDCl$_3$, δ in ppm): 9.04 (s, 1H), 7.72 (d, J=8.5 Hz, 2H), 7.70 (m, 1H), 7.67 (m, 1H), 7.52 (d, J=8.5 Hz, 2H), 7.24 (dd, J=8.5, 8.5 Hz, 1H), 4.03 (m, 1H), 3.88 (s, 2H), 3.80 (m, 1H), 3.66 (m, 1H), 3.56 (m, 2H), 2.02 (m, 2H), 1.89 (m, 2H). LC-MS (IE, m/z): 431 [M+1]$^+$.

Example 11

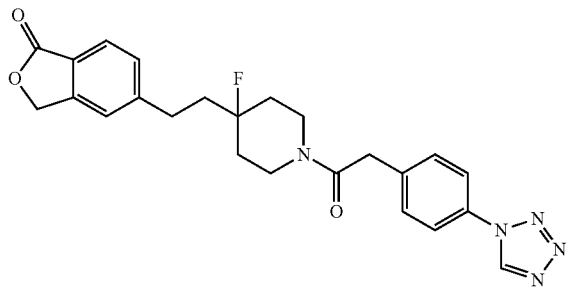 [SMILES: O=C1OCc2cc(CCC3(F)CCN(C(=O)Cc4ccc(-n5cnnn5)cc4)CC3)ccc21]

5-[2-(4-fluoro-1-{[4-(1H-tetrazol-1-yl)phenyl]
acetyl}piperidin-4-yl)ethyl]-2-benzofuran-1(3H)-one To a solution of DAST (5.3 µl, 0.040 mmol) in dichloromethane (1 ml) at −78° C. was added a solution of 5-[2-(4-hydroxy-1-{[4-(1H-tetrazol-1-yl)phenyl]acetyl}piperidin-4-yl)ethyl]-2-benzofuran-1(3H)-one (9.0 mg, 0.020 mmol) in dichloromethane (1 ml). The reaction stirred 1 h at −78 C, then 2 h at 0° C. The reaction mixture was diluted with ethyl acetate and washed with saturated NaHCO$_3$ and brine, then dried (Na$_2$SO$_4$), filtered and concentrated. Preparative-TLC (2% MeOH in EtOAc eluent system) provided 5-[2-(4-fluoro-1-{[4-(1H-tetrazol-1-yl)phenyl]acetyl}piperidin-4-yl)ethyl]-2-benzofuran-1(3H)-one.

$^1$H NMR (500 MHz, CDCl$_3$, δ in ppm): 9.02 (s, 1H), 7.88 (d, J=8 Hz, 1H), 7.72 (d, J=8.5 Hz, 2H), 7.53 (d, J=8.5 Hz, 2H), 7.40 (s, 1H), 7.37 (d, J=8 Hz, 1H), 5.32 (s, 2H), 4.61 (m, 1H), 4.05 (m, 1H), 3.85 (s, 2H), 3.60-3.45 (m, 2H), 3.04 (m, 2H), 2.91 (m, 2H), 2.03 (m, 2H), 1.95 (m, 2H). LC-MS (IE, m/z): 450 [M+1]$^+$.

Example 12

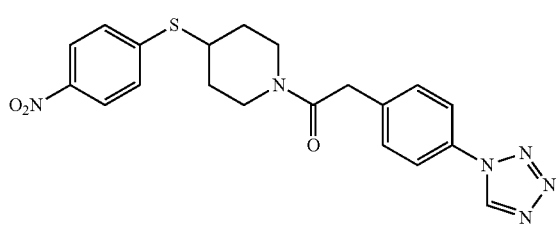 [SMILES: O=C(Cc1ccc(-n2cnnn2)cc1)N1CCC(Sc2ccc([N+](=O)[O-])cc2)CC1]

1-{4-[(4-Nitrophenyl)sulfanyl]piperidin-1-yl}-2-[4-(1H-tetrazol-1-yl)phenyl]ethanone To a solution of tert-butyl 4-[(4-nitrophenyl)sulfanyl]piperidine-1-carboxylate (0.23 g, 0.84 mmol) in 20 mL of anhydrous DCM was added sequentially [4-(1H-tetrazol-1-yl)phenyl]acetic acid (171 mg, 0.84 mmol), EDC (1980 mg, 1 mmol), HOBt (136 mg, 1 mmol) and triethylamine (0.51 g, 5.0 mmol) and the mixture was stirred at ambient temperature for 12 hours. When the reaction was complete, DCM (20 mL) was added and then the mixture was washed with brine. The organic layer was dried over anhydrous Na$_2$SO$_4$ and concentrated. The residue was purified by preparative TLC to afford 1-{4-[(4-nitrophenyl)sulfanyl]piperidin-1-yl}-2-[4-(1H-tetrazol-1-yl)phenyl]ethanone.

$^1$H-NMR (300 MHz, CDCl$_3$) δ ppm 9.0 (s, 1H), 8.14 (d, J=8.6 Hz, 2H), 7.67 (d, J=8.6 Hz, 2H), 7.38~7.48 (m, 4H), 4.27~4.35 (m, 1H), 3.81~3.91 (m, 3H), 3.52~3.61 (m, 3H), 3.27~3.37 (m, 1H), 3.13~3.23 (m, 1H), 1.97~2.12 (m, 2H), 1.58~1.70 (m, 2H).

Example 13

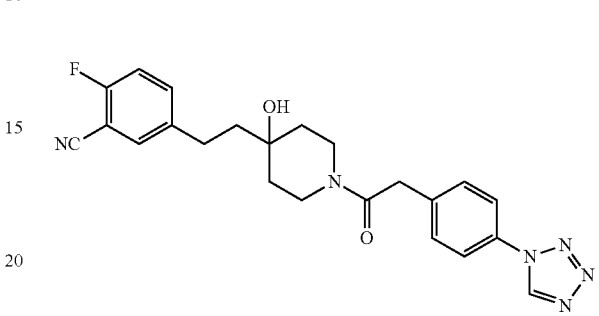

2-Fluoro-5-[2-(4-hydroxy-1-{[4-(1H-tetrazol-1-yl)phenyl]acetyl}piperidin-4-yl)ethyl]benzonitrile A mixture of 2-fluoro-5-[(4-hydroxy-1-{[4-(1H-tetrazol-1-yl)phenyl]acetyl}piperidin-4-yl)ethynyl]benzonitrile (140 mg, 0.33 mmol) and palladium on carbon (70 mg, 0.066 mmol) in methanol (10 mL) was stirred under a hydrogen atmosphere (1 atm) for 12 h. The mixture was filtered through a pad of diatomaceous earth and concentrated. Purification by prep-TLC (2% MeOH in EtOAc eluent) provided 2-fluoro-5-[2-(4-hydroxy-1-{[4-(1H-tetrazol-1-yl)phenyl]acetyl}piperidin-4-yl)ethyl]benzonitrile. $^1$H NMR (500 MHz, CDCl$_3$, δ in ppm): 9.06 (s, 1H), 7.65 (d, J=8.5 Hz, 2H), 7.45 (d, J=8.5 Hz, 2H), 7.41-7.38 (overlapping m's, 2H), 7.43 (dd, J=8.5, 8.5 Hz, 1H), 4.37 (m, 1H), 3.81 (s, 2H), 3.69 (m, 1H), 3.49 (m, 1H), 3.09 (m, 1H), 2.72 (m, 2H), 1.99 (br s, 1H), 1.74 (m, 2H), 1.64 (m, 2H), 1.54 (m, 2H). LC-MS (IE, m/z): 435 [M+1]$^+$.

Example 14

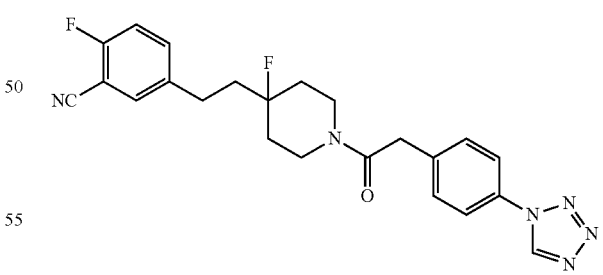

2-Fluoro-5-[2-(4-fluoro-1-{[4-(1H-tetrazol-1-yl)phenyl]acetyl}piperidin-4-yl)ethyl]benzonitrile 2-Fluoro-5-[2-(4-fluoro-1-{[4-(1H-tetrazol-1-yl)phenyl]acetyl}piperidin-4-yl)ethyl]benzonitrile was prepared in a similar fashion to that described for the synthesis of EXAMPLE 11 starting from 2-fluoro-5-[2-(4-hydroxy-1-{[4-(1H-tetrazol-1-yl)phenyl]acetyl}piperidin-4-yl)ethyl]

benzonitrile. ¹H NMR (500 MHz, CDCl₃, δ in ppm): 9.04 (s, 1H), 7.71 (d, J=8.5 Hz, 2H), 7.51 (d, J=8.5 Hz, 2H), 7.47-7.43 (overlapping m's, 2H), 7.17 (dd, J=8.5, 8.5 Hz, 1H), 4.35 (m, 1H), 3.87 (s, 2H), 3.75 (m, 1H), 3.53 (m, 1H), 3.12 (m, 1H), 2.77 (m, 2H), 1.79 (m, 2H), 1.71 (m, 2H), 1.55 (m, 2H). LC-MS (IE, m/z): 437 [M+1]⁺.

Example 15

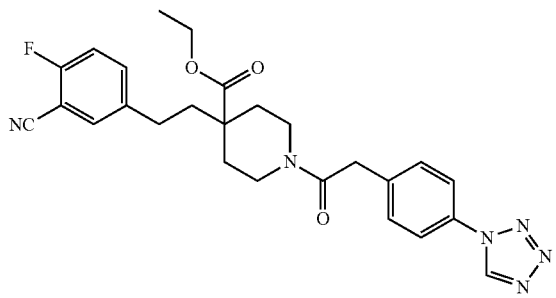 [SMILES: CCOC(=O)C1(CCc2ccc(F)c(C#N)c2)CCN(C(=O)Cc2ccc(-n3cnnn3)cc2)CC1]

Ethyl 4-[2-(3-cyano-4-fluorophenyl)ethyl]-1-{[4-(1H-tetrazol-1-yl)phenyl]acetyl}piperidine-4-carboxylate Ethyl 4-[2-(3-cyano-4-fluorophenyl)ethyl]-1-{[4-(1H-tetrazol-1-yl)phenyl]acetyl}piperidine-4-carboxylate was prepared in a similar fashion to that described for the synthesis of EXAMPLE 5 starting from 4-[2-(3-cyano-4-fluorophenyl)ethyl]-4-(ethoxycarbonyl)piperidinium chloride and (3-chloro-4-cyanophenyl)acetic acid. ¹H-NMR (400 MHz, CDCl₃) δ ppm 9.00 (s, 1H), 7.71 (d, J=8.6 Hz, 2H), 7.46 (d, J=7.5 Hz, 2H), 7.30~7.36 (m, 2H), 7.15 (dd, J=9.0, 9.0 Hz, 1H), 4.43 (m, 1H), 4.05~4.23 (m, 2H), 3.75~3.86 (m, 3H), 2.80 (dd, J=11.6, 11.6 Hz, 1H), 2.51 (dd, J=8.4, 8.4 Hz, 2H), 2.24 (m, 1H), 1.98~2.11 (m, 2H), 1.72~1.84 (m, 2H), 1.41 (m, 1H), 1.27 (m, 3H).

Example 16

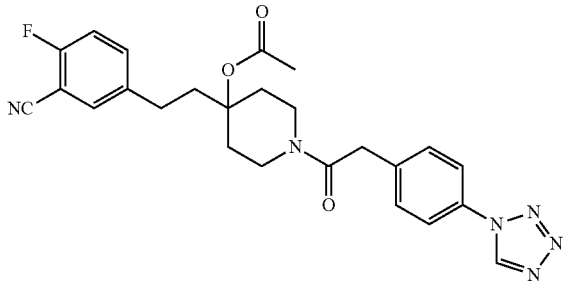 [SMILES: CC(=O)OC1(CCc2ccc(F)c(C#N)c2)CCN(C(=O)Cc2ccc(-n3cnnn3)cc2)CC1]

4-[2-(3-Cyano-4-fluorophenyl)ethyl]-1-{[4-(1H-tetrazol-1-yl)phenyl]acetyl}piperidin-4-yl acetate To a solution of 2-fluoro-5-[2-(4-hydroxy-1-{[4-(1H-tetrazol-1-yl)phenyl]acetyl}piperidin-4-yl)ethyl]benzonitrile (10 mg, 0.023 mmol) in DCM (1 ml) at room temperature was added acetic anhydride (4.3 μl, 0.046 mmol) followed by 4-dimethylaminopyridine (0.56 mg, 4.6 μmol). The mixture stirred 12 h at rt, then was washed with water and concentrated in vacuo to provide 4-[2-(3-cyano-4-fluorophenyl)ethyl]-1-{[4-(1H-tetrazol-1-yl)phenyl]acetyl}piperidin-4-yl acetate. ¹H NMR (500 MHz, CDCl₃, δ in ppm): 9.02 (s, 1H), 7.72 (d, J=8 Hz, 2H), 7.52 (d, J=8 Hz, 2H), 7.44-7.41 (overlapping m's, 2H), 7.17 (dd, J=8.5, 8.5 Hz, 1H), 4.50 (m, 1H), 3.86 (s, 2H), 3.78 (m, 1H), 3.34 (m, 1H), 2.98 (m, 1H), 2.62 (m, 2H), 2.40 (m, 2H), 2.23 (m, 2H), 2.09 (s, 3H), 1.54 (m, 2H). LC-MS (IE, m/z): 477 [M+1]⁺.

Example 17

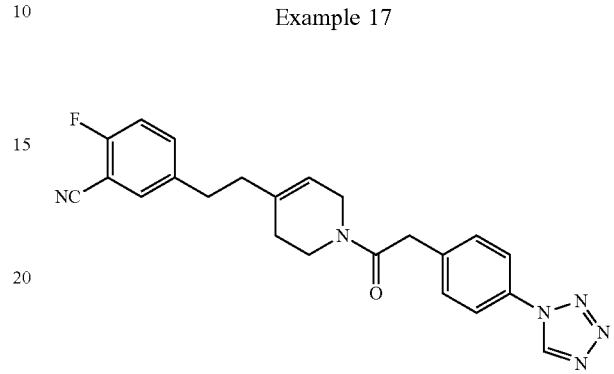

2-Fluoro-5-[2-(1-{[4-(1H-tetrazol-1-yl)phenyl]acetyl}-1,2,3,6-tetrahydropyridin-4-yl)ethyl]benzonitrile Toluenesulfonic acid (11 mg, 0.058 mmol) was added to a stirred mixture of 2-fluoro-5-[2-(4-hydroxy-1-{[4-(1H-tetrazol-1-yl)phenyl]acetyl}piperidin-4-yl)ethyl]benzonitrile (3.0 mg, 6.7 μM) in benzene (0.5 mL) and the mixture was heated at reflux for 12 h. The mixture was cooled and concentrated, then purified by prep-TLC (2% MeOH in EtOAc eluent) to provide 5-[2-(1-{[4-(1H-Tetrazol-1-yl)phenyl]acetyl}-1,2,3,6-tetrahydropyridin-4-yl)ethyl]-2-benzofuran-1(3H)-one. ¹H NMR (500 MHz, CDCl₃, δ in ppm): 9.04 (s, 1H), 7.72 (d, J=8 Hz, 2H), 7.51 (d, J=8 Hz, 2H), 7.47-7.40 (overlapping m's, 2H), 7.17 (dd, J=8.5, 8.5 Hz, 1H), 5.43 (m, 1H), 4.06 (m, 2H), 3.89 (s, 2H), 3.71 (m, 2H), 2.78 (m, 2H), 2.34 (m, 2H), 2.13 (m, 2H). LC-MS (IE, m/z): 417 [M+1]⁺.

Example 18

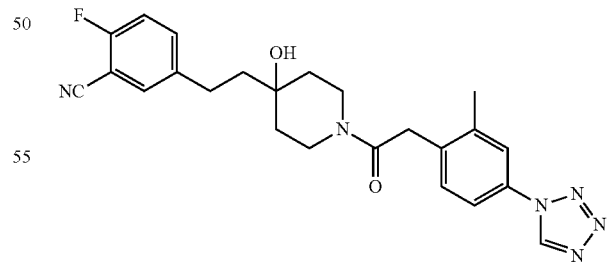

2-Fluoro-5-[2-(4-hydroxy-1-{[2-methyl-4-(1H-tetrazol-1-yl)phenyl]acetyl}piperidin-4-yl)ethyl]benzonitrile 2-fluoro-5-[2-(4-hydroxy-1-{[2-methyl-4-(1H-tetrazol-1-yl)phenyl]acetyl}piperidin-4-yl)ethyl]benzonitrile was prepared in a similar fashion to that described for the synthesis of EXAMPLE 4 starting from 4-[2-(3-cyano-4-fluorophenyl)ethyl]-4-hydroxypiperidinium chloride and [2-methyl-4-(1H-tetrazol-1-yl)phenyl]acetic acid. $^1$H NMR (500 MHz, CDCl$_3$, δ in ppm): 9.02 (s, 1H), 7.58 (s, 1H), 7.53-7.44 (overlapping m's, 3H), 7.35 (d, J=8.5 Hz, 1H), 7.18 (dd, J 9.9 Hz, 1H), 4.48 (m, 1H), 3.82 (s, 2H), 3.70 (m, 1H), 3.58 (m, 1H), 3.19 (m, 1H), 2.79 (m, 2H), 2.42 (s, 3H), 1.82 (m, 2H), 1.77 (m, 2H), 1.61 (m, 2H). LC-MS (IE, m/z): 449 [M+1]$^+$.

Example 19

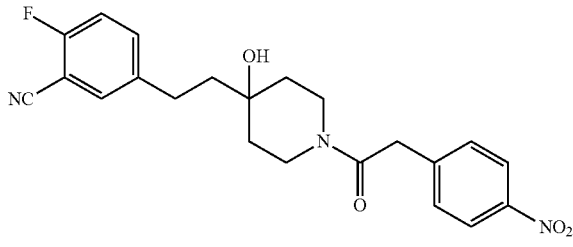 [SMILES: N#Cc1cc(CCC2(O)CCN(C(=O)Cc3ccc([N+](=O)[O-])cc3)CC2)ccc1F]

2-Fluoro-5-(2-{4-hydroxy-1-[(4-nitrophenyl)acetyl]piperidin-4-yl}ethyl)benzonitrile 2-Fluoro-5-[2-(4-hydroxy-1-[(4-nitrophenyl)acetyl]piperidin-4-yl}ethyl)benzonitrile was prepared in a similar fashion to that described for the synthesis of EXAMPLE 4 starting from 4-[2-(3-cyano-4-fluorophenyl)ethyl]-4-hydroxypiperidinium chloride and (4-nitrophenyl)acetic acid. $^1$H-NMR (CDCl$_3$, 400 MHz) δ ppm 8.17 (d, J=8.8 Hz, 2H), 7.38~7.47 (m, 4H), 7.12 (dd, J=8.8, 8.8 Hz, 1H), 4.40 (m, 1H), 3.84 (s, 2H), 3.66 (m, 1H), 3.49 (m, 1H), 3.11 (m, 1H), 2.68~2.75 (m, 2H), 1.69~1.79 (m, 2H), 1.50~1.67 (m, 3H), 1.40 (m, 1H).

Example 20

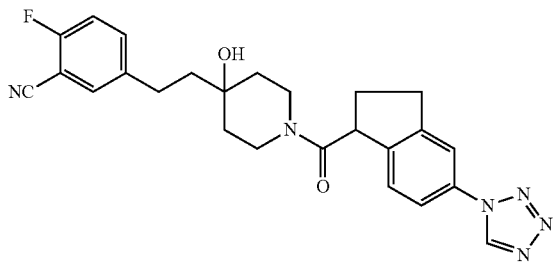 [SMILES: N#Cc1cc(CCC2(O)CCN(C(=O)C3CCc4cc(-n5cnnn5)ccc43)CC2)ccc1F]

2-Fluoro-5-[2-(4-hydroxy-1-{[5-(1H-tetrazol-1-yl)-2,3-dihydro-1H-inden-1-yl]carbonyl}piperidin-4-yl)ethyl]benzonitrile 2-fluoro-5-[2-(4-hydroxy-1-{[5-(1H-tetrazol-1-yl)-2,3-dihydro-1H-inden-1-yl]carbonyl}piperidin-4-yl)ethyl]benzonitrile was prepared in a similar fashion to that described for the synthesis of EXAMPLE 4 starting from 4-[2-(3-cyano-4-fluorophenyl)ethyl]-4-hydroxypiperidinium chloride and 5-(1H-tetrazol-1-yl)-2,3-dihydro-1H-indene-1-carboxylic acid. $^1$H NMR (500 MHz, CDCl$_3$, δ in ppm): 9.03 (s, 1H), 7.62 (s, 1H), 7.54-7.49 (overlapping m's, 3H), 7.38 (m, 1H), 7.19 (dd, J=8.5, 8.5 Hz, 1H), 4.49 (m, 1H), 4.47 (m, 1H), 4.00 (m, 1H), 3.25 (m, 2H), 3.09 (m, 1H), 2.83 (m, 2H), 2.56 (m, 1H), 2.41 (m, 1H), 1.86 (m, 2H), 1.77 (m, 2H), 1.69 (m, 2H). LC-MS (IE, m/z): 461 [M+1]$^+$.

Example 21

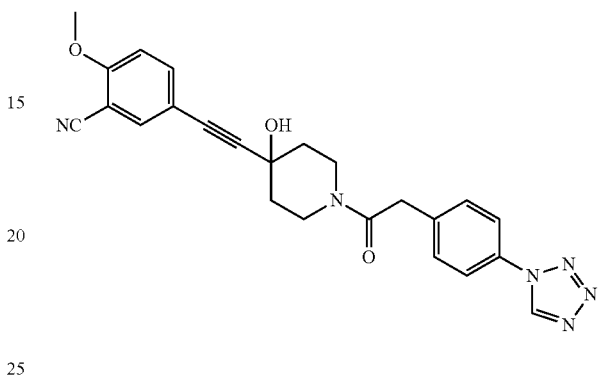

5-[(4-Hydroxy-1-{[4-(1H-tetrazol-1-yl)phenyl]acetyl}piperidin-4-yl)ethynyl]-2-methoxybenzonitrile 5-[(4-Hydroxy-1-{[4-(1H-tetrazol-1-yl)phenyl]acetyl}piperidin-4-yl)ethynyl]-2-methoxybenzonitrile was prepared in a similar fashion to that described for the synthesis of EXAMPLE 10 starting from 1-(4-ethynyl-4-hydroxypiperidin-1-yl)-2-[4-(1H-tetrazol-1-yl)phenyl]ethanone and 5-bromo-2-methoxybenzonitrile. $^1$H NMR (500 MHz, CDCl$_3$, δ in ppm): 9.02 (s, 1H), 7.72 (d, J=8.5 Hz, 2H), 7.65 (s, 1H), 7.61 (m, 1H), 7.52 (d, J=8.5 Hz, 2H), 6.97 (d, J=8.5 Hz, 1H), 4.07 (m, 1H), 3.99 (s, 3H), 3.88 (s, 2H), 3.76 (m, 1H), 3.58 (m, 1H), 3.33 (m, 1H), 2.02 (m, 2H), 1.83 (m, 2H). LC-MS (IE, m/z): 443 [M+1]$^+$.

Example 22

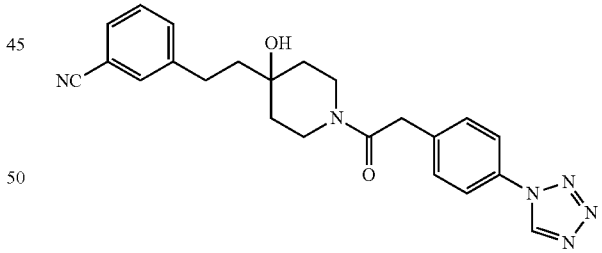

3-[2-(4-Hydroxy-1-{[4-(1H-tetrazol-1-yl)phenyl]acetyl}piperidin-4-yl)ethyl]benzonitrile Step A: 3-[(4-Hydroxy-1-{[4-(1H-tetrazol-1-yl)phenyl]acetyl}piperidin-4-yl)ethynyl]benzonitrile 3-[(4-hydroxy-1-{[4-(1H-tetrazol-1-yl)phenyl]acetyl}piperidin-4-yl)ethynyl]benzonitrile was prepared in a similar fashion to that described for the synthesis of EXAMPLE 10 starting from 1-(4-ethynyl-4-hydroxypiperidin-1-yl)-2-[4-(1H-tetrazol-1-yl)phenyl]ethanone and 3-bromobenzonitrile. $^1$H NMR (500 MHz, CDCl$_3$, δ in ppm): 9.03 (s, 1H), 7.73-7.66 (overlapping m's, 5H), 7.53-

7.48 (overlapping m's, 3H), 4.06 (m, 1H), 3.88 (s, 2H), 3.81 (m, 1H), 3.65 (m, 1H), 3.57 (m, 1H), 2.05 (m, 2H), 1.90 (m, 2H). LC-MS (IE, m/z): 413 [M+1]⁻¹.

Step A: 3-[(4-Hydroxy-1-{[4-(1H-tetrazol-1-yl)phenyl]acetyl}piperidin-4-yl)ethyl]benzonitrile 3-[2-(4-Hydroxy-1-{[4-(1H-tetrazol-1-yl)phenyl]acetyl}piperidin-4-yl)ethyl]benzonitrile was prepared in a similar fashion to that described for the synthesis of EXAMPLE 13 starting from 3-[(4-hydroxy-1-{[4-(1H-tetrazol-1-yl)phenyl]acetyl}piperidin-4-yl)ethynyl]benzonitrile.

¹H NMR (500 MHz, CDCl₃, δ in ppm): 9.04 (s, 1H), 7.71 (d, J=8.5 Hz, 2H), 7.51 (m, 4H), 7.46-7.40 (overlapping m's, 2H), 7.43 (dd, J=8.5, 8.5 Hz, 1H), 4.44 (m, 1H), 3.86 (s, 2H), 3.74 (m, 1H), 3.54 (m, 1H), 3.15 (m, 1H), 2.79 (m, 2H), 1.80 (m, 2H), 1.71 (m, 2H), 1.55 (m, 2H). LC-MS (IE, m/z): 417 [M+1]⁺.

Example 23

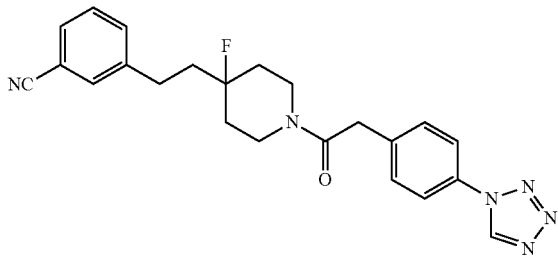 [SMILES: N#Cc1cccc(CCC2(F)CCN(C(=O)Cc3ccc(-n4cnnn4)cc3)CC2)c1]

3-[2-(4-Fluoro-1-{[4-(1H-tetrazol-1-yl)phenyl]acetyl}piperidin-4-yl)ethyl]benzonitrile 3-[2-(4-Fluoro-1-{[4-(1H-tetrazol-1-yl)phenyl]acetyl}piperidin-4-yl)ethyl]benzonitrile was prepared in a similar fashion to that described for the synthesis of EXAMPLE 11 starting from 3-[2-(4-Hydroxy-1-{[4-(1H-tetrazol-1-yl)phenyl]acetyl}piperidin-4-yl)ethyl]benzonitrile.

¹H NMR (500 MHz, CDCl₃, δ in ppm): 9.04 (s, 1H), 7.71 (m, 3H), 7.54-7.42 (overlapping m's, 5H), 4.52 (m, 1H), 3.99 (m, 1H), 3.88 (s, 2H), 3.68 (m, 1H), 3.47 (m, 1H), 3.02 (m, 1H), 2.81 (m, 2H), 2.36 (m, 2H), 1.92 (m, 2H), 1.57 (m, 2H).

Example 24

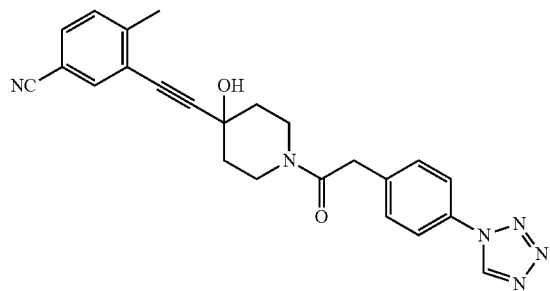 [SMILES: Cc1ccc(C#N)cc1C#CC1(O)CCN(C(=O)Cc2ccc(-n3cnnn3)cc2)CC1]

3-[(4-Hydroxy-1-{[4-(1H-tetrazol-1-yl)phenyl]acetyl}piperidin-4-yl)ethynyl]-4-methylbenzonitrile 3-[(4-Hydroxy-1-{[4-(1H-tetrazol-1-yl)phenyl]acetyl}piperidin-4-yl)ethynyl]-4-methylbenzonitrile was prepared in a similar fashion to that described for the synthesis of EXAMPLE 10 starting from 1-(4-ethynyl-4-hydroxypiperidin-1-yl)-2-[4-(1H-tetrazol-1-yl)phenyl]ethanone and 3-bromo-4-methylbenzonitrile. ¹H NMR (500 MHz, CDCl₃, δ in ppm): 9.02 (s, 1H), 7.72 (d, J=8.5 Hz, 2H), 7.61 (s, 1H), 7.52 (d, J=8.5 Hz, 2H), 7.36 (m, 2H), 4.06 (m, 1H), 3.89 (s, 2H), 3.76 (m, 1H), 3.59 (m, 1H), 3.35 (m, 1H), 2.51 (s, 3H), 2.08 (m, 2H), 1.91 (m, 2H).

Example 25

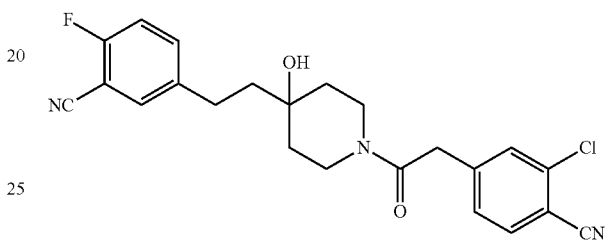

2-Chloro-4-(2-{4-[2-(3-cyano-4-fluorophenyl)ethyl]-4-hydroxypiperidin-1-yl}-2-oxoethyl)benzonitrile 2-Chloro-4-(2-{4-[2-(3-cyano-4-fluorophenyl)ethyl]-4-hydroxypiperidin-1-yl}-2-oxoethyl)benzonitrile was prepared in a similar fashion to that described for the synthesis of EXAMPLE 4 starting from 4-[2-(3-cyano-4-fluorophenyl)ethyl]-4-hydroxypiperidinium chloride and (3-chloro-4-cyanophenyl)acetic acid. ¹H NMR (500 MHz, CDCl₃, δ in ppm): 7.67 (d, J=8 Hz, 1H), 7.45 (m, 3H), 7.29 (m, 1H), 7.17 (dd, J=8.5, 8.5 Hz, 1H), 4.43 (m, 1H), 3.84 (s, 2H), 3.67 (m, 1H), 3.52 (m, 2H), 3.10 (m, 1H), 2.76 (m, 2H), 1.78 (m, 2H), 1.67 (m, 2H), 1.54 (m, 2H). LC-MS (IE, m/z): 426 [M+1]⁺.

Example 26

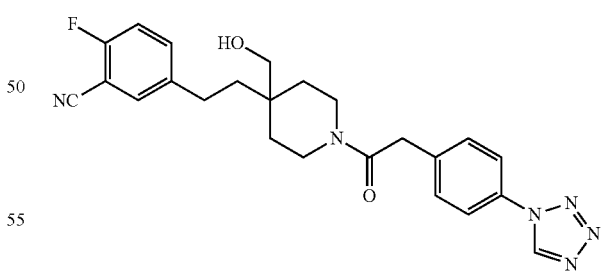

2-Fluoro-5-{2-[4-(hydroxymethyl)-1-{[4-(1H-tetrazol-1-yl)phenyl]acetyl}piperidin-4-yl]ethyl}benzonitrile A solution of compound ethyl 4-[2-(3-cyano-4-fluorophenyl)ethyl]-1-{[4-(1H-tetrazol-1-yl)phenyl]acetyl}piperidine-4-carboxylate (0.20 g, 0.41 mmol) in THF (10 mL) was treated with sodium borohydride (0.076 g, 2.1 mmol) and lithium chloride (0.087 g, 2.1 mmol), then 10 mL of ethanol was added to the suspended solution, and the mixture was allowed to react under an nitrogen atmosphere at room temperature for 20 h. The mixture was concentrated in vacuo, and the resulting residue was partitioned between EtOAc and water. The organic phase was washed with brine, dried over anhydrous sodium sulfate and concentrated. The resulting residue was purified by preparative TLC to provide 2-fluoro-5-{2-[4-(hydroxymethyl)-1-{[4-(1H-tetrazol-1-yl)phenyl]acetyl}piperidin-4-yl]ethyl}benzonitrile. $^{1}$H-NMR (400 MHz, MeOD) δ ppm 9.72 (s, 1H), 7.82 (d, J=8.3 Hz, 2H), 7.49~7.60 (m, 4H), 7.25 (dd, J=9.0, 9.0 Hz, 1H), 3.89 (s, 2H), 3.55~3.71 (m, 4H), 3.29~3.34 (m, 2H), 2.56~2.62 (m, 2H), 1.41~1.51 (m, 4H).

Example 27

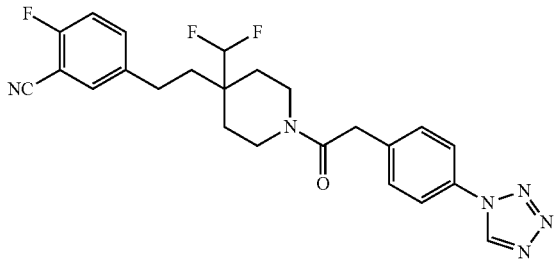 [SMILES: N#Cc1cc(CCC2(C(F)F)CCN(C(=O)Cc3ccc(-n4cnnn4)cc3)CC2)ccc1F]

5-{2-[4-(Difluoromethyl)-1-{[4-(1H-tetrazol-1-yl)phenyl]acetyl}piperidin-4-yl]ethyl}-2-fluorobenzonitrile Step A: 2-Fluoro-5-[2-(4-formyl-1-{[4-(1H-tetrazol-1-yl)phenyl]acetyl}piperidin-4-yl)ethyl]benzonitrile To a solution of 2-fluoro-5-{2-[4-(hydroxymethyl)-1-{[4-(1H-tetrazol-1-yl)phenyl]acetyl}piperidin-4-yl]ethyl}benzonitrile (50 mg, 0.13 mmol) in 10 mL of anhydrous DCM was added Dess-Martin periodinane (110 mg, 0.26 mmol) at 0° C. under a nitrogen atmosphere. The reaction mixture was allowed to warm to ambient temperature and stirred overnight. The reaction mixture was filtered, and the filtrate was concentrated to provide 2-fluoro-5-[2-(4-formyl-1-{[4-(1H-tetrazol-1-yl)phenyl]acetyl}piperidin-4-yl)ethyl]benzonitrile, which was used directly without further purification.

Step B: 5-{2-[4-(Difluoromethyl)-1-{[4-(1H-tetrazol-1-yl)phenyl]acetyl}piperidin-4-yl]ethyl}-2-fluorobenzonitrile A solution of 2-fluoro-5-[2-(4-formyl-1-{[4-(1H-tetrazol-1-yl)phenyl]acetyl}piperidin-4-yl)ethyl]benzonitrile (50 mg, 0.12 mmol) in 10 mL of anhydrous DCM was treated with DAST (0.04 mL, 0.28 mmol) at 0° C. under a nitrogen atmosphere and the mixture was stirred at ambient temperature overnight. The mixture was quenched with water and diluted with DCM. After separation, the organic phase was washed with brine, dried over anhydrous sodium sulfate and concentrated. The resulting residue was purified by preparative TLC and then prep-HPLC to provide 5-{2-[4-(difluoromethyl)-1-{[4-(1H-tetrazol-1-yl)phenyl]acetyl}piperidin-4-yl]ethyl}-2-fluorobenzonitrile. $^{1}$H-NMR (400 MHz, CD$_{3}$OD) δ ppm 9.75 (s, 1H), 7.84 (d, J=8.4 Hz, 2H), 7.49~7.65 (m, 4H), 7.26 (dd, J=8.8 Hz, 1H), 5.84 (dd, J=56, 56 Hz, 1H), 4.08 (m, 1H), 3.91 (s, 2H), 3.75~3.81 (m, 2H), 3.45~3.52 (m, 2H), 3.33 (m, 1H), 2.68~2.72 (m, 2H), 1.80~1.86 (m, 2H), 1.63~1.71 (m, 2H), 1.41~1.45 (m, 2H).

Example 28

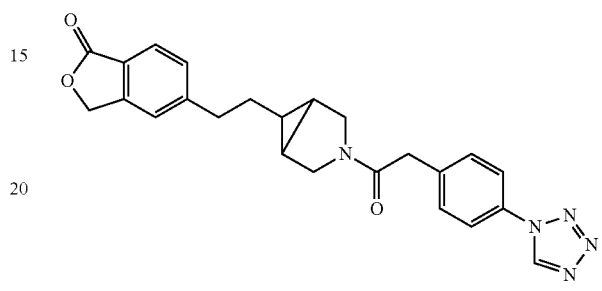

5-[2-(3-{[4-(1H-Tetrazol-1-yl)phenyl]acetyl}-3-azabicyclo[3.1.0]hex-6-yl)ethyl]-2-benzofuran-1(3H)-one Step A: 5-[(3-{[4-(1H-Tetrazol-1-yl)phenyl]acetyl}-3-azabicyclo[3.1.0]hex-6-yl)ethynyl]-2-benzofuran-1(3H)-one 5-[(3-{[4-(1H-tetrazol-1-yl)phenyl]acetyl}-3-azabicyclo[3.1.0]hex-6-yl)ethynyl]-2-benzofuran-1(3H)-one was prepared in a similar fashion to that described for the synthesis of EXAMPLE 10 starting from 1-(6-ethynyl-3-azabicyclo[3.1.0]hex-3-yl)-2-[4-(1H-tetrazol-1-yl)phenyl]ethanone and 5-bromo-2-benzofuran-1(3H)-one. $^{1}$H NMR (500 MHz, CDCl$_{3}$, δ in ppm): 9.02 (s, 1H), 7.87 (d, J=8.5 Hz, 2H), 7.72 (d, J=8.5 Hz, 2H), 7.54 (m, 2H), 7.52 (d, J=8.0 Hz, 2H), 5.31 (s, 2H), 4.03 (d, J=12.5 Hz, 1H), 3.83 (d, J=10.5 Hz, 1H), 3.74 (s, 2H), 3.71 (m, 1H), 3.57 (m, 1H), 2.12 (m, 2H), 1.31 (m, 1H). LC-MS (IE, m/z): 426 [M+1]$^{+}$.

Step B: 5-[2-(3-{[4-(1H-Tetrazol-1-yl)phenyl]acetyl}-3-azabicyclo[3.1.0]hex-6-yl)ethyl]-2-benzofuran-1(3H)-one 5-[2-(3-{[4-(1H-tetrazol-1-yl)phenyl]acetyl}-3-azabicyclo[3.1.0]hex-6-yl)ethyl]-2-benzofuran-1(3H)-one was prepared in a similar fashion to that described for the synthesis of EXAMPLE 13 starting from 5-[(3-{[4-(1H-tetrazol-1-yl)phenyl]acetyl}-3-azabicyclo[3.1.0]hex-6-yl)ethynyl]-2-benzofuran-1(3H)-one. $^{1}$H NMR (500 MHz, CDCl$_{3}$, δ in ppm): 9.05 (s, 1H), 7.87 (d, J=7 Hz, 1H), 7.69 (d, J=8.5 Hz, 2H), 7.43 (d, J=8.5 Hz, 2H), 7.33 (m, 2H), 5.32 (s, 2H), 3.84 (m, 1H), 3.69 (s, 2H), 3.61 (m, 2H), 3.46 (m, 1H), 2.87 (m, 2H), 1.73 (m, 2H), 1.60 (m, 1H), 0.92 (m, 1H).

Example 29

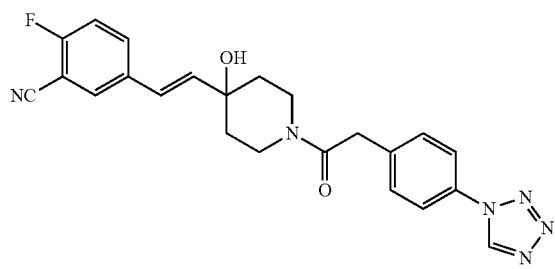 [SMILES: N#Cc1cc(/C=C/C2(O)CCN(C(=O)Cc3ccc(-n4cnnn4)cc3)CC2)ccc1F]

2-Fluoro-5-[(E)-2-(4-hydroxy-1-{[4-(1H-tetrazol-1-yl)phenyl]acetyl}piperidin-4-yl)ethenyl]benzonitrile 2-Fluoro-5-[(E)-2-(4-hydroxy-1-{[4-(1H-tetrazol-1-yl)phenyl]acetyl}piperidin-4-yl)ethenyl]benzonitrile was prepared in a similar fashion to that described for the synthesis of EXAMPLE 4 starting 4-[(E)-2-(3-cyano-4-fluorophenyl)ethenyl]-4-hydroxypiperidine and [4-(1H-tetrazol-1-yl)phenyl]acetic acid.

$^1$H-NMR (400 MHz, CDCl$_3$) δ ppm 9.02 (s, 1H), 7.67 (d, J=8.6 Hz, 2H), 7.55~7.59 (m, 2H), 7.48 (d, J=8.3 Hz, 2H), 7.17 (dd, J=8.3, 8.3 Hz, 1H), 6.58 (d, J=15.8 Hz, 1H), 6.23 (d, J=16.2 Hz, 1H), 4.45 (m, 1H), 3.67~3.84 (m, 3H), 3.54 (m, 1H), 3.15 (m, 1H), 1.66~1.74 (m, 4H).

Example 30

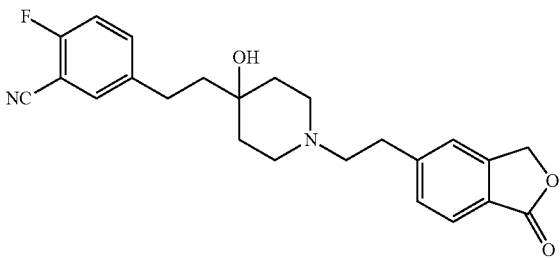 [SMILES: N#Cc1cc(CCC2(O)CCN(CCc3ccc4c(c3)COC4=O)CC2)ccc1F]

2-Fluoro-5-(2-{4-hydroxy-1-[2-(1-oxo-1,3-dihydro-2-benzofuran-5-yl)ethyl]piperidin-4-yl}ethyl)benzonitrile To a microwave tube were added 5-(2-bromoethyl)-2-benzofuran-1(3H)-one (50 mg, 0.35 mmol), 2-fluoro-5-[2-(4-hydroxypiperidin-4-yl)ethyl]benzonitrile hydrochloride (50 mg, 0.18 mmol), cesium carbonate (170 mg, 0.53 mmol) and ethanol (3.0 mL). The mixture was heated in the microwave for 30 min at 150° C. The solvent was evaporated and the crude product was purified by mass directed reverse-phase HPLC Chromatography to provide 2-fluoro-5-(2-{4-hydroxy-1-[2-(1-oxo-1,3-dihydro-2-benzofuran-5-yl)ethyl]piperidin-4-yl}ethyl)benzonitrile (TFA salt). LC-MS (IE, m/z): 409 [M+1]$^+$.

Example 31

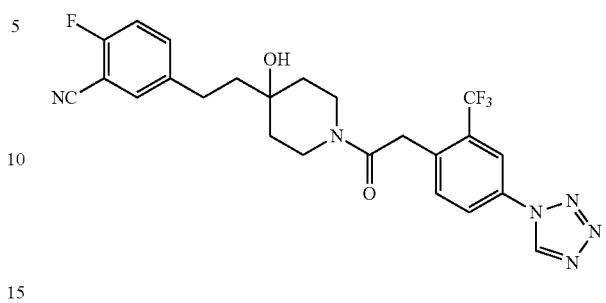

2-Fluoro-5-[2-(4-hydroxy-1-{[4-(1H-tetrazol-1-yl)-2-(trifluoromethyl)phenyl]acetyl}piperidin-4-yl)ethyl]benzonitrile 2-Fluoro-5-[2-(4-hydroxy-1-{[4-(1H-tetrazol-1-yl)-2-(trifluoromethyl)phenyl]acetyl}piperidin-4-yl)ethyl]benzonitrile was prepared in a similar fashion to that described for the synthesis of EXAMPLE 4 starting 4-[2-(3-cyano-4-fluorophenyl)ethyl]-4-hydroxypiperidinium chloride and [4-(1H-tetrazol-1-yl)-2-(trifluoromethyl)phenyl]acetic acid.

$^1$H-NMR (400 MHz, CD$_3$OD) δ ppm 9.89 (s, 1H), 8.24 (s, 1H), 8.12 (d, J=7.5 Hz, 1H), 7.66 (d, J=7.5 Hz, 1H), 7.59 (m, 2H), 7.27 (dd, J=9.0, 9.0 Hz, 1H), 4.27 (m, 1H), 4.11 (m, 1H), 4.09 (s, 2H), 3.85 (m, 1H), 3.59 (m, 1H), 3.32 (m, 1H), 3.19 (m, 1H), 2.79 (m, 2H), 1.79 (m, 2H), 1.72 (m, 2H), 1.60 (m, 1H), 1.28 (m, 1H). LC-MS (IE, m/z): 503 [M+1]$^+$.

Example 32

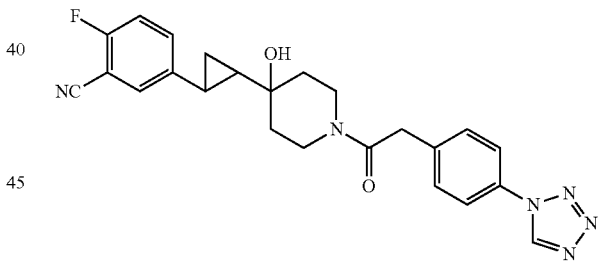

2-Fluoro-5-[2-(4-hydroxy-1-{[4-(1H-tetrazol-1-yl)phenyl]acetyl}piperidin-4-yl)cyclopropyl]benzonitrile A solution of 2-fluoro-5-[(E)-2-(4-hydroxy-1-{[4-(1H-tetrazol-1-yl)phenyl]acetyl}piperidin-4-yl)ethenyl]benzonitrile (20 mg, 0.050 mmol) in 5 ml of EtOAc at 0° C. was treated successively with a solution of diazomethane in 2 mL of diethyl ether followed by palladium acetate (10 mg). The resulting mixture was stirred at room temperature overnight. The reaction mixture was filtered and purified by prep-TLC to afford 2-fluoro-5-[2-(4-hydroxy-1-{[4-(1H-tetrazol-1-yl)phenyl]acetyl}piperidin-4-yl)cyclopropyl]benzonitrile.

$^1$H-NMR (400 MHz, CDCl$_3$) δ ppm 8.97 (s, 1H), 7.67 (d, J=6.6 Hz, 2H), 7.46~7.5 (m, 2H), 7.27~7.29 (m, 2H), 7.10 (dd, J=9.0, 9.0 Hz, 1H), 4.46 (m, 1H), 3.83 (s, 2H), 3.73 (m, 1H), 3.47 (m, 1H), 3.08 (m, 1H), 1.99 (m, 1H), 1.45~1.58 (m, 4H), 1.08~1.16 (m, 2H), 0.86 (m, 1H).

Example 33

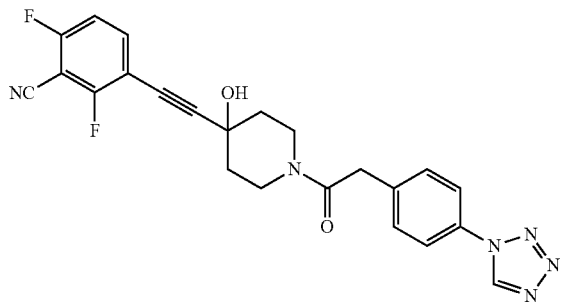 [SMILES: N#Cc1c(F)ccc(C#CC2(O)CCN(C(=O)Cc3ccc(-n4cnnn4)cc3)CC2)c1F]

2,6-Difluoro-3-[(4-hydroxy-1-{[4-(1H-tetrazol-1-yl)phenyl]acetyl}piperidin-4-yl)ethynyl]benzonitrile 2,6-Difluoro-3-[(4-hydroxy-1-{[4-(1H-tetrazol-1-yl)phenyl]acetyl}piperidin-4-yl)ethynyl]benzonitrile was prepared in a similar fashion to that described for the synthesis of EXAMPLE 10 starting from 1-(4-ethynyl-4-hydroxypiperidin-1-yl)-2-[4-(1H-tetrazol-1-yl)phenyl]ethanone and 3-bromo-2,6-difluorobenzonitrile. $^1$H-NMR (400 MHz, CDCl$_3$) δ ppm 8.98 (s, 1H), 7.61~7.69 (m, 3H), 7.46~7.49 (m, 2H), 7.05 (m, 1H), 4.06 (m, 1H), 3.74~3.83 (m, 3H), 3.47~3.57 (m, 2H), 1.95~2.06 (m, 2H), 1.74~1.88 (m, 2H).

Example 34

2,6-Difluoro-3-[2-(4-hydroxy-1-{[4-(1H-tetrazol-1-yl)phenyl]acetyl}piperidin-4-yl)ethyl]benzonitrile 2,6-Difluoro-3-[2-(4-hydroxy-1-{[4-(1H-tetrazol-1-yl)phenyl]acetyl}piperidin-4-yl)ethyl]benzonitrile was prepared in a similar fashion to that described for the synthesis of EXAMPLE 11 starting from 2,6-Difluoro-3-[(4-hydroxy-1-{[4-(1H-tetrazol-1-yl)phenyl]acetyl}piperidin-4-yl)ethynyl]benzonitrile. $^1$H-NMR (400 MHz, CDCl$_3$) δ ppm 8.91 (s, 1H), 7.59~7.61 (m, 2H), 7.33~7.42 (m, 3H), 6.91 (m, 1H), 4.33 (m, 1H), 3.62~3.75 (m, 3H), 3.42 (m, 1H), 3.05 (m, 1H), 2.66~2.70 (m, 2H), 1.54~1.67 (m, 6H).

Example 35

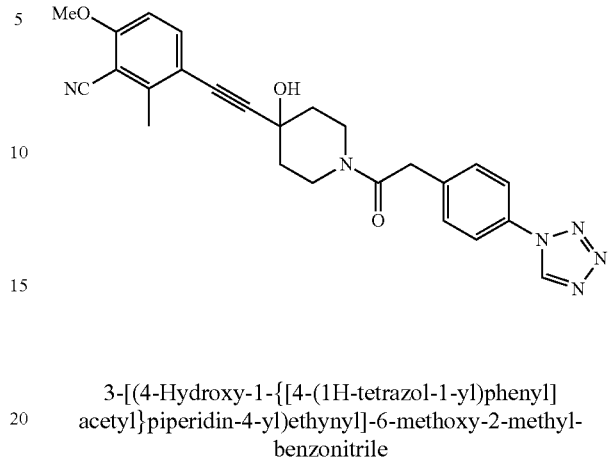

3-[(4-Hydroxy-1-{[4-(1H-tetrazol-1-yl)phenyl]acetyl}piperidin-4-yl)ethynyl]-6-methoxy-2-methylbenzonitrile 3-[(4-Hydroxy-1-{[4-(1H-tetrazol-1-yl)phenyl]acetyl}piperidin-4-yl)ethynyl]-6-methoxy-2-methylbenzonitrile was prepared in a similar fashion to that described for the synthesis of EXAMPLE 10 starting from 1-(4-ethynyl-4-hydroxypiperidin-1-yl)-2-[4-(1H-tetrazol-1-yl)phenyl]ethanone and 3-bromo-6-methoxy-2-methylbenzonitrile. $^1$H-NMR (400 MHz, CDCl$_3$) δ ppm 8.94 (s, 1H), 7.59~7.61 (m, 2H), 7.4~7.46 (m, 3H), 6.69 (d, J=8.6 Hz, 1H), 3.99 (m, 1H), 3.86 (s, 3H), 3.69~3.77 (m, 3H), 3.42~3.51 (m, 2H), 2.40 (s, 3H), 1.88~2.0 (m, 2H), 1.67~1.81 (m, 2H).

Example 36

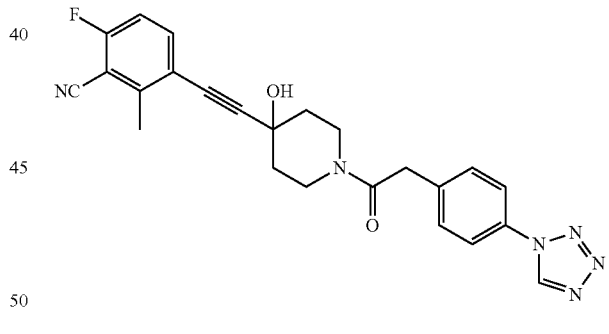

6-Fluoro-3-[(4-hydroxy-1-{[4-(1H-tetrazol-1-yl)phenyl]acetyl}piperidin-4-yl)ethynyl]-2-methylbenzonitrile 6-Fluoro-3-[(4-hydroxy-1-{[4-(1H-tetrazol-1-yl)phenyl]acetyl}piperidin-4-yl)ethynyl]-2-methylbenzonitrile was prepared in a similar fashion to that described for the synthesis of EXAMPLE 10 starting from 1-(4-ethynyl-4-hydroxypiperidin-1-yl)-2-[4-(1H-tetrazol-1-yl)phenyl]ethanone and 3-bromo-6-fluoro-2-methylbenzonitrile. $^1$H-NMR (400 MHz, CDCl$_3$) δ ppm 8.95 (s, 1H), 7.65~7.67 (m, 2H), 7.57 (m, 1H), 7.45~7.47 (m, 2H), 7.01 (m, 1H), 4.01 (m, 1H), 3.73~3.82 (m, 3H), 3.47~3.61 (m, 2H), 2.66 (s, 3H), 1.75~2.07 (m, 4H).

Example 37

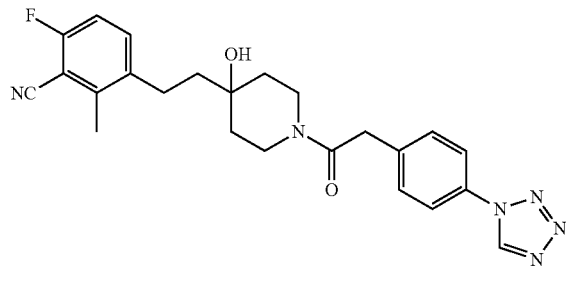 [SMILES: Cc1c(CCC2(O)CCN(C(=O)Cc3ccc(-n4cnnn4)cc3)CC2)ccc(F)c1C#N]

6-Fluoro-3-[2-(4-hydroxy-1-{[4-(1H-tetrazol-1-yl)phenyl]acetyl}piperidin-4-yl)ethyl]-2-methylbenzonitrile 6-Fluoro-3-[2-(4-hydroxy-1-{[4-(1H-tetrazol-1-yl)phenyl]acetyl}piperidin-4-yl)ethyl]-2-methylbenzonitrile was prepared in a similar fashion to that described for the synthesis of EXAMPLE 11 starting from 6-fluoro-3-[(4-hydroxy-1-{[4-(1H-tetrazol-1-yl)phenyl]acetyl}piperidin-4-yl)ethynyl]-2-methylbenzonitrile.

$^1$H-NMR (400 MHz, CDCl$_3$) δ ppm 8.90 (s, 1H), 7.59~7.61 (m, 2H), 7.40~7.42 (m, 2H), 7.24 (m, 1H), 6.90 (m, 1H), 4.36 (m, 1H), 3.71~3.80 (m, 2H), 3.65 (m, 1H), 3.43 (m, 1H), 3.03 (m, 1H), 2.61~2.66 (m, 2H), 2.43 (s, 3H), 1.44~1.46 (m, 6H).

Example 38

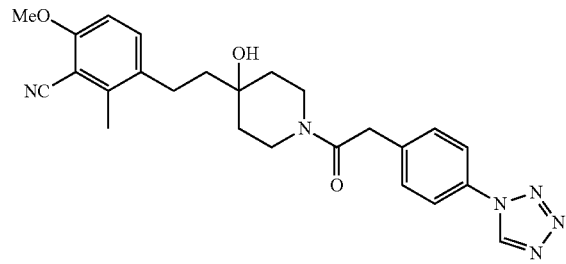 [SMILES: COc1ccc(CCC2(O)CCN(C(=O)Cc3ccc(-n4cnnn4)cc3)CC2)c(C)c1C#N]

3-[2-(4-Hydroxy-1-{[4-(1H-tetrazol-1-yl)phenyl]acetyl}piperidin-4-yl)ethyl]-6-methoxy-2-methylbenzonitrile 3-[2-(4-Hydroxy-1-{[4-(1H-tetrazol-1-yl)phenyl]acetyl}piperidin-4-yl)ethyl]-6-methoxy-2-methylbenzonitrile was prepared in a similar fashion to that described for the synthesis of EXAMPLE 11 starting from 6-fluoro-3-[(4-hydroxy-1-{[4-(1H-tetrazol-1-yl)phenyl]acetyl}piperidin-4-yl)ethynyl]-2-methylbenzonitrile.

$^1$H-NMR (400 MHz, CDCl$_3$) δ ppm 8.95 (s, 1H), 7.59 (d, J=8.6 Hz, 2H), 7.4 (d, J=8.6 Hz, 2H), 7.17 (d, J=8.6 Hz, 1H), 6.65 (d, J=8.6 Hz, 1H), 4.31 (m, 1H), 3.80 (s, 3H), 3.76 (s, 2H), 3.63 (m, 1H), 3.42 (m, 1H), 3.04 (m, 1H), 2.56~2.61 (m, 2H), 2.37 (s, 3H), 1.34~1.64 (m, 6H).

Example 39

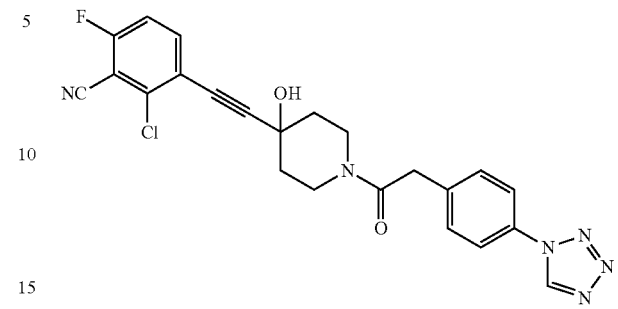

2-Chloro-6-fluoro-3-[(4-hydroxy-1-{[4-(1H-tetrazol-1-yl)phenyl]acetyl}piperidin-4-yl)ethynyl]benzonitrile A solution of 2-chloro-6-fluoro-3-iodobenzonitrile (220 mg, 0.79 mmol) in 5 mL of anhydrous DMF was added 1-(4-ethynyl-4-hydroxypiperidin-1-yl)-2-[4-(1H-tetrazol-1-yl)phenyl]ethanone (210 mg, 0.66 mmol), tetrakis(triphenylphosphine palladiumdichloride (60 mg), copper (I) iodide (60 mg), triethylamine (200 mg, 2.0 mmol) and triphenylphosphine (150 mg), and the mixture was heated to 60~70° C. under a nitrogen atmosphere overnight. The reaction mixture was cooled to room temperature and poured into water and the layers separated. The aqueous layer was extracted with ethyl acetate, and the combined extracts were washed with brine, dried over anhydrous sodium sulfate and concentrated. The resulting residue was purified by prep-TLC to provide 2-chloro-6-fluoro-3-[(4-hydroxy-1-{[4-(1H-tetrazol-1-yl)phenyl]acetyl}piperidin-4-yl)ethynyl]benzonitrile.

$^1$H-NMR (400 MHz, CDCl$_3$) δ 9.01 (s, 1H), 7.65~7.69 (m, 3H), 7.48~7.50 (m, 2H), 7.15 (m, 1H), 4.12 (m, 1H), 3.78~3.85 (m, 3H), 3.49~3.56 (m, 3H), 1.80~2.07 (m, 4H).

Example 40

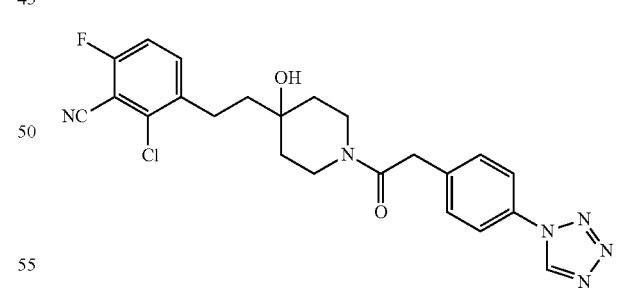

2-Chloro-6-fluoro-3-[2-(4-hydroxy-1-{[4-(1H-tetrazol-1-yl)phenyl]acetyl}piperidin-4-yl)ethyl]benzonitrile 2-Chloro-6-fluoro-3-[2-(4-hydroxy-1-{[4-(1H-tetrazol-1-yl)phenyl]acetyl}piperidin-4-yl)ethyl]benzonitrile was prepared in a similar fashion to that described for the synthesis of EXAMPLE 11 starting from 2-chloro-6-fluoro-3-[(4-hydroxy-1- {[4-(1H-tetrazol-1-yl)phenyl]acetyl}piperidin- 4-yl)ethynyl]benzonitrile. ¹H-NMR (400 MHz, CDCl₃) δ 8.95 (s, 1H), 7.62 (d, J=8.61 Hz, 2H), 7.41 (d, J=8.61 Hz, 2H), 7.37 (m, 1H), 7.03 (dd, J=8.8, 8.8 Hz, 1H), 4.38 (m, 1H), 3.82 (s, 2H), 3.61~3.65 (m, 2H), 3.43~3.49 (m, 2H), 3.08 (m, 1H), 2.75~2.80 (m, 2H), 1.62~1.67 (m, 2H), 1.56 (m, 1H), 1.41 (m, 1H).

Example 41

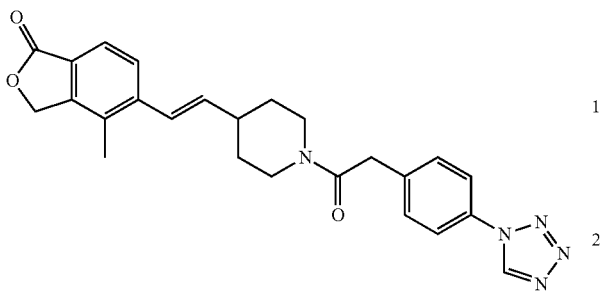

4-Methyl-5-[(E)-2-(1-{[4-(1H-tetrazol-1-yl)phenyl]acetyl}piperidin-4-yl)ethenyl]-2-benzofuran-1(3H)-one 4-Methyl-5-[(E)-2-(1-{[4-(1H-tetrazol-1-yl)phenyl]acetyl}piperidin-4-yl)ethenyl]-2-benzofuran-1(3H)-one was prepared in a similar fashion to that described for the synthesis of EXAMPLE 5 starting from 4-[(E)-2-(4-methyl-1-oxo-1,3-dihydro-2-benzofuran-5-yl)ethenyl]piperidinium chloride and [4-(1H-tetrazol-1-yl)phenyl]acetic acid. ¹H NMR (500 MHz, CDCl₃, δ in ppm): 9.00 (s, 1H), 7.68 (m, 3H), 7.55 (d, J=8.2 Hz, 2H), 7.48 (d, J=8.2 Hz, 2H), 6.63 (d, J=16.0 Hz, 1H), 6.15 (dd, J=7.1, 16.0 Hz, 1H), 5.22 (s, 2H), 4.69 (m, 1H), 3.97 (m, 1H), 3.83 (s, 2H), 3.16 (m, 1H), 2.73 (m, 2H), 2.47 (m, 1H), 2.25 (s, 3H), 1.87 (m, 2H), 1.14 (m, 1H). LC-MS (IE, m/z): 434 [M+1]⁺.

Example 42

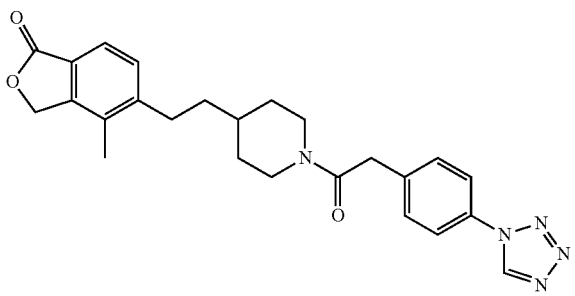

4-Methyl-5-[2-(1-{[4-(1H-tetrazol-1-yl)phenyl]acetyl}piperidin-4-yl)ethyl]-2-benzofuran-1(3H)-one 4-Methyl-5-[2-(1-{[4-(1H-tetrazol-1-yl)phenyl]acetyl}piperidin-4-yl)ethyl]-2-benzofuran-1(3H)-one was prepared in a similar fashion to that described for the synthesis of EXAMPLE 7 starting from 4-methyl-5-[(E)-2-(1-{[4-(1H-tetrazol-1-yl)phenyl]acetyl}piperidin-4-yl)ethenyl]-2-benzofuran-1(3H)-one. ¹H NMR (500 MHz, CDCl₃, δ in ppm): 9.00 (s, 1H), 7.66 (m, 3H), 7.46 (d, J=8.2 Hz, 2H), 7.26 (m, 1H), 5.22 (s, 2H), 4.66 (m, 1H), 3.92 (m, 1H), 3.81 (s, 2H), 3.06 (m, 1H), 2.72 (m, 2H), 2.60 (m, 1H), 2.23 (s, 3H), 1.1-1.9 (m, 7H). LC-MS (IE, m/z): 446 [M+1]⁺.

Example 43

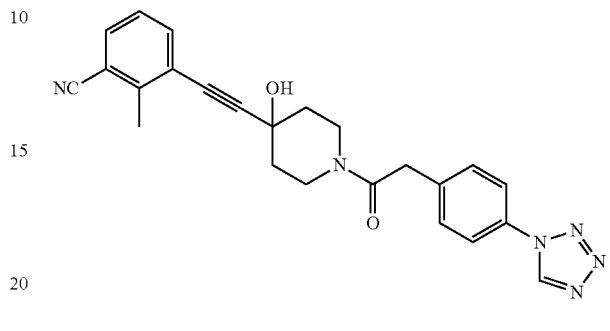

3-[(4-Hydroxy-1-{[4-(1H-tetrazol-1-yl)phenyl]acetyl}piperidin-4-yl)ethynyl]-2-methylbenzonitrile 3-[(4-Hydroxy-1-{[4-(1H-tetrazol-1-yl)phenyl]acetyl}piperidin-4-yl)ethynyl]-2-methylbenzonitrile was prepared in a similar fashion to that described for the synthesis of EXAMPLE 39 starting from 1-(4-ethynyl-4-hydroxypiperidin-1-yl)-2-[4-(1H-tetrazol-1-yl)phenyl]ethanone and 3-iodo-2-methylbenzonitrile. ¹H-NMR (400 MHz, CDCl₃) δ ppm 8.97 (s, 1H), 7.65~7.67 (m, 2H), 7.55~7.58 (m, 2H), 7.45~7.47 (m, 2H), 7.23 (m, 1H), 4.04 (m, 1H), 3.71~3.82 (m, 3H), 3.47~3.59 (m, 2H), 2.60 (s, 3H), 1.95~2.05 (m, 2H), 1.76~1.88 (m, 2H).

Example 44

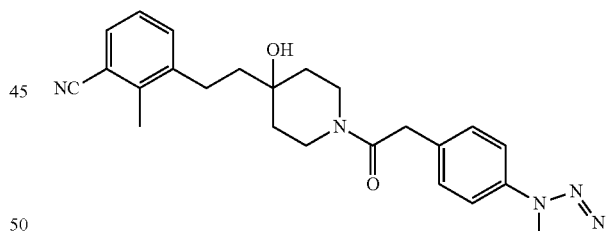

3-[2-(4-Hydroxy-1-{[4-(1H-tetrazol-1-yl)phenyl]acetyl}piperidin-4-yl)ethynyl]-2-methylbenzonitrile 3-[2-(4-Hydroxy-1-{[4-(1H-tetrazol-1-yl)phenyl]acetyl}piperidin-4-yl)ethynyl]-2-methylbenzonitrile was prepared in a similar fashion to that described for the synthesis of EXAMPLE 11 starting from 3-[(4-hydroxy-1-{[4-(1H-tetrazol-1-yl)phenyl]acetyl}piperidin-4-yl)ethynyl]-2-methylbenzonitrile. ¹H-NMR (400 MHz, CDCl₃) δ ppm 8.91 (s, 1H), 7.59~7.61 (m, 2H), 7.39~7.42 (m, 3H), 7.26 (m, 1H), 7.13 (m, 1H), 3.76 (s, 2H), 3.40 (m, 1H), 3.10 (m, 1H), 2.65~2.69 (m, 2H), 2.43 (s, 3H), 1.36~1.63 (m, 8H).

Example 45

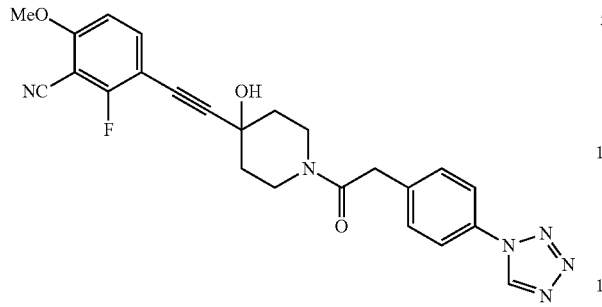

2-Fluoro-3-[(4-hydroxy-1-{[4-(1H-tetrazol-1-yl)phenyl]acetyl}piperidin-4-yl)ethynyl]-6-methoxybenzonitrile 2-Fluoro-3-[(4-hydroxy-1-{[4-(1H-tetrazol-1-yl)phenyl]acetyl}piperidin-4-yl)ethynyl]-6-methoxybenzonitrile was prepared in a similar fashion to that described for the synthesis of EXAMPLE 39 starting from 1-(4-ethynyl-4-hydroxypiperidin-1-yl)-2-[4-(1H-tetrazol-1-yl)phenyl]ethanone and 3-bromo-2-fluoro-6-methoxybenzonitrile. $^1$H-NMR (400 MHz, CDCl$_3$) δ ppm 8.91 (s, 1H), 7.60~7.62 (m, 2H), 7.40~7.50 (m, 3H), 6.67 (m, 1H), 4.05 (m, 1H), 3.90 (s, 3H), 3.69~3.77 (m, 3H), 3.39~3.46 (m, 2H), 1.88~1.98 (m, 2H), 1.53~1.81 (m, 2H).

Example 46

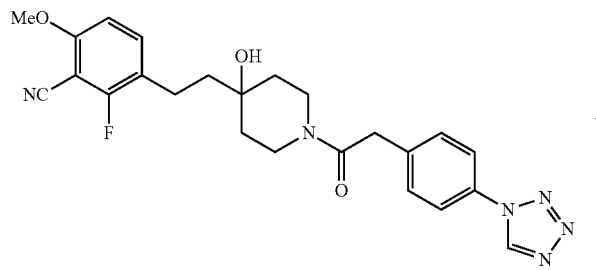

2-Fluoro-3-[2-(4-hydroxy-1-{[4-(1H-tetrazol-1-yl)phenyl]acetyl}piperidin-4-yl)ethyl]-6-methoxybenzonitrile 2-Fluoro-3-[2-(4-hydroxy-1-{[4-(1H-tetrazol-1-yl)phenyl]acetyl}piperidin-4-yl)ethyl]-6-methoxybenzonitrile was prepared in a similar fashion to that described for the synthesis of EXAMPLE 11 starting from 2-fluoro-3-[(4-hydroxy-1-{[4-(1H-tetrazol-1-yl)phenyl]acetyl}piperidin-4-yl)ethynyl]-6-methoxybenzonitrile. $^1$H-NMR (400 MHz, CDCl$_3$) δ ppm 8.91 (s, 1H), 7.59~7.61 (m, 2H), 7.40~7.42 (m, 2H), 7.25 (m, 1H), 6.61 (m, 1H), 4.00 (m, 1H), 3.84 (s, 3H), 3.75 (s, 2H), 2.59~2.64 (m, 2H), 1.40~1.65 (m, 8H).

Example 47

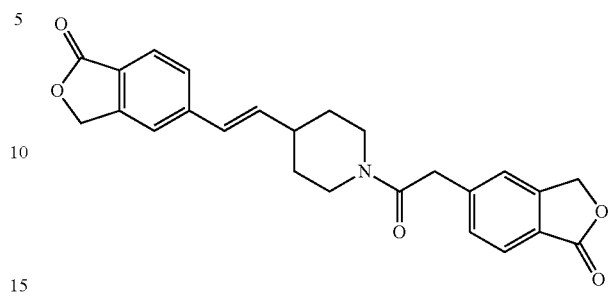

5-[(E)-2-{1-[(1-Oxo-1,3-dihydro-2-benzofuran-5-yl)acetyl]piperidin-4-}ethenyl]-2-benzofuran-1(3H)-one 5-[(E)-2-{1-[(1-Oxo-1,3-dihydro-2-benzofuran-5-yl)acetyl]piperidin-4-}ethenyl]-2-benzofuran-1(3H)-one was prepared in a similar fashion to that described for the synthesis of EXAMPLE 5 starting from 4-[(E)-2-(1-oxo-1,3-dihydro-2-benzofuran-5-yl)ethenyl]piperidinium chloride and (1-oxo-1,3-dihydro-2-benzofuran-5-yl)acetic acid.
$^1$H NMR (500 MHz, CDCl$_3$, δ in ppm): 7.4-8.0 (m, 6H), 6.2-6.6 (m, 2H), 5.34 (s, 2H), 5.31 (s, 2H), 4.73 (m, 1H), 4.00 (m, 1H), 3.90 (s, 2H), 1.2-3.3 (m, 7H). LC-MS (IE, m/z): 418 [M+1]$^+$.

Example 48

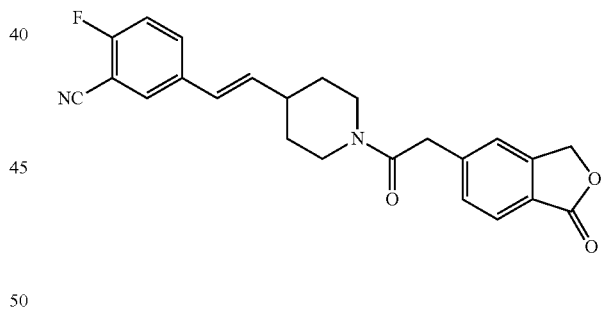

2-Fluoro-5-[(E)-2-{1-[(1-oxo-1,3-dihydro-2-benzofuran-5-yl)acetyl]piperidin-4-yl}ethenyl]benzonitrile 2-Fluoro-5-[(E)-2-{1-[(1-oxo-1,3-dihydro-2-benzofuran-5-yl)acetyl]piperidin-4-yl}ethenyl]benzonitrile was prepared in a similar fashion to that described for the synthesis of EXAMPLE 5 starting from 4-[(E)-2-(3-cyano-4-fluorophenyl)ethenyl]piperidinium chloride and (1-oxo-1,3-dihydro-2-benzofuran-5-yl)acetic acid. $^1$H NMR (500 MHz, CDCl$_3$, δ in ppm): 7.87 (d, J=7.8 Hz, 1H), 7.54 (m, 2H), 7.42 (m, 2H), 7.15 (m, 1H), 6.32 (d, J=15.8 Hz, 1H)), 6.09 (dd, J=6.9 Hz, J=15.8 Hz, 1H), 5.30 (s, 2H), 4.67 (s, 1H), 3.95 (m, 1H), 3.86 (s, 2H), 3.13 (m, 1H), 2.70 (m, 1H), 2.40 (m, 1H), 1.83 (m, 2H), 1.20-1.40 (m, 2H). LC-MS (IE, m/z): 405 [M+1]$^+$.

Example 49

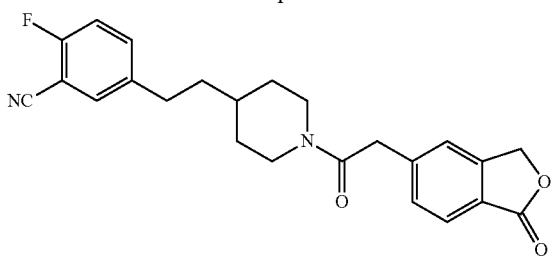

2-Fluoro-5-(2-{1-[(1-oxo-1,3-dihydro-2-benzofuran-5-yl)acetyl]piperidin-4-yl}ethyl)benzonitrile 2-Fluoro-5-(2-{1-[(1-oxo-1,3-dihydro-2-benzofuran-5-yl)acetyl]piperidin-4-yl}ethyl)benzonitrile was prepared in a similar fashion to that described for the synthesis of EXAMPLE 7 starting from 2-fluoro-5-[(E)-2-{1-[(1-oxo-1,3-dihydro-2-benzofuran-5-yl)acetyl]piperidin-4-yl}ethenyl]benzonitrile. LC-MS (IE, m/z): 407 [M+1]$^+$.

Example 50

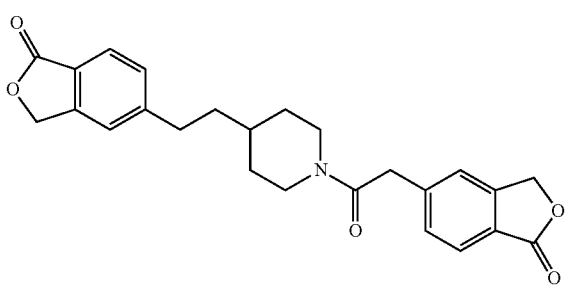 [SMILES: O=C1OCc2cc(CCC3CCN(C(=O)Cc4ccc5c(c4)COC5=O)CC3)ccc21]

5-(2-{1-[(1-Oxo-1,3-dihydro-2-benzofuran-5-yl)acetyl]piperidin-4-yl}ethyl)-2-benzofuran-1(3H)-one 5-(2-{1-[(1-Oxo-1,3-dihydro-2-benzofuran-5-yl)acetyl]piperidin-4-yl}ethyl)-2-benzofuran-1(3H)-one was prepared in a similar fashion to that described for the synthesis of EXAMPLE 7 starting from 5-[(E)-2-{1-[(1-oxo-1,3-dihydro-2-benzofuran-5-yl)acetyl]piperidin-4-}ethenyl]-2-benzofuran-1(3H)-one.

$^1$H NMR (500 MHz, CDCl$_3$, δ in ppm): 7.87 (d, J=7.8 Hz, 1H), 7.83 (d, J=7.8 Hz, 1H), 7.41 (1H, s), 7.39 (d, J=8.0 Hz, 1H), 7.26 (m, 1H), 5.29 (s, 2H), 5.28 (2H, s), 4.64 (m, 1H), 3.89 (m, 1H), 3.84 (s, 2H), 1.0-3.3 (m, 1H). LC-MS (IE, m/z): 420 [M+1]$^+$.

Example 51

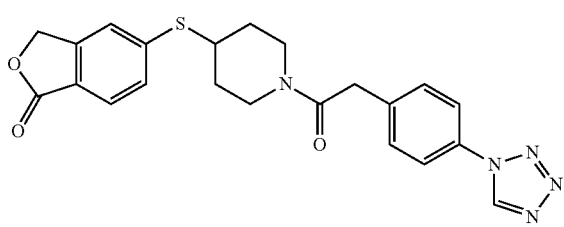 [SMILES: O=C1OCc2cc(SC3CCN(C(=O)Cc4ccc(-n5cnnn5)cc4)CC3)ccc21]

5-[(1-{[4-(1H-Tetrazol-1-yl)phenyl]acetyl}piperidin-4-yl)sulfanyl]-2-benzofuran-1(3H)-one 5-[(1-{[4-(1H-Tetrazol-1-yl)phenyl]acetyl}piperidin-4-yl)sulfanyl]-2-benzofuran-1(3H)-one was prepared in a similar fashion to that described for the synthesis of EXAMPLE 5 starting from 4-[(1-oxo-1,3-dihydro-2-benzofuran-5-yl)sulfanyl]piperidinium chloride and [4-(1H-tetrazol-1-yl)phenyl]acetic acid. $^1$H-NMR (400 MHz, CD$_3$OD) δ ppm 9.72 (s, 1H), 7.82 (d, J=8.6 Hz, 2H), 7.74 (d, J=8.6 Hz, 1H), 7.57 (s, 1H), 7.49~7.51 (m, 3H), 5.32 (s, 2H), 4.32 (m, 1H), 4.00 (m, 1H), 3.89 (s, 2H), 3.71 (m, 1H), 3.35 (m, 1H), 3.08 (m, 1H), 2.03~2.89 (m, 2H), 1.49 (m, 1H).

Example 52

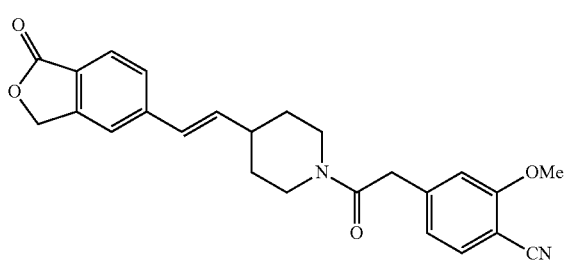 [SMILES: COc1cc(CC(=O)N2CCC(/C=C/c3ccc4c(c3)COC4=O)CC2)ccc1C#N]

2-Methoxy-4-(2-oxo-2-(4-[(E)-2-(1-oxo-1,3-dihydro-2-benzofuran-5-yl)ethenyl]piperidin-1-yl}ethyl]benzonitrile 2-Methoxy-4-(2-oxo-2-(4-[(E)-2-(1-oxo-1,3-dihydro-2-benzofuran-5-yl)ethenyl]piperidin-1-yl}ethyl]benzonitrile was prepared in a similar fashion to that described for the synthesis of EXAMPLE 5 starting from 4-[(E)-2-(1-oxo-1,3-dihydro-2-benzofuran-5-yl)ethenyl]piperidinium chloride and (4-cyano-3-methoxyphenyl)acetic acid. $^1$H NMR (500 MHz, CDCl$_3$, δ in ppm): 7.81 (m, 1H), 7.52 (m, 2H), 7.40 (s, 1H), 6.91 (s, 1H), 6.87 (m, 1H), 6.42 (m, 1H), 6.23 (m, 1H), 5.27 (s, 2H), 4.64 (m, 1H), 3.85 (m, 4H), 3.78 (s, 2H), 3.05 (m, 1H), 2.70 (m, 1H), 2.42 (m, 1H), 1.82 (m, 2H), 1.2-1.5 (m, 2H). LC-MS (IE, m/z): 417 [M+1]$^+$.

Example 53

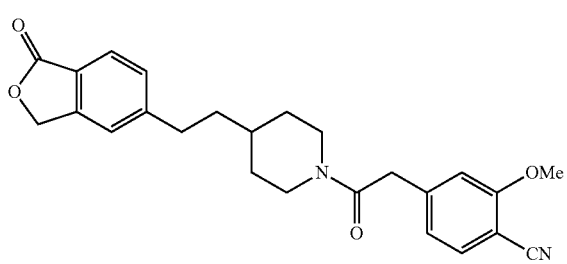 [SMILES: COc1cc(CC(=O)N2CCC(CCc3ccc4c(c3)COC4=O)CC2)ccc1C#N]

2-Methoxy-4-(2-oxo-2-(4-[2-(1-oxo-1,3-dihydro-2-benzofuran-5-yl)ethyl]piperidin-1-yl}ethyl]benzonitrile 2-Methoxy-4-(2-oxo-2-(4-[2-(1-oxo-1,3-dihydro-2-benzofuran-5-yl)ethyl]piperidin-1-yl}ethyl]benzonitrile was prepared in a similar fashion to that described for the synthesis of EXAMPLE 7 starting from 2-methoxy-4-(2-oxo-2-(4-[(E)-2-(1-oxo-1,3-dihydro-2-benzofuran-5-yl)ethenyl]piperidin-1-yl}ethyl]benzonitrile. LC-MS (IE, m/z): 419 [M+1]+.

Example 54 A & B

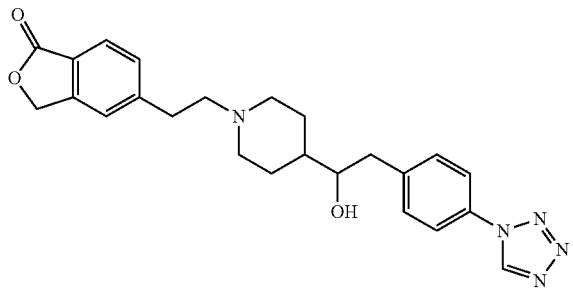 [SMILES: O=C1OCc2cc(CCN3CCC(C(O)Cc4ccc(-n5cnnn5)cc4)CC3)ccc21]

5-[2-(4-{1-Hydroxy-2-[4-(1H-tetrazol-1-yl)phenyl]ethyl}piperidin-1-yl)ethyl]-2-benzofuran-1(3H)-one A mixture of 1-(piperidin-4-yl)-2-[4-(1H-tetrazol-1-yl)phenyl]ethanol (70 mg, 0.23 mmol), oxo-1,3-dihydro-2-benzofuran-5-yl)acetaldehyde (60 mg, 0.34 mmol), acetic acid (28 mg, 0.46 mmol), and DCM/MeOH (1 mL/1 mL) was treated with sodium cyanoborohydride (21 mg, 0.34 mmol) and stirred for 2 hours at room temperature. The mixture was diluted with methanol, and filtered. The filtrate was concentrated in vacuo to 2 mL, and purified by prep-HPLC to provide 5-[2-(4-{1-hydroxy-2-[4-(1H-tetrazol-1-yl)phenyl]ethyl}piperidin-1-yl)ethyl]-2-benzofuran-1(3H)-one. $^1$H-NMR (DMSO-d6, 400 Hz) δ: 9.50 (s, 1H), 7.69~7.71 (m, 1H), 7.62~7.64 (m, 2H), 7.32~7.36 (m, 4H), 5.36 (s, 2H), 4.27 (s, 1H), 3.51~3.53 (m, 1H), 2.95~3.15 (m, 2H), 2.61~2.95 (m, 4H), 2.21 (brs, 2H), 1.88~1.91 (m, 1H), 1.69~1.72 (m, 1H), 1.41~1.56 (m, 4H). LC-MS (IE, m/z): 434 [M+1]+.

The enantiomerically pure products (isomer A & B) were obtained via SFC resolution (Instrument: Berger Multi-Gram™ SFC, Mettler Toledo Co, Ltd; Column: AD 250 mm*30 mm, 5 um; Mobile phase: A: Supercritical CO2, B: MeOH (0.05% DEA), A/B=60/40 at 70 mL/min; Wavelength: 220 nm).

Isomer A (faster eluting) $^1$H-NMR (400 MHz, CD$_3$OD) δ ppm 9.71 (s, 1H), 7.76-7.83 (m, 3H), 7.51-7.56 (m, 4H), 5.36 (s, 2H), 3.58-3.64 (m, 2H), 3.18-3.30 (m, 6H), 2.64-2.95 (m, 3H), 2.10-2.14 (m, 1H), 1.92-1.96 (m, 1H), 1.62-1.82 (m, 3H). LC-MS (IE, m/z): 434 [M+1]+.

Isomer B (slower eluting) $^1$H-NMR (400 MHz, CD$_3$OD) δ ppm 9.71 (s, 1H), 7.75-7.80 (m, 3H), 7.46-7.52 (m, 4H), 5.35 (s, 2H), 3.60-3.70 (m, 2H), 3.18-3.30 (m, 3H), 2.96-3.04 (m, 3H), 2.70-2.82 (m, 1H), 1.96-2.02 (m, 1H), 1.78-1.84 (m, 1H), 1.45-1.68 (m, 3H). LC-MS (IE, m/z): 434 [M+1]+.

Example 55

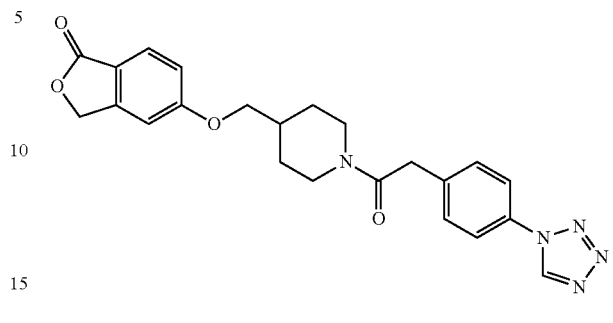

5-[(1-{[4-(1H-Tetrazol-1-yl)phenyl]acetyl}piperidin-4-yl)methoxy]-2-benzofuran-1(3H)-one To 4-{[(1-oxo-1,3-dihydro-2-benzofuran-5-yl)oxy]methyl}piperidine hydrochloride salt (25 mg, ~0.10 mmol) in DCM (5 mL) under nitrogen was added [4-(1H-tetrazol-1-yl)phenyl]acetic acid (41 mg, 0.20 mmol), DIPEA (0.088 mL, 0.50 mmol), pyridine (0.088 mL, 0.50 mmol), and then EDC (39 mg, 0.20 mmol). The reaction was stirred at rt for 16 hours. The mixture was diluted with water, acidified with 18% citric acid and extracted 3 times with DCM. The organic layers were washed with brine, dried over sodium sulfate and evaporated. The residue was taken up in 1:1 acetonitrile:water for reverse phase chromatography (gradient of 10-75% acetonitrile/water with 0.1% TFA) to provide 5-[(1-{[4-(1H-tetrazol-1-yl)phenyl]acetyl}piperidin-4-yl)methoxy]-2-benzofuran-1(3H)-one. LC/MS (M+1-28)+= 406 (100%), (M+1)+=434.

Example 56

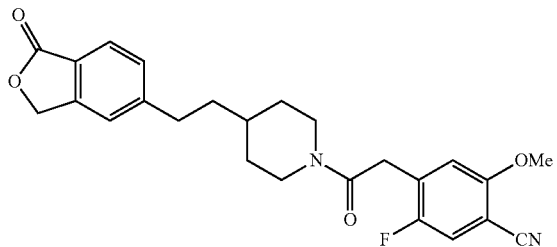 [SMILES: COc1cc(CC(=O)N2CCC(CCc3ccc4c(c3)COC4=O)CC2)c(F)cc1C#N]

5-Fluoro-2-methoxy-4-(2-oxo-2-{4-[2-(1-oxo-1,3-dihydro-2-benzofuran-5-yl)ethyl]piperidin-1-yl}ethyl)benzonitrile 5-Fluoro-2-methoxy-4-(2-oxo-2-{4-[2-(1-oxo-1,3-dihydro-2-benzofuran-5-yl)ethyl]piperidin-1-yl}ethyl)benzonitrile was prepared in a similar fashion to that described for the synthesis of EXAMPLE 5 starting from 4-[2-(1-oxo-1,3-dihydro-2-benzofuran-5-yl)ethyl]piperidinium chloride and (4-cyano-2-fluoro-5-methoxyphenyl)acetic acid. LC-MS (IE, m/z): 437 [M+1]+.

Example 57

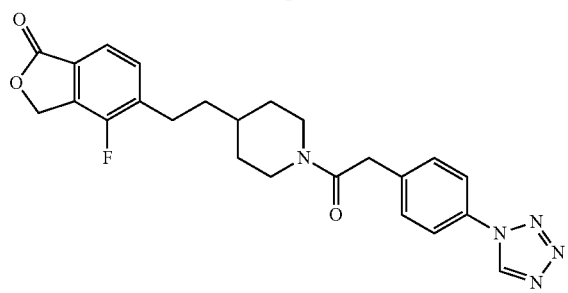 [SMILES: O=C1OCc2c1ccc(CCC1CCN(C(=O)Cc3ccc(-n4cnnn4)cc3)CC1)c2F]

4-Fluoro-5-[2-(1-{[4-(1H-tetrazol-1-yl)phenyl]
acetyl}piperidin-4-yl)ethyl]-2-benzofuran-1(3H)-one 4-Fluoro-5-[2-(1-{[4-(1H-tetrazol-1-yl)phenyl]
acetyl}piperidin-4-yl)ethyl]-2-benzofuran-1(3H)-one was prepared in a similar fashion to that described for the synthesis of EXAMPLE 5 starting from 4-[2-(4-fluoro-1-oxo-1,3-dihydro-2-benzofuran-5-yl)ethyl]piperidinium chloride and [4-(1H-tetrazol-1-yl)phenyl]acetic acid. LC-MS (IE, m/z): 450 [M+1]$^+$.

Example 58

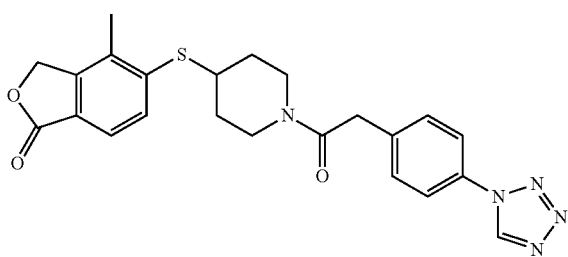 [SMILES: Cc1c(SC2CCN(C(=O)Cc3ccc(-n4cnnn4)cc3)CC2)ccc2c1COC2=O]

4-Methyl-5-[(1-{[4-(1H-tetrazol-1-yl)phenyl]
acetyl}piperidin-4-yl)sulfanyl]-2-benzofuran-1(3H)-one 4-Methyl-5-[(1-{[4-(1H-tetrazol-1-yl)phenyl]
acetyl}piperidin-4-yl)sulfanyl]-2-benzofuran-1(3H)-one was prepared in a similar fashion to that described for the synthesis of EXAMPLE 5 starting from 4-[(4-methyl-1-oxo-1,3-dihydro-2-benzofuran-5-yl)sulfanyl]piperidinium chloride and [4-(1H-tetrazol-1-yl)phenyl]acetic acid. $^1$H-NMR (400 MHz, CDCl$_3$) δ ppm 8.90 (s, 1H), 7.59~7.64 (m, 3H), 7.37~7.41 (m, 3H), 5.16 (s, 2H), 4.28 (m, 1H), 3.72~3.86 (m, 3H), 3.44 (m, 1H), 3.04~3.22 (m, 2H), 2.25 (s, 3H), 1.93~2.00 (m, 2H).

Examples 59 And 60

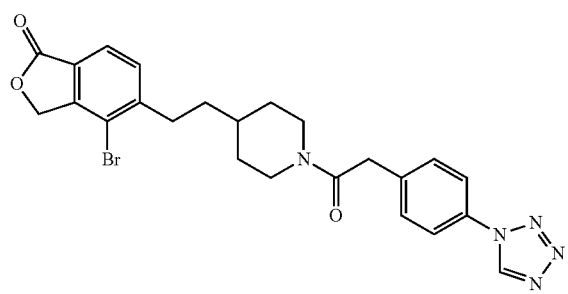

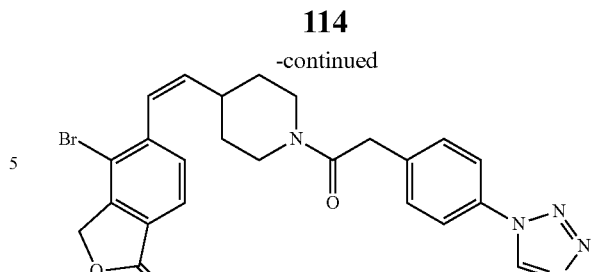

4-Bromo-5-[2-(1-{[4-(1H-tetrazol-1-yl)phenyl]
acetyl}piperidin-4-yl)ethyl]-2-benzofuran-1(3H)-one
and 4-Bromo-5-[(Z)-2-(1-{[4-(1H-tetrazol-1-yl)phenyl]acetyl}piperidin-4-yl)ethenyl]-2-benzofuran-1(3H)-one 4-Bromo-5-[2-(1-{[4-(1H-tetrazol-1-yl)phenyl]
acetyl}piperidin-4-yl)ethyl]-2-benzofuran-1(3H)-one and 4-bromo-5-[(Z)-2-(1-{[4-(1H-tetrazol-1-yl)phenyl]acetyl}piperidin-4-yl)ethenyl]-2-benzofuran-1(3H)-one were obtained after separation (mass-directed HPLC) of the product mixture prepared in a similar fashion to that described for the synthesis of EXAMPLE 5 starting from [4-(1H-tetrazol-1-yl)phenyl]acetic acid and the mixture of 4-[2-(4-bromo-1-oxo-1,3-dihydro-2-benzofuran-5-yl)ethyl]piperidinium chloride and 4-[(Z)-2-(4-bromo-1-oxo-1,3-dihydro-2-benzofuran-5-yl)ethenyl]piperidinium chloride which was obtained as INTERMEDIATES 35 and 36.

4-Bromo-5-[2-(1-{[4-(1H-tetrazol-1-yl)phenyl]
acetyl}piperidin-4-yl)ethyl]-2-benzofuran-1(3H)-one $^1$H-NMR (500 MHz, CDCl$_3$) δ ppm 9.08 (s, 1H), 7.83 (d, J=7.5 Hz, 1H), 7.73 (d, J=8.0 Hz, 2H), 7.51 (d, J=8.0 Hz, 2H), 7.42 (d, J=7.5 Hz, 1H), 5.23 (s, 2H), 4.71 (d, J=8.5 Hz, 1H), 3.96 (m, 1H), 3.93 (s, 2H), 3.14 (m, 1H), 2.91 (m, 2H), 2.74 (t, J=12 Hz, 1H), 1.92 (m, 2H), 1.63 (m, 2H), 1.27 (m, 1H), 1.14 (m, 1H).

4-Bromo-5-[(Z)-2-(1-{[4-(1H-tetrazol-1-yl)phenyl]
acetyl}piperidin-4-yl)ethenyl]-2-benzofuran-1(3H)-one $^1$H-NMR (500 MHz, CDCl$_3$) δ ppm 9.05 (s, 1H), 7.83 (d, J=8.0 Hz, 1H), 7.72 (d, J=8.5 Hz, 2H), 7.50 (d, J=8.5 Hz, 2H), 7.45 (d, J=8.0 Hz, 1H), 6.73 (dd, J=8.0, 1.5 Hz, 1H), 5.24 (s, 2H), 5.07 (dd, J=8.0, 3.0 Hz, 1H), 4.11 (m, 1H), 3.94 (s, 2H), 3.58 (m, 1H), 2.97 (m, 2H), 2.38 (m, 1H), 2.10 (m, 1H), 1.72 (m, 2H).

Example 61

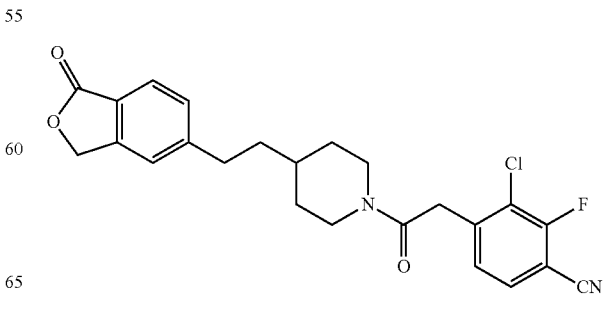

3-Chloro-2-fluoro-4-(2-oxo-2-{4-[2-(1-oxo-1,3-di-hydro-2-benzofuran-5-yl)ethyl]piperidin-1-yl}ethyl) benzonitrile 3-Chloro-2-fluoro-4-(2-oxo-2-{4-[2-(1-oxo-1,3-dihydro-2-benzofuran-5-yl)ethyl]piperidin-1-yl}ethyl)benzonitrile was prepared in a similar fashion to that described for the synthesis of EXAMPLE 5 starting from 4-[2-(1-oxo-1,3-dihydro-2-benzofuran-5-yl)ethyl]piperidinium chloride and (2-chloro-4-cyano-3-fluorophenyl)acetic acid. LC-MS (IE, m/z): 442 [M+1]$^+$.

Example 62

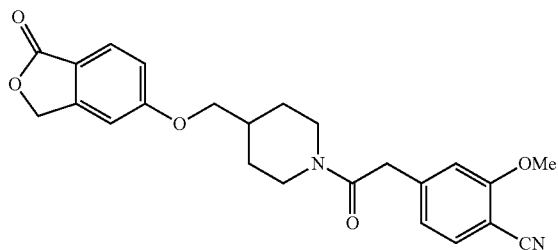 [SMILES: COc1cc(CC(=O)N2CCC(COc3ccc4c(c3)COC4=O)CC2)ccc1C#N]

2-Methoxy-4-[2-oxo-2-(4-{[(1-oxo-1,3-dihydro-2-benzofuran-5-yl)oxy]methyl}piperidin-1-yl)ethyl] benzonitrile To 4-{[(1-oxo-1,3-dihydro-2-benzofuran-5-yl)oxy] methyl}piperidinium chloride (22 mg, 0.089 mmol) in DCM (5 mL) under nitrogen was added 4-cyano-3-methoxyacetic acid (43 mg, 0.22 mmol), DIPEA (0.078 mL, 0.45 mmol), pyridine (0.036 mL, 0.45 mmol), and then EDC (43 mg, 0.22 mmol). The reaction was stirred at rt for 16 hours. The mixture was diluted with water, acidified with 18% citric acid and extracted 3 times with DCM. The organic layers were washed with brine, dried over sodium sulfate and evaporated. The residue was taken up in 1:1 acetonitrile: water for reverse phase chromatography (gradient of 10-75% acetonitrile/water with 0.1% TFA) to provide 2-Methoxy-4-[2-oxo-2-(4-{[(1-oxo-1,3-dihydro-2-benzofuran-5-yl)oxy]methyl}piperidin-1-yl)ethyl]benzonitrile. LC-MS (IE, m/z): 421 [M+1]$^+$.

Example 63

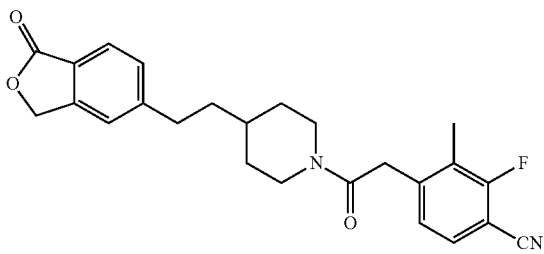 [SMILES: Cc1c(CC(=O)N2CCC(CCc3ccc4c(c3)COC4=O)CC2)ccc(C#N)c1F]

2-Fluoro-3-methyl-4-(2-oxo-2-{4-[2-(1-oxo-1,3-dihydro-2-benzofuran-5-yl)ethyl]piperidin-1-yl}ethyl)benzonitrile 2-Fluoro-3-methyl-4-(2-oxo-2-{4-[2-(1-oxo-1,3-dihydro-2-benzofuran-5- yl)ethyl]piperidin-1-yl}ethyl)benzonitrile was prepared in a similar fashion to that described for the synthesis of EXAMPLE 5 starting from 4-[2-(1-oxo-1,3-dihydro-2-benzofuran-5-yl)ethyl]piperidinium chloride and (4-cyano-3-fluoro-2-methylphenyl)acetic acid. LC-MS (IE, m/z): 421 [M+1]$^+$.

Example 64

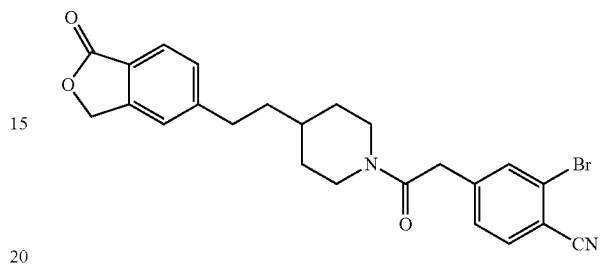

2-Bromo-4-[2-oxo-2-[4-[2-(1-oxo-3H-isobenzo-furan-5-yl)ethyl]-1-piperidyl]ethyl]benzonitrile 2-Bromo-4-[2-oxo-2-[4-[2-(1-oxo-3H-isobenzofuran-5-yl)ethyl]-1-piperidyl]ethyl]benzonitrile was prepared in a similar fashion to that described for the synthesis of EXAMPLE 5 starting from (3-bromo-4-cyanophenyl)acetic acid and 5-[2-(piperidin-4-yl)ethyl]-2-benzofuran-1(3H)-one hydrochloride. LC-MS (IE, m/z): 469 [M+1]$^+$.

Example 65

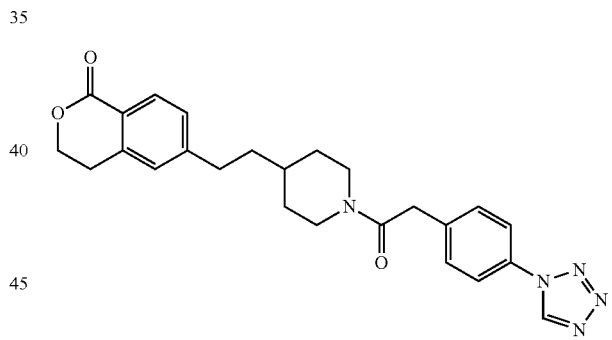

6-[2-(1-{[4-(1H-tetrazol-1-yl)phenyl] acetyl}piperidin-4-yl)ethyl]-3,4-dihydro-1H-iso-chromen-1-one To a solution of 6-[2-(piperidin-4-yl)ethyl]-3,4-dihydro-1H-isochromen-1-one (51 mg, 0.17 mmol) in DCM (10 ml) was added [4-(1H-tetrazol-1-yl)phenyl]acetic acid (53 mg, 0.26 mmol), EDC (67 mg, 0.35 mmol), and triethylamine (48 μl, 0.35 mmol). The reaction was stirred for 16 hrs. The reaction mixture was washed with brine, dried (Na$_2$SO$_4$), filtered and concentrated. The resulting residue was purified by mass directed HPLC to provide 6-[2-(1-{[4-(1H-tetrazol-1-yl)phenyl]acetyl}piperidin-4-yl)ethyl]-3,4-dihydro-1H-isochromen-1-one.
$^1$H NMR (500 MHz, DMSO): δ 10.07 (s, 1H), 7.83 (d, J=8.5 Hz, 2H), 7.82 (d, J=6.5 Hz, 1H), 7.49 (d, J=8.4 Hz, 2H), 7.26 (d, J=8.0 Hz, 1H), 7.24 (s, 1H), 4.47 (t, J=4.9 Hz, 2H), 4.39 (d, J=13 Hz, 1H), 3.98 (d, J=14 Hz, 1H), 3.83 (s, 2H), 3.02 (t, J=5.9 Hz, 2H), 2.99 (t, J=13 Hz, 1H), 2.66 (t, J=7.6 Hz, 2H), 2.56 (t, J=13 Hz, 1H), 1.73 (d, J=12 Hz, 2H), 1.5-1.54 (m, 3H), 0.95-1.04 (m, 2H). LC-MS (IE, m/z): 446 [M+1]⁺.

Example 66

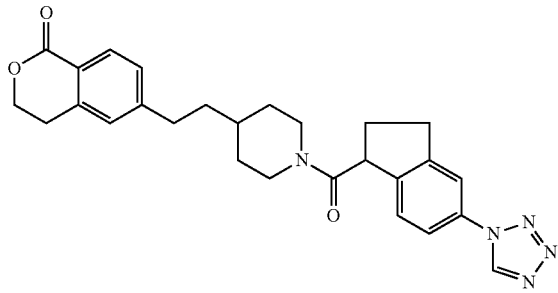 [SMILES: O=C1OCCc2cc(CCC3CCN(C(=O)C4CCc5cc(-n6cnnn6)ccc54)CC3)ccc21]

6-[2-(1-{[5-1H-Tetrazol-1-yl)-2,3-dihydro-1H-inden-1-yl]carbonyl}piperidin-4-yl)ethyl]-3,4-dihydro-1H-isochromen-1-one 6-[2-(1-{[5-(1H-Tetrazol-1-yl)-2,3-dihydro-1H-inden-1-yl]carbonyl}piperidin-4-yl)ethyl]-3,4-dihydro-1H-isochromen-1-one was prepared in a similar fashion to the synthesis previously described for EXAMPLE 65 starting from 4-[2-(1-oxo-3,4-dihydro-1H-isochromen-6-yl)ethyl]piperidinium chloride and 5-(1H-tetrazol-1-yl)-2,3-dihydro-1H-indene-1-carboxylic acid. ¹H NMR (500 MHz, DMSO): δ 10.04 (s, 1H), 7.84 (d, J=8.0 Hz, 1H), 7.77 (s, 1H), 7.67 (dd, J=11.5, 8.5 Hz, 1H), 7.31 (t, J=8.4 Hz, 2H), 7.27 (s, 1H), 4.52 (t, J=5.7 Hz, 1H), 4.48 (t, J=6.0 Hz, 2H), 4.38-4.44 (m, 1H), 4.20 (t, J=11.4 Hz, 1H), 2.95-3.21 (m, 5H) 2.69~2.725 (m, 1H), 2.62 (t, J=12 Hz, 1H), 2.37 (m, 1H), 2.12-2.26 (m, 1H), 1.86 (t, J=10.5 Hz, 1H), 1.78 (b, 1H), 1.5-1.62 (m, 3H), 0.98-1.35 (m, 2H). LC-MS (IE, m/z): 472 [M+1]⁺.

Example 67

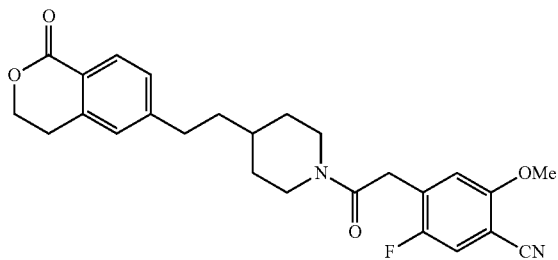 [SMILES: COc1cc(CC(=O)N2CCC(CCc3ccc4c(c3)CCOC4=O)CC2)c(F)cc1C#N]

5-Fluoro-2-methoxy-4-(2-oxo-2-{4-[2-(1-oxo-3,4-dihydro-1H-isochromen-6-yl)ethyl]piperidin-1-yl}ethyl)benzonitrile 5-Fluoro-2-methoxy-4-(2-oxo-2-{4-[2-(1-oxo-3,4-dihydro-1H-isochromen-6-yl)ethyl]piperidin-1-yl}ethyl)benzonitrile was prepared in a similar fashion to the synthesis previously described for EXAMPLE 65 starting from 4-[2-(1-oxo-3,4-dihydro-1H-isochromen-6-yl)ethyl]piperidinium chloride and (4-cyano-2-fluoro-5-methoxyphenyl)acetic acid.

¹H NMR (500 MHz, DMSO): δ 7.84 (d, J=8.0 Hz, 1H), 7.67 (d, J=9.0 Hz, 1H), 7.28 (d, J=8 Hz, 1H), 7.26 (s, 1H), 7.18 (d, J=5.7 Hz, 1H), 4.48 (t, J=6.1 Hz, 2H), 4.33 (d, J=13 Hz, 1H), 3.96 (d, J=14 Hz, 1H), 3.87 (s, 3H), 3.82 (s, 2H), 3.04 (t, J=13 Hz, 1H), 3.03 (t, J=6.2 Hz, 2H), 2.68 (t, J=3.5 Hz, 2H), 2.56 (t, J=13 Hz, 1H), 1.73-1.78 (m, 2H), 1.5-1.58 (m, 3H), 1.16 (m, 1H), 0.98-1.35 (m, 1H). LC-MS (IE, m/z): 451 [M+1]⁺.

Example 68

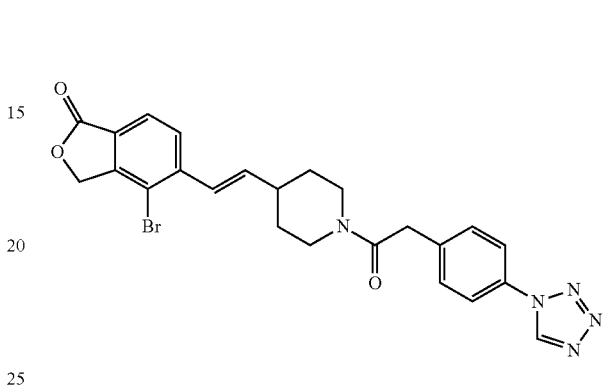

4-Bromo-5-[(E)-2-(1-{[4-(1H-tetrazol-1-yl)phenyl]acetyl}piperidin-4-yl)ethenyl]-2-benzofuran-1(3H)-one 4-Bromo-5-[(E)-2-(1-{[4-(1H-tetrazol-1-yl)phenyl]acetyl}piperidin-4-yl)ethenyl]-2-benzofuran-1(3H)-one was prepared in a similar fashion to that described for the synthesis of EXAMPLE 5 starting from 4-[(E)-2-(4-bromo-1-oxo-1,3-dihydro-2-benzofuran-5-yl)ethenyl]piperidinium chloride and [4-(1H-tetrazol-1-yl)phenyl]acetic acid.

¹H-NMR (500 MHz, CDCl₃) δ ppm 9.04 (s, 1H), 7.83 (d, J=8.0 Hz, 1H), 7.30 (d, J=8.5 Hz, 2H), 7.68 (d, J=8.0 Hz, 1H), 7.53 (d, J=8.5 Hz, 2H), 6.83 (d, J=16 Hz, 1H), 6.31 (dd, J=16, 7.0 Hz, 1H), 5.24 (s, 2H), 4.75 (d, J=16 Hz, 1H), 4.03 (d, J=13.5 Hz, 1H), 3.91 (s, 2H), 3.23 (t, J=12 Hz, 1H), 2.57 (m, 1H), 1.99 (m, 2H), 1.50 (m, 1H), 1.39 (m, 1H).

Example 69

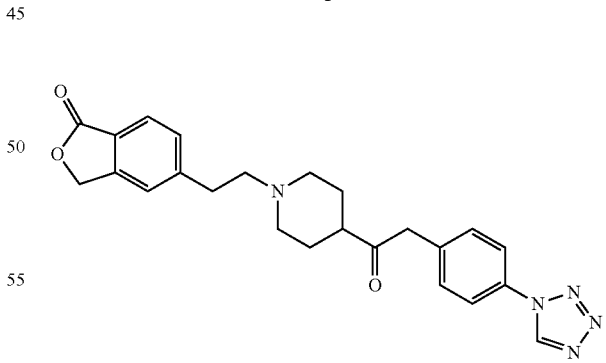

5-[2-(4-{[4-(1H-Tetrazol-1-yl)phenyl]acetyl}piperidin-1-yl)ethyl]-2-benzofuran-1(3H)-one A solution of 5-[2-(4-{1-hydroxy-2-[4-(1H-tetrazol-1-yl)phenyl]ethyl}piperidin-1-yl)ethyl]-2-benzofuran-1(3H)-one (10 mg, 0.023 mmol) in DMF (0.5 mL) was added pyridinium chlorochromate (70 mg, 0.197 mmol) and the mixture was stirred at room temperature for 6 hours. The resulting mixture was diluted with saturated sodium bicarbonate solution and extracted with ethyl acetate. The organic layer was washed with brine, dried (Na$_2$SO$_4$), filtered and concentrated. The resulting residue was purified by prep-HPLC to provide 5-[2-(4-{[4-(1H-tetrazol-1-yl)phenyl]acetyl}piperidin-1-yl)ethyl]-2-benzofuran-1(3H)-one.

$^1$H-NMR (DMSO-d6, 400 Hz) δ 9.50 (s, 1H), 7.69~7.71 (m, 1H), 7.62~7.64 (m, 2H), 7.32~7.36 (m, 4H), 2.135 (s, 2H), 4.27 (s, 1H), 3.61~3.64 (m, 1H), 2.95~3.15 (m, 2H), 2.61~2.95 (m, 4H), 2.21 (s, 2H), 1.88~1.91 (m, 1H), 1.69~1.72 (m, 1H), 1.41~1.56 (m, 4H).

Example 70

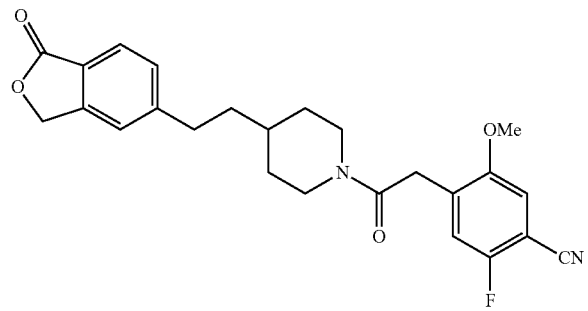 [SMILES: COc1cc(C#N)c(F)cc1CC(=O)N1CCC(CCc2ccc3c(c2)COC3=O)CC1]

2-Fluoro-5-methoxy-4-(2-oxo-2-{4-[2-(1-oxo-1,3-dihydro-2-benzofuran-5-yl)ethyl]piperidin-1-yl}ethyl)benzonitrile 2-Fluoro-5-methoxy-4-(2-oxo-2-{4-[2-(1-oxo-1,3-dihydro-2-benzofuran-5-yl)ethyl]piperidin-1-yl}ethyl)benzonitrile was prepared in a similar fashion to that described for the synthesis of EXAMPLE 5 starting from (4-cyano-5-fluoro-2-methoxyphenyl)acetic acid and 5-[2-(piperidin-4-yl)ethyl]-2-benzofuran-1(3H)-one hydrochloride.

$^1$H NMR (500 MHz, CDCl$_3$, δ in ppm): 7.80 (m, 1H), 7.38 (m, 1H), 7.32 (m, 1H), 7.10 (m, 1H), 6.98 (m, 1H), 5.23 (s, 2H), 4.60 (m, 1H), 3.82 (m, 4H), 3.63 (m, 2H), 3.01 (m, 1H), 2.78 (m, 2H), 2.58 (m, 1H), 1.00-1.90 (m, 5H). LC-MS (IE, m/z): 437 [M+1]$^+$.

Example 71

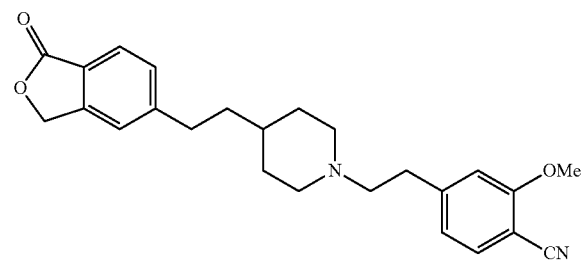 [SMILES: COc1cc(CCN2CCC(CCc3ccc4c(c3)COC4=O)CC2)ccc1C#N]

2-Methoxy-4-(2-{4-[2-(1-oxo-1,3-dihydro-2-benzofuran-5-yl)ethyl]piperidin-1-yl}ethyl)benzonitrile To a mixture of 5-[2-(piperazin-1-yl)ethyl]-2-benzofuran-1(3H)-one methyl (31 mg, 0.11 mmol) and 2-methoxy-4-(2-oxoethyl)benzonitrile (16 mg, 0.091 mmol) in methanol (1.0 mL) at 0° C. was added sodium cyanoborohydride (8.0 mg, 0.13 mmol) and the mixture was stirred at room temperature for 12 hours. The reaction mixture was concentrated and purified by mass-directed HPLC to provide 2-methoxy-4-(2-{4-[2-(1-oxo-1,3-dihydro-2-benzofuran-5-yl)ethyl]piperidin-1-yl}ethyl)benzonitrile. LC-MS (IE, m/z): 406 [M+1]$^+$.

Example 72

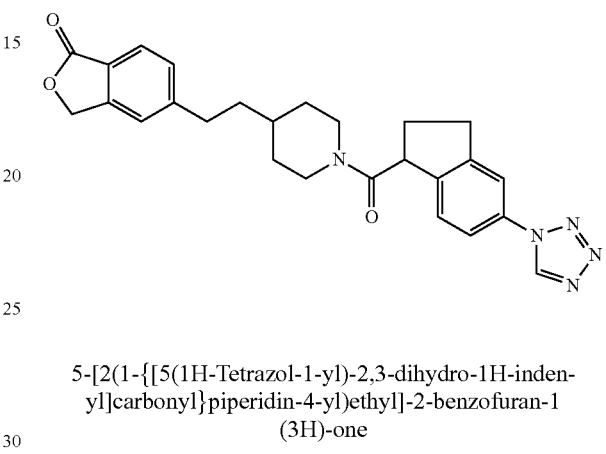

5-[2(1-{[5(1H-Tetrazol-1-yl)-2,3-dihydro-1H-inden-yl]carbonyl}piperidin-4-yl)ethyl]-2-benzofuran-1(3H)-one 5-[2-(1-{[5-(1H-Tetrazol-1-yl)-2,3-dihydro-1H-inden-1-yl]carbonyl}piperidin-4-yl)ethyl]-2-benzofuran-1(3H)-one was prepared in a similar fashion to that described for the synthesis of EXAMPLE 5 starting from (3-bromo-4-cyanophenyl)acetic acid and 5-(1H-tetrazol-1-yl)-2,3-dihydro-1H-indene-1-carboxylic acid. $^1$H NMR (500 MHz, DMSO): δ 10.04 (s, 1H), 7.77 (s, 2H), 7.67 (dd, J=11.5, 8.6 Hz, 1H), 7.53 (s, 1H), 7.46 (d, J=7.6 Hz, 1H), 7.33 (dd, J=8.0, 3.8 Hz, 1H), 5.40 (s, 2H), 4.53 (t, J=8.0, 1H), 4.43 (dd, J=22.5, 14 Hz, 1H), 4.20 (t, J=13 Hz, 1H), 3.17 (m, 1H) 3.02-3.10 (m, 1H), 2.92-3.0 (m, 1H), 2.76-2.82 (m, 2H), 2.62 (t, J=12.5 Hz, 1H), 2.35-2.42 (m, 1H), 2.12-2.26 (m, 1H), 1.86 (t, J=11.2 Hz, 1H), 1.72-1.82 (m, 1H), 1.52-1.64 (m, 3H), 1.0-1.2 (m, 2H). LC-MS (IE, m/z): 458 [M+1]$^+$.

Example 73

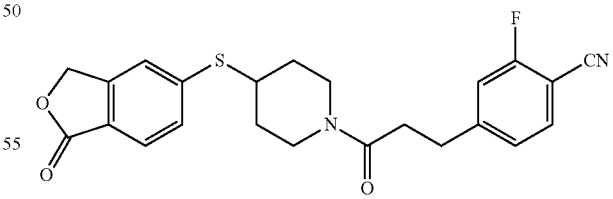

2-Fluoro-4-(3-oxo-3-{4-[(1-oxo-1,3-dihydro-2-benzofuran-5-yl)sulfanyl]piperidin-1-yl}propyl)benzonitrile 2-Fluoro-4-(3-oxo-3-{4-[(1-oxo-1,3-dihydro-2-benzofuran-5-yl)sulfanyl]piperidin-1-yl}propyl)benzonitrile was prepared in a similar fashion to that described for the synthesis of EXAMPLE 5 starting from 4-[(1-oxo-1,3- dihydro-2-benzofuran-5-yl)sulfanyl]piperidinium chloride and 3-(4-cyano-3-fluorophenyl)propanoic acid. LC-MS (IE, m/z): 425 [M+1]⁺.

Example 74

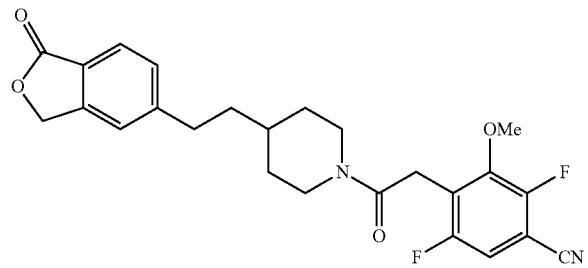 [SMILES: COc1c(F)c(C#N)cc(F)c1CC(=O)N1CCC(CCc2ccc3c(c2)COC3=O)CC1]

2,5-Difluoro-3-methoxy-4-(2-oxo-2-{4-[2-(1-oxo-1, 3-dihydro-2-benzofuran-5-yl)ethyl]piperidin-1-yl}ethyl)benzonitrile 2,5-Difluoro-3-methoxy-4-(2-oxo-2-{4-[2-(1-oxo-1,3-dihydro-2-benzofuran-5-yl)ethyl]piperidin-1-yl}ethyl)benzonitrile was prepared in a similar fashion to that described for the synthesis of EXAMPLE 5 starting from (4-cyano-3,6-difluoro-2-methoxyphenyl)acetic acid and 5-[2-(piperidin-4-yl)ethyl]-2-benzofuran-1(3H)one hydrochloride.

¹H NMR (500 MHz, CDCl₃, δ in ppm): 7.84 (1H, d, J=7.8 Hz), 7.35 (1H, d, J=7.8 Hz), 7.30 (1H, s), 7.02 (1H, dd, J=4.3, 8.0 Hz), 5.29 (2H, s), 4.59 (1H, m), 3.98 (4H, m), 3.73 (2H, s), 3.14 (1H, m), 2.80 (2H, m), 2.61 (1H, m), 1.20-1.90 (7H, m). LC-MS (IE, m/z): 455 [M+1]⁺.

Example 75

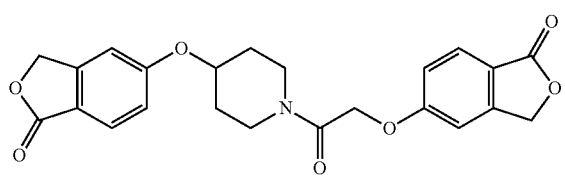 [SMILES: O=C1OCc2cc(OCC(=O)N3CCC(Oc4ccc5c(c4)COC5=O)CC3)ccc21]

5-[(1-{[(1-Oxo-1,3-dihydro-2-benzofuran-5-yl)oxy] acetyl}piperidin-4-yl)oxy]-2-benzofuran-1(3H)-one 5-[(1-{[(1-Oxo-1,3-dihydro-2-benzofuran-5-yl)oxy] acetyl}piperidin-4-yl)oxy]-2-benzofuran-1(3H)-one was prepared in a similar fashion to that described for the synthesis of EXAMPLE 5 starting from 4-[(1-oxo-1,3-dihydro-2-benzofuran-5-yl)oxy]piperidinium chloride and [(1-oxo-1,3-dihydro-2-benzofuran-5-yl)oxy]acetic acid. LC-MS (IE, m/z): 424 [M+1]⁺.

Example 76

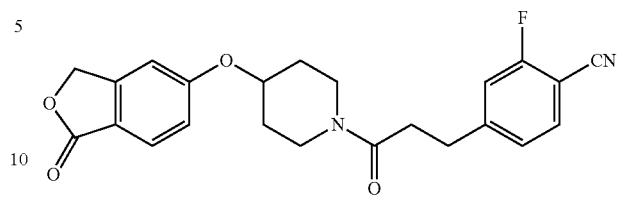

2-Fluoro-4-(3-oxo-3-{4-[(1-oxo-1,3-dihydro-2-benzofuran-5-yl)oxy]piperidin-1-yl}propyl)benzonitrile 2-Fluoro-4-(3-oxo-3-{4-[(1-oxo-1,3-dihydro-2-benzofuran-5-yl)oxy]piperidin-1-yl}propyl)benzonitrile was prepared in a similar fashion to that described for the synthesis of EXAMPLE 5 starting from 4-[(1-oxo-1,3-dihydro-2-benzofuran-5-yl)oxy]piperidinium chloride and 3-(4-cyano-3-fluorophenyl)propanoic acid. LC-MS (IE, m/z): 409 [M+1]⁺.

Example 77

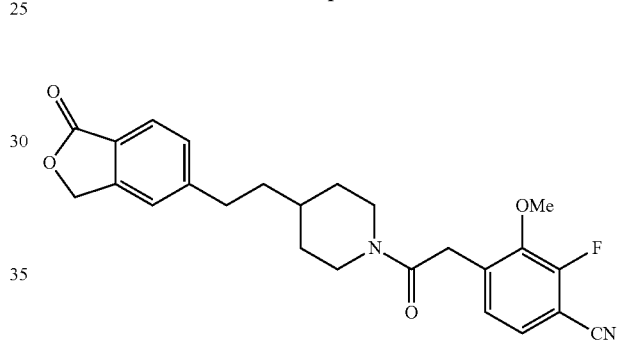

2-Fluoro-3-methoxy-4-(2-oxo-2-{4-[2-(1-oxo-1,3-dihydro-2-benzofuran-5-yl)ethyl]piperidin-1-yl}ethyl)benzonitrile 2-Fluoro-3-methoxy-4-(2-oxo-2-{4-[2-(1-oxo-1,3-dihydro-2-benzofuran-5-yl)ethyl]piperidin-1-yl}ethyl)benzonitrile was prepared in a similar fashion to that described for the synthesis of EXAMPLE 5 starting from (4-cyano-3-fluoro-2-methoxyphenyl)acetic acid and 5-[2-(piperidin-4-yl)ethyl]-2-benzofuran-1(3H)-one hydrochloride. LC-MS (IE, m/z): 437 [M+1]⁺.

Example 78

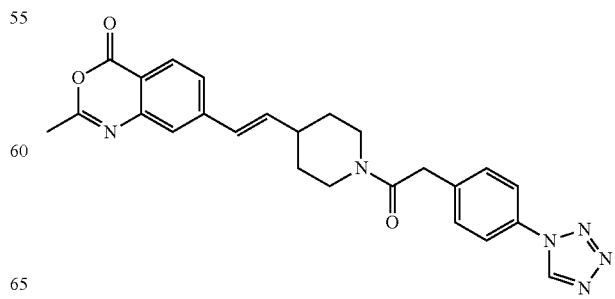

2-Methyl-7-[(E)-2-(1-{[4-(1H-tetrazol-1-yl)phenyl]
acetyl}piperidin-4-yl)ethenyl]-4H-3,1-benzoxazin-4-
one 2-Methyl-7-[(E)-2-(1-{[4-(1H-tetrazol-1-yl)phenyl]
acetyl}piperidin-4-yl)ethenyl]-4H-3,1-benzoxazin-4-one
was prepared in a similar fashion to that described for the
synthesis of EXAMPLE 5 starting 4-[(E)-2-(2-methyl-4-
oxo-4H-3,1-benzoxazin-7-yl)ethenyl]piperidinium chloride
and [4-(1H-tetrazol-1-yl)phenyl]acetic acid. LC-MS (IE,
m/z): 457 [M+1]⁺.

Example 79

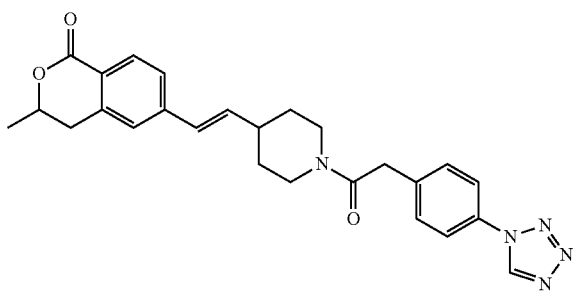 [SMILES: CC1Cc2cc(/C=C/C3CCN(C(=O)Cc4ccc(-n5cnnn5)cc4)CC3)ccc2C(=O)O1]

3-Methyl-6-[(E)-2-(1-{[4-(1H-tetrazol-1-yl)phenyl]
acetyl}piperidin-4-yl)ethenyl]-3,4-dihydro-1H-iso-
chromen-1-one 3-Methyl-6-[(E)-2-(1-{[4-(1H-tetrazol-1-yl)phenyl]
acetyl}piperidin-4-yl)ethenyl]-3,4-dihydro-1H-isochromen-
1-one was prepared in a similar fashion to that described for
the synthesis of EXAMPLE 5 starting 4-[(E)-2-(2-methyl-
4-oxo-4H-3,1-benzoxazin-7-yl)ethenyl]piperidinium chloride and [4-(1H-tetrazol-1-yl)phenyl]acetic acid. LC-MS
(IE, m/z): 457 [M+1]⁺.

Example 80

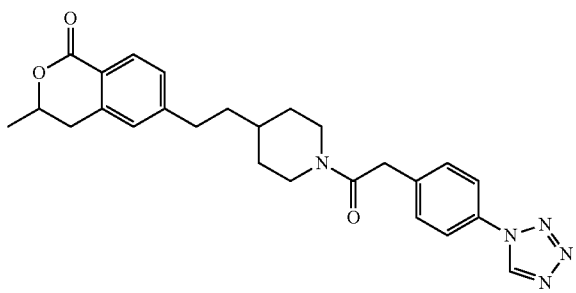 [SMILES: CC1Cc2cc(CCC3CCN(C(=O)Cc4ccc(-n5cnnn5)cc4)CC3)ccc2C(=O)O1]

3-Methyl-6-[2-(1-{[4-(1H-tetrazol-1-yl)phenyl]
acetyl}piperidin-4-yl)ethyl]-3,4-dihydro-1H-iso-
chromen-1-one 3-Methyl-6-[2-(1-{[4-(1H-tetrazol-1-yl)phenyl]
acetyl}piperidin-4-yl)ethyl]-3,4-dihydro-1H-isochromen-1-
one was prepared in a similar fashion to that described for
the synthesis of EXAMPLE 7 starting from 3-methyl-6-[(E)-

2-(1-{[4-(1H-tetrazol-1-yl)phenyl]acetyl}piperidin-4-yl)
ethenyl]-3,4-dihydro-1H-isochromen-1-one. LC-MS (IE,
m/z): 460 [M+1]⁺.

Example 81

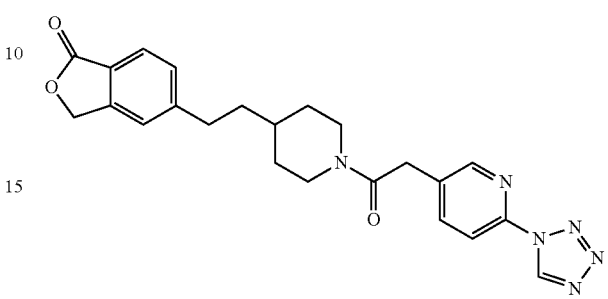

5-[2-(1-{[6-(1H-tetrazol-1-yl)pyridin-3-yl]
acetyl}piperidin-4-yl)ethyl]-2-benzofuran-1(3H)-one 5-[2-(1-{[6-(1H-tetrazol-1-yl)pyridin-3-yl]
acetyl}piperidin-4-yl)ethyl]-2-benzofuran-1(3H)-one was
prepared in a similar fashion to that described for the
synthesis of EXAMPLE 5 starting from 4-[2-(1-oxo-1,3-
dihydro-2-benzofuran-5-yl)ethyl]piperidinium chloride and
[6-(1H-tetrazol-1-yl)pyridin-3-yl]acetic acid. 1H NMR LC-
MS (IE, m/z): 433 [M+1]⁺.

Example 82

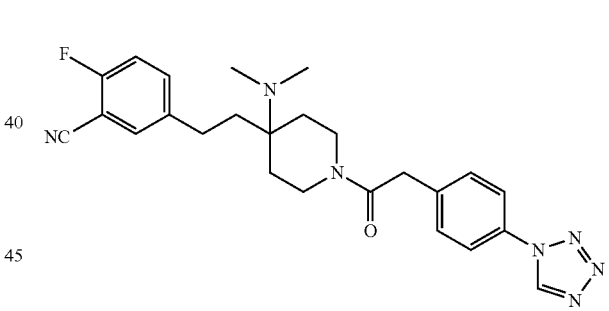

5-{2-[4-(Dimethylamino)-1-{[4-(1H-tetrazol-1-yl)
phenyl]acetyl}piperidin-4-yl]ethyl}-2-fluorobenzo-
nitrile Step A: Benzyl {4-[2-(3-cyano-4-fluorophenyl)
ethyl]-1-[4-(1H-tetrazol-1-yl)phenylacetyl]piperidin-
4-yl}carbamate To a solution of benzyl {4-[2-(3-cyano-4-fluorophenyl)
ethyl]piperidin-4-yl}carbamate hydrochloride salt (110 mg,
0.26 mmol), [4-(1H-tetrazol-1-yl)phenyl]acetic acid (81 mg,
0.40 mmol) and EDC (100 mg, 0.53 mmol) in acetonitrile
(1.0 mL) was added DIPEA (0.23 mL, 1.3 mmol) and
pyridine (0.11 mL, 1.3 mmol). The solution was stirred at rt
for 4 hours when another aliquot of EDC (30 mg) was added
and the reaction was stirred overnight. The mixture was
separated directly on reverse phase chromatography (gradient of 10-75% acetonitrile/water with 0.1% TFA) to afford Benzyl {4-[2-(3-cyano-4-fluorophenyl)ethyl]-1-[4-(1H-tetrazol-1-yl)phenylacetyl]piperidin-4-yl}carbamate.

¹H-NMR (500 MHz, CDCl₃) δ ppm 9.06 (s, 1H), 7.70 (d, J=8.5 Hz, 1H), 7.47 (d, J=8.4 Hz, 1H), 7.2~7.4 (2m, 7H), 7.09 (dd, J=8.5, 8.5 Hz, 1H), 7.09 (dd, J=8.5, 8.5 Hz, 1H), 5.10 (br s, 2H), 4.70 (br s, 1H), 4.41 (br d, J=14 Hz, 1H), 3.89 (s, 2H), 3.74 (br d, J=14 Hz, 1H), 3.36 (m, 1H), 3.05 (m, 1H), 2.4-2.6 (m, 2H), 2.3-2.4 (m, 1H), 2.1-2.2 (m, 1H), 2.0-2.1 (m, 1H), 1.8-1.9 (m, 1H), 1.58 (m, 1H), 1.45 (m, 1H). LC-MS (IE, m/z): 568 [M+1]⁺.

Step B: 1-{4-[2-(3-Cyano-4-fluorophenyl)ethyl]-4-(amino)piperidin-1-yl}-2-[4-(1H-tetrazol-1-yl)phenyl]ethanone A solution of benzyl {4-[2-(3-cyano-4-fluorophenyl)ethyl]-1-[4-(1H-tetrazol-1-yl)phenylacetyl]piperidin-4-yl}carbamate (100 mg, 0.18 mmol) in ethanol (6 mL) in a hydrogenation tube was flushed with nitrogen and Pd/C (25 mg) was added. The mixture was shaken under hydrogen (40 psi) for 2 hours. The catalyst was removed by filtration and rinsed well with MeOH/DCM. Evaporation of the volatiles and vacuum drying gave 1-{4-[2-(3-cyano-4-fluorophenyl)ethyl]-4-(amino)piperidin-1-yl}-2-[4-(1H-tetrazol-1-yl)phenyl]ethanone.

LC-MS (IE, m/z): 434 [M+1]⁺.

Step C: 1-{4-[2-(3-Cyano-4-fluorophenyl)ethyl]-4-(dimethylamino)piperidin-1-yl}-2-[4-(1H-tetrazol-1-yl)phenyl]ethanone To a solution of 1-{4-[2-(3-cyano-4-fluorophenyl)ethyl]-4-(amino)piperidin-1-yl}-2-[4-(1H-tetrazol-1-yl)phenyl]ethanone (20 mg, 0.046 mmol) in dichloroethane (3 mL) was added sodium triacetoxyborohydride (20 mg, 0.092 mmol) and acetic acid (0.003 mL, 0.046 mmol). The reaction was stirred at rt for 16 hours and then evaporated. The residue was purified on reverse phase chromatography (gradient of 10-75% acetonitrile/water with 0.1% TFA) to provide 1-{4-[2-(3-cyano-4-fluorophenyl)ethyl]-4-(dimethylamino)piperidin-1-yl}-2-[4-(1H-tetrazol-1-yl)phenyl]ethanone. LC-MS (IE, m/z): 462 [M+1]⁺.

Example 83

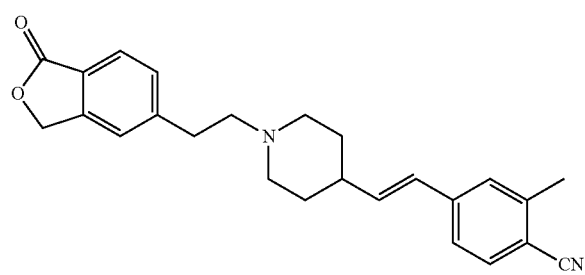 [SMILES: Cc1cc(/C=C/C2CCN(CCc3ccc4c(c3)COC4=O)CC2)ccc1C#N]

4-[(E)-2-{1-[2-(1-Oxo-1,3-dihydro-2-benzofuran-5-yl)ethyl]piperidin-4-yl}ethenyl]benzonitrile To a flask containing 4-[(E)-2-(4-cyano-3-methylphenyl)ethenyl]piperidinium chloride (110 mg, 0.33 mmol) was added oxo-1,3-dihydro-2-benzofuran-5-yl)acetaldehyde (57 mg, 0.33 mmol) and DCM (1.3 mL). The mixture was allowed to stir for 20 minutes before sodium triacetoxyborohydride (210 mg, 0.97 mmol) was added and the mixture stirred for 36 h. The reaction was quenched with methanol, stirred an additional 30 minutes, and concentrated in vacuo. The resulting residue was redissolved in dichloromethane, filtered, concentrated and purified via MPLC (30-100% (10% IPA in DCM/DCM) to afford 4-[(E)-2-{1-[2-(1-oxo-1,3-dihydro-2-benzofuran-5-yl)ethyl]piperidin-4-yl}ethenyl]benzonitrile.

LC-MS (IE, m/z): 387 [M+1]⁺.

Example 84

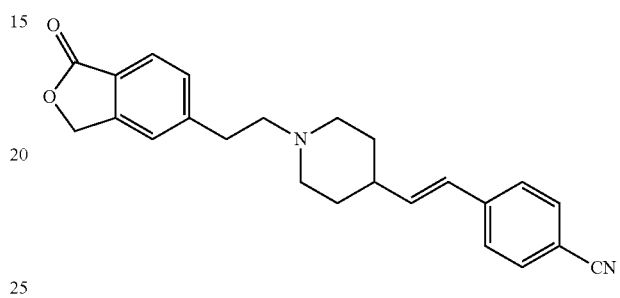

4-[(E)-2-{1-[2-(1-Oxo-1,3-dihydro-2-benzofuran-5-yl)ethyl]piperidin-4-yl}ethenyl]benzonitrile 4-[(E)-2-{1-[2-(1-Oxo-1,3-dihydro-2-benzofuran-5-yl)ethyl]piperidin-4-yl}ethenyl]benzonitrile was prepared in a similar fashion to the synthesis previously described in EXAMPLE 83 starting from 4-[(E)-2-(4-cyanophenyl)ethenyl]piperidinium chloride and oxo-1,3-dihydro-2-benzofuran-5-yl)acetaldehyde. LC-MS (IE, m/z): 373 [M+1]⁺.

Example 85

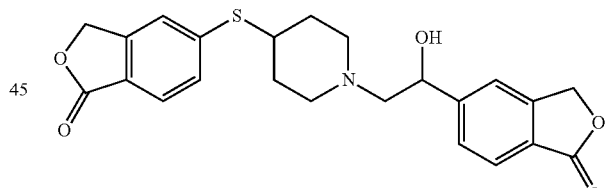

5-({1-[2-hydroxy-2-(1-oxo-1,3-dihydro-2-benzofuran-5-yl)ethyl]piperidin-4-yl}sulfanyl)-2-benzofuran-1(3H)-one 4-methyl-5-oxiran-2-yl-2-benzofuran-1(3H)-one (50 mg, 0.20 mmol) was combined with the free base generated from 4-[(1-oxo-1,3-dihydro-2-benzofuran-5-yl)sulfanyl]piperidinium chloride in a microwave vial and treated with ethanol (2.5 mL). The resulting mixture was then heated at 150° C. for 30 min. The reaction mixture was concentrated to dryness, re-dissolved in MeOH, filtered and purified by mass-directed HPLC to yield 5-({1-[2-hydroxy-2-(1-oxo-1,3-dihydro-2-benzofuran-5-yl)ethyl]piperidin-4-yl}sulfanyl)-2-benzofuran-1(3H)-one.

LC-MS (IE, m/z): 440 [M+1]⁺.

Example 86

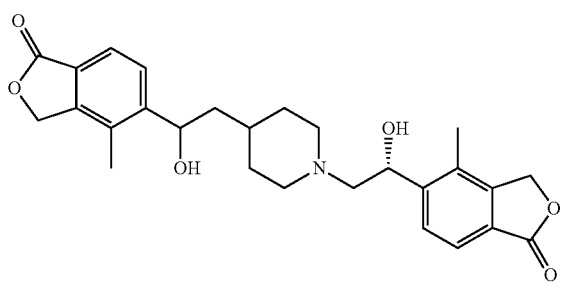 [SMILES: Cc1c(C(O)CC2CCN(C[C@H](O)c3ccc4c(c3C)COC4=O)CC2)ccc2c1COC2=O]

5-[(1R)-1-Hydroxy-2-{4-[2-hydroxy-2-(4-methyl-1-oxo-1,3-dihydro-2-benzofuran-5-yl)ethyl]piperidin-1-yl}ethyl]-4-methyl-2-benzofuran-1(3H)-one (2-Diastereomers)

To a flask charged with 5-[1-hydroxy-2-(piperidin-4-yl)ethyl]-4-methyl-2-benzofuran-1(3H)-one TFA salt was added aqueous sodium bicarbonate. The solution was extracted three times with CHCl$_3$-IPA (3:1). The combined extracts were dried over Na$_2$SO$_4$, filtered and concentrated to produce the free base. The free base (41 mg, 0.15 mmol) was transferred into a 5 mL microwave tube. To the tube was added 4-methyl-5-[(2R)-oxiran-2-yl]-2-benzofuran-1(3H)-one (59 mg, 0.31 mmol), ethanol (3 mL), and a stir bar. The tube was sealed and heated to 150° C. for 1 hour. LC showed formation of the desired product, which was separated by mass-directed HPLC to provide 5-[(1R)-1-hydroxy-2-{4-[2-hydroxy-2-(4-methyl-1-oxo-1,3-dihydro-2-benzofuran-5-yl)ethyl]piperidin-1-yl}ethyl]-4-methyl-2-benzofuran-1(3H)-one as a mixture of two diastereomers. LC-MS (IE, m/z): 466 [M+1]$^+$.

Example 87

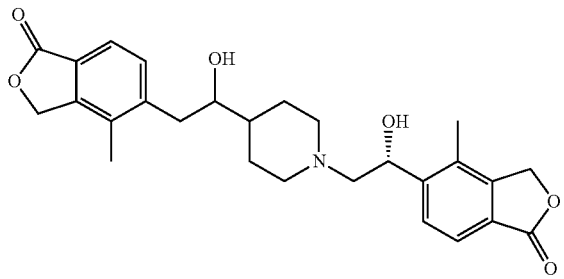 [SMILES: Cc1c(CC(O)C2CCN(C[C@H](O)c3ccc4c(c3C)COC4=O)CC2)ccc2c1COC2=O]

5-[(1R)-1-Hydroxy-2-{4-[1-hydroxy-2-(4-methyl-1-oxo-1,3-dihydro-2-benzofuran-5-yl)ethyl]piperidin-1-yl}ethyl]-4-methyl-2-benzofuran-1(3H)-one (2 Diastereomers)

5-[(1R)-1-Hydroxy-2-{4-[1-hydroxy-2-(4-methyl-1-oxo-1,3-dihydro-2-benzofuran-5-yl)ethyl]piperidin-1-yl}ethyl]-4-methyl-2-benzofuran-1(3H)-one (mixture of two diastereomers) was prepared in a similar fashion to the synthesis previously described for EXAMPLE 86 starting from 5-[2-hydroxy-2-(piperidin-4-yl)ethyl]-4-methyl-2-benzofuran-1(3H)-one and 4-methyl-5-[(2R)-oxiran-2-yl]-2-benzofuran-1(3H)-one. LC-MS (IE, m/z): 466 [M+1]$^+$.

Example 88

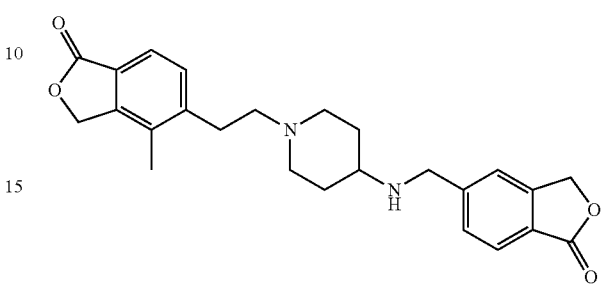

4-Methyl-5-[2-(4-{[(1-oxo-1,3-dihydro-2-benzofuran-5-yl)methyl]amino}piperidin-1-yl)ethyl]-2-benzofuran-1(3H)-one To a solution of 4-{[(1-oxo-1,3-dihydro-2-benzofuran-5-yl)methyl]amino}piperidinium chloride (40 mg, 0.13 mmol) in methanol (3 ml) was added (4-methyl-1-oxo-1,3-dihydro-2-benzofuran-5-yl)acetaldehyde (36 mg, 0.19 mmol) at rt. The mixture was left to stir for 10 min, and then sodium cyanoborohydride (12 mg, 0.19 mmol) was added to the mixture at room temperature. 10% Acetic acid (0.40 ml, 7.0 mmol) was then added dropwise to help with solubility. The reaction mixture was left to stir at room temperature overnight. The mixture was concentrated, and the residue was purified by prep TLC (silica gel; 10% MeOH/DCM) to provide 4-methyl-5-[2-(4-{[(1-oxo-1,3-dihydro-2-benzofuran-5-yl)methyl]amino}piperidin-1-yl)ethyl]-2-benzofuran-1(3H)-one. LC-MS (IE, m/z): 421 [M+1]$^+$.

Example 89

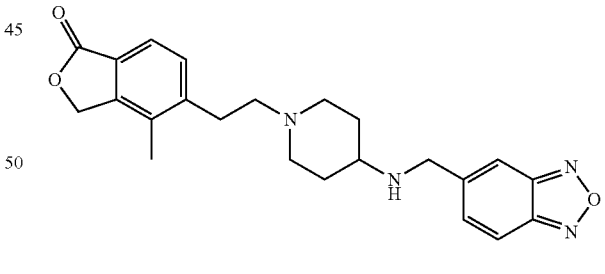

5-(2-{4-[(2,1,3-Benzoxadiazol-5-ylmethyl)amino]piperidin-1-yl}ethyl)-4-methyl-2-benzofuran-1(3H)-one To a solution of 1-[2-(4-methyl-1-oxo-1,3-dihydro-2-benzofuran-5-yl)ethyl]piperidin-4-aminium chloride (40 mg, 0.13 mmol) in methanol (3 ml) was added (4-methyl-1-oxo-1,3-dihydro-2-benzofuran-5-yl)acetaldehyde (36 mg, 0.19 mmol) at room temperature. The mixture was left to stir for 10 min, and then sodium cyanoborohydride (12 mg, 0.19 mmol) was added to the mixture at room temperature. 10% Acetic acid (0.40 ml, 7.0 mmol) was then added dropwise to help with solubility. The reaction mixture was left to stir at room temperature overnight. The mixture was concentrated, and the residue was purified by prep-TLC (silica gel; 10% MeOH/DCM) to provide 5-(2-{4-[(2,1,3-benzoxadiazol-5-ylmethyl)amino]piperidin-1-yl}ethyl)-4-methyl-2-benzofuran-1(3H)-one. LC-MS (IE, m/z): 407 [M+1]⁺.

Example 90

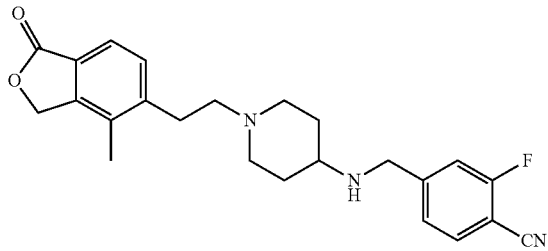 [SMILES: Cc1c(CCN2CCC(NCc3ccc(C#N)c(F)c3)CC2)ccc2c1COC2=O]

2-Fluoro-4-[({1-[2-(4-methyl-1-oxo-1,3-dihydro-2-benzofuran-5-yl)ethyl]piperidin-4-yl}amino)methyl]benzonitrile 2-Fluoro-4-[({1-[2-(4-methyl-1-oxo-1,3-dihydro-2-benzofuran-5-yl)ethyl]piperidin-4-yl}amino)methyl]benzonitrile was prepared in a similar fashion to the previously described synthesis of INTERMEDIATE 89 starting from 1-[2-(4-methyl-1-oxo-1,3-dihydro-2-benzofuran-5-yl)ethyl]piperidin-4-aminium chloride and 2-fluoro-4-formylbenzonitrile.

LC-MS (IE, m/z): 408 [M+1]⁺.

Example 91

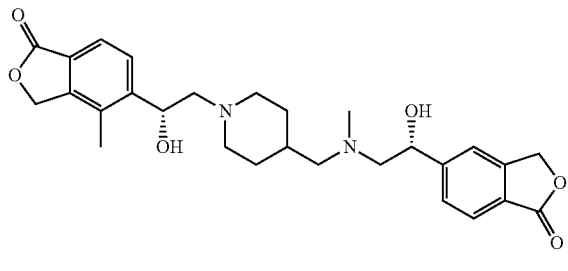 [SMILES: Cc1c([C@@H](O)CN2CCC(CN(C)C[C@H](O)c3ccc4c(c3)COC4=O)CC2)ccc2c1COC2=O]

5-{(1R)-1-Hydroxy-2-[4-({[(2R)-2-hydroxy-2-(1-oxo-1,3-dihydro-2-benzofuran-5-yl)ethyl](methyl)amino}methyl)piperidin-1-yl]ethyl}-4-methyl-2-benzofuran-1(3H)-one A solution of 4-methyl-5-[(2R)-oxiran-2-yl]-2-benzofuran-1(3H)-one (38 mg, 0.20 mmol) in 0.50 mL of ethanol was prepared. Separately, 5-[(1R)-1-hydroxy-2-{4-[(methylamino)methyl]piperidin-1-yl}ethyl]-4-methyl-2-benzofuran-1(3H)-one (62 mg, 0.20 mmol) was dissolved in 1 mL of ethanol followed by addition of 200 mg of MP-CO₃ resin and heating. The two solutions, along with the resin, were combined and microwaved at 140° C. for fifty-five minutes. The solvent was removed in vacuo and the remaining solids were dissolved in 1 mL DMSO. Purification by HPLC afforded 5-{(1R)-1-hydroxy-2-[4-({[(2R)-2-hydroxy-2-(4-methyl-1-oxo-1,3-dihydro-2-benzofuran-5-yl)ethyl](methyl)amino}methyl)piperidin-1-yl]ethyl}-4-methyl-2-benzofuran-1(3H)-one. ¹H NMR (500 MHz, CD₃OD), δ 8.56 (s, 1H), 7.77 (m, 4H), 5.38 (m, 4H), 5.23 (m, 2H), 3.46 (d, J=12.0 Hz, 1H), 3.31 (d, J=12.0 Hz, 1H), 2.88 (m, 2H), 2.68 (s, 6H), 2.63 (m, 2H), 2.47 (s, 3H), 2.38 (d, J=5.0 Hz, 4H), 1.98 (d, J=13.0 Hz, 1H), 1.72 (m, 2H), 1.41 (m, 2H). LC-MS (IE, m/z): 495 [M+1]⁺.

Example 92

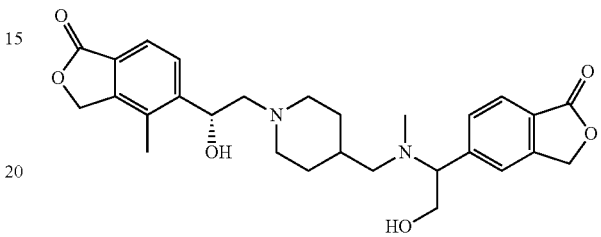

5-{(1R)-1-Hydroxy-2-[4-({[2-hydroxy-1-(1-oxo-1,3-dihydro-2-benzofuran-5-yl)ethyl](methyl)amino}methyl)piperidin-1-yl]ethyl}-4-methyl-2-benzofuran-1(3H)-one 5-{(1R)-1-Hydroxy-2-[4-({[2-hydroxy-1-(1-oxo-1,3-dihydro-2-benzofuran-5-yl)ethyl](methyl)amino}methyl)piperidin-1-yl]ethyl}-4-methyl-2-benzofuran-1(3H)-one was isolated as a separate peak from the reaction mixture described in EXAMPLE 91.

LC-MS (IE, m/z): 495 [M+1]⁺.

Example 93

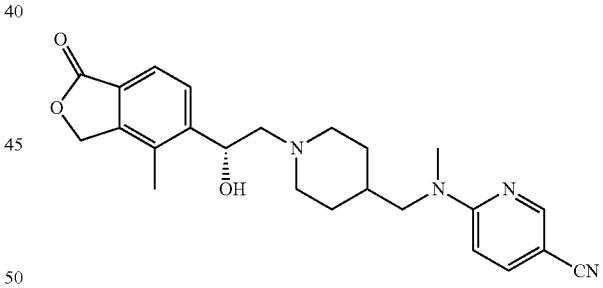

6-[({1-[(2R)-2-Hydroxy-2-(4-methyl-1-oxo-1,3-dihydro-2-benzofuran-5-yl)ethyl]piperidin-4-yl}methyl)(methyl)amino]pyridine-3-carbonitrile A dry reaction flask was charged with 5-[(1R)-1-hydroxy-2-{4-[(methylamino)methyl]piperidin-1-yl}ethyl]-4-methyl-2-benzofuran-1(3H)-one (32 mg, 0.10 mmol), 6-chloropyridine-3-carbonitrile (17 mg, 0.12 mmol), DIPEA (87 µL, 0.50 mmol), and DMF (0.5 mL) and the mixture was shaken at room temperature overnight. The reaction mixture was concentrated in vacuo and the resulting residue purified by mass-directed HPLC to provide 6-[({1-[(2R)-2-hydroxy-2-(4-methyl-1-oxo-1,3-dihydro-2-benzofuran-5-yl)ethyl]piperidin-4-yl}methyl)(methyl)amino]pyridine-3-carbonitrile. LC-MS (IE, m/z): 421 [M+1]⁺.

Example 94

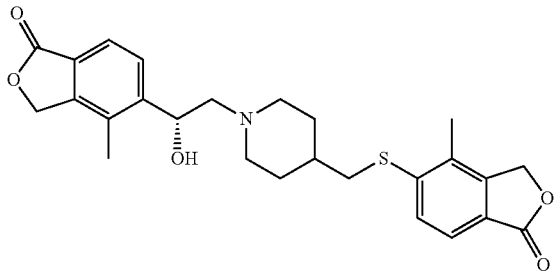 [SMILES: Cc1c(SCC2CCN(C[C@H](O)c3ccc4c(c3C)COC4=O)CC2)ccc2c1COC2=O]

5-[({1-[(2R)-2-Hydroxy-2-(4-methyl-1-oxo-1,3-dihydro-2-benzofuran-5-yl)ethyl]piperidin-4-yl}methyl)sulfanyl]-4-methyl-2-benzofuran-1(3H)-one 4-{[(4-methyl-1-oxo-1,3-dihydro-2-benzofuran-5-yl)sulfanyl]methyl}piperidinium trifluoroacetate (93 mg, 0.24 mmol) was mixed with DIEA (0.08 mL, 0.46 mmol) in ethanol (2 mL). 4-Methyl-5-[(2R)-oxiran-2-yl]-2-benzofuran-1(3H)-one (66 mg, 0.35 mmol) in ethanol (2 mL) was added and the mixture was heated at 145° C. in a microwave reactor for 30 minutes. After cooling down to room temperature, the solvent was removed under reduced pressure and the resulting residue was purified by prep-TLC (2000 microns silica gel, 5% MeOH/DCM) to provide 5-[({1-[(2R)-2-Hydroxy-2-(4-methyl-1-oxo-1,3-dihydro-2-benzofuran-5-yl)ethyl]piperidin-4-yl}methyl)sulfanyl]-4-methyl-2-benzofuran-1(3H)-one. $^1$H NMR (500 MHz, Acetone-d$_6$): δ 7.79 (d, J=8.0 Hz, 1H), 7.64 (dd, J=18.3, 8.0 Hz, 1H), 7.53 (d, J=8.1 Hz, 1H), 5.33 (4H, s), 5.16 (d, J=9.5 Hz, 1H), 3.18 (m, 1H), 3.08 (d, J=6.8 Hz, 2H), 2.93 (m, 1H), 2.53 (m, 1H), 2.47-2.37 (m, 1H), 2.34 (s, 3H), 2.30 (s, 3H), 2.27 (m, 1H), 2.08 (m, 1H), 1.94 (m, 2H), 1.68 (m, 1H), 1.54-1.37 (m, 2H). LC-MS (IE, m/z): 468 [M+1]$^+$.

Example 95

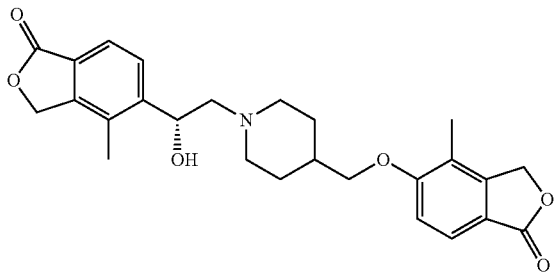 [SMILES: Cc1c(OCC2CCN(C[C@H](O)c3ccc4c(c3C)COC4=O)CC2)ccc2c1COC2=O]

5-({1-[(2R)-2-Hydroxy-2-(4-methyl-1-oxo-1,3-dihydro-2-benzofuran-5-yl)ethyl]piperidin-4-yl}methoxy)-4-methyl-2-benzofuran-1(3H)-one 4-Methyl-5-[(2R)-oxiran-2-yl]-2-benzofuran-1(3H)-one (51 mg, 0.27 mmol) and 4-methyl-5-(piperidin-4-ylmethoxy)-2-benzofuran-1(3H)-one (47 mg, 0.18 mmol) were mixed in ethanol (4 mL) and was heated at 135° C. in a microwave reactor for 50 minutes. After cooling to room temperature, the reaction mixture was concentrated under reduced pressure and the resulting residue was purified by prep-TLC (eluent: 10% MeOH/DCM) to provide 5-({1-[(2R)-2-hydroxy-2-(4-methyl-1-oxo-1,3-dihydro-2-benzofuran-5-yl)ethyl]piperidin-4-yl}methoxy)-4-methyl-2-benzofuran-1(3H)-one. $^1$H NMR (500 MHz, Acetone d$_6$), δ 7.81 (d, J=8.0 Hz, 1H), 7.65 (t, J=9.0 Hz, 2H), 7.18 (d, J=8.4 Hz, 1H), 5.34 (d, J=2.1 Hz, 2H), 5.28 (s, 2H), 5.18 (dd, J=9.55, 3.5 Hz, 1H), 4.04 (d, J=5.9 Hz, 2H), 3.23 (d, J=11.2 Hz, 1H), 2.98 (d, J=11.3 Hz, 1H), 2.56 (dd, J=12.8, 3.5 Hz, 1H), 2.45 (dd, J=12.8, 9.6 Hz, 1H), 2.35 (s, 3H), 2.37-2.31 (m, 1H), 2.21-2.19 (s, 3H), 2.19-2.13 (m, 1H), 1.95-1.86 (m, 3H), 1.61-1.46 (m, 2H). LC-MS (IE, m/z): 452 [M+1]$^+$.

Example 96A & B

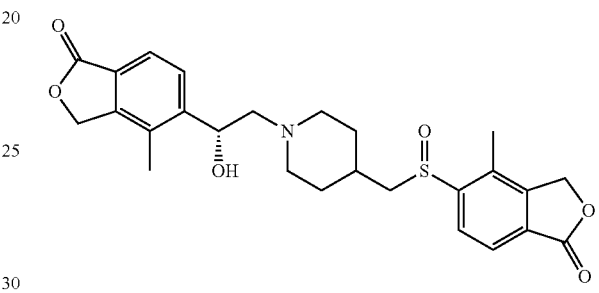

5-[({1-[(2R)-2-Hydroxy-2-(4-methyl-1-oxo-1,3-dihydro-2-benzofuran-5-yl)ethyl]piperidin-4-yl}methoxy)-4-methyl-2-benzofuran-1(3H)-one 4-methyl-5-[(piperidin-4-ylmethyl)sulfinyl]-2-benzofuran-1(3H)-one (55 mg, 0.19 mmol) was dissolved in ethanol (4 mL) and was mixed with 4-methyl-5-[(2R)-oxiran-2-yl]-2-benzofuran-1(3H)-one (71 mg, 0.38 mmol) in a microwave vial. The mixture was heated in a microwave reactor at 135° C. for 40 minutes. After cooling to room temperature, the solvent was removed under reduced pressure and the resulting residue was purified by prep-TLC (eluent 5% MeOH/DCM) to provide 5-[({1-[(2R)-2-hydroxy-2-(4-methyl-1-oxo-1,3-dihydro-2-benzofuran-5-yl)ethyl]piperidin-4-yl}methoxy)-4-methyl-2-benzofuran-1(3H)-one. LC-MS (IE, m/z): 484 [M+1]$^+$.

The mixture of diastereomers of 5-[({1-[(2R)-2-hydroxy-2-(4-methyl-1-oxo-1,3-dihydro-2-benzofuran-5-yl)ethyl]piperidin-4-yl}methyl)sulfinyl]-4-methyl-2-benzofuran-1(3H)-one was separated by SFC-HPLC (Column: As 30×250 mm, 60% MeOH (0.2% DEA)/CO2, 70 mL/min, 100 bar, 35° C., 220 nm):

EXAMPLE 96A (faster eluting): $^1$H NMR (500 MHz, CDCl$_3$), δ 8.14 (d, J=8.0 Hz, 1H), 8.00 (d, J=8.0 Hz, 1H), 7.79 (s, 2H), 5.31 (d, J=3.4 Hz, 2H), 5.25 (s, 2H), 5.08 (dd, J=10.6, 3.1 Hz, 1H), 4.09 (br, 1H), 3.26 (d, J=11.2 Hz, 1H), 2.84 (d, J=11.2 Hz, 1H), 2.78 (dd, J=13.2, 4.0 Hz, 1H), 2.62-2.53 (m, 2H), 2.46-2.38 (m, 2H), 2.37 (s, 3H), 2.29 (s, 3H), 2.23-2.14 (m, 2H), 1.77 (d, J=13.0 Hz, 1H), 1.54-1.46 (m, 2H); LC-MS (IE, m/z): 484 [M+1]$^+$. Rt=5.5 minutes.

Fraction B (slower eluting): $^1$H NMR (500 MHz, CDCl$_3$), δ 8.14 (d, J=8.0 Hz, 1H), 8.00 (d, J=8.0 Hz, 1H), 7.79 (s, 2H), 5.31 (d, J=3.4 Hz, 2H), 5.25 (s, 2), 5.06 (dd, J=10.5, 3.1 Hz, 1H), 4.08 (br, 1H), 3.21 (d, J=11.1 Hz, 1H), 2.90 (d, J=11.4 Hz, 1H), 2.78 (dd, J=13.3, 3.9 Hz, 1H), 2.62-2.52 (m, 2H), 2.48-2.38 (m, 2H), 2.37 (s, 3H), 2.28 (s, 3H), 2.26-2.21 (m, 1H), 2.20-2.12 (m, 2H), 1.80 (d, J=13.1 Hz, 1H), 1.54-1.41 (m, 2H); LC-MS (IE, m/z): 484 [M+1]⁺. Rt=7.0 minutes.

Example 97

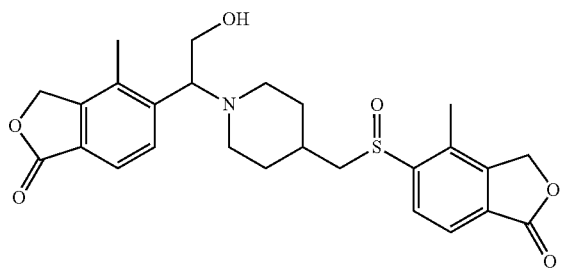 [SMILES: Cc1c(C(CO)N2CCC(CS(=O)c3ccc4c(c3C)COC4=O)CC2)ccc2c1COC2=O]

5-[({1-[2-Hydroxy-1-(4-methyl-1-oxo-1,3-dihydro-2-benzofuran-5-yl)ethyl]piperidin-4-yl}methyl)sulfinyl]-4-methyl-2-benzofuran-1(3H)-one 5-[({1-[(1S)-2-hydroxy-1-(4-methyl-1-oxo-1,3-dihydro-2-benzofuran-5-yl)ethyl]piperidin-4-yl}methyl)sulfinyl]-4-methyl-2-benzofuran-1(3H)-one isolated as a third eluting fraction from the separation described above in EXAMPLE 96.

¹H NMR (500 MHz, CDCl₃), δ 8.11 (d, J=8.0 Hz, 1H), 7.97 (d, J=8.0 Hz, 1H), 7.75 (d, J=8.0 Hz, 1H), 7.56 (d, J=8.0 Hz, 1H), 5.31-5.25 (m, 5H), 3.98 (t, J=5.8 Hz, 1H), 3.92 (t, J=6.8 Hz, 1H), 3.82-3.77 (m, 1H), 3.19 (d, J=11.0 Hz, 1H), 2.82 (d, J=11.4 Hz, 1H), 2.72 (dd, J=13.2, 4.1 Hz, 1H), 2.55 (dd, J=13.2, 9.8 Hz, 1H), 2.35 (s, 3H), 2.34 (s, 3H), 2.27-2.20 (m, 2H), 2.00-1.95 (m, 1H), 1.38-1.31 (m, 2H); LC-MS (IE, m/z): 484 [M+1]⁺. Rt=7.0 minutes.

Example 98

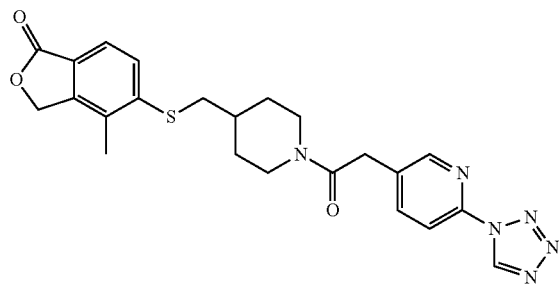 [SMILES: Cc1c(SCC2CCN(C(=O)Cc3ccc(-n4cnnn4)nc3)CC2)ccc2c1COC2=O]

4-Methyl-5-{[(1-{[6-(1H-tetrazol-1-yl)pyridin-3-yl]acetyl}piperidin-4-yl)methyl]sulfanyl}-2-benzofuran-1(3H)-one 4-{[(4-methyl-1-oxo-1,3-dihydro-2-benzofuran-5-yl)sulfanyl]methyl}piperidinium trifluoroacetate (37 mg, 0.095 mmol) was dissolved in DMF (1 mL) and was mixed with [6-(1H-tetrazol-1-yl)pyridin-3-yl]acetic acid (23 mg, 0.11 mmol). DIEA (0.033 mL, 0.19 mmol) and HATU (54 mg, 0.14 mmol) were added. The resulting mixture was stirred at 25° C. over night. The reaction mixture was put on prep-HPLC for purification. (10-100% AcCN/H2O+0.1% TFA gradient, column). Lyophilization provided 4-methyl-5-{[(1-{[6-(1H-tetrazol-1-yl)pyridin-3-yl]acetyl}piperidin-4-yl)methyl]sulfanyl}-2-benzofuran-1(3H)-one. ¹H NMR (500 MHz, CDCl₃), δ 9.55 (s, 1H), 8.41 (s, 1H), 8.08 (d, J=8.4 Hz, 1H), 7.91 (dd, J=8.4, 2.3 Hz, 1H), 7.72 (d, J=8.1 Hz, 1H), 7.32 (d, J=8.1 Hz, 1H), 5.25 (s, 2H), 4.69 (d, J=13.0 Hz, 1H), 3.99 (d, J=12.8 Hz, 1H), 3.86 (s, 2H), 3.16 (m, 1H), 2.97 (t, J=6.5 Hz, 2H), 2.69 (m, 1H), 2.29 (s, 3H), 2.03 (m, 2H), 1.92 (m, 1H), 1.35-1.23 (m, 2H). LC-MS (IE, m/z): 463 [M+1]⁺.

Example 99

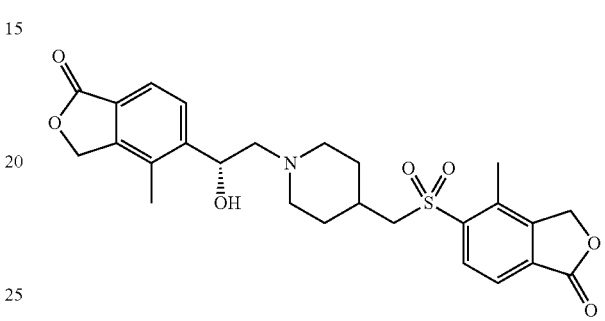

5-({1-[(2R)-2-Hydroxy-2-(4-methyl-1-oxo-1,3-dihydro-2-benzofuran-5-yl)ethyl]piperidin-4-yl}methyl)sulfonyl]-4-methyl-2-benzofuran-1-(3H)-one 4-{[(4-methyl-1-oxo-1,3-dihydro-2-benzofuran-5-yl)sulfonyl]methyl}piperidinium trifluoroacetate (50 mg, 0.12 mmol), 4-methyl-5-[(2R)-oxiran-2-yl]-2-benzofuran-1(3H)-one (34 mg, 0.18 mmol) and DIEA (0.041 mL, 0.24 mmol) were mixed in ethanol (2 mL) and were heated at 78° C. over night. The resulting reaction mixture was diluted with dichloromethane and transferred to a round bottom flask and concentrated in vacuo. The resulting residue was purified by prep-TLC (eluent: 5% MeOH/DCM). To provide 5-({1-[(2R)-2-Hydroxy-2-(4-methyl-1-oxo-1,3-dihydro-2-benzofuran-5-yl)ethyl]piperidin-4-yl}methyl)sulfonyl]-4-methyl-2-benzofuran-1(3H)-one. ¹H NMR (500 MHz, CDCl₃), δ ¹H NMR δ (ppm): 8.23 (d, J=8.0 Hz, 1H), 7.95 (d, J=8.0 Hz, 1H), 7.78 (s, 2H), 5.36 (s, 2H), 5.24 (s, 2H), 5.05 (dd, J=10.5, 3.1 Hz, 1H), 3.18 (d, J=11.1 Hz, 1H), 3.11 (d, J=6.4 Hz, 2H), 2.82 (d, J=11.2 Hz, 1H), 2.70 (s, 3H), 2.51 (dd, J=12.7, 3.1 Hz, 1H), 2.41-2.32 (m, 2H), 2.27 (s, 3H), 2.22-2.10 (m, 2H), 2.06-1.94 (m, 3H), 1.60-1.45 (m, 2H). LC-MS (IE, m/z): 500 [M+1]⁺.

Example 100

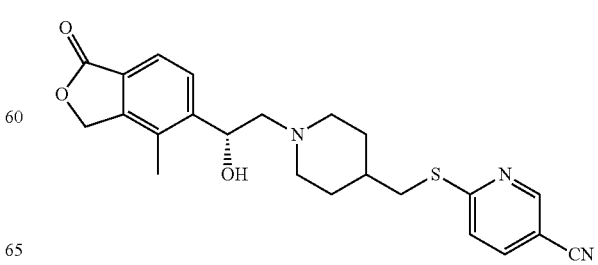

6-[({1-[(2R)-2-Hydroxy-2-(4-methyl-1-oxo-1,3-dihydro-2-benzofuran-5-yl)ethyl]piperidin-4-yl}methyl)sulfanyl]pyridine-3-carbonitrile 6-[(piperidin-4-ylmethyl)sulfanyl]pyridine-3-carbonitrile (100 mg, 0.30 mmol) was mixed with DIEA (0.11 mL, 0.60 mmol) at room temperature in ethanol (4 mL). 4-methyl-5-[(2R)-oxiran-2-yl]-2-benzofuran-1(3H)-one (68 mg, 0.36 mmol) was added and the reaction mixture was heated at 80° C. over night. The solvent was removed under reduced pressure and the resulting residue was purified by prep-TLC (eluent: 100% EtOAc) to provide 6-[({1-[(2R)-2-hydroxy-2-(4-methyl-1-oxo-1,3-dihydro-2-benzofuran-5-yl)ethyl]piperidin-4-yl}methyl)sulfanyl]pyridine-3-carbonitrile. $^1$H NMR δ (ppm) (500 Hz, CDCl$_3$): 8.65 (d, J=2.2 Hz, 1H), 7.81-7.78 (s, 2H), 7.65 (dd, J=8.5, 2.2 Hz, 1H), 5.24 (d, 2.5 Hz, 2H), 5.07 (d, J=10.4 Hz, 1H), 3.21 (m, 3H), 2.84 (d, J=11 Hz, 1H), 2.51 (dd, J=12.7, 3.1 Hz, 1H), 2.37-2.28 (m, 2H), 2.27 (s, 3H), 2.07 (m, 1H), 1.92 (m, 2H), 1.70-1.67 (m, 1H), 1.41 (m, 2H). LC-MS (IE, m/z): 424 M+1]$^+$.

Example 101 A & B

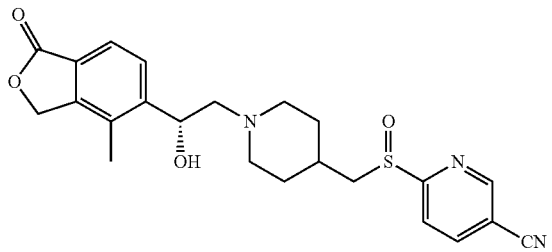 [SMILES: Cc1c([C@@H](O)CN2CCC(CS(=O)c3ccc(C#N)cn3)CC2)ccc2c1COC2=O]

6-[({1-[(2R)-2-Hydroxy-2-(4-methyl-1-oxo-1,3-dihydro-2-benzofuran-5-yl)ethyl]piperidin-4-yl}methyl)sulfinyl]pyridine-3-carbonitrile 6-[({1-[(2R)-2-Hydroxy-2-(4-methyl-1-oxo-1,3-dihydro-2-benzofuran-5-yl)ethyl]piperidin-4-yl}methyl)sulfinyl]pyridine-3-carbonitrile was prepared in a similar fashion to the synthesis previously described for EXAMPLE 96 starting from 6-[(piperidin-4-ylmethyl)sulfinyl]pyridine-3-carbonitrile and 4-methyl-5-[(2R)-oxiran-2-yl]-2-benzofuran-1 (3H)-one.

$^1$H NMR δ (ppm) (500 Hz, CDCl$_3$): 8.93 (1H, s), 8.30-8.24 (m, 2H), 7.84 (d, J=1.8 Hz, 2H), 5.30 (s, 2H), 5.14 (d, J=8.4 Hz, 1H), 3.23 (m, 1H), 3.06 (m, 1H), 2.94-2.80 (m, 2H), 2.54 (m, 1H), 2.40 (m, 2H), 2.28 (d, J=5.0 Hz, 3H), 2.24-2.10 (m, 3H), 1.78 (m, 1H), 1.55-1.45 (m, 2H). LC-MS (IE, m/z): 440 M+1]$^+$.

The diastereomers were separated by SFC Chiral-HPLC (Column: ChiralCel OJ-H, 250×30 mm I.D, 60:40 2-propanol (0.2% DEA):CO2, 50 mL/min) to give two isomers: fast elutor (99.6% e.e.) has retention time as 3.46 min and slow elutor (99.67% e.e.) has Rt as 5.52 min (Thar analytical SFC, ChiralCel OJ-H, 250×4.6 mm I.D., 40% isopropanol (0.05% DEA)/CO2, 2.4 mL/min, 220 nm).

EXAMPLE 101 A (faster eluting): LC-MS (IE, m/z): 440 M+1]$^+$.

EXAMPLE 101 B (slower eluting): LC-MS (IE, m/z): 440 M+1]$^+$.

Example 102

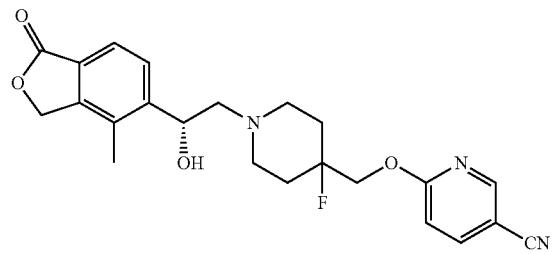 [SMILES: Cc1c([C@@H](O)CN2CCC(F)(COc3ccc(C#N)cn3)CC2)ccc2c1COC2=O]

6-({4-Fluoro-1-[(2R)-2-hydroxy-2-(4-methyl-1-oxo-1,3-dihydro-2-benzofuran-5-yl)ethyl]piperidin-4-yl}methoxy)pyridine-3-carbonitrile 6-({4-Fluoro-1-[(2R)-2-hydroxy-2-(4-methyl-1-oxo-1,3-dihydro-2-benzofuran-5-yl)ethyl]piperidin-4-yl}methoxy)pyridine-3-carbonitrile was prepared in a similar fashion to the synthesis previously described for EXAMPLE 96 starting from 6-[(4-fluoropiperidin-4-yl)methoxy]pyridine-3-carbonitrile and 4-methyl-5-[(2R)-oxiran-2-yl]-2-benzofuran-1(3H)-one. $^1$H NMR δ (ppm)(500 Hz, CHCl$_3$-d): 8.48 (d, J=2.3 Hz, 1H), 7.84~7.81 (dd, J=8.5 Hz, 2.5 Hz, 1H), 7.80 (s, 2H), 6.91 (d, J=8.7 Hz, 1H), 5.25 (s, 2H), 5.10 (dd, J=10.6, 3.1 Hz, 1H), 4.45 (d, J=19.5 Hz, 2H), 3.10-3.04 (m, 1H), 2.76-2.70 (m, 2H), 2.60 (dd, J=12.7, 3.1 Hz, 1H), 2.52-2.40 (m, 2H), 2.28 (s, 3H), 2.11-2.02 (m, 2H), 1.95-1.78 (m, 2H); LC-MS (IE, m/z): 426 M+1]$^+$.

Example 103

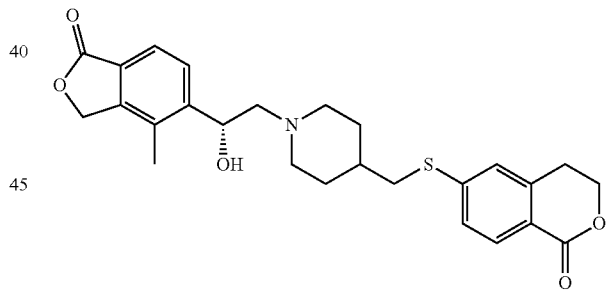

6-[({1-[(2R)-2-Hydroxy-2-(4-methyl-1-oxo-1,3-dihydro-2-benzofuran-5-yl)ethyl]piperidin-4-yl}methyl)sulfanyl]-3,4-dihydro-1H-isochromen-1-one 6-[({1-[(2R)-2-Hydroxy-2-(4-methyl-1-oxo-1,3-dihydro-2-benzofuran-5-yl)ethyl]piperidin-4-yl}methyl)sulfanyl]-3,4-dihydro-1H-isochromen-1-one was prepared in a similar fashion to the synthesis previously described for EXAMPLE 96 starting from 4-{[(1-oxo-3,4-dihydro-1H-isochromen-6-yl)sulfanyl]methyl}piperidinium trifluoroacetate and 4-methyl-5-[(2R)-oxiran-2-yl]-2-benzofuran-1(3H)-one.

$^1$H NMR δ (ppm) (500 Hz, CDCl$_3$): 8.00 (d, J=8.2 Hz, 1H), 7.83-7.74 (m, 2H), 7.26-7.22 (m, 2H), 5.65 (d, J=10.6 Hz, 1H), 5.24 (d, J=5.3 Hz, 2H), 4.53 (t, J=6.0 Hz, 2H), 4.16 (d, J=12.0 Hz, 1H), 3.84 (d, J=11.4 Hz, 1H), 3.15 (t, J=11.9

Hz, 1H), 3.06-2.95 (m, 5H), 2.80 (m, 2H), 2.29 (s, 3H), 2.23-2.07 (m, 2H), 2.10-1.80 (m, 3H); LC-MS (IE, m/z): 468 M+1]+.

Example 104 A & B

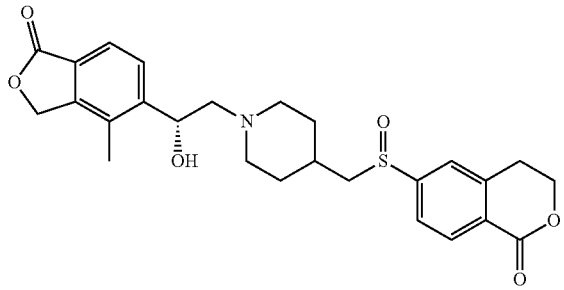 [SMILES: Cc1c([C@@H](O)CN2CCC(CS(=O)c3ccc4c(c3)CCOC4=O)CC2)ccc2c1COC2=O]

6-[({1-[(2R)-2-Hydroxy-2-(4-methyl-1-oxo-1,3-dihydro-2-benzofuran-5-yl)ethyl]piperidin-4-yl}methyl)sulfinyl]-3,4-dihydro-1H-isochromen-1-one 6-[({1-[(2R)-2-Hydroxy-2-(4-methyl-1-oxo-1,3-dihydro-2-benzofuran-5-yl)ethyl]piperidin-4-yl}methyl)sulfinyl]-3,4-dihydro-1H-isochromen-1-one was prepared in a similar fashion to the synthesis previously described for EXAMPLE 96 starting from 6-[(piperidin-4-ylmethyl)sulfinyl]-3,4-dihydro-1H-isochromen-1-one and 4-methyl-5-[(2R)-oxiran-2-yl]-2-benzofuran-1(3H)-one.

LC/MS: (M+1)+=484.06; $^1$H NMR δ (ppm)(500 Hz, CDCl$_3$): 8.24 (d, J=8.1 Hz, 1H), 7.79 (s, 2H), 7.66 (s, 1H), 7.55 (d, J=8.2 Hz, 1H), 5.25 (s, 2H), 5.10-5.04 (m, 1H), 4.59 (t, J=6.0 Hz, 2H), 3.27-3.18 (m, 1H), 3.18-3.14 (t, J=6.5 Hz, 2H), 2.92-2.81 (m, 2H), 2.63-2.51 (m, 2H), 2.45-2.33 (m, 2H), 2.28 (d, J=5.1 Hz, 3H), 2.23-2.07 (m, 3H), 1.79 (m, 1H), 1.58-1.42 (m, 2H). The two diastereomers were separated by SFC chiral prep-HPLC (AS, 30×250 mm, 40% MeOH (0.2% DEA)/CO2, 70 mL/min, 100 bar, 20 mg/mL in DCM/MeOH, 35° C., 220 nm). On analytical chiral-HPLC (AS-H, 4.6×250 mm column, 40% (MeOH+0.2% DEA)/CO2, 2.1 mL/min, 100 bar, 40° C.).

EXAMPLE 104 A: LC-MS (IE, m/z): 484 M+1]+.
EXAMPLE 104 B: LC-MS (IE, m/z): 484 M+1]+.

Example 105

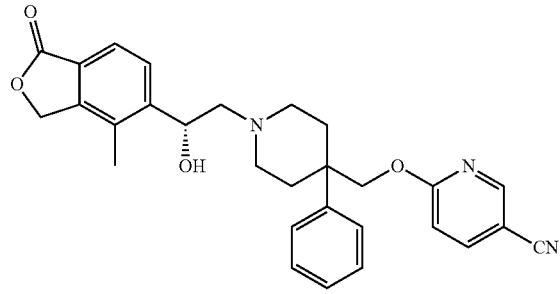 [SMILES: Cc1c([C@@H](O)CN2CCC(COc3ccc(C#N)cn3)(c3ccccc3)CC2)ccc2c1COC2=O]

6-[({1-[(2R)-2-Hydroxy-2-(4-methyl-1-oxo-1,3-dihydro-2-benzofuran-5-yl)ethyl]-4-phenylpiperidin-4-yl}methoxy)pyridine-3-carbonitrile 6-[({1-[(2R)-2-Hydroxy-2-(4-methyl-1-oxo-1,3-dihydro-2-benzofuran-5-yl)ethyl]-4-phenylpiperidin-4-yl}methoxy)pyridine-3-carbonitrile was prepared in a similar fashion to the synthesis previously described for EXAMPLE 96 starting from 6-[(4-phenylpiperidin-4-yl)methoxy]pyridine-3-carbonitrile and 4-methyl-5-[(2R)-oxiran-2-yl]-2-benzofuran-1(3H)-one. $^1$H NMR δ (ppm) (500 Hz, CDCl$_3$): 8.39 (d, J=2.29 Hz, 1H), 7.78 (d, J=2.5 Hz, 2H), 7.75-7.71 (m, 1H), 7.43-7.32 (m, 4H), 7.26-7.22 (m, 1H), 6.75 (d, J=9.0 Hz, 1H), 5.25-5.20 (d, J=3.0 Hz, 2H), 5.06 (dd, J=10.5, 3.1 Hz, 1H), 4.36 (s, 2H), 3.03-2.97 (m, 1H), 2.69-2.57 (m, 2H), 2.49-2.43 (m, 1H), 2.42-2.26 (m, 4H), 2.22 (s, 3H), 2.21-2.07 (m, 2H); LC-MS (IE, m/z): 484 M+1]+.

Example 106

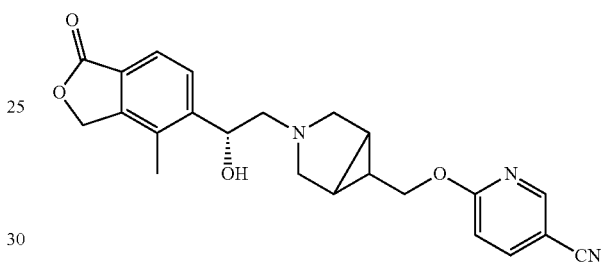

6-({3-[(2R)-2-Hydroxy-2-(4-methyl-1-oxo-1,3-dihydro-2-benzofuran-5-yl)ethyl]-3-azabicyclo[3.1.0]hex-6-yl}methoxy)pyridine-3-carbonitrile 6-({3-[(2R)-2-Hydroxy-2-(4-methyl-1-oxo-1,3-dihydro-2-benzofuran-5-yl)ethyl]-3-azabicyclo[3.1.0]hex-6-yl}methoxy)pyridine-3-carbonitrile was prepared in a similar fashion to the synthesis previously described for EXAMPLE 96 starting from 6-(3-azabicyclo[3.1.0]hex-6-ylmethoxy)pyridine-3-carbonitrile and 4-methyl-5-[(2R)-oxiran-2-yl]-2-benzofuran-1(3H)-one. LC-MS (IE, m/z): 406 M+1]+.

Example 107

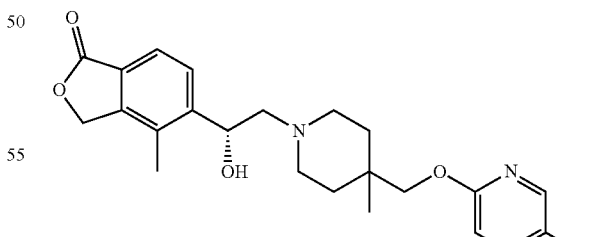

6-[({1-[(2R)-2-Hydroxy-2-(4-methyl-1-oxo-1,3-dihydro-2-benzofuran-5-yl)ethyl]-4-methylpiperidin-4-yl}methoxy)pyridine-3-carbonitrile 6-[({1-[(2R)-2-Hydroxy-2-(4-methyl-1-oxo-1,3-dihydro-2-benzofuran-5-yl)ethyl]-4-methylpiperidin-4-yl}methoxy)

pyridine-3-carbonitrile was prepared in a similar fashion to the synthesis previously described for EXAMPLE 96 starting from 6-[(4-methylpiperidin-4-yl)methoxy]pyridine-3-carbonitrile and 4-methyl-5-[(2R)-oxiran-2-yl]-2-benzofuran-1(3H)-one. ¹H NMR δ (ppm) (500 Hz, CHCl₃-d): 8.47 (d, J=2.3 Hz, 1H), 7.82-7.78 (m, 3H), 6.85 (d, J=8.7 Hz, 1H), 5.24 (s, 2H), 5.08 (dd, J=10.6, 3.1 Hz, 1H), 4.17 (s, 2H), 2.89 (m, 1H), 2.70 (t, J=10.3 Hz, 1H), 2.56 (m, 2H), 2.44-2.34 (m, 2H), 2.28 (s, 2H), 1.77 (m, 2H), 1.56-1.50 (m, 2H), 1.09 (s, 3H). LC-MS (IE, m/z): 422 M+1]⁺.

Example 108

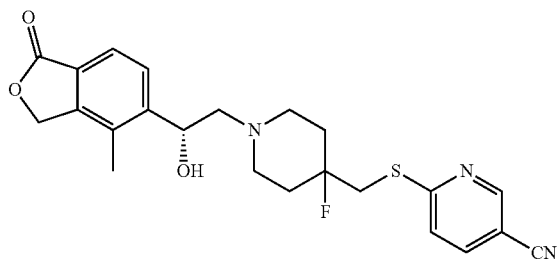 [SMILES: Cc1c([C@@H](O)CN2CCC(F)(CSc3ccc(C#N)cn3)CC2)ccc2c1COC2=O]

6-({4-Fluoro-1-[(2R)-2-hydroxy-2-(4-methyl-1-oxo-1,3-dihydro-2-benzofuran-5-yl)ethyl]piperidin-4-yl}methyl)sulfanyl]pyridine-3-carbonitrile 6-({4-Fluoro-1-[(2R)-2-hydroxy-2-(4-methyl-1-oxo-1,3-dihydro-2-benzofuran-5-yl)ethyl]piperidin-4-yl}methyl)sulfanyl]pyridine-3-carbonitrile was prepared in a similar fashion to the synthesis previously described for EXAMPLE 96 starting from 4-{[(5-cyanopyridin-2-yl)sulfanyl]methyl}-4-fluoropiperidinium trifluoroacetate and 4-methyl-5-[(2R)-oxiran-2-yl]-2-benzofuran-1(3H)-one.

¹H NMR δ (ppm) (500 Hz, CDCl₃): 8.66 (s, 1H), 7.79 (s, 2H), 7.69 (dd, J=8.4, 2.2 Hz, 1H), 7.32 (d, J=8.4 Hz, 1H), 5.24 (s, 2H), 5.07 (dd, J=10.6, 3.1 Hz, 1H), 3.66 (d, J=20 Hz, 1H), 3.03 (d, J=10.9 Hz, 1H), 2.67 (d, J=8.3 Hz, 2H), 2.57 (dd, J=12.7, 3.1 Hz, 1H), 2.45-2.37 (m, 2H), 2.27 (s, 3H), 2.07-1.97 (m, 2H), 1.96-1.76 (m, 2H); LC-MS (IE, m/z): 442 M+1]⁺.

Example 109

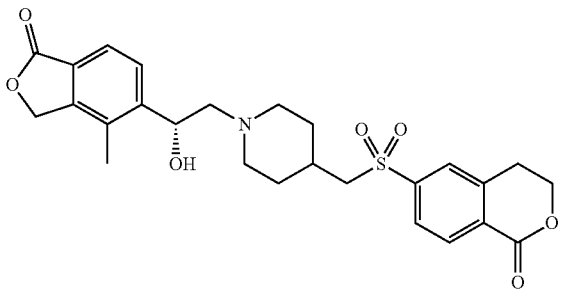 [SMILES: Cc1c([C@@H](O)CN2CCC(CS(=O)(=O)c3ccc4c(c3)CCOC4=O)CC2)ccc2c1COC2=O]

6-[({1-[(2R)-2-Hydroxy-2-(4-methyl-1-oxo-1,3-dihydro-2-benzofuran-5-yl)ethyl]piperidin-4-yl}methyl)sulfonyl]-3,4-dihydro-1H-isochromen-1-one 6-[({1-[(2R)-2-Hydroxy-2-(4-methyl-1-oxo-1,3-dihydro-2-benzofuran-5-yl)ethyl]piperidin-4-yl}methyl)sulfonyl]-3,4-dihydro-1H-isochromen-1-one was prepared in a similar fashion to the synthesis previously described for EXAMPLE 96 starting from 4-{[(1-oxo-3,4-dihydro-1H-isochromen-6-yl)sulfonyl]methyl}piperidinium trifluoroacetate and 4-methyl-5-[(2R)-oxiran-2-yl]-2-benzofuran-1(3H)-one. ¹H NMR δ (ppm) (500 Hz, CDCl₃): 8.31 (d, J=8.1 Hz, 1H), 7.94 (d, J=8.3 Hz, 1H), 7.87 (s, 1H), 7.78 (s, 2H), 5.24 (s, 2H), 5.05 (dd, J=10.6, 3.2 Hz, 1H), 4.61 (t, J=6.0 Hz, 1H), 3.19 (m, 3H), 3.07 (d, J=6.4 Hz, 1H), 2.82 (d, J=11.4 Hz, 1H), 2.51 (dd, J 12.6, 3.3 Hz, 1H), 2.42-2.32 (m, 2H), 2.27 (s, 3H), 2.19-2.09 (m, 2H), 2.04-1.94 (m, 2H), 1.56-1.42 (m, 2H); LC-MS (IE, m/z): 500 M+1]⁺.

Example 110 A & B

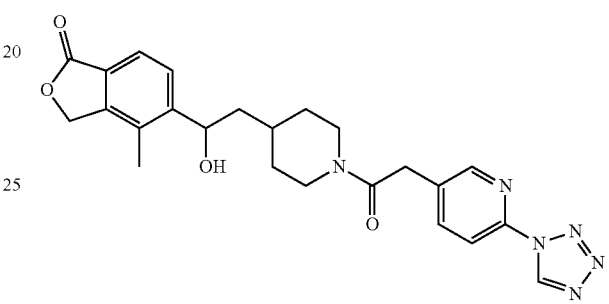

5-[1-Hydroxy-2-(1-{[6-(1H-tetrazol-1-yl)pyridin-3-yl]acetyl}piperidin-4-yl)ethyl]-4-methyl-2-benzofuran-1(3H)-one 5-[1-hydroxy-2-(1-{[6-(1H-tetrazol-1-yl)pyridin-3-yl]acetyl}piperidin-4-yl)ethyl]-4-methyl-2-benzofuran-1(3H)-one was prepared in a similar fashion to that described for the synthesis of EXAMPLE 5 starting from 4-[2-hydroxy-2-(4-methyl-1-oxo-1,3-dihydro-2-benzofuran-5-yl)ethyl]piperidinium chloride and [6-(1H-tetrazol-1-yl)pyridin-3-yl]acetic acid. LC-MS (IE, m/z): 435 [M−28]⁺. The mixture of enantiomers was separated using a chiral SFC system (OD-H, 4.6×250 mm, 40% (MeOH+0.2% DEA)/CO₂, 2.1 mL/min, 100 bar, 40° C.

Fast enantiomer: ¹H NMR (500 MHz, CDCl₃): 9.5 (s, 1H), 8.4 (s, 1H), 8.15 (m, 1H) 7.9 (m, 1H), 7.8 (m, 1H), 7.4 (m, 1H), 5.35 (s, 1H), 5.25 (m, 1H), 4.6-4.7 (m, 2H), 3.9-4.0 (m, 2H), 3.8 (broad s, 2H), 3.2-3.3 (m, 2H), 2.6-2.7 (m, 2H), 2.3, (s, 3H), 1.5-2.0 (m, 5H). LC-MS (IE, m/z): 435 [M−28]⁺.

Slow enantiomer: ¹H NMR (500 MHz, CDCl₃): 9.5 (s, 1H), 8.4 (s, 1H), 8.15 (m, 1H) 7.9 (m, 1H), 7.8 (m, 1H), 7.4 (m, 1H), 5.35 (s, 1H), 5.25 (m, 1H), 4.6-4.7 (m, 2H), 3.9-4.0 (m, 2H), 3.8 (broad s, 2H), 3.2-3.3 (m, 2H), 2.6-2.7 (m, 2H), 2.3, (s, 3H), 1.5-2.0 (m, 5H). LC-MS (IE, m/z): 435 [M−28]⁺.

Example 111

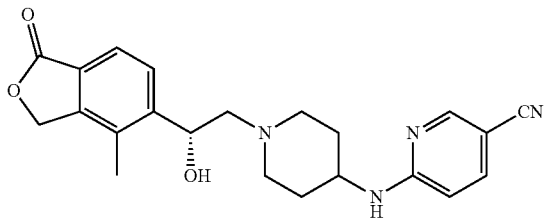 [SMILES: Cc1c([C@@H](O)CN2CCC(Nc3ccc(C#N)cn3)CC2)ccc2c1COC2=O]

(R)-6-(1-(2-Hydroxy-2-(4-methyl-1-oxo-1,3-dihydroisobenzofuran-5-yl)ethyl)piperidin-4-ylamino)nicotinonitrile To a mixture of (R)-5-(2-(4-aminopiperidin-1-yl)-1-hydroxyethyl)-4-methylisobenzofuran-1(3H)-one hydrochloride (60 mg, 0.16 mmol) and 5-cyano-2-fluoropyridine (20 mg, 0.16 mmol) in N-methylpyrrolidinone (550 µl) was added DIEA (57 µl, 0.33 mmol) in a microwave tube at room temperature. The tube was sealed and heated at 100° C. for 4 h. The mixture was cooled and partitioned between EtOAc/hexanes (2:1) and water. The aqueous layer was extracted with EtOAc (2×). The combined organic phase was washed with brine, dried (MgSO$_4$), filtered and concentrated. The resulting residue was purified by prep TLC (silica gel, 10% MeOH/DCM) to provide (R)-6-(1-(2-hydroxy-2-(4-methyl-1-oxo-1,3-dihydroisobenzofuran-5-yl)ethyl)piperidin-4-ylamino)nicotinonitrile. $^1$H-NMR (CDCl$_3$, 500 MHz), δ 8.39 (m, 1H), 7.82 (s, 2H), 7.60 (m, 1H), 6.41 (m, 1H), 5.29 (s, 2H), 4.92 (m, 1H), 3.23 (m, 1H), 2.96 (m, 1H), 2.39-2.46 (m, 4H), 2.18 (s, 3H), 2.02 (m, 4H); LC-MS (IE, m/z): 393 [M+1]$^+$.

Example 112

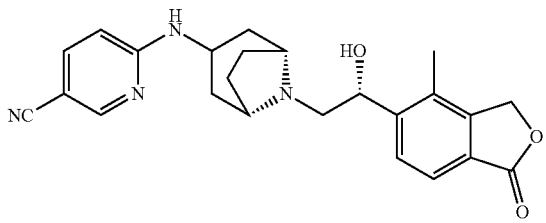 [SMILES: Cc1c([C@@H](O)CN2[C@@H]3CC[C@H]2CC(Nc2ccc(C#N)cn2)C3)ccc2c1COC2=O]

6-((1R,5S)-8-((R)-2-Hydroxy-2-(4-methyl-1-oxo-1,3-dihydroisobenzofuran-5-yl)ethyl)-8-azabicyclo[3.2.1]octan-3-ylamino)nicotinonitrile 6-((1R,5S)-8-((R)-2-Hydroxy-2-(4-methyl-1-oxo-1,3-dihydroisobenzofuran-5-yl)ethyl)-8-azabicyclo[3.2.1]octan-3-ylamino)nicotinonitrile was prepared in a similar fashion to that described for the synthesis of EXAMPLE 111 starting from 5-41R)-2-((1R,5S)-3-amino-8-azabicyclo[3.2.1]octan-8-yl)-1-hydroxyethyl)-4-methylisobenzofuran-1(3H)-one hydrochloride and 6-chloropyridine-3-carbonitrile. LC-MS (IE, m/z): 419 [M+1]$^+$.

Example 113

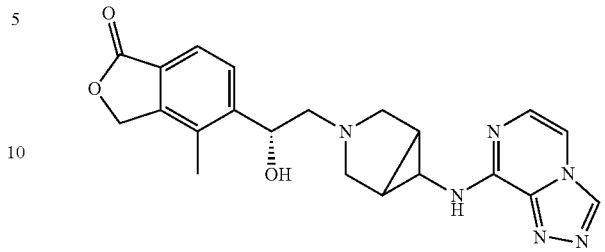

5-((1R)-2-(6-([1,2,4]Triazolo[4,3-a]pyrazin-8-ylamino)-3-azabicyclo[3.1.0]hexan-3-yl)-1-hydroxyethyl)-4-methylisobenzofuran-1(3H)-one 5-((1R)-2-(6-([1,2,4]Triazolo[4,3-a]pyrazin-8-ylamino)-3-azabicyclo[3.1.0]hexan-3-yl)-1-hydroxyethyl)-4-methylisobenzofuran-1(3H)-one was prepared in a similar fashion to that described for the synthesis of EXAMPLE 111 starting from 5-((1R)-2-(6-Amino-3-azabicyclo[3.1.0]hexan-3-yl)-1-hydroxyethyl)-4-methylisobenzofuran-1(3H)-one hydrochloride and 8-chloro-[1,2,4]triazolo[4,3-a]pyrazine. LC-MS (IE, m/z): 407 [M+1]$^+$.

Example 114

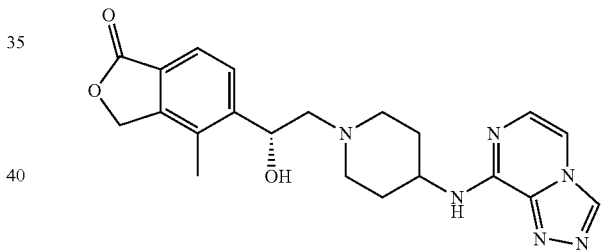

(R)-5-(2-(4-([1,2,4]Triazolo[4,3-a]pyrazin-8-ylamino)piperidin-1-yl)-1-hydroxyethyl)-4-methylisobenzofuran-1(3H)-one (R)-5-(2-(4-([1,2,4]Triazolo[4,3-c]pyrazin-8-ylamino)piperidin-1-yl)-1-hydroxyethyl)-4-methylisobenzofuran-1(3H)-one was prepared in a similar fashion to that described for the synthesis of EXAMPLE 111 starting from (R)-5-(2-(4-aminopiperidin-1-yl)-1-hydroxyethyl)-4-methylisobenzofuran-1(3H)-one hydrochloride and 8-chloro-[1,2,4]triazolo[4,3-c]pyrazine. LC-MS (IE, m/z): 409 [M+1]$^+$.

Several assays may be used to measure functional inhibition of the ROMK channel by compounds of the instant invention. One primary assay that can be used is a functional $^{86}$Rb$^+$ efflux assay that measures the ability of ROMK to permeate $^{86}$Rb$^+$, in the absence or presence of test compound. Under control conditions, cells loaded with $^{86}$Rb$^+$ and incubated in Rb$^+$-free medium display a time-dependent efflux of the isotope, the rate of which depends on number of functional channels. When cells are incubated in the presence of a channel inhibitor, efflux of $^{86}$Rb$^+$ is prevented in a concentration-dependent manner, and IC$_{50}$ values of inhibition by compounds can be accurately determined. This assay has been established with cell lines expressing either human, rat or dog ROMK channels, and can operate in 96- or 384-well format. Importantly, the human, rat, and dog $^{86}Rb^+$ efflux assays can be carried out in the presence of up to 100% serum allowing, therefore, an accurate estimation of the effect of protein binding on the inhibitory activity of compounds of interest. Another ROMK functional assay makes use of the ability of thallium to permeate through open ROMK channels and increase the fluorescence of a dye previously loaded into the cells. Under control conditions, cells loaded with dye and exposed to thallium-containing medium display a time-dependent increase in fluorescence, the rate of which depends on number of functional channels. When cells are incubated in the presence of a channel inhibitor, the increase in fluorescence is attenuated in a concentration-dependent manner, and $IC_{50}$ values of inhibition by compounds can be accurately determined. This assay has been established with cell lines expressing either human, or rat ROMK channels, and operates in 384-well format. Another assay for evaluation of the compounds of the instant invention and for evaluation of mechanism of action of compounds of Formula I relies on the measurement of the electrical current that is generated as potassium permeates through the channel. For these electrophysiological experiments, three different platforms, IonWorks, QPatch, or manual patch clamp, are used, depending on the experimental protocol under consideration. IonWorks operates in a 384-well format and allows accurate determination of $IC_{50}$ values for inhibitors. Examples of compounds of the present invention (listed above) all had potencies of at least 1 µM or lower in one or more of the three assays described herein.

The following Thallium Flux Assay and/or the $^{86}Rb^+$ Efflux Assay were performed on the final product compounds in the Examples.

Thallium Flux Assay

Cell Culture Conditions—

HEK293 cells stably expressing hROMK ($hK_{ir}1.1$) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, media was aspirated from the flask and rinsed with 10 ml Calcium/Magnesium-free PBS. 5 ml of 1× trypsin (prepared in Ca/Mg Free PBS) was added to T-225 flask and flask returned to 37° C./$CO_2$ incubator for 2-3 minutes. To dislodge the cell, the side of the flask was gently banged by hand. Cells were completely triturated and then transferred to 25 ml complete media, and centrifuged at 1,500 rpm for 6 min followed by resuspension in complete growth media and cell concentration determined. For typical re-seeding, 4E6 cells/T-225 flask attained >80% confluency in 4 days. Under ideal growth conditions and appropriate tissue culture practices, this cell line was stable for 40-45 passages.

FluxOR™ Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample was kept at −20° C. Water soluble, 100× after solubilization in 1 ml water. Store at 4° C.
  FluxOR™ Chloride-free Buffer (Component E)—5× Concentrate
  Potassium sulfate ($K_2SO_4$) Concentrate (Component F)—125 mM in water. Stored at 4° C.
  Thallium sulfate ($Tl_2SO_4$) Concentrate (Component G)—50 mM in water. Stored at 4° C.
  DMSO (dimethyl sulfoxide, Component H)—1 ml (100%)

Reagent Preparation—
FluxOR Working Solutions
  1000× FluxOR™ Reagent: Reconstituted a vial of component A in 100 µl DMSO; Mixed well; Stored 10 µl aliquots at −20° C.
  1× FluxOR™ Assay Buffer: Diluted Component B 10-fold with water; Adjusted pH to 7.4 with Hepes/NaOH; Filtered and stored at 4° C.
  Probenecid/Assay Buffer: 100 ml of 1× FluxOR™ Assay Buffer; 1 ml of reconstituted component D; Stored at 4° C.
  Loading Buffer (per microplate): 10 µl 1000× FluxOR™ Reagent; 100 µl component C; 10 ml Probenecid/Assay Buffer
  Compound Buffer (per microplate): 20 ml Probenecid/Assay Buffer; 0.3 mM ouabain (10 mM ouabain in water stored in amber bottle/aluminum foil at room temperature); Tested compound
  1× FluxOR™ Chloride-Free Buffer: Prepared 1× working solution in water. Stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Stored at 4° C. when not in use. When kept sterile, the solution was good for months.

Assay Protocol—

The ROMK channel functional thallium flux assay was performed in 384 wells, using the FLIPR-Tetra instrument. HEK-hKir1.1 cells were seeded in Poly-D-Lysine microplates and kept in a 37° C.-10% $CO_2$ incubator overnight. On the day of the experiment, the growth media was replaced with the FluxOR™ reagent loading buffer and incubated, protected from light, at ambient temperature (23-25° C.) for 90 min. The loading buffer was replaced with assay buffer±test compound followed by 30 min incubation at ambient temperature, where the Thallium/Potassium stimulant was added to the microplate.

Step Protocol
1. Seeded HEK-hKir1.1 cells (50 µl at 20,000 cells/well) in 384-well PDL coated Microplates
2. Allowed cells to adhere overnight in humidified 37° C./10% $CO_2$ incubator
3. Completely removed cell growth media from microplate and replaced with 25 µl loading buffer
4. Incubated Microplate at room temperature, protected form light, for 90 min
5. Removed loading buffer and replaced with 25 µl 1× Assay Buffer±test compound.
6. Incubated microplate at room temperature, protected form light, for 30 min
7. At FLIPR-Tetra 384: Added stimulant (Thallium/Potassium) solution to microplate and monitor fluorescence. Excitation=400 nm, Emission=460 & 580 nm. Collected data for 10 min.

Data Calculation—

The fluorescence intensity of wells containing 3 µM of a standard control ROMK inhibitor of the present invention was used to define the ROMK-sensitive component of thallium flux. Fluorescence in the presence of test compounds was normalized to control values to provide % fluorescence change. $IC_{50}$ values represented the concentration of compound that inhibits 50% of the ROMK thallium flux signal.

Assay Standard—

Normally, a control compound was included to support that the assay was giving consistent results compared to previous measurements, although the control was not required to obtain the results for the test compounds. The control was any compound of Formula I of the present invention, preferably with an $IC_{50}$ potency of less than 1 μM in this assay. Alternatively, the control was another compound (outside the scope of Formula I) that had an $IC_{50}$ potency in this assay of less than 1

Compounds listed above and tested according to the Thalium Flux Assay were found to have $IC_{50}$ potency falling within the μM potency ranges shown below:

≤0.7—Examples 85-114.
≤0.2—Examples 85-90, 93-96, 99-100, 102-104, 106-107, 109-112.
≤0.1—Examples 86-88, 94-96, 99-100, 104, 106-107, 109-112.

$^{86}Rb^+$ Efflux Assay

Cell Culture Conditions—

CHO-DHFR-cells stably expressing hROMK1 ($K_{ir}$1.1) were grown at 37° C. in a 10% $CO_2$ humidified incubator in Iscove's Modified Dulbecco's Medium (Gibco 12440) supplemented with HT Supplement, Penicillin/Streptomycin/Glutamine, G418 (500 μg/ml) and 10% FBS. Cells were seeded in Sterile and Tissue Culture Treated Packard CulturPlate White Opaque Microplates at a concentration of 5.0E5-7.0E5 cells/ml—PerkinElmer 6005680 (96-well); Corning 3707 (384 well) in complete media containing 1.5 μCi/ml Rubidium-86. Cells were incubated in 37° C.-10% $CO_2$ incubator overnight. On the day of the experiment, the media was removed and cells washed with low K assay buffer. $^{86}Rb^+$ efflux was initiated after addition of assay buffer±test compound followed by 35 min incubation at room temperature. ROMK-sensitive component of efflux was defined in the presence of 10 mM $BaCl_2$. Assay buffer was removed and transferred to a plate and cells were solubilized in the presence of SDS. Radioactivity associated with assay and cell plate was determined.

Step Protocol
1. Removed cell media and washed cells with low K assay buffer (126.9 mM NaCl, 4.6 mM KCl, 2 mM $CaCl_2$, 1 mM $MgCl_2$, 10 mM Hepes/NaOH; pH 7.4)
   200 μl for 96-well plate; 70 μl for 384-well plate
2. Added assay buffer (121.5 mM NaCl, 10 mM KCl, 2 mM $CaCl_2$, 1 mM $MgCl_2$, 10 mM Hepes/NaOH; pH 7.4)±test compound to cells
   100 μl for 96-well plate; 50 μl for 384-well plate
3. Incubated at ambient temperature (22-24° C.) for 35 min
4. Removed assay buffer and added it to a 96- or 384-well plate containing Microscint-20
   96-well Plate: 100 μl buffer, 170 μl MicroScint 20 (for TopCount)
   384-well plate: 20 μl buffer, 50 μl Optiphiase (for MicroLux)
5. Completely removed remaining assay buffer from cell plate
6. Solubilized cells with 1% SDS; then add MicroScint or Optiphase
   96-well Plate: 30 μl SDS, 170 μl MicroScint 20 (for TopCount)
   384-well plate: 20 μl SDS, 50 μl Optiphiase (for MicroLux)
7. Sealed both cell and supernatant plates and count Data Calculation—

Radioactivity associated with the assay plate was normalized to the total radioactivity (assay+ cell plates) to provide % efflux, under each condition. % efflux in the presence of 10 mM $BaCl_2$ was subtracted from each experimental point to provide the ROMK-sensitive component of $^{86}Rb^+$ efflux. In the absence of test compound, this number corresponded to 100% control efflux. $IC_{50}$ values represented the concentration of compound that inhibits 50% of ROMK efflux.

Normally, a control compound was included to support that the assay was giving consistent results compared to previous measurements, although the control is not required to obtain results for the test compounds. The control was any compound of Formula I of the present invention, preferably with an $IC_{50}$ potency of less than 1 μM in this assay, or the control was another compound (outside the scope of Formula I) that has an $IC_{50}$ potency in this assay of less than 1 μM.

Compounds listed above and tested according to the $^{86}Rb^+$ Efflux Assay were found to have $IC_{50}$ potency falling within the μM potency ranges shown below:

≤1.1—Examples 1-90.
≤0.5—Examples 1-8, 10-15, 18, 26-27, 29-31, 33-34, 36-37, 39-42, 47-48, 50-53, 55-57, 59, 64-68, 70-72, 79-90.
≤0.2—Examples 1-6, 11-12, 30, 41-42, 55, 57, 59, 65-66, 70-72, 79-81, 83, 86-88.

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 ml of Versene (Invitrogen 15040-066) for approximately 6 min at 37° C. and suspended in 10 ml of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 ml of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/ml amphotericin B for 4 min. Amphotericin B (Sigma A-4888) was prepared as a 40 mg/ml solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control was any compound of Formula I of the present invention, preferably with an $IC_{50}$ potency of less than 1 µM in this assay, or another compound (outside the scope of Formula I) that has an $IC_{50}$ potency in this assay of less than 1 µM.

Compounds of the Examples were tested in the electrophysiology assay and found to have a therapeutic level of potency.

Rat Diuresis Assay

Experimental protocols for evaluating diuretic efficacy of compounds of the present invention in Sprague-Dawley (SD) rats is described below:
1. Adult male SD rats were acclimated to single housing in metabolism cages for at least three (3) days before their use in the diuresis screen. Rats had at lib access to food and water.
2. For most studies the procedure was to remove food hoppers and water bottles from the metabolic cages 1-2 h before the start of the diuresis screen. Rats were dosed with compound (see below) and 30 minutes later dosed with water or saline orally at 18 mL/kg to induce voiding and placed in the metabolic cage where urine was collected over the next 4 hours.
For selected studies an overnight fast was necessary if saline/water loads larger than those described above were required. For these studies a saline or water dose of up to 27 mL/kg was be given.
3. Following the fasting period (usually 1-2 hours but sometimes overnight), animals were removed from the metabolism cages and temporarily housed in shoebox cages for dosing. Compound or vehicle was dosed in 70% PEG200 or Imwitor:Tween (depending on the physical properties of the compound) at 1 mL/Kg PO.
4. The 30 min time period between compound dosing and water/saline loading was modified depending on the bioavailability of the compound being tested.
5. Urine was collected from each animal for up to 4 hrs at room temperature.
6. The urine volume collected from each animal was measured and recorded. Urine was centrifuged, aliquoted and frozen (−20° C.) until analyzed.
7. Blood (150-200 µL) was obtained from treated animals by jugular vein bleed for compound plasma exposure levels.

Note: Rats were re-tested with additional compounds after 1 week of recovery while housed in metabolism cages. Data=Mean/sem. Data was analyzed by one way ANOVA and Dunnett's comparison of treatments to vehicle. The known diuretic, hydrochlorothiazide, dosed PO at 10 or 25 mg/kg, was used as a positive control in this model.

Compounds of the Examples were tested in the electrophysiology assay and found to have a therapeutic level of potency.

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:
1. A compound having structural Formula I:

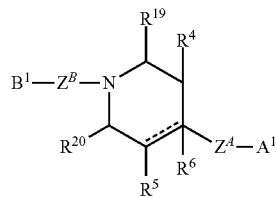

I or a pharmaceutically acceptable salt thereof, wherein:
$B^1$—$Z^B$— is $B^1$—$CHR^1CH_2$—, $B^1$—$CHR^1C(O)$—, $B^1$—$C(O)$—, $B^1$—$CHR^1CH_2C(O)$—, $B^1$—$OCH_2C(O)$—, or $B^1$—$CH(CH_2OH)$—;
—$Z^A$-$A^1$ is $CHR^{21}CR^2R^{22}$-$A^1$, —CH=$CR^2$-$A^1$, —C≡C-$A^1$, —S-$A^1$, —$CH_2O$-$A^1$, —C(O)$CHR^2$-$A^1$, —O-$A^1$, —NHCHR$^2$-$A^1$, —$CH_2N(CH_3)CH_2CH(OH)$-$A^1$, —$CH_2N(CH_3)CH(CH_2OH)$-$A^1$, —$CH_2N(CH_3)$-$A^1$, —$CH_2S$-$A^1$, —$CH_2O$-$A^1$, $CH_2S(O)$-$A^1$, —$CH_2S(O_2)$-$A^1$, or —NH-$A^1$;
$A^1$ is

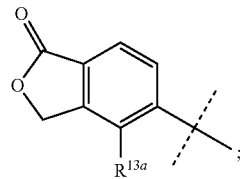

;

$B^1$ is

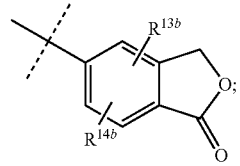

X is O or S;
$R^1$ is —H, —$C_{1-6}$ alkyl, —$C_{3-6}$ cycloalkyl, $CF_3$, —OH, F, —$CH_2OH$, —C(O)OH, —C(O)O$C_{1-6}$ alkyl, or $R^1$ may be joined with $R^{13b}$ by 2-3 carbon atoms or 1-2 carbon atoms and one heteroatom to form a ring;
$R^2$ is —H, —$C_{1-6}$ alkyl, —$C_{3-6}$ cycloalkyl, $CF_3$, —OH, F, —$CH_2OH$, —C(O)OH, —C(O)O$C_{1-6}$ alkyl, or $R^2$ may be joined with $R^{13a}$ by 2-3 carbon atoms or 1-2 carbon atoms and one heteroatom to form a ring;
$R^4$ is H, —OH, F, —O—$C_{1-6}$ alkyl, or —$C_{1-6}$ alkyl, or may be joined with $R^5$ by a bond, or by 1-4 carbon atoms, to form a ring;
$R^5$ is H, —OH, F, —O—$C_{1-6}$ alkyl, or —$C_{1-6}$ alkyl, or may be joined with $R^4$ by a bond, or by 1-4 carbon atoms to form a ring;

$R^6$ is —H, —C(O)OCH$_3$, C(O)OCH$_2$CH$_3$, —OC(O)CH$_3$—CH$_2$OH, —OH, —CHF$_3$, —N(CH$_3$)$_2$, —CH$_3$, —C$_6$H$_5$, or F;

$R^{13a}$ is —H, —C$_{1-6}$ alkyl, —C$_{3-6}$ cycloalkyl, -halogen, CF$_3$, —CH$_2$OH, —CO$_2$R$^{16a}$, —OR$^{16a}$, —SR$^{16a}$, —CN, -aryl, -heterocycle, —NR$^{16a}$R$^{18a}$, or R$^{13a}$ may be joined with R$^2$ by 2-3 carbon atoms or 1-2 carbon atoms and one heteroatom to form a ring, or R$^{13a}$ may be joined with R$^{14a}$ by 3-4 carbon atoms or 2-3 carbon atoms and one heteroatom to form a ring;

$R^{13b}$ is —H, —C$_{1-6}$ alkyl, —C$_{3-6}$ cycloalkyl, -halogen, CF$_3$, —CH$_2$OH, —CO$_2$R$^{16b}$, —OR$^{16b}$, —SR$^{16b}$, —CN, -aryl, -heterocycle, —NR$^{16b}$R$^{18b}$, or R$^{13b}$ may be joined with R$^1$ by 2-3 carbon atoms or 1-2 carbon atoms and one heteroatom to form a ring, or R$^{13b}$ may be joined to R$^{14b}$ by 3-4 carbon atoms or 2-3 carbon atoms and one heteroatom to form a ring;

$R^{14a}$ is —H, —C$_{1-6}$ alkyl, —C$_{3-6}$ cycloalkyl, -halogen, CF$_3$, —CH$_2$OH, —CO$_2$R$^{17a}$, —OR$^{17a}$, —SR$^{17a}$, —CN, -aryl, -heterocycle, or R$^{14a}$ may be joined to R$^{13a}$ by 3-4 carbon atoms or 2-3 carbon atoms and one heteroatom to form a ring;

$R^{14b}$ is —H, —C$_{1-6}$ alkyl, —C$_{3-6}$ cycloalkyl, -halogen, CF$_3$, —CH$_2$OH, —CO$_2$R$^{17b}$, —OR$^{17b}$, —SR$^{17b}$, —CN, -aryl, -heterocycle, or R$^{14b}$ may be joined to R$^{13b}$ by 3-4 carbon atoms or 2-3 carbon atoms and one heteratom to form a ring;

$R^{15a}$ is —H, halogen, —C$_{1-6}$ alkyl, C$_{3-6}$ cycloalkyl, —OC$_{1-6}$ alkyl, or —CF$_3$;

$R^{15b}$ is —H, halogen, —C$_{1-6}$ alkyl, C$_{3-6}$ cycloalkyl, —OC$_{1-6}$ alkyl, or —CF$_3$;

$R^{16a}$, $R^{16b}$, $R^{17a}$, $R^{17b}$, $R^{18a}$, and $R^{18b}$ are independently —H, —C$_{1-6}$ alkyl, or —C$_{3-6}$ cycloalkyl;

$R^{19}$ and $R^{20}$ are H, or may be joined by a bond or 1-2 carbon atoms, to form a 4-5-membered ring; and $R^{21}$ and $R^{22}$ are H, or, together with carbon atom to which they are attached, form —C$_{3-6}$ cycloalkyl.

2. A compound of claim 1, wherein

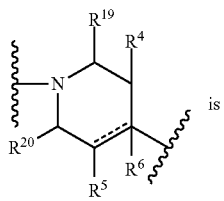

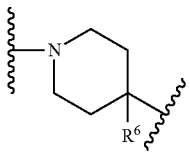

is or a pharmaceutically acceptable salt thereof.

3. A compound of claim 1, wherein, R$^{13a}$ is H, F, Br, Cl, CH$_3$, or —OCH$_3$; R$^{14a}$ is H or F; and R$^{15a}$ is H or CH$_3$, or a pharmaceutically acceptable salt thereof.

4. A compound of claim 3, wherein, R$^{13a}$ is H or CH$_3$, or a pharmaceutically acceptable salts thereof.

5. A compound of claim 1, wherein R$^{13b}$ is H, F, Br, Cl, —CF$_3$, —CH$_3$ or —OCH$_3$; R$^{14b}$ is H or Cl; and R$^{15b}$ is H or F, or a pharmaceutically acceptable salt thereof.

6. A compound of claim 1, wherein, where B$^1$—Z$^B$— is B$^1$—CH$_2$CH$_2$—, B$^1$—CHR$^1$C(O)—, B$^1$—C(O)—, B$^1$—CH$_2$CH$_2$C(O)—, B$^1$—OCH$_2$C(O)—, B$^1$—CH(OH)CH$_2$—, or B$^1$—CH(CH$_2$OH)—, or a pharmaceutically acceptable salts thereof.

7. A compound of claim 6, wherein, B$^1$—Z$^B$— is B$^1$—CH$_2$CH$_2$—, B$^1$—CHR$^1$C(O)— or B$^1$—CH(OH)CH$_2$—, or a pharmaceutically acceptable salts thereof.

8. A compound of claim 1, wherein —Z$^A$-A$^1$ is —CHR$^{21}$CR$^2$R$^{22}$-A$^1$, —CH=CH-A$^1$, —S-A$^1$, —CH$_2$O-A$^1$, —C(O)CH$_2$-A$^1$, —O-A$^1$, —CH$_2$CH(OH)-A$^1$, —NHCH$_2$-A$^1$, —CH$_2$N(CH$_3$)CH$_2$CH(OH)-A$^1$, —CH$_2$N(CH$_3$)CH(CH$_2$OH)-A$^1$, —CH$_2$N(CH$_3$)-A$^1$, —CH$_2$S-A$^1$, —CH$_2$O-A$^1$, CH$_2$S(O)-A$^1$, —CH$_2$S(O)$_2$-A$^1$, or —NH-A$^1$, or a pharmaceutically acceptable salt thereof.

9. A compound of claim 8, wherein, —Z$^A$-A$^1$ is —CH$_2$CH$_2$-A$^1$, —CH$_2$O-A$^1$, or —CH$_2$CH(OH)-A$^1$, or a pharmaceutically acceptable salt thereof.

10. A compound of claim 1, which is

5-[(E)-2-{1-[(1-Oxo-1,3-dihydro-2-benzofuran-5-yl)acetyl]piperidin-4-}ethenyl]-2-benzofuran-1(3H)-one, 5-(2-{1-[(1-Oxo-1,3-dihydro-2-benzofuran-5-yl)acetyl]piperidin-4-yl}ethyl)-2-benzofuran-1(3H)-one, 5-[(1-{[(1-Oxo-1,3-dihydro-2-benzofuran-5-yl)oxy]acetyl}piperidin-4-yl)oxy]-2-benzofuran-1(3H)-one, 5-({1-[2-hydroxy-2-(1-oxo-1,3-dihydro-2-benzofuran-5-yl)ethyl]piperidin-4-yl}sulfanyl)-2-benzofuran-1(3H)-one, 5-[(1R)-1-Hydroxy-2-{4-[2-hydroxy-2-(4-methyl-1-oxo-1,3-dihydro-2-benzofuran-5-yl)ethyl]piperidin-1-yl}ethyl]-4-methyl-2-benzofuran-1(3H)-one, 5-[(1R)-1-Hydroxy-2-{4-[1-hydroxy-2-(4-methyl-1-oxo-1,3-dihydro-2-benzofuran-5-yl)ethyl]piperidin-1-yl}ethyl]-4-methyl-2-benzofuran-1(3H)-one, 4-Methyl-5-[2-(4-{[(1-oxo-1,3-dihydro-2-benzofuran-5-yl)methyl]amino}piperidin-1-yl)ethyl]-2-benzofuran-1(3H)-one, 5-{(1R)-1-Hydroxy-2-[4-({[(2R)-2-hydroxy-2-(1-oxo-1,3-dihydro-2-benzofuran-5-yl)ethyl](methyl)amino}methyl)piperidin-1-yl]ethyl}-4-methyl-2-benzofuran-1(3H)-one, 5-{(1R)-1-Hydroxy-2-[4-({[2-hydroxy-1-(1-oxo-1,3-dihydro-2-benzofuran-5-yl)ethyl](methyl)amino}methyl)piperidin-1-yl]ethyl}-4-methyl-2-benzofuran-1(3H)-one, 5-[({1-[(2R)-2-Hydroxy-2-(4-methyl-1-oxo-1,3-dihydro-2-benzofuran-5-yl)ethyl]piperidin-4-yl}methyl)sulfanyl]-4-methyl-2-benzofuran-1(3H)-one, 5-({1-[(2R)-2-Hydroxy-2-(4-methyl-1-oxo-1,3-dihydro-2-benzofuran-5-yl)ethyl]piperidin-4-yl}methoxy)-4-methyl-2-benzofuran-1(3H)-one, 5-[({1-[(2R)-2-Hydroxy-2-(4-methyl-1-oxo-1,3-dihydro-2-benzofuran-5-yl)ethyl]piperidin-4-yl}methoxy)-4-methyl-2-benzofuran-1(3H)-one, 5-[(1-[2-Hydroxy-1-(4-methyl-1-oxo-1,3-dihydro-2-benzofuran-5-yl)ethyl]piperidin-4-yl}methyl)sulfinyl]-4-methyl-2-benzofuran-1(3H)-one, 5-({1-[(2R)-2-Hydroxy-2-(4-methyl-1-oxo-1,3-dihydro-2-benzofuran-5-yl)ethyl]piperidin-4-yl}methyl)sulfonyl]-4-methyl-2-benzofuran-1(3H)-one, or a pharmaceutically acceptable salt thereof.

11. A composition comprised of a compound of claim 1, or a pharmaceutically acceptable salt thereof, and a pharmaceutically acceptable carrier.

* * * * *